(12) United States Patent
Goldsmith

(10) Patent No.: US 11,013,858 B2
(45) Date of Patent: May 25, 2021

(54) NONJACKETING SIDE-ENTRY CONNECTORS AND PROSTHETIC DISORDER RESPONSE SYSTEMS

(71) Applicant: David S. Goldsmith, Atlanta, GA (US)

(72) Inventor: David S. Goldsmith, Atlanta, GA (US)

( * ) Notice: Subject to any disclaimer, the term of this patent is extended or adjusted under 35 U.S.C. 154(b) by 958 days.

(21) Appl. No.: 14/998,495

(22) Filed: Jan. 12, 2016

(65) Prior Publication Data

US 2017/0197028 A1 Jul. 13, 2017

(51) Int. Cl.
*A61M 5/158* (2006.01)
*A61M 39/02* (2006.01)
(Continued)

(52) U.S. Cl.
CPC ........ *A61M 5/158* (2013.01); *A61M 39/0247* (2013.01); *A61B 18/22* (2013.01);
(Continued)

(58) Field of Classification Search
CPC .... A61M 2205/057; A61M 2205/0286; A61M 2039/0276; A61M 2039/0282; A61M 39/0247; A61M 39/02; A61M 39/0208; A61M 5/158; A61M 2005/1586; A61M 2025/0286; A61M 25/04; A61M 2205/054; A61M 2039/0286; A61M 2025/0233; A61M 2017/3484; A61M 2039/0273; A61M 2039/0264; A61M 2039/0261; A61M 2039/0279; A61M 25/00; A61M 2025/028; A61M 2205/04; A61N 1/05; A61B 5/6839; A61B 17/064; A61B 2017/3484; A61B 18/22

See application file for complete search history.

(56) References Cited

U.S. PATENT DOCUMENTS

| 6,620,139 B1 * | 9/2003 | Plicchi | A61B 18/1477 604/103.1 |
| 2006/0178647 A1 * | 8/2006 | Stats | A61M 39/0208 604/288.01 |

(Continued)

*Primary Examiner* — Tiffany Legette-Thompson
(74) *Attorney, Agent, or Firm* — Meunier Carlin & Curfman LLC

(57) ABSTRACT

Provided is a connector suitable for securely infixing a catheter, electrode, hollow needle, probe, or other styliform device with its tip stabilized within a nontubular anatomical structure. Secure junctions between fluid lines and/or electrodes and tissue are essential for automatic controls and permanent nephrostomies and suprapubic cystostomies, for example, using synthetic materials. These can be made self-contained and fully implanted to treat one chronic condition, or represent but one module controlled as an axis or channel of control in an adaptive ambulatory hierarchical prosthetic disorder response system used to automatically coordinate the treatment of chronic comorbid disease. Such applications require prosthesis-to-native tissue junctions which are secure, immobile, unsusceptible to leaks or microbial intrusion, and require little if any maintenance. Connection for securely and least disruptively merging catheteric and native lumina is described in nonprovisional application Ser. No. 14/121,365, entitled Ductus Side-entry Jackets and Prosthetic Disorder Response Systems, filed on 25 Aug. 2014.

17 Claims, 21 Drawing Sheets

(51) Int. Cl.
*A61N 1/05* (2006.01)
*A61M 25/02* (2006.01)
*A61B 18/22* (2006.01)

(52) U.S. Cl.
CPC ............ *A61M 2005/1586* (2013.01); *A61M 2025/0233* (2013.01); *A61M 2025/0286* (2013.01); *A61M 2039/0276* (2013.01); *A61M 2039/0282* (2013.01); *A61M 2205/04* (2013.01); *A61M 2205/054* (2013.01); *A61M 2205/057* (2013.01); *A61N 1/05* (2013.01)

(56) References Cited

U.S. PATENT DOCUMENTS

| | | | |
|---|---|---|---|
| 2007/0240721 A1* | 10/2007 | Ho | A61M 16/06 128/207.13 |
| 2010/0018534 A1* | 1/2010 | Veliss | A61M 16/06 128/206.24 |
| 2011/0098662 A1* | 4/2011 | Zinn | A61M 39/0208 604/288.01 |
| 2011/0238034 A1* | 9/2011 | Kalpin | A61M 5/14276 604/500 |
| 2012/0172800 A1* | 7/2012 | Dudar | A61M 5/36 604/123 |
| 2014/0171899 A1* | 6/2014 | Rosenberg | A61M 25/02 604/500 |
| 2015/0005733 A1* | 1/2015 | Le | A61M 25/02 604/500 |

* cited by examiner

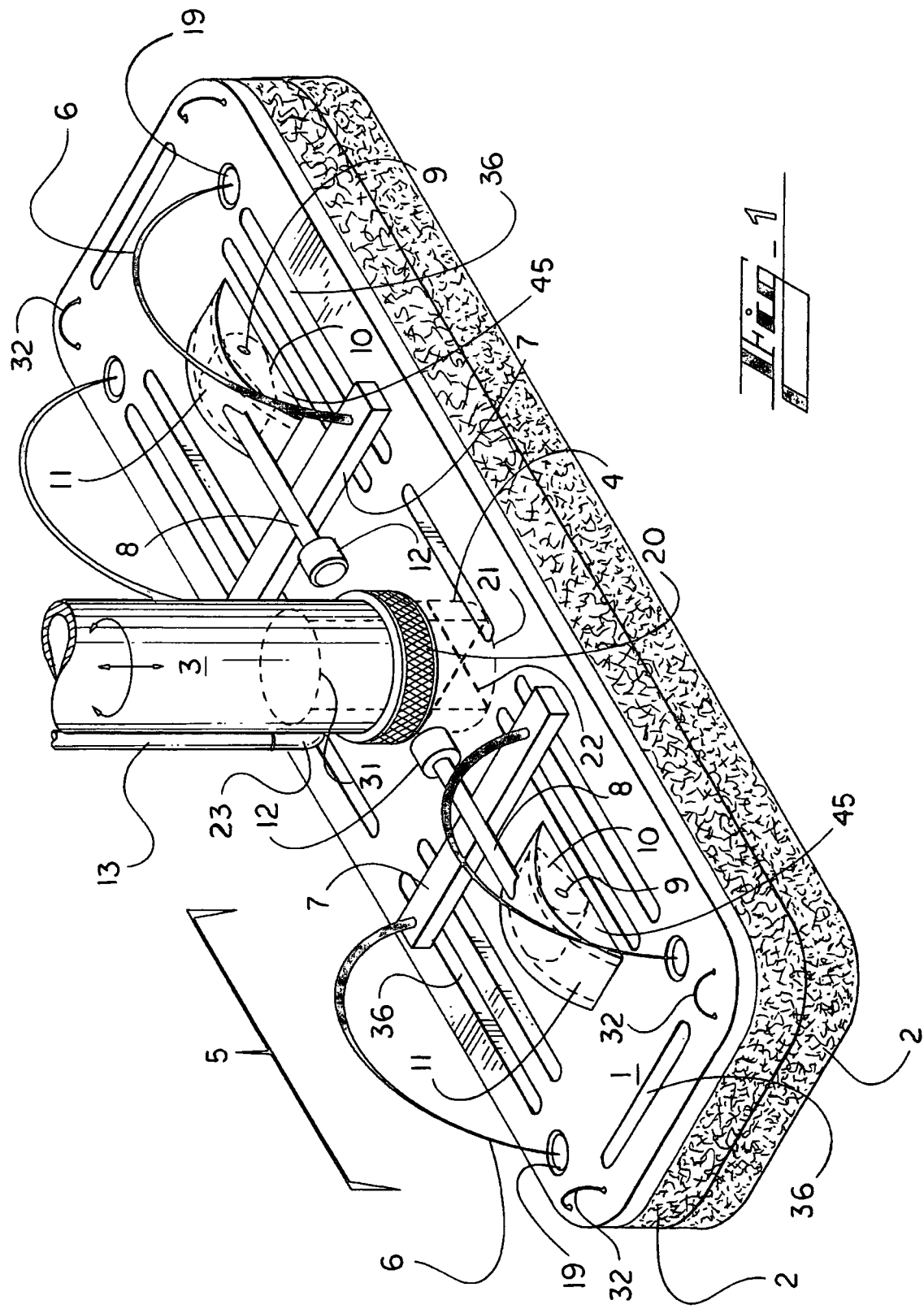

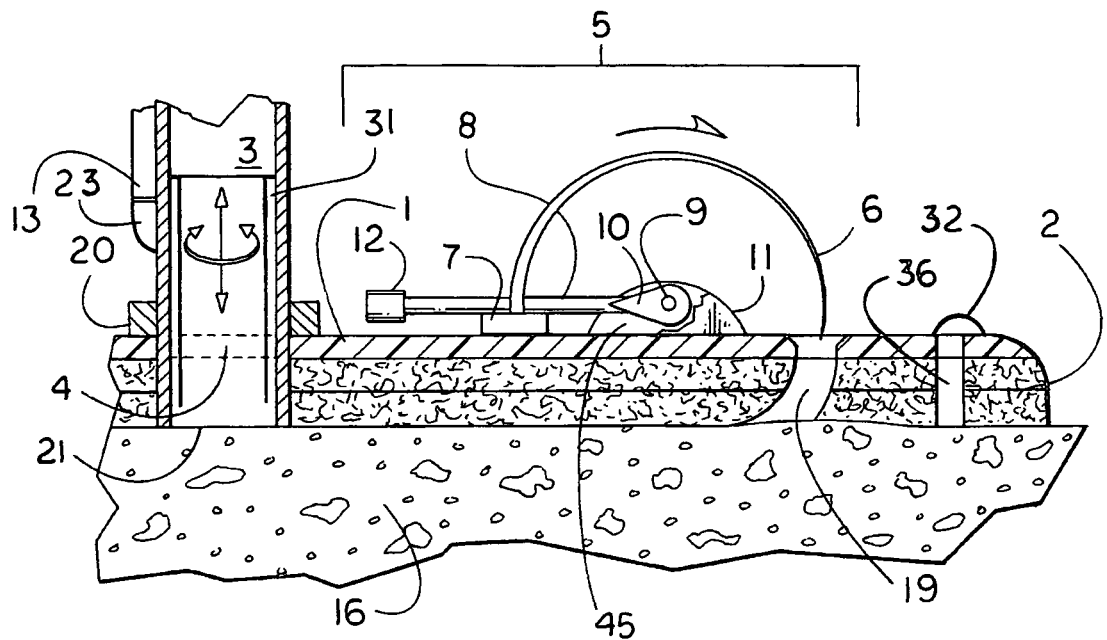
FIG_2
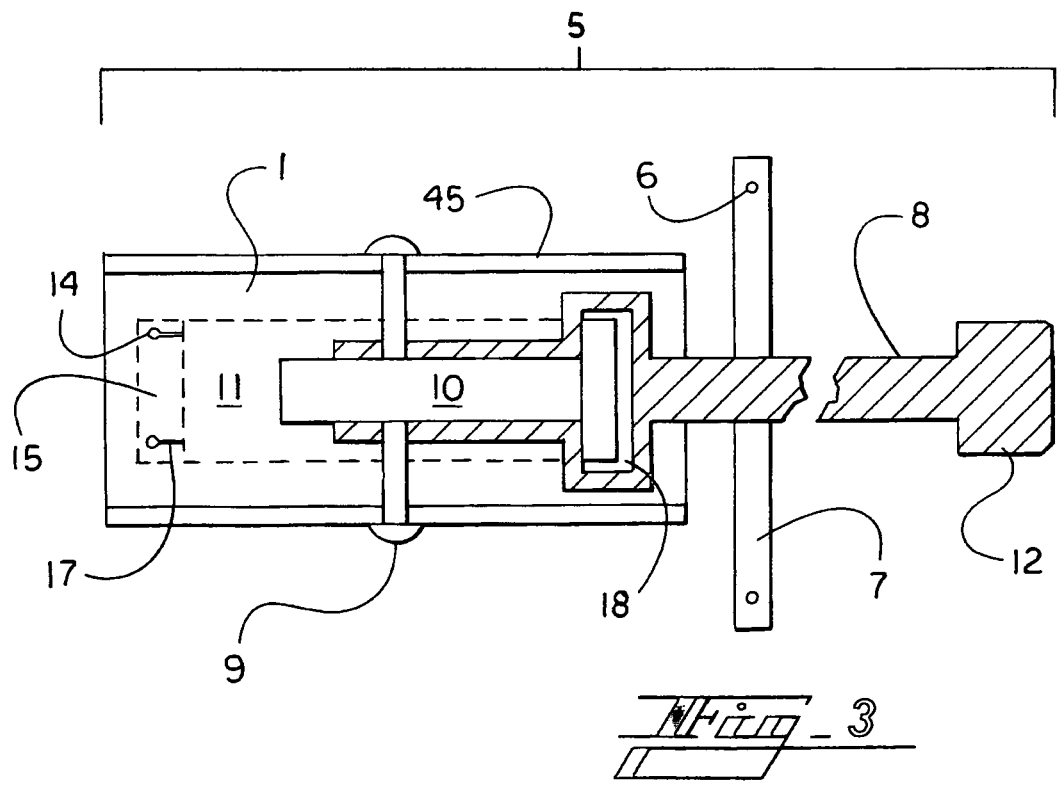
FIG_3

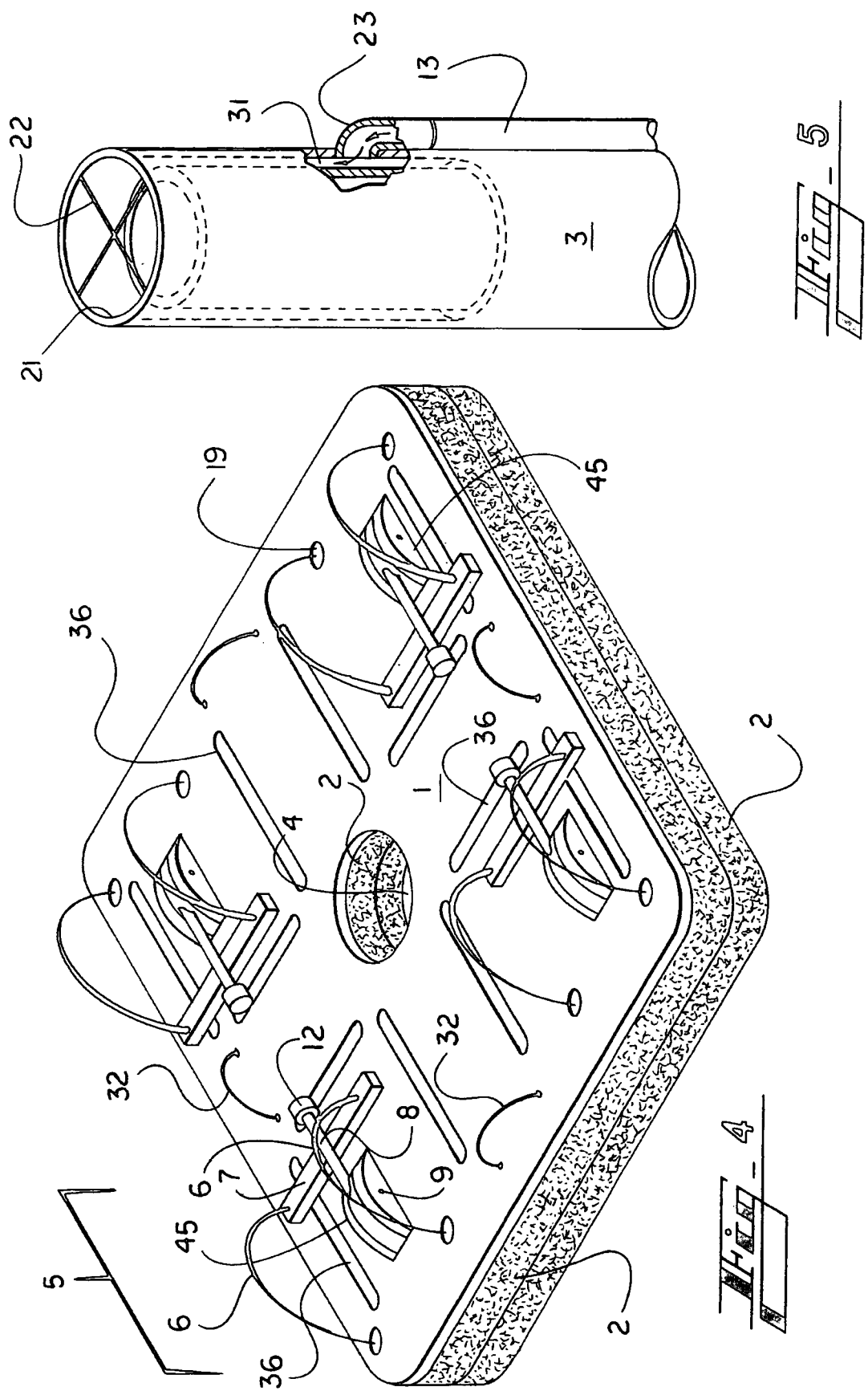

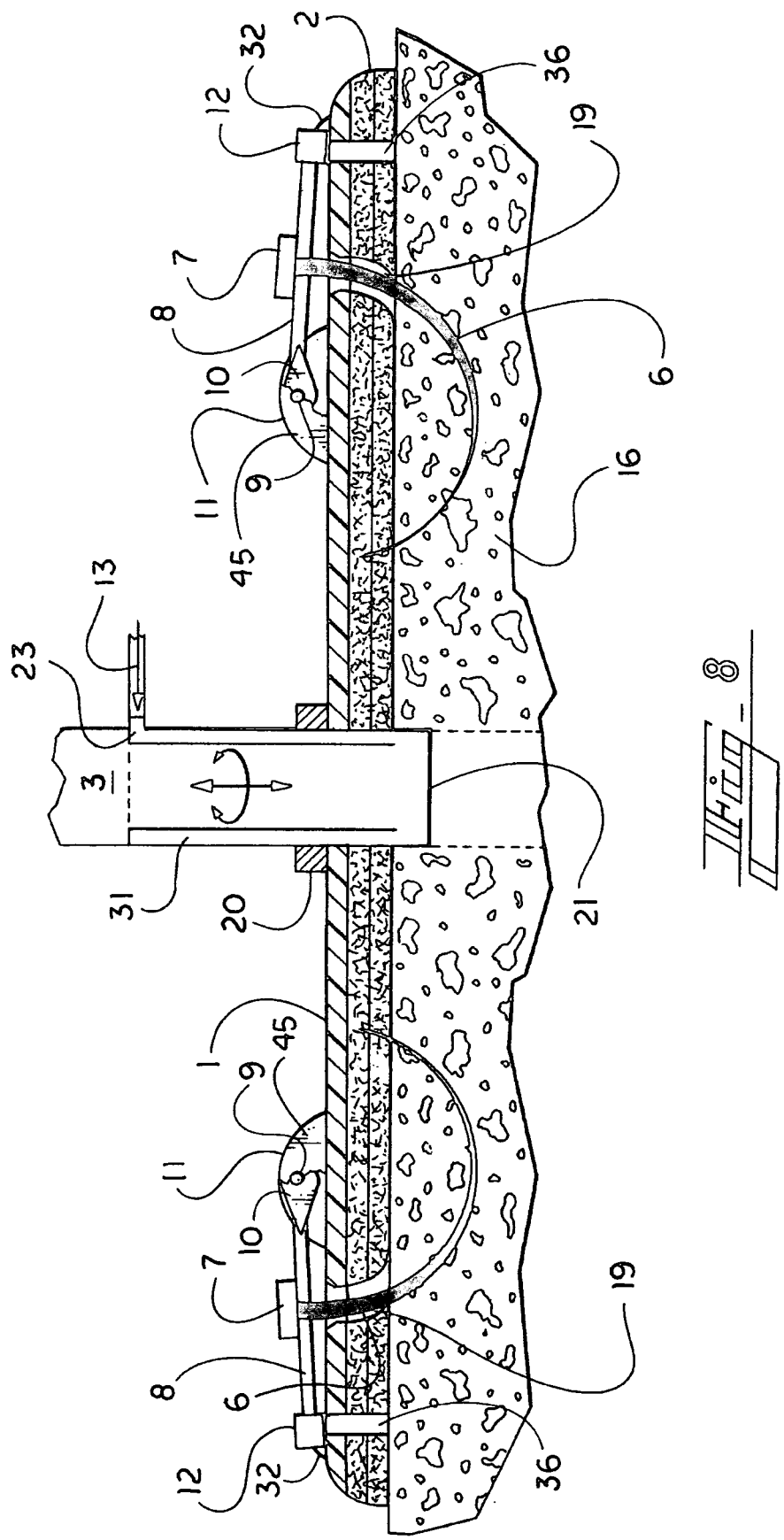

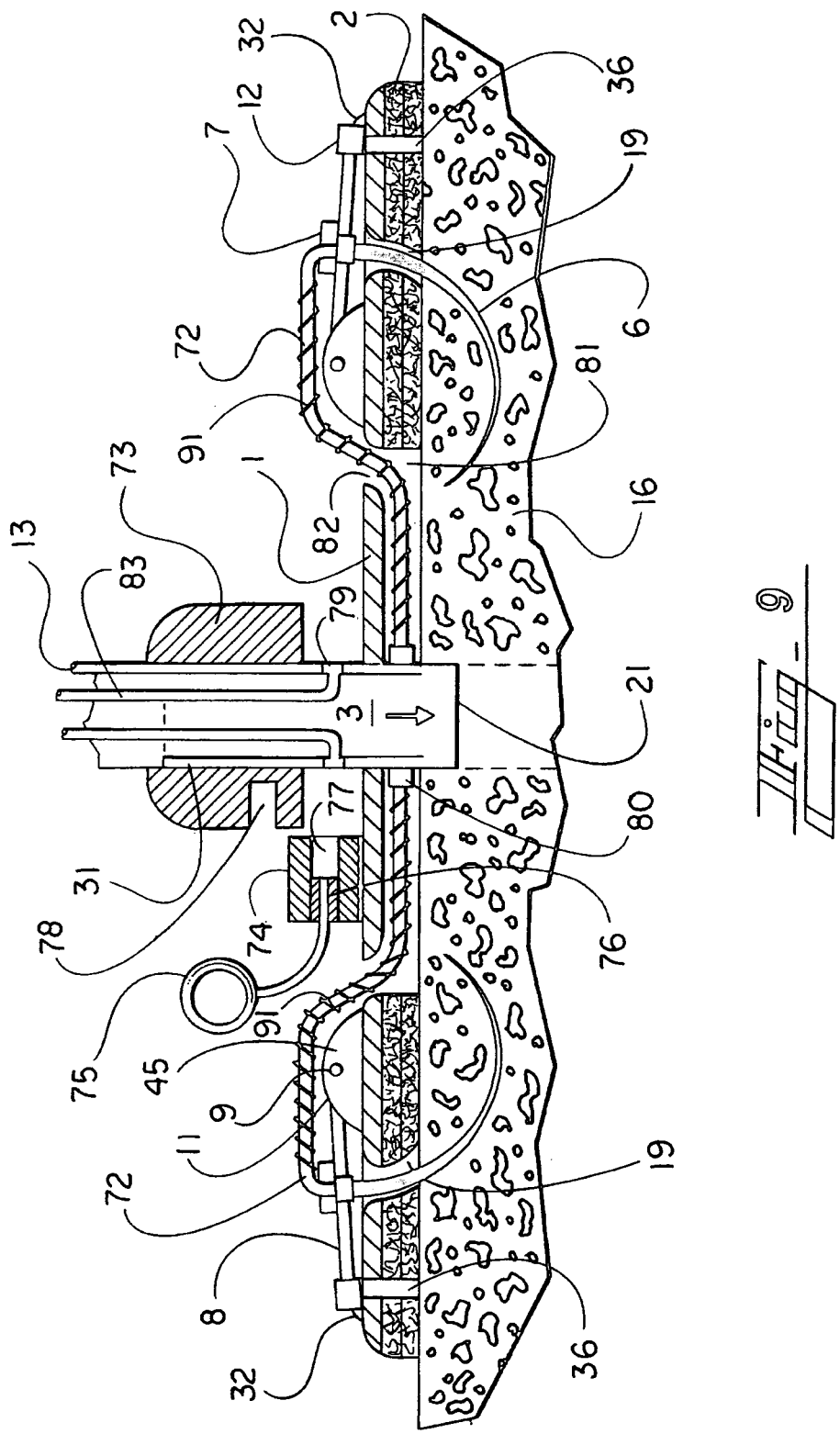

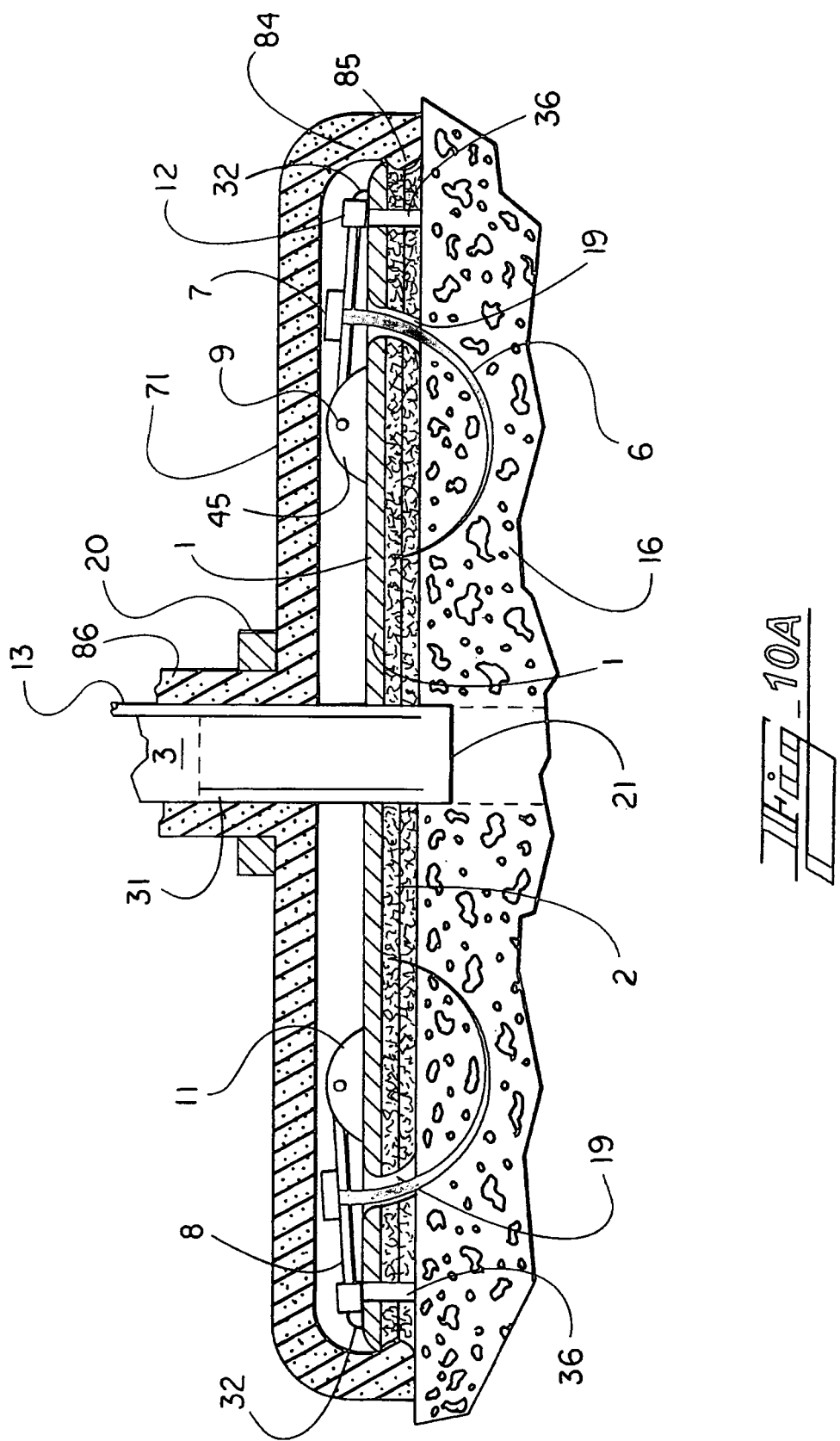

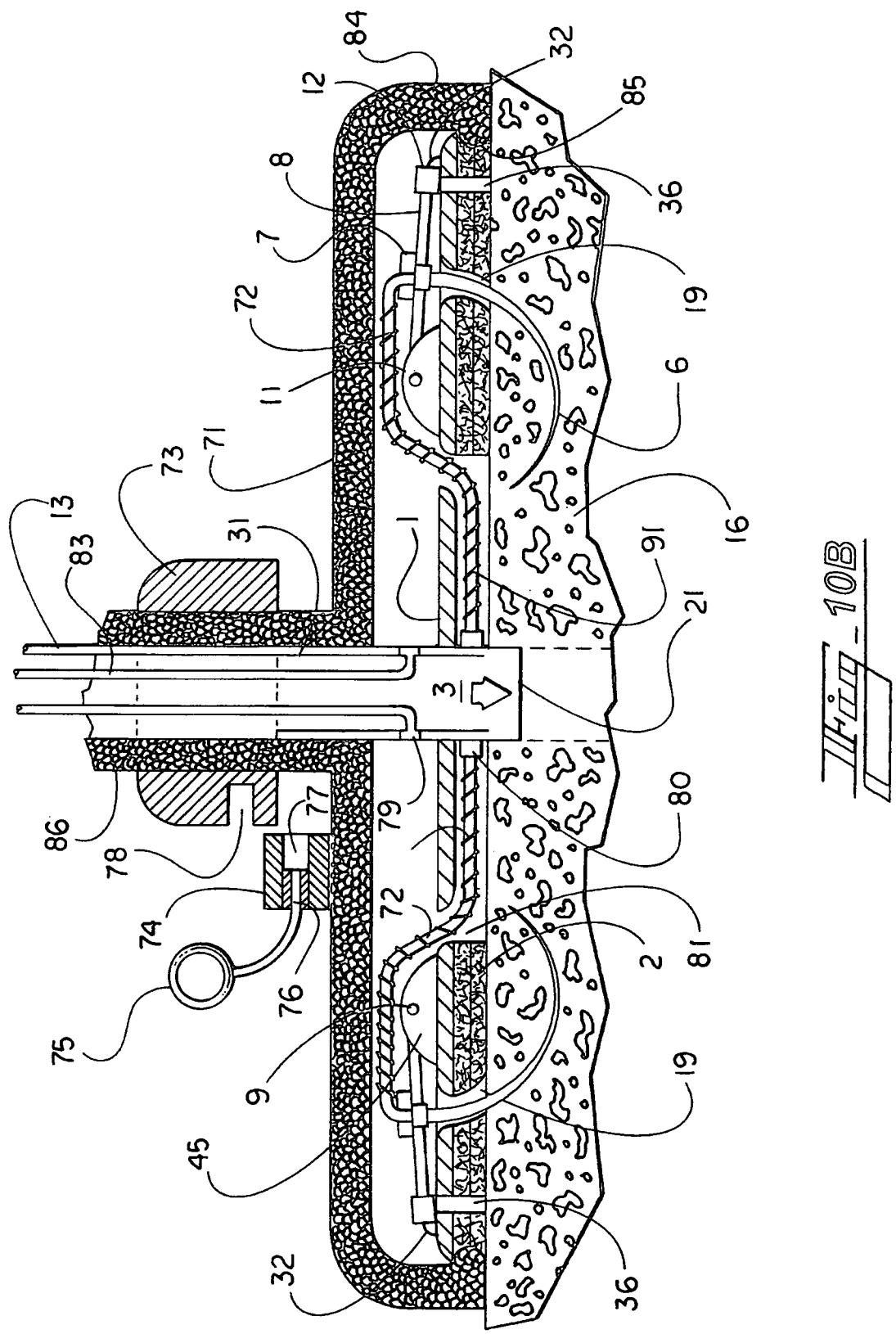

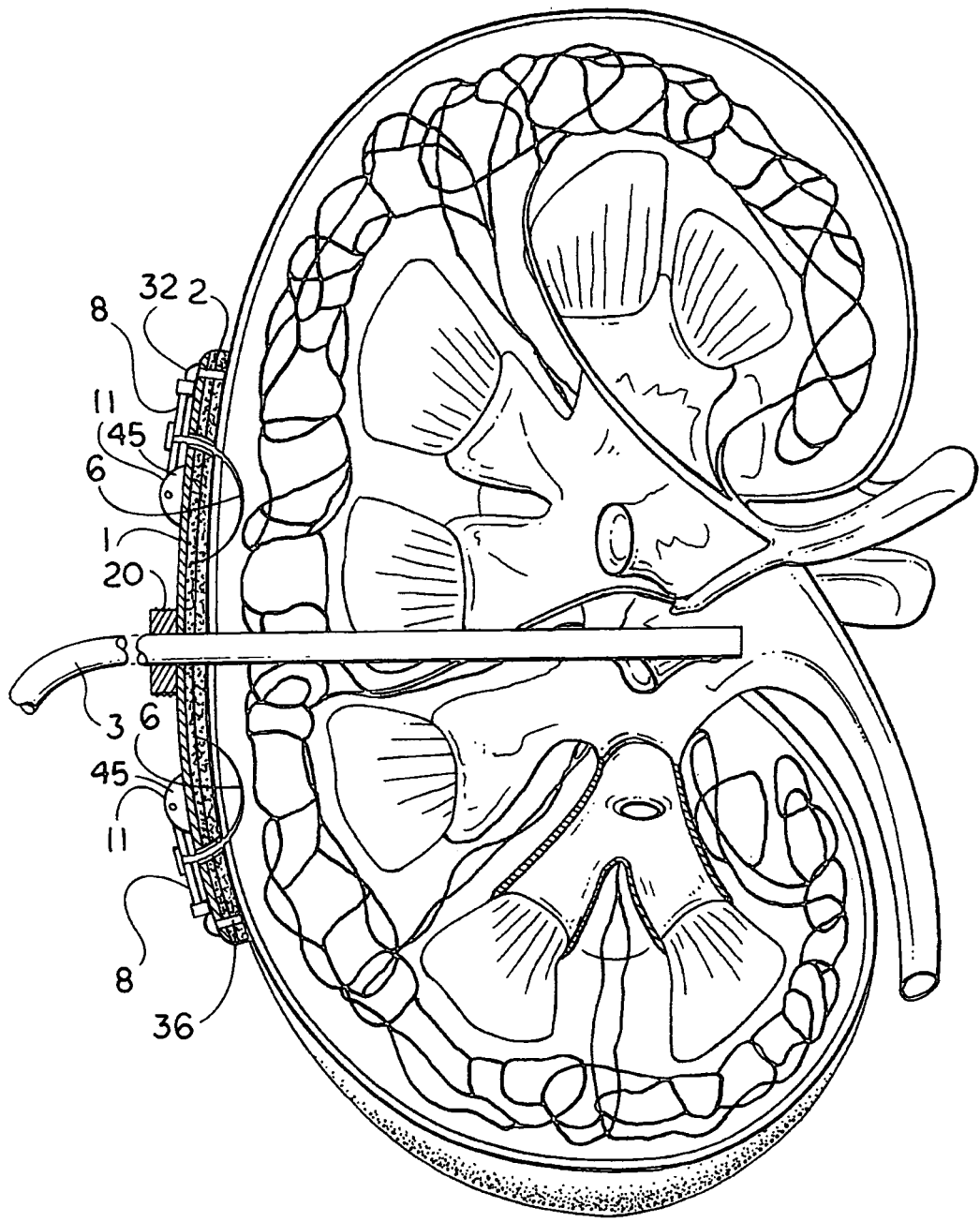
Fig_11

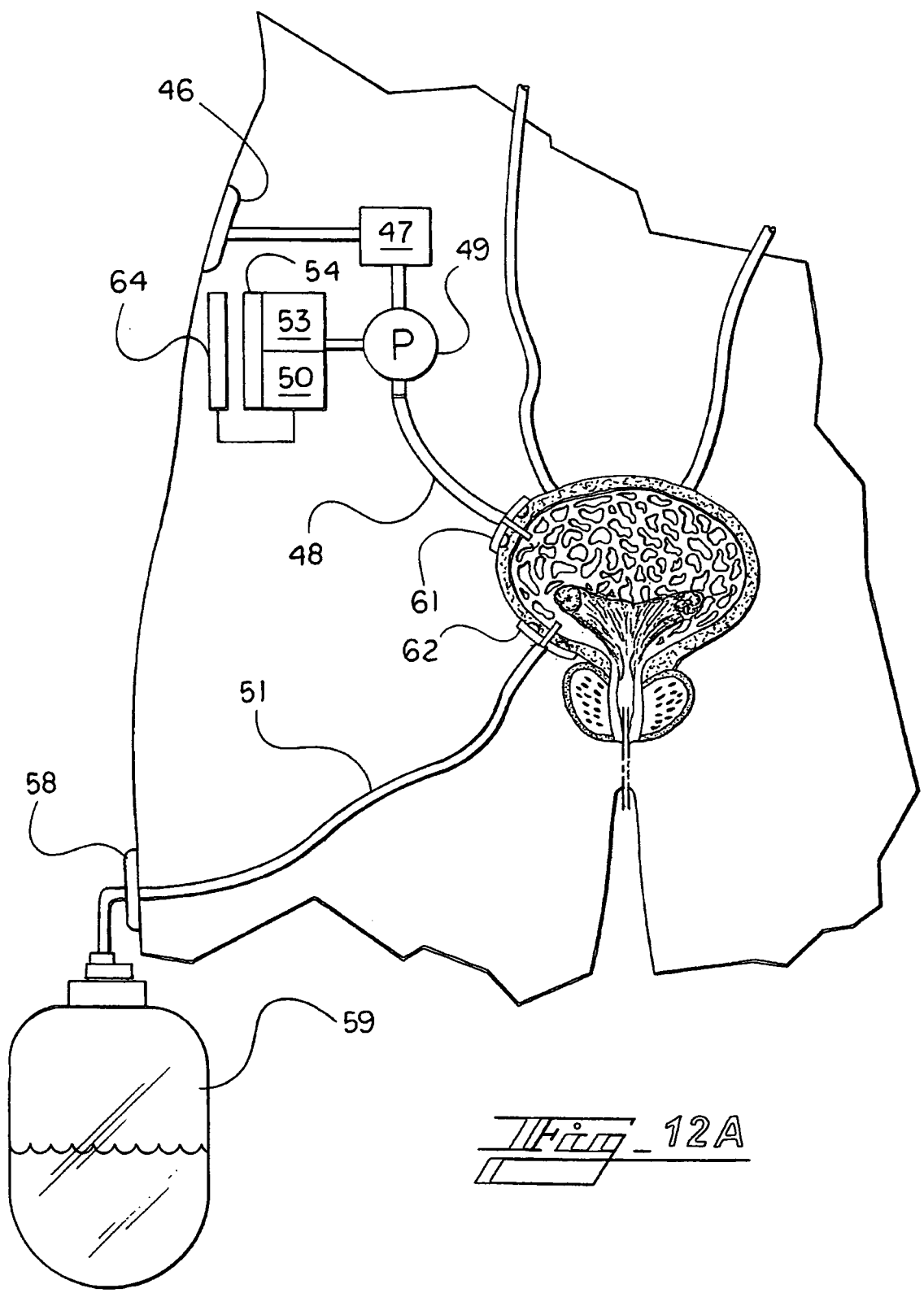
Fig_12A

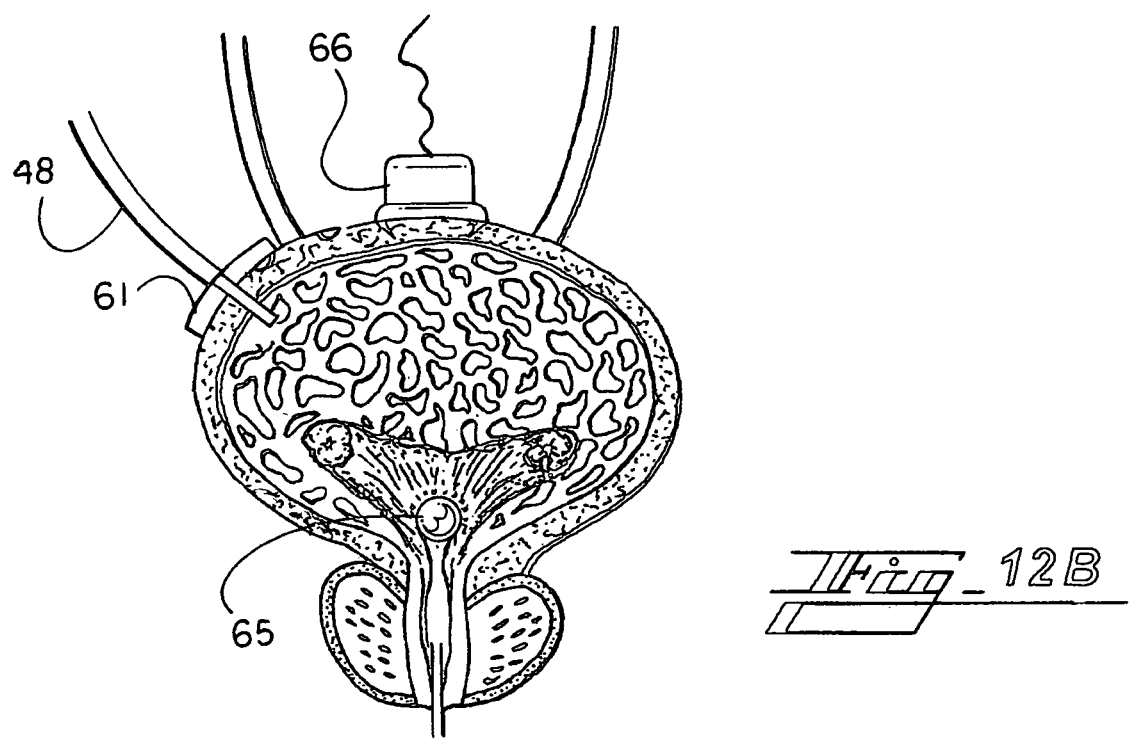
Fig_12B

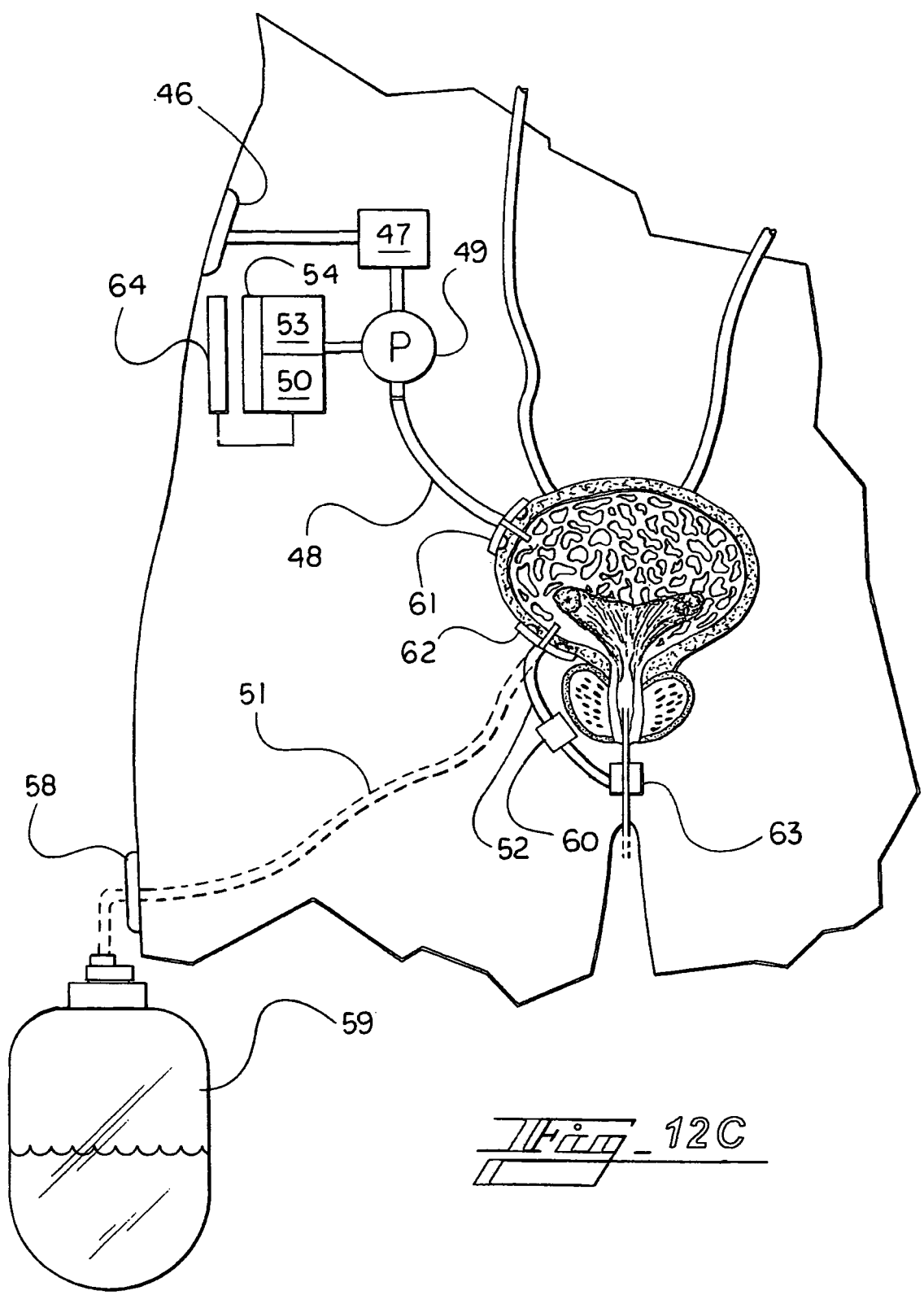

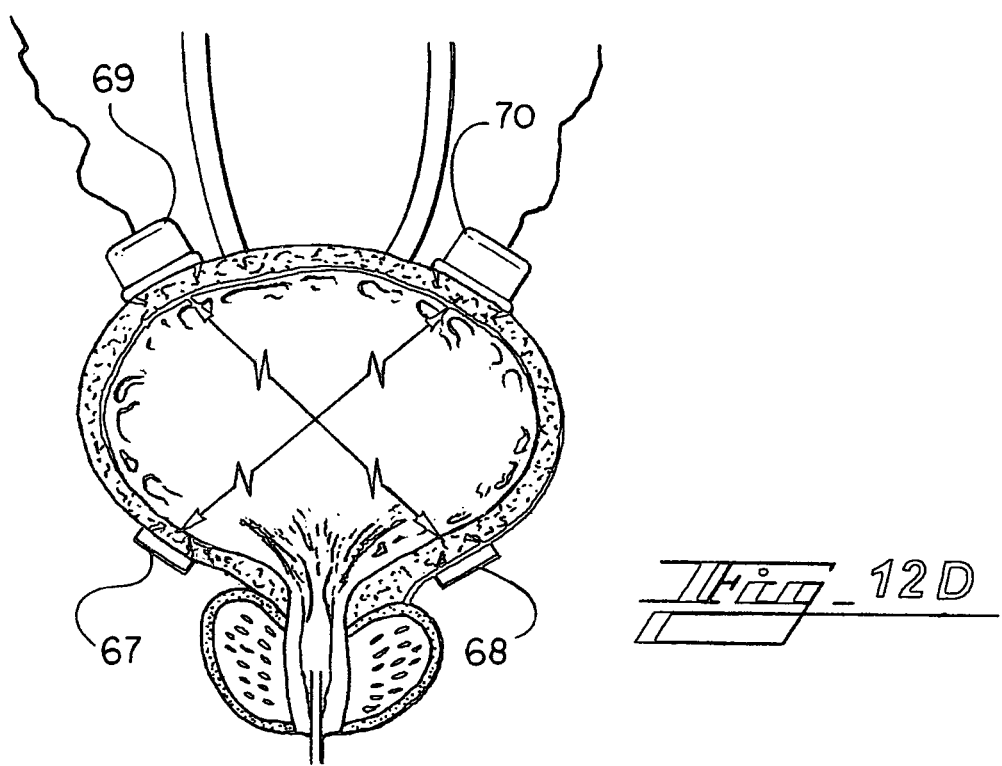
Fig_12D

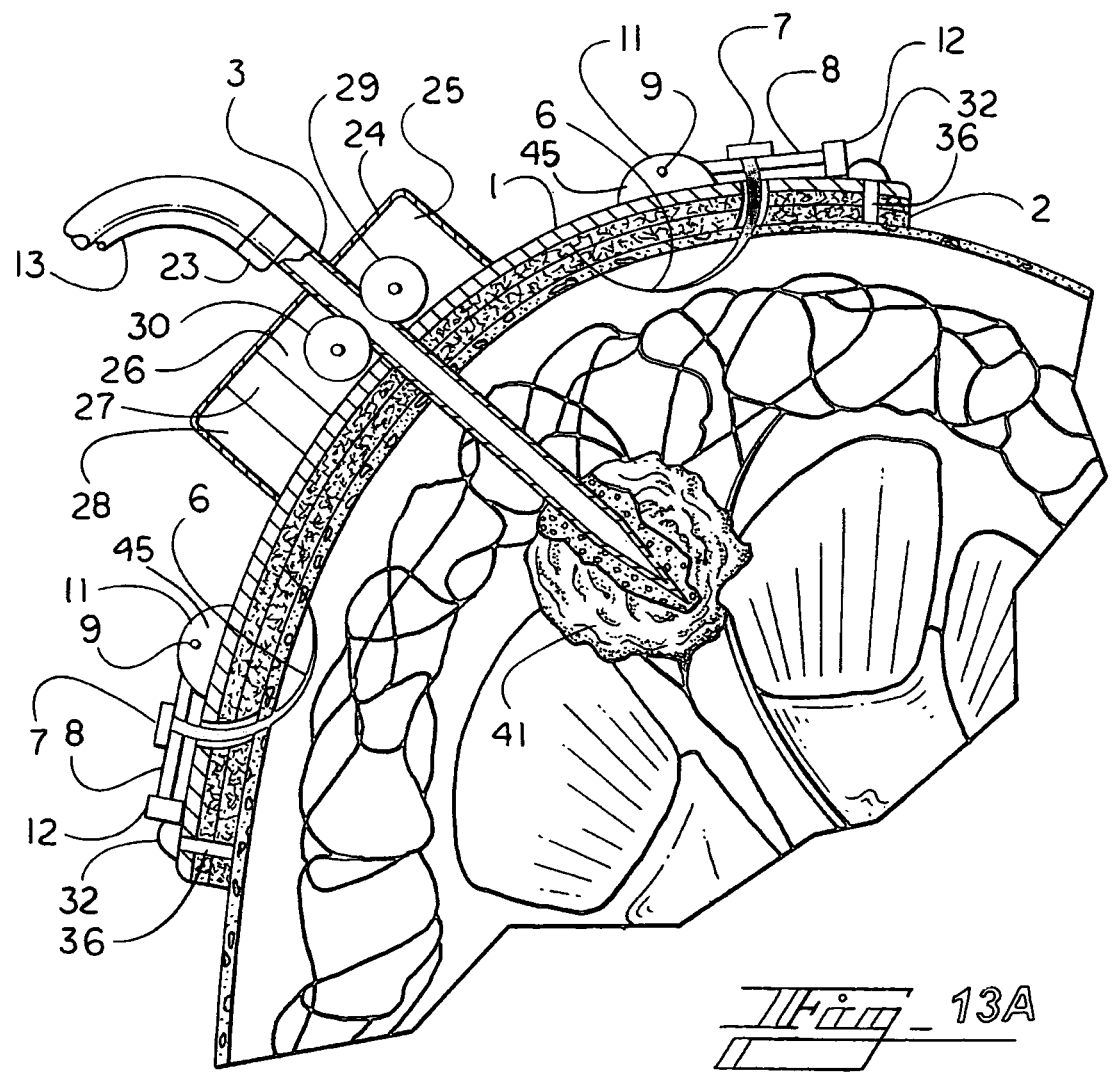
Fig_13A

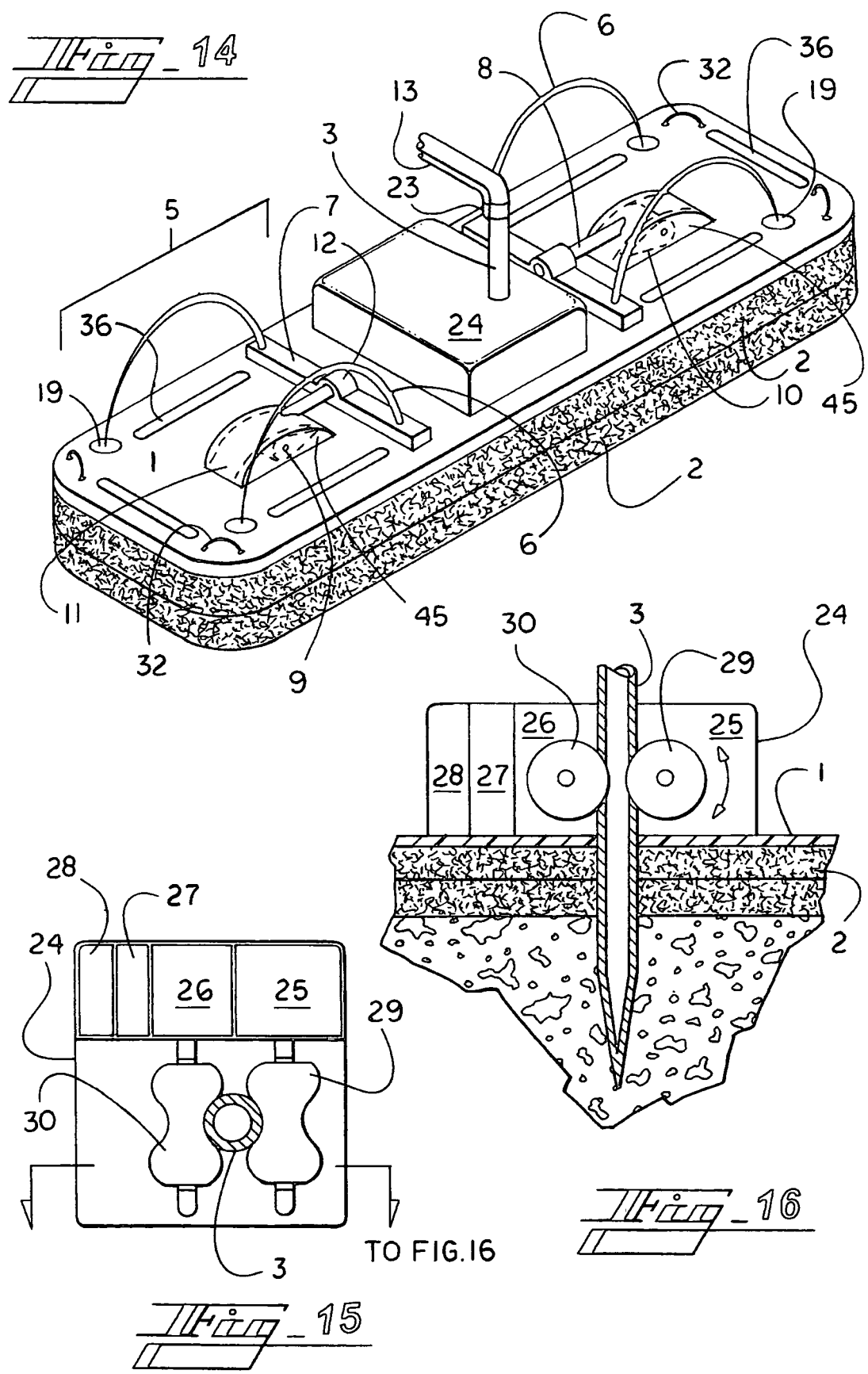

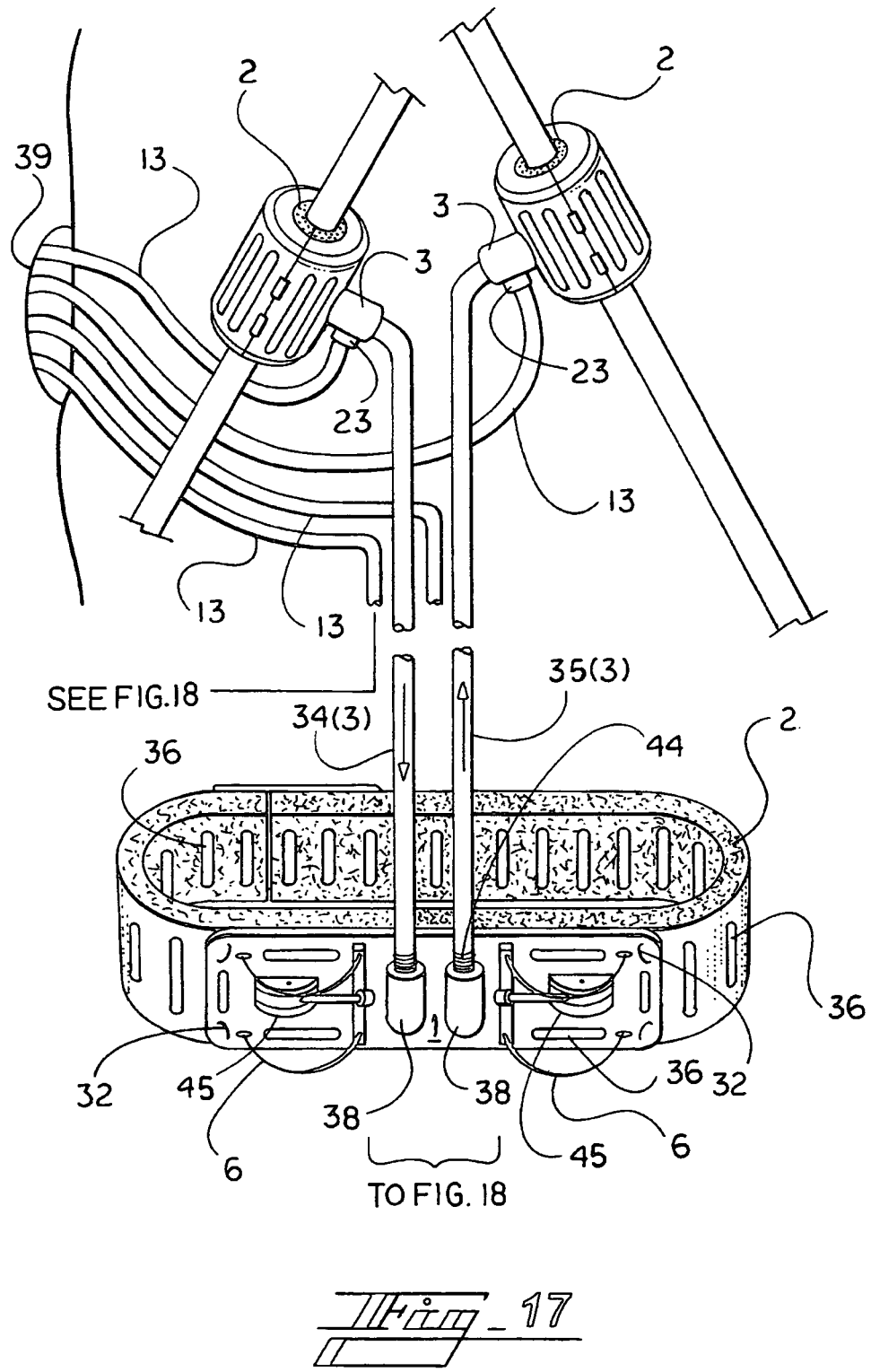

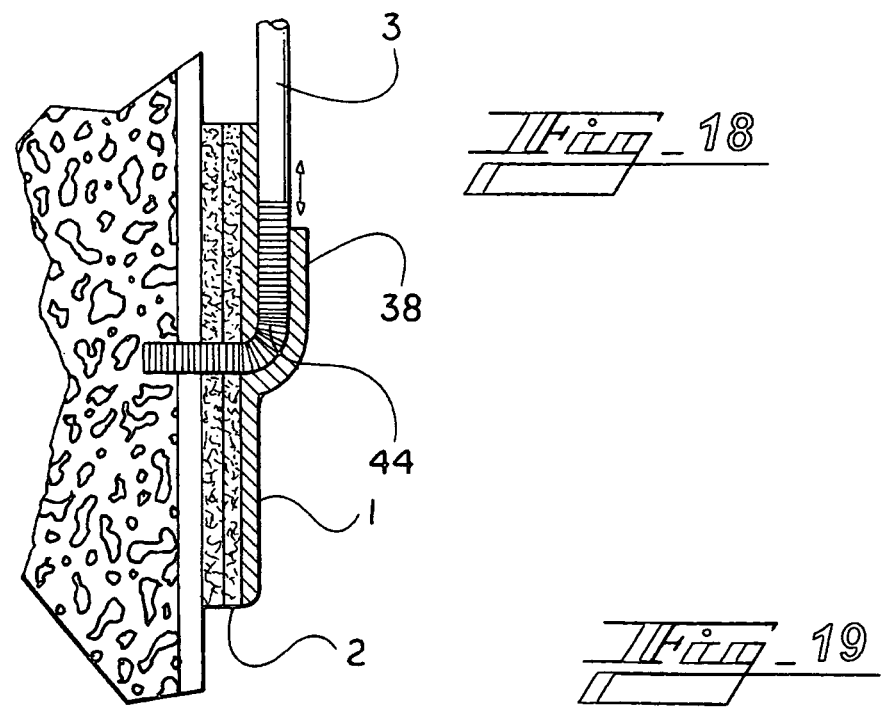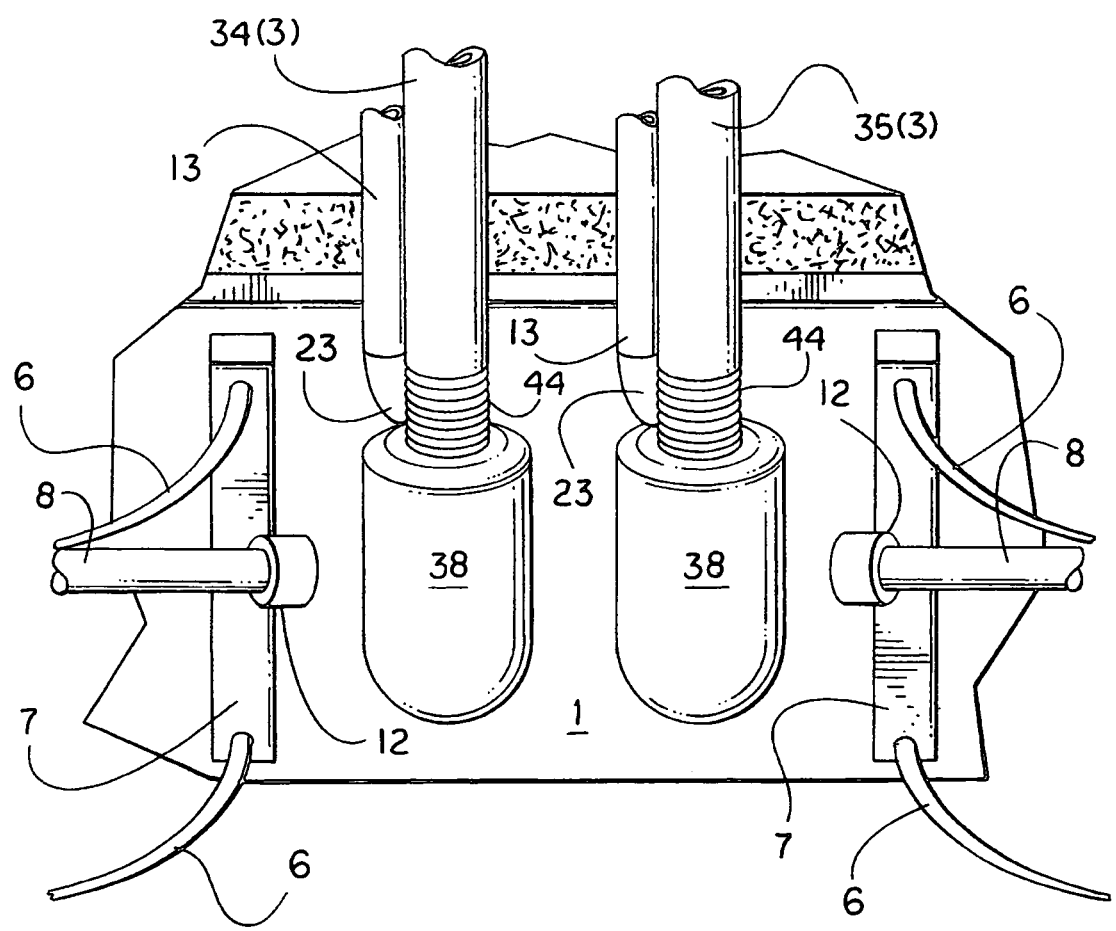

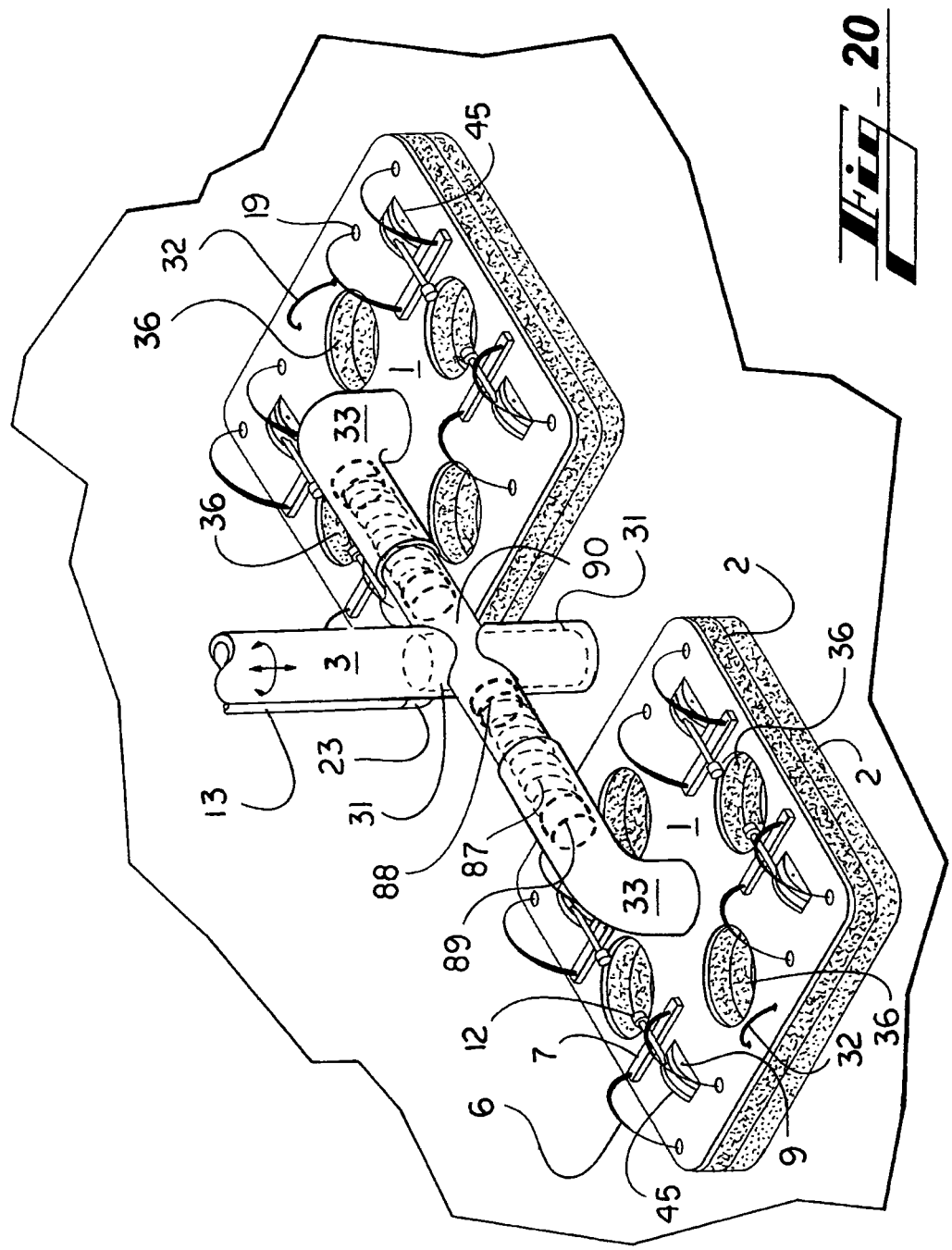

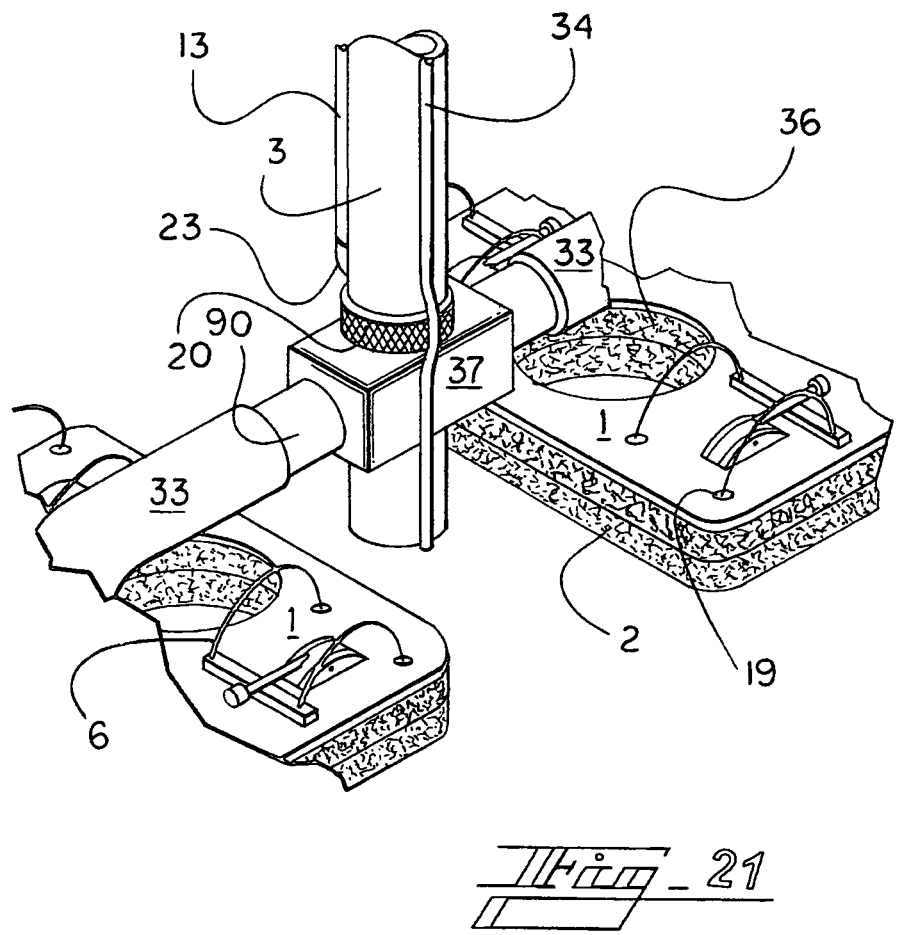
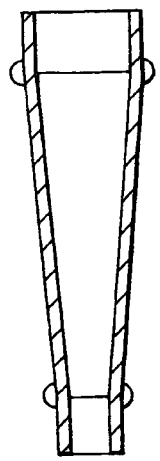
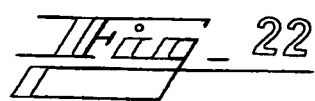

NONJACKETING SIDE-ENTRY CONNECTORS AND PROSTHETIC DISORDER RESPONSE SYSTEMS

This nonprovisional application follows and claims the benefit of Provisional Patent Application 62/282,183, originally entitled Nonductus Side-entry Connectors and Prosthetic Disorder Response Systems filed on 27 Jul. 2015 under 35 U.S.C. 119(e), the entire disclosure thereof incorporated by reference. Pursuant to provisional patent application Ser. No. 62/282,183, the present nonprovisional application changes the title from Nonductus Side-entry Connectors and Prosthetic Disorder Response Systems to Nonjacketing Side-entry Connectors and Prosthetic Disorder Response Systems and claims the benefit of Provisional patent Application 62/282,183.

BACKGROUND OF THE INVENTION

1. Field of the Invention

The methods and apparatus to be described are intended for use by veterinary specialists, nephrologists, urologists, gastroenterologists, general, endocrine, neurological, pediatric, and cardiothoracic surgeons, interventional cardiologists, and interventional radiologists to allow the direct delivery of drugs, other therapeutic substances, or functional electrical stimulation into, or to provide drainage or obtain diagnostic testing samples from bodily organs and tissues of nontubular, or nonductal, conformation, or ductal but large and traumatizing to encircle. Copending application Ser. No. 14/121,365, entitled Ductus Side-entry Jackets and Prosthetic Disorder Response Systems, filed on 25 Aug. 2014 described means for creating secure junctions between catheters, or ductus produced by tissue engineering or tissue expansion, and native ductus, to include those vascular, gastrointestinal, and urogenital.

Copending nonprovisional application Ser. No. 14/121,365 was directed to the creation of passages between synthetic and native ductus and the reverse by means of dependable connectors and durable connections able to remain in place indefinitely, and if necessary, adapt to growth over a period of years. Copending application Ser. No. 14/121,365 also addressed means for securely fastening catheteric lines, injection needles, and electrodes, for example, to native ductus through an entry wound for the long term treatment of chronic conditions, and delineated the assignment of axes in a hierarchical control system to different organs or organ systems in the treatment of comorbid disease, for example. A side-entry connector must provide a junction which is durable, positionally durable, and leak free. Nonjacketing side-entry connectors extend this capability to ductal structures such as the heart, stomach and colon, which abruptly motile and large in diameter, need not be jacketed or collared, as well as to nonductal tissue, prompting revision of the title from 'nonductus' to 'nonjacketing.'

Accordingly, this application extends from tubular to nontubular and large caliber tubular anatomical structures the capabilities of ductus side-entry jackets described in copending nonprovisional application Ser. No. 14/121,365. The junction created may be conventional and singular or support one in a number of disease process treatment control axes or channels of an automatic ambulatory prosthetic disorder response system placed to act as a backup 'immune' system.' Autonomic motor assist devices mentioned in passing are deferred for full description in an application to follow, that present concerned with electrical and pharmacological applications of nonjacketing side-entry connectors.

2. Concept of the Invention

As well as to fix the angle of an electrode or an injection needle, for example, within underlying tissue, nonjacketing side-entry connectors can be used to connect synthetic to native conduits or the reverse, as when creating a shunt or bypass. The long term sustainability of any such connection within the body is no less dependent upon the ability to protect the junction formed as it is upon the security of the mechanical joint. These connectors are thus no less directed to the delivery of maintenance solutions and medication to maintain the integrity and sterility of the junction as well as to treat the affected tissue. Nonjacketing side-entry connectors securely and sustainably connect and maintain the angle of insertion within tissue or large conduits such as in the lower intestinal tract, of catheters, styliform, and/or cabled devices regardless of type.

Nonjacketing and ductus side-entry connectors differ from 'dumb' surgical fasteners such as staples in seven major respects:

1. The implementation of direct drug targeting by mechanical means not dependent upon intrinsic chemical affinity, thus allowing drug concentrations greater than might be allowed into the general circulation without exposing vulnerable tissue and so that drug drug, drug food, and adverse tissue reactions would result.
2. Thermally responsive viscoelastic polyurethane foam cushioning is provided to protect the fine vessels and nervelets of the adventitia or fibrosa;
3. The mounting platform, or baseplate of the connector, is pliant to conform to the contour of the surface to which the connector is attached, minimizing stresses on the tissue and dislodging forces on the connector;
4. Apertures entirely through the baseplate to include the foam cushion are always provided to avoid the complete isolation from the interior environment of the tissue;
5. An accessory fluid delivery line is provided to supply reagents essential to maintain the implant itself by countering the adverse phenomena that have limited the use of synthetic conduits as shunts and bypasses, to include contamination with or without the formation of a biofilm, clot, crystal accretion, or the accumulation of precipitants;
6. The availability of the accessory channel to target adjuvant or subsequent medication from a subdermally implanted port directly to the connector without the need for invasive reentry; and
7/ Backward integrability into an implanted automatic disorder response system controlled by a drug prescription programmed microcontroller to coordinate the direct delivery of drugs to the nidi and secondary sites of comorbid disease.

Nonjacketing side-entry connectors not only allow the dependable connection of synthetic tubing to native tissue or the reverse, but fix the angle and depth of a catheter or styloid device within the tissue. The long term dependability of these connectors is not, and could not be, imparted simply by secure means of mechanical fastening but are made possible by an accessory or service channel which allows the delivery to the junction and the lumen of the catheter or the native conduit of pharmaceuticals. To protect both the synthetic and native components, these normally include antimicrobials, anti-inflammatories, and other drugs and solutions as necessary to treat not only the affected tissue but the junction itself as well as the synthetic lumen. The sustainability of the junction and line depend upon sterility and freedom from clot or crystallization according to the application. Affording no means for the direct targeting of maintenance substances to the junction and lumina to keep these free of accretions and contaminants, smaller diameter synthetic lines have always been limited in useful life.

Essentially, side-entry connectors make possible the direct delivery of any fluid medication and/or any electrical discharge pattern to any location in the body. That side-entry connectors can be fluidically and/or electrically connected in series, daisy-chained, or connected together according to any other circuit arrangement rather than separately is considered obvious. Multiple side-entry connectors applied to the heart or stomach, for example, to deliver electrostimulation, drugs, and/or these in coordination, for example, can be controlled in unison as a group. To optimize most medical applications requires that each connector if not each anchoring needle as will be explained, be separately controllable. For this reason, when hollow to allow injection and/or able to conduct electricity, each anchoring needle seen as part number 6 in the accompanying drawings will often respond to an independent channel of control.

Differential control is especially pertinent in connection with electrostimulation, where differential and coordinated control over the discharge pattern of each needle of each side-entry connector can be significant. Absent conductive needles, the overall dimensions of any one connector will seldom recommend independent control among the hollow anchoring needles of the same connector. Where electrostimulation and drug delivery are to be precisely coordinated, however, this will not be so. A discrete channel of control for each needle makes possible coordination among the discharges of each needle in a given connector as well as coordination with each needle in any neighboring side-entry connectors. In this way, various arrangements of connectors about the post myocardial infarction heart, for example, can be programmed to vary the type and pattern of stimulation among the needles in the same and neighboring connectors as monophasic, biphasic, or pulsed polyphasic, for example.

The radius of any one semicircular tissue engaging and retaining, or anchoring, needle 6 in FIGS. 1, 2, 4, 6 thru 11, 13A thru 14, 17, and 19, thru 21 depends upon the physical properties and depth of the tissue to be fastened but is typically 5 millimeters. For tissue that changes in thickness, the radius of the needles is adapted, so that some connectors will be asymmetrical as to needle radius. An exception to series connection is a train of nonjacketing side-entry connectors, generally three to a ring, strung at intervals along a motility-impaired urogenital or digestive ductus. There the connectors in each successive ring are separately energized in the timing sequence programmed but series connected within each ring to discharge and/or deliver a drug circumferentially as a unit.

To simulate the action of the intrinsic, or enteric, nervous system appropriate to the metabolic function as peristaltic, segmentative, haustral churning, catastalsis, gastroileal reflex, gastrocolic reflex, or mass movement, for example, the microcontroller implant must energize the rings and individual side-entry jackets with electrical discharge anchoring needles and/or electrode, in different sequential patterns. When it is considered that the detailed action at each connector in a body-wide constellation of connectors such as these and applied to other organ systems can be coordinated with each of the others by an implanted microcontroller governing the action of miniature reversible pumps connected to miniaturized reservoirs positioned in a remote pocket or pockets, the therapeutic potential of such an arrangement compared to conventional methods of treatment becomes apparent.

Electrostimulation to a depth greater than the anchoring needles penetrate is through an electrode incorporated as the side-entry connector or a component thereof. If hollow and connected to a drug delivery, or fluid drug feedline, as shown in FIGS. 9 and 10B and to be described, the tissue-engaging or anchoring needles seen as part number 6 in the drawing figures can be used for timed injections at precise locations from implanted pumps under the control of an implanted microcontroller programmed to adjust the schedule according to inputs received from implanted sensors. Injection of the same or different drugs, for example, can proceed simultaneously or alternately through both anchoring needles 6 and a hollow needle as side connector 3. Fully, or closed-skin implanted, such a system, detects and responds to morbidity or comorbidity automatically, so that the wearer may not even be aware of it. Directly targeted to the junction, these drugs are kept apart from the systemic circulation and the risk of inducing adverse side effects. The potential advantages over a dumb infusion and recovery syringe driver or syringe pump of discretionary treatment in detail thus are considerable.

Reversal of the pump allows aspiration therapeutic or to extract a biopsy test sample. If drug delivery through infected tissue has contaminated the needle used, a neighboring needle is used. If perforated along the sides as a sieve, injectants are more uniformly emitted at points along the outer surface of the needle and not just at the distal tip. Anchoring needles to passively (nonelectromagnetically) attract a superparamagnetic iron oxide nanoparticulate drug carrier-bound ferrofluid injected by another needle, for example, incorporate magnetized neodymium iron boron. Whether put to the same use but so that the magnetic field can be controlled, a needle continuous with the core or armature of a solenoid coil wound above the level of tissue entry can be used as the distally extended probe of an electromagnet. Needles that include copper or silver matter and connected to an electrical discharge pulsation pattern generator or a microcontroller discharge the electrostimulation.

Needles can inject and retrieve a diagnostic solution for analysis with, in tight timing coordination with, or without the application to the injected tissue of electrical current. Needles can be used to inject a ferrofluid, setting the locus for heat to be generated in a radiofrequency alternated magnetic field. The number of uses to which conductive needles, styloid diagnostic and/or therapeutic probes, stimulatory or analytic electrodes, and fully implantable cabled devices attached as the side connector, seen as part number 3 in the accompanying drawings, can be put is very large. The number, combinations, and permutations of the uses to which fully implanted styloid and cabled devices might be put in conjunction with the delivery of drugs, electrostimulation, magnetic heating, and external beam radiation, to name a few, considerably exceeds the present scope. Probes, electrodes, injection needles, and so on can also be run alongside or down through the side connector as conduit to reach a greater depth.

The depth to which an electrode, for example, extends into the subjacent tissue is set by tightening lock nut 20 in the drawing figures to the length required. When the depth of the probe or electrode, for example, must be precisely adjusted during automated therapy following full implantation, the embodiment shown in FIGS. 14 thru 16 and described below in this section and that entitled Description of the Preferred Embodiments of the Invention is used. Rather than to incorporate a costly ratcheting mechanism, for example, or to produce numerous such devices set to different angles, the probes, electrodes, and injection needles, for example, to be used are made bendable. This has the additional benefit of allowing the operator to set the angle midprocedurally with the site for placement in view.

Ductus side-entry jackets and nonjacketing side-entry connectors not only improve upon conventional means such as used in a suprapubic cystostomy, which is limited to temporary use, but make possible the direct targeting of any tissue requiring treatment, to include sources of hormonal and autonomic motor dysfunction. Digestive hormones can be metered out directly to the gastric antrum with the stomach motile and the patient oblivious. The ability to target drugs directly to the junction allows protection not only against the formation of clot and biofilm (references below in this section) but means that any blood borne disease contracted later can be fought directly as well as systemically. Along the urinary tract, the accretion of minerals along the inside walls of any synthetic tubing used presages obstruction.

If the disease is systemic and the nidus directly targeted, then a background dose of the drug or drugs is circulated. In a simple configuration, a subdermal portacath, usually positioned in the pectoral region, is injected with these substances. Side effects, drug-drug, and drug-food interactions substantially eliminated, the benefits of direct-to-nidus and/or localized affected tissue of drugs such as antineoplastic chemotherapeutics, immunosuppressives, steroids, and amiodarone (delivered directly to the cardioneural nodes of the cardionector (electrical conduction system of the heart, cardionecteur), for example, are fundamental and substantial. Trace amounts that enter the systemic circulation able to inflict harm can often be neutralized with a reversal agent delivered at the excurrent vein, for example.

In more elaborate configurations, injection is of multiple doses held within an implanted reservoir, administration discharged automatically by a small reversible pump under the control of a microcontroller, which in a still more elaborate system, acts in direct response to feedback from implanted sensors. To cite one example, the patency rates of synthetic vascular bypasses in the lower extremities, which ideally would serve well for life, have always proven unsatisfactory, these patients having to be kept on systemically circulated warfarin (Taylor, L. M. Jr., Porter, J. M., and Masser, P. A. 1997. "Femoropopliteal and Infrapopliteal Occlusive Disease," Chapter 85, page 1823 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven). This exposes these patients to bleeding risk, which can be reversed with vitamin K but not before a 2 to 5 day delay. Directly targeted to a segment along a vessel, the coagulability of the blood overall is affected little if at all.

By contrast, the ability to securely fasten prosthetic conduits directly to native conduits and tissues allows synthetic shunts and bypasses to be introduced into the vascular tree and urinary tract, usually with drug support directly targeted to the junction and conduit. This makes possible diversions or rechannelings of luminal contents past diseased or missing anatomy not otherwise practicable, and without the need to harvest healthy autologous tissue and reassign it to a function for which it is not adapted. A reversal agent not yet approved, the clotting factor Xa direct thrombin inhibitor anticoagulants intended primarily for thromboprophylaxis by preventing venous thromboembolism (dabigatran, rivaroxaban, and apixaban now marketed, and betrixaban, darexaban, and edoxaban currently under study), likewise pose the potential for causing a bleeding problem anywhere along the vascular tree. However, with direct targeting, the fact that by the time of filing, no reversal agent for the newer oral anticoagulants dabigitran, rivaroxiban, and apixaban, for example, had been approved or that ximelagatran had been removed from the market is likewise rendered moot.

Delivery of an anticoagulant by the means described herein pertain to chronic conditions such as congestive heart failure or genetic and acquired hypercoagulability, not exigent pulmonary embolism, deep vein thrombosis, venous thromboembolism, stroke, or a myocardial infarction. Treatment of the causative factor of atrial fibrillation presumed whether a valve disorder, cardiomyopathy, hyperthyroidism, thyrotoxicosis, or pericarditis, for example, and alternative or concurrent treatment modalities, such as cardioversion, ablation, therapy, or the use of beta blocker or calcium antagonist accepted (see, for example, Josephson, M. E. and Zimetbaum, P. 2005. "The Tachyarrhythmias," in Harrison's Principles of Internal Medicine, New York, N.Y.: McGraw-Hill, 16th Edition, pages 1345-1347; The Merck Manual 18th edition, 2006, Section 75, pages 696-699), confining consideration to the use of an anticoagulant, ductus side-entry connectors as described in copending application Ser. No. 14/121,365 allow the direct targeting of the anticoagulant to the pulmonary veins, for example, (see, for example, Harrison, Op cit., page 1346), and nonjacketing side-entry connectors as described herein allow secure delivery of drugs to the atrial myocardium as well as allow the treatment of cardiomyopathy by attachment at any location or locations about the heart. The targeted fraction of an anticoagulant is usually more concentrated and supported by a less concentrated systemic dose.

Considering the time delay of 2 to 5 days for vitamin K to reverse warfarin, the lack of a reversal agent leaves the patient who needs emergency surgery or is involved in a traffic collision, for example, little more vulnerable than does warfarin in patients eligible for vitamin K therapy. Significantly, when direct targeting of all but a systemically circulated background dose of any anticoagulant can be delivered to a circumscribed region or segment such as the lower legs, the overall amount used is too small to result in a bleeding problem, so that the inability to reverse these drugs is materially reduced as a problem. While hypercoagulability demands the systemic administration of anticoagulants, the risk of deep venous thrombosis in the lower legs and the risk of pulmonary embolism, for example, can be averted using the arrangement shown in FIGS. 17 thru 19.

In addition to temporary delivery through the accessory channels of an anticoagulant to prevent a deep vein thrombosis, or a thrombolytic to break up a thrombus using above-skin mainlines, FIGS. 17 thru 19 pertain to the long term treatment using subcutaneously tunneled bloodlines of intractable arterial and venous stasis ulcers of the crus which persist despite repair of the native venous valves and the use of compression stockings. As shown in the side view of FIG. 18, for use over a limited interval, the fluid supply lines are not tunneled nor the connector implanted subdermally. However, the majority of venous ulcers recur, so that the device is placed subdermally. The need for a pressure equalization opening in fluid lines is assumed throughout, such too small to allow leakage of any medical significance. By comparison, a dose of any drug targeted to a side-entry connector, even were there zero takeup, if dispersed throughout the systemic circulation could not induce side effects and certainly not a generalized state of reduced coagulability. The ability to directly deliver drugs and prosthetic conduit maintaining substances such as antimicrobials and anti-inflammatories to the junction and conduit, or line, mean that once placed, nonjacketing side-entry connectors and ductus side-entry jackets need seldom if ever be revisited.

Provided sufficient slack can be given the lines, such connectors and lines placed in childhood should remain functional throughout life. The lines and connectors coated with contrast allow these to be checked from year to year. Nonjacketing side-entry connectors are intended to make possible positionally durable connections of catheters to native tissue with minimal complications. The term ductus is used in the widest sense of any bodily conduit and not just to denote a duct such as of a gland. Durable connection to an abruptly excursive myocardium or gastric wall can be accomplished by increasing the number and adjusting the angular orientation of the anchoring half-round needles. Placed with the patient under local or general anesthesia, coating of the needles with a topical anesthetic should never be necessary.

When hollow and electrically conductive, the anchoring needles can also be used to inject drugs and/or deliver electrical discharges, where drug and discharge delivery are coordinated in time. For long term placement, and if not to allow injection and/or electrical conductivity, the needles are made of titanium and given an outer textured surface with undercuts to encourage tissue ingrowth. Acid etching is inadequate for this purpose, machining allowing the production of undercuts. Interim adhesion pending ingrowth will seldom be needed, but can be provided by wetting the needles with an absorbable adhesive. If necessary, adverse reaction-suppressive and anti-inflammatory substances, such as phosphorylcholine, dexamethasone, and/or curcumin are added.

The direct targeting into the impaired myocardium or stomach of inotropic or other drugs, such as antineoplastic, antimicrobial, and/or anti-inflammatory, and/or electrostimulation requires the tenacity and chemical as well as chemical durability to withstand strong dislodging forces over a long time. Ductus and nonjacketing side-entry connectors have been devised to realize this level of tenacity and durability. Connecting such needles to separate sources of fluid medication or electrical discharge as a discrete channel allows pharmacological and/or electrical treatment at the affected organ locally and in detail. A simple arrangement to target a single organ requires a portacath, a reservoir or reservoirs, and microcontroller controlled pump from each reservoir to the target.

A switching arrangement as shown in copending application Ser. No. 14/121,365, entitled Ductus Side-entry Jackets and Prosthetic Disorder Response Systems can be inserted at various junctions along this circuit; however, to eliminate this as a potential source of malfunction, and because some drugs should not be mixed before delivery, separate channels from portacath to target is preferred. As shown in FIG. 4, if necessary, individual nonjacketing side-entry connectors can be expanded, or as shown in FIG. 20, connected in tandem or ganged to achieve long term adhesion, fixation to the abruptly discursive heart and stomach necessitating high tenacity.

In cases of refractory ulceration, as in metastatic Zollinger-Ellison disease unresponsive to oral proton pump inhibitors or monthly injections of octreotide and/or where the patient cannot take these drugs, leaving radical resection such as a gastrectomy the only remaining option, the prepositioning of nonjacketing side-entry connectors with electrically conductive needles as shown in FIGS. 9 and 10B and described below in the section entitled Description of the Preferred Embodiments of the Invention is suggested. Placement of these at intervals about the stomach and duodenum to treat gastric and/or duodenal ulcers is readily accomplished endoscopically. For uncomplicated disease where treatment of the condition does not represent but one therapeutic channel under the control of a hierarchically programmed microcontroller, a conventional electrical pulse generator is implanted in the pectoral region. The combination of directly targeted drug and electrical discharge delivery means encourages the study of means for the effective combination of these treatment modalities.

The device to treat venous stasis ulcers of the crus (see, for example, Carmel, J. E. and Bryant, R. A. 2016. "Venous Ulcers," Chapter 12, pages 204-226, in Bryant, R. A. and Nix, D. H. (eds.), Acute and Chronic Wounds: Current Management Concepts, St. Louis, Mo.: Elsevier) shown in FIGS. 17 thru 19 can be placed subdermally or externally and is compatible with skin transplantation; or dermagraft (see, for example, PLOS [Public Library of Science] One Staff 2015. "Correction: Acute Cutaneous Wounds Treated with Human Decellularised Dermis Show Enhanced Angiogenesis during Healing," PLoS One 10(3):e0121503; Greaves, N. S., Lqbal, S. A., Morris, J., Benatar, B., Alonso-Rasgado, T., Baguneid, M., and Bayat, A. 2015. "Acute Cutaneous Wounds Treated with Human Decellularised Dennis Show Enhanced Angiogenesis during Healing," PLoS One 10(1):e0113209; Jones, J. E., Nelson, E. A., and Al-Hity, A. 2013. "Skin Grafting for Venous Leg Ulcers," Cochrane Database of Systematic Reviews 1:CD001737; Hart, C. E., Snyder, D. L., Sullivan, N., and Schoelles, K. M. (eds.) 2012. "Skin Substitutes for Treating Chronic Wounds," Rockville Md. Agency for Healthcare Research and Quality (US) Technology Assessments (online); Loewen-Rodriguez, A., and Lessem, J. 2012. "Dermagraft: Use in the Treatment of Chronic Wounds," Advances in Wound Care (New Rochelle) 1(3):138-141; Landsman, A. S., Cook, J., Cook, E., Landsman, A. R., Garrett, P., Yoon, J., Kirkwood, A., and Desman, E. 2011. "A Retrospective Clinical Study of 188 Consecutive Patients to Examine the Effectiveness of a Biologically Active Cryopreserved Human Skin Allograft (TheraSkin®) on the Treatment of Diabetic Foot Ulcers and Venous Leg Ulcers," Foot and Ankle Specialist 4(1):29-41; Hogsberg, T., Bjarnsholt, T., Thomsen, J. S., and Kirketerp-Moller, K. 2011. "Success Rate of Split-thickness Skin Grafting of Chronic Venous Leg Ulcers Depends on the Presence of *Pseudomonas aeruginosa*: A Retrospective Study," PLOS [Public Library of Science] One 6(5):e20492; Jankunas, V., Bagdonas, R., Samsanavicius, D., and Rimdeika, R. 2007. "An Analysis of the Effectiveness of Skin Grafting to Treat Chronic Venous Leg Ulcers," Wounds 19(5):128-137; Curran, M. P. and Plosker, G. L. 2002. "Bilayered Bioengineered Skin Substitute (Apligraf): A Review of Its Use in the Treatment of Venous Leg Ulcers and Diabetic Foot Ulcers," BioDrugs 16(6):439-455; Turczynski, R. and Tarpila, E. 1999. "Treatment of Leg Ulcers with Split Skin Grafts: Early and Late Results," Scandinavian Journal of Plastic and Reconstructive Hand Surgery 33(3):301-305; Kilner, R. S., Mata, S. M., Falanga, V., and Kerdel, F. A. 1995. "Split-thickness Skin Autografting of Leg Ulcers. The University of Miami Department of Dermatology's Experience (1990-1993)," Dermatological Surgery 21(8):701-703).

These side-entry connectors can deliver electrostimulation as has been found to exert a curative effect on ulcers. The coordinated delivery to each connector of medication requires but the addition of a fluid to the electrical line. That these lines must be routed to prevent future strangulation of tissue from the electrical control pulse generator or microcontroller is superfluous. Moreover, as addressed below in this section, the device shown in FIGS. 17 thru 19 can deliver antimicrobials to reduce the burden of graft jeopardizing bacteria such as *Pseudomonas aeruginosa* to levels incapable of forming a biofilm.

Electrical means should afford a measure of effective treatment whether the ulcerative wounds are the result of hyperacidity or obstruction to perfusion that results in a venous stasis ulcer, the curative effect of electrical current for such wounds having multidisciplinary confirmation (Ud-Din, S., Sebastian, A., Giddings, P., Colthurst, J., Whiteside, S., Morris, J., Nuccitelli, R., Pullar, C., Baguneid, M., and Bayat, A. 2015. "Angiogenesis is Induced and Wound Size is Reduced by Electrical Stimulation in an Acute Wound Healing model in Human Skin," PLoS [Public Library of Science] One 10(4): e0124502; Taghian, T., Narmoneva, D. A., and Kogan, A. B. 2015. "Modulation of Cell Function by Electric Field: A High-resolution Analysis," Journal of the Royal Society, Interface 12(107) pii: 20150153; Liu, Q. and Song, B. 2014. "Electric Field Regulated Signaling Pathways," International Journal of Biochemistry and Cell Biology 55:264-268; Sheikh, A. Q., Taghian, T., Hemingway, B., Cho, H., Kogan, A. B., and Narmoneva, D. A. 2013. "Regulation of Endothelial MAPK/ERK [mitogen-activated protein kinase/extracellular signal-regulated kinase] Signalling and Capillary Morphogenesis by Low-amplitude Electric Field," Journal of the Royal Society, Interface 10(78): 20120548; Ud-Din, S., Perry, D., Giddings, P., Colthurst, J., Zaman, K., Cotton, S., Whiteside, S., Morris, J., and Bayat, A. 2012. "Electrical Stimulation Increases Blood Flow and Haemoglobin Levels in Acute Cutaneous Wounds without Affecting Wound Closure Time: Evidenced by Non-invasive Assessment of Temporal Biopsy Wounds in Human Volunteers," Experimental Dermatology 21(10):758-764; Sebastian, A., Syed, F., Perry, D., Balamurugan, V., Colthurst, J., Chaudhry, I. H., and Bayat, A. 2011. "Acceleration of Cutaneous Healing by Electrical Stimulation: Degenerate Electrical Waveform Down-regulates Inflammation, Up-regulates Angiogenesis and Advances Remodeling in Temporal Punch Biopsies in a Human Volunteer Study," Wound Repair and Regeneration 19(6):693-708).

The facilitation of yet other therapeutic approaches made possible by nonjacketing side-entry connectors, to include the direct delivery of pentoxifillin and vacuum sealing drainage combined with oxygen loaded fluid, is addressed later in this section. To treat leg ulcers, the embodiment shown in FIGS. 17 thru 19 incorporates electrically conductive anchoring needles, accessory channels 13 used to deliver drugs through the needles when hollow to allow injection. The electrification and configuration of the half round anchoring needles for injection is described and illustrated below in conjunction with the connectors shown in FIGS. 9 and 10B. For standardization and to eliminate the need for another invasive procedure at a later date, the embodiment depicted in FIGS. 17 thru 19 always includes both electrical and fluid supply lines, as do most other nonjacketing side-entry connectors.

To afford flexibility across mobile tissue surfaces so that the drug delivery catheter or other cylindrical device such as an injection needle or excimer laser, will remain more stationary, the embodiment depicted in FIG. 20 situates spring-loaded anchoring pads or footings to either side of the device connected, or side connector, labeled 3 in the drawing figures. The side connector separated from the anchoring pads off to its sides, such an embodiment, whether double as shown or quadruple in a cruciate arrangement, does not afford the continuity essential to include electrical wires or subsidiary drug supply lines for connection to the anchoring needles. Where the side connector is centered among the anchoring needles, such as shown in FIGS. 1 and 4, for example, these connections are made as shown in FIGS. 9 and 10B described below.

There, electrical and catheteric fluid lines are run down through a common conduit as side connector, of which the distal end is situated beneath the baseplate or support platform 1, allowing these lines to be connected to the needles. The term 'pad' denotes the baseplate 1 and other components to include anchoring needles 6 and foam lining 2, arranged along the horizontal plane and to exclude the side connector 3. Such an embodiment is therefore not compatible with the configurations shown in FIGS. 9 and 10B. Where the surface to which a catheter, for example, is to be fastened is abruptly mobile, separate side-entry connectors as shown in FIGS. 9 and 10B are used. Because the embodiment shown in FIG. 20 isolates the side connector from the anchoring pad to either side, only the side connector itself requires local radiation shielding to allow the delivery of radionuclides.

The delivery of any type inotropic or immunosuppressive drug, for example, and/or electrotherapy such as stimulatory or synchronizing (synergizing) requires not only adhesion at the connector-tissue interface to prevent shake-off but high flexibility in the fluid and electrical lines to prevent fatigue fracture. For telemetric and noninvasive diagnostic purposes, such lines are not limited to the unidirectionally incurrent but can output implanted sensor readings to an implant microcontroller. Supplementation with an implantable micro total analysis system, or microfluidic devices with one or more lab-on-a-chip generated diagnostics, allows the microcontroller to respond to diagnostic inputs in accordance with the prescription-program.

The terms ductus and nonductus are pertinent to only the majority of applications. Ductus jackets, which fully encircle the conduit treated, tend to gain in obtrusiveness in proportion to the size of the substrate conduit, and therefore tend to be smaller. In fact, ductus side-entry jackets can be configured to perform the functions of a nonjacketing connector, and might be placed anywhere along the gastrointestinal tract, for example. The preference for nonductus connectors over ductus jackets for use along the gastrointestinal tract is based not just upon size but upon the availability of electrified anchoring needles able to deliver electrostimulation as well as fluid lines to deliver any drugs needed. Nonjacketing side-entry connectors in an array used to stimulate peristalsis are positioned at intervals along the tract, generally in an encircling ring of three at each level so as to take up the least space.

Direct delivery from a subdermally implanted portacath directly to the junction and synthetic line at the origin or takeoff connector through its service channel (accessory channel, sideline) and/or the junction and native tissue at the insertion connector through its service channel allow any drug or line maintaining substance to be targeted to these sites without exposure to other tissue. These are suitable for conventional applications, such as a percutaneous catheteric nephrostomy or a suprapubic cystostomy (vesicostomy) for urinary diversion. Equally important is that used in conjunction with other components described in this and in copending applications entitled Integrated System for the Ballistic and Nonballistic Infixion and Retrieval of Implants with or without Drug Targeting and Ductus Side-entry Jackets and Prosthetic Disorder Response Systems, these connectors make possible the realization of automatic ambulatory prosthetic disorder response systems.

Such a system makes possible the continuous automatic monitoring and application of therapy that previously could be applied only while the patient remained confined to the clinic. Moreover, the therapy itself is availed of the fundamental benefits of directly piped targeting, to include the ability to optimize dosages without exposure to nontargeted tissue, and therewith, the avoidance of adverse side effects, drug drug, and drug food interactions. Even in the clinic, to implement such a system requires stable and durable junctions between synthetic materials and native tissue. This is the central object in ductus side-entry jackets and nonjacketing side-entry tissue connectors. Ideally, the patient is ambulatory and oblivious to the system.

Because the control system is equipped and programmed to maintain its own components as well as to monitor and treat the disease, provided the drugs required if any are replenished as necessary, and except for periodic charging, usually by means of transdermal energy transfer, it is meant to function autonomously for years. To treat symptomatically complex multivariable disease, which may elude diagnosis, such a negative feedback system assigns lower level closed loops to the control of individual symptom values, such as characterize a key metabolic pathway or process. The conventional treatment regimen established, inputs from symptom or variable sensor implants provide feedback, to which the controller responds by adjusting the delivery in dose level and interval of pharmaceutical and/or electrical therapy to recover to the programmed target set point as the normal value.

Where the regimen is unestablished, different drugs and electrical discharge patterns are first established in the clinic. In the treatment of comorbid disease, higher level control is applied to monitor the summary condition and if necessary, apply adjustments among the control axes, such as to adjust the subordinate set points. Ideally, such a system is fully or closed-skin implanted. Where the summary condition is unfamiliar, this 'bottom up' self-optimizing empirical approach may serve not only to treat but to diagnose the condition. In a fully implanted system, this process of self-optimization proceeds unconstrained by limitations of time as would prevail in a busy clinic.

Further use of the term 'comorbid' is intended to denote coexisting disease conditions whether or not these are related or cooriginal. For use in such a system, the catheteric line connectors must positively infix the line and allow the line to flex up to its entry into the baseplate (platform, stage), thus minimizing if not eliminating abrasive or erosive contact with neighboring tissue. While the mixed involuntary/voluntary and therefore sensed functions of voiding can be relegated to control by a patient with normal internal sensation and of sound mind, it cannot be entrusted to a small child or quadriplegic not so, nor for any other dysfunction of endocrine, enzymatic, or autonomic motor action, all involuntary and unsensed in a normal individual.

The detection of involuntary dysfunction whether of autonomic motor or metabolic function cannot depend upon sensory nerve endings. For this reason, a system that automatically responds to unsensed malfunction, an implanted backup 'immune system,' must initiate remedial action immediately on the basis of sensor inputs without the participation of the patient. Unsensed aberrations of physiology must be entrusted to sensor inputs chosen and positioned to detect indicia associated with the disorder or disorders and to implanted electrical, mechanical, and chemical effectors. Side-entry jackets and connectors can fix the position of sensors that would otherwise lack positional stability, at the same time delivering drugs and/or electrical current to the site of implantation.

Neuromodulation through electrostimulation, implementing cardiac resynchonization in the form of pacemakers and cardioverter defibrillators, relief from cephalalgia, and the support of voiding, most unsensed dysfunction remains to be addressed. Side-entry connectors must be long-lived, reasonably accessible for iatrogenic examination and devised for automated self-maintenance, precise and stable in dimensions, nondeformable, minimally excite rejection reactions (see for example, Su, J., Todorov, M., Perez Gonzalez, H., Perkins, L., Kojouharov, H., Weng, H., and Tang, L. 2011. "A Predictive Tool for Foreign Body Fibrotic Reactions Using a Two-Dimensional Computational Model," Open Access Bioinformatics January, 2011), non-enroaching upon surrounding tissue or otherwise causing discomfort, not degraded in a hydrolytic and/or enzymatic environment, and configured for being fitted with drug releasing, electrical pulsation, and styliform therapeutic devices as necessary.

A key factor in this treatment is that drug and electrical discharge delivery is targeted, that is, conveyed directly to the treatment site or sites, eliminating electrical or drug takeup and reaction within nontargeted tissues. By allowing dosing that substantially omits nontargeted tissue, targeting considerably expands the utility of existing drugs used in smaller doses with fewer complications and less expense. Moreover, the avoidance of a dependency upon intrinsic affinity, such as that of the thyroid gland for iodine, along with adverse side effects in nonthyroid tissue, for example, will expedite the approval of new drugs, fundamentally easing the burden of pharmaceutical development. Ductus side-entry connectors allow the secure connection of synthetic tubing to anatomical tubular structures, to include blood vessels and digestive conduits.

A larger mainline catheter, or side connector, injection or aspiration hollow needle, hypotube, miniature cabled device such as a laser, or other styloid device generically referred to as the side connector, when a catheter used as a circulatory or digestive shunt, for example, conveys the luminal contents, while a sideline, or accessory channel, is available to deliver adjuvant drugs into the mainline when reason exists to avoid upstream mixing of the drug with the luminal contents passed through the mainline. In FIGS. 1, 2, 6, 7, 8, 9, 13, 13A, 13B, 14, 20, and 21, the side connector with accompanying accessory channel is shown erect for clarity; it is actually flexible so that it can be flexed to avoid encroachment on neighboring tissue.

By contrast, the embodiment shown in FIG. 10A which includes nondistegrating tungsten radiation shielding to allow the delivery of radioactive substances is of limited pliancy, and that with disintegrating shielding shown in 10B is as flexible as the matrix binding the overlapping tungsten plates allows, several suitable materials specified below in the section entitled Description of the Preferred Embodiments of the Invention. Were catheteric side connector 3 shield 86 encased entirely down to where it is in contact with the upper surface of baseplate 1, shielding would seldom be needed; however, removal and reentry of side connector 3 during placement could result in spillage onto the upper surface of baseplate 1. Otherwise, shielding adds weight, expense, and is best avoided. Shielding is then, almost always an extra precaution taken in case a high dose rate and/or long half life radioactive substance is used and spillage or leaking may occur. A nonjacketing side-entry connector as described herein is essentially equivalent to a ductus side-entry connector in allowing the joining of a synthetic tube shunting blood, luminal contents, or drugs, to a nontubular organ or other tissue with little if any irritation at the entry wound.

The composition of temporary or disintegrating shielding is addressed in copending application Ser. No. 14/121,365, entitled Ductus Side-entry Jackets and Prosthetic Disorder Response Systems, Thus, a shunt to pass blood from an artery to hypoxic tissue would be connected to the source artery with a ductus side-entry jacket, with a nonjacketing side-entry connector used to securely infix the excurrent end of the shunt to the target tissue. The potential uses for such connectors are extensive, ranging from central venous catheters that allow the patient complete freedom of movement, to synthetic circulatory shunts that avoid the need to appropriate and divert unaffected tissue toward surgical construction of a conduit which can lead to adverse sequelae for the donor as well as the recipient site, to the delivery of neuromodulatory stimulation to prod correct sequential timing of peristaltic and sphincteric function. Where the shunt is synthetic, direct synthetic-to-native anastomosis is avoided, and should an adverse tissue reaction arise anyway, the connector, made of nonproteinaceous synthetics, can deliver medication to the junction.

A LeVeen, or peritoneovenous, shunt, or a Denver, or pleurovenous shunt, if joined to the vein by such a connector, or various gut and other digestive system duct shunts, for example, can be supplied with antimicrobials, anticoagulants, and/or anti-inflammatories as necessary by injection into a portacath or Ommaya type reservoir, for example, delivery therefrom into the shunt of the medication through the accessory channel, or sideline, as will be described. As will be addressed, with transdermal charging, such a shunt can be fully, or closed-skin, implanted. A small reversible pump is used to draw off the antimicrobial, anticoagulant, and/or anti-inflammatory from the reservoir for delivery into the shunt through the accessory channel according to the schedule for administration programmed.

When the patient is likely to present secondary or additional disorders at a later date, an initial procedure responsive to incontinence, just as any to treat a singular disorder, is responded to by initial treatment using componentry that except for placing a body surface rather than subdermally positioned injection port, or portacath, allows the introduction of additional control channels as may later become necessary. If secondary or sequelary morbidity is likely to affect the same region or organ and the connection—unlike one that conveys blood or a drug to be delivered continuously—the different viewing, diagnostic, and therapeutic devices to be used are of like diameter, allowing these to be inserted interchangeably through aperture 4 in FIGS. 1, 2, 4, and 7 thru 10.

If the number of drugs to provided for the same or different disease necessitates, an external port with multiple entryways, each clearly marked is used. Prepositioning a connector with piping and electrical conductor or conductors and control electronics—but not a portacath, reservoir, or pump, which can be placed later—allows testing electrostimulation as the first and best option. Not requiring a portacath, reservoir, or pump, for example, electrical means involve the fewest components, take up the least space, and generally allow placement with the least dissection. Provided unintended function of like innervation is unaffected, the lead or leads can be positioned at a functionally and anatomically higher level. A sacral neuromodulator, for example, may exert an effect on rectal as well as bladder function where only one or the other called for treatment.

In such a circumstance, more highly resolved stimulation farther along the neural circuit once the nerve divides to send the target organ its respective branch or ramus is therapeutically selective in eliminating unwanted concurrent stimulation of another organ, such as the rectum where the bladder had been intended. Then, however meticulous was the testing before implantation, even tiny movement of the lead, whether tined or barbed, cannot shift the distribution of stimulation. Using an electrode, lead, or leads to stimulate the innervation, electrostimulatory neuromodulation is least invasive of a native sphincter, and least susceptible to the complications associated with pharmacological treatment, to include adverse side effects, drug-food, and drug-drug interactions.

At the same time, including at the outset fluid lines that may later become necessary allows for the addition of other components as necessary without the need to access and replace the connector or to place additional lines at a later date (see, for example, Kim, S. W., Shin, I. S., Kim, J. M., Kang, H. C., Mun, J. U., Yang, S. J., and Yoon, J. S. 2006. "Mirtazapine for Severe Gastroparesis Unresponsive to Conventional Prokinetic Treatment," Psychosomatics 47(5): 440-442). Initial placement best enables the delivery of treatment beyond that contemplated at the outset, not just to allow adjustment in a single therapeutic modality but in the modality or combination of modalities. The concept of making it possible for the therapy to be adjusted without the need to revise the initial procedure or replace the original implants at a later date applies not just to disease able to induce secquelary pathology but to specific disorders for which the best therapeutic regimen will need to be adjusted, as well as when the optimal result can be found only through empirical testing.

To cite one instance, with a refractory gastric reflux that resists treatment with a proton pump inhibitor and/or induces unwanted side effects at the oral (systemic) dose necessary, delivery through a side-entry jacket or nonjacketing side-entry connector at the lower esophageal (cardiac, gastroesophageal0 sphincter, at the gastroesophageal junction allows the dose to be increased to a level that if circulated would be likely to cause adverse side effects. If the decision is made to resort to electrostimulation of the sphincter, in lieu of or in combination with medication, the connector, already in place, can be used to test numerous modes of electrical pulsation or drug based treatments with or without concurrent or intermittent electrostimulation. The ability to directly target familiar drugs, hormones, and enzymes allows the use of these in novel ways that can advance pharmaceutical science no less than the discovery of new drugs.

Baclofen, for example, is effective at suppressing lower esophageal sphincter relaxations giving rise to acid reflux (Piche, T. and Galmiche, J. P. 2005. "Pharmacological Targets in Gastro-oesophageal Reflux Disease," Basic and Clinical Pharmacology and Toxicology 97(6):333-341); administered orally or by intrathecal or intramuscular injection, however, baclofen too often induces serious side effects, to include drowsiness, depression, fatigue, dizziness, nausea, abdominal pain, paresthesias, dystonias, ataxias, tremors, syncope, hallucinations, psychosis, and several others (Hsieh, M. J., Chen, S. C., Weng, T. I., Fang, C. C., and Tsai, T. J. 2012. "Treating Baclofen Overdose by Hemodialysis," American Journal of Emergency Medicine 30(8):1654.e5-e7; Chawla, J. M. and Sagar, R. 2006. "Baclofen-induced Psychosis," Annals of Pharmacotherapy 40(11):2071-2073; Kofler, M., Matzak, H., and Saltuari, L. 2002. "The Impact of Intrathecal Baclofen on Gastrointestinal Function," Brain Injury 16(9):825-836; Ryan, D. M. and Blumenthal, F. S. 1993. "Baclofen-induced Dyskinesia," Archives of Physical Medicine and Rehabilitation 74(7):766-767; Yassa, R. Y. and Iskandar, H. L. 1988. "Baclofen-induced Psychosis: Two Cases and a Review," Journal of Clinical Psychiatry 49(8):318-320).

This is especially pertinent to disorders that call for the administration of hormones, of which the potentially adverse side effects are many, serious, and difficult to treat. In patients with renal impairment in addition to acid reflux, the side effects of baclofen are often more problematic (see, for example, Meillier, A., Heller, C., and Patel, S. 2015. "Baclofen-induced Encephalopathy in End Stage Renal Disease," Case Reports in Medicine 2015:203936; Ijaz, M., Tariq, H., Kashif, M., and Marquez, J. G. 2015. "Encephalopathy and Hypotonia Due to Baclofen Toxicity in a Patient with End-stage Renal Disease," American Journal of Case Reports 16:232-235; Mousavi, S. S., Mousavi, M. B., and Motemednia, F. 2012. "Baclofen-induced Encephalopathy in Patient with End Stage Renal Disease: Two Case Reports," Indian Journal of Nephrology 22(3):210-212). In FIGS. 6, 13A, and 13B and the section below entitled Description of the Preferred Embodiments of the Invention are described means for directly targeting the kidneys; however, to treat systemic comorbidities such as multiple sclerosis and spinal spasticity, systemic circulation is essential.

Acid reflux common, transesophageal endoscopic treatments such as radiofrequency and polymer injection bulking of the lower esophageal sphincter, and fundoplication have been developed (see, for example, Yew, K. C. and Chuah, S. K. 2013. 'Antireflux Endoluminal Therapies: Past and Present," Gastroenterology Research and Practice 2013:481417; Jobe, B. A. 2012. "Endoscopic Treatments for Gastroesophageal Reflux Disease," Gastroenterology and Hepatology (New York) 8(1):42-44; Schwartz, M. P. and Smout, A. J. 2007. "Review Article: The Endoscopic Treatment of Gastro-oesophageal Reflux Disease," Alimentary Pharmacology and Therapeutics 26 Supplement 2:1-6; Fry, L. C., Monkemuller, K., and Malfertheiner, P. 2007. "Systematic Review: Endoluminal Therapy for Gastro-oesophageal Reflux Disease: Evidence from Clinical Trials," European Journal of Gastroenterology and Hepatology 19(12):1125-1139; Ozawa, S., Yoshida, M., Kumai, K., and Kitajima, M. 2005. "New Endoscopic Treatments for Gastroesophageal Reflux Disease," Annals of Thoracic and Cardiovascular Surgery 11(3):146-153). Through laparoscopic access (laparoscopic reflux surgery, LARS), the same methods could be applied to the treatment of other sphincters.

The long term durability of these new treatments remains to be established. Polymer injection was terminated in 2005 due to iatrogenic procedural errors that resulted in mispositioning of the polymer or perforation of the esophagus. Treatment of a dysfunctional sphincter as an isolated problem with the Stretta radiofrequency bulking method (Mederi Therapeutics Inc.), for example, is eventually satisfactory (see, for example, Ych, R. W. and Triadafilopoulos, G. 2005. "Endoscopic Antireflux Therapy: The Stretta Procedure," Thoracic Surgery Clinics 15(3):395-403); but the improvement in symptoms is realized only after the interval during which the sphincter recovers and strengthens to reduce inappropriate transient relaxations, which can take up to half a year.

Appraisals of the Stretta procedure are mixed (see, for example, Bosworth, T. 2015. "New Study Reignites Debate Over Stretta—Meta-analysis Suggests Lack of Clinical Benefit for Endoscopic Procedure; Some Experts Disagree," General Surgery News January (42):01; Triadafilopoulos, G. 2014. "Stretta: A Valuable Endoscopic Treatment Modality for Gastroesophageal Reflux Disease," World Journal of Gastroenterology 20(24):7730-7738; Jafri, S. M., Arora, G., and Triadafilopoulos, G. 2009. "What is Left of the Endoscopic Antireflux Devices?," Current Opinion in Gastroenterology 25(4):352-357). Where the dysfunction is not one of inadequate sphincteric pressure with otherwise unimpaired motile function but rather of dysmotility seen as atony or dyssynergia, treatment must be keyed to the sphincter.

If part of a more extensive disorder that includes gastroparesis, for example, contextual symptoms other than appurtenant of the spincter per se require treatment, not just bulking, which may even interfere with relaxation to pass food. In some cases, appropriately timed forcible closure of the sphincter through electrostimulation of the innervation or constriction by an autonomic motor assist device will be necessary. Gastroparesis is another condition treatable with the means to be described. Because side-entry connectors are not limited to electrical or pharmacological therapy but implement the coordination of the two for delivery at a higher level or for differential application at lower levels, treatment of condition overall is more refined.

"The pathophysiology behind delayed gastric emptying is still not well-understood, but encompasses abnormalities at 3 levels—autonomic nervous system, smooth muscle cells, and enteric neurons." (Tang, D. M. and Friedenberg, F. K. 2011. "Gastroparesis: Approach, Diagnostic Evaluation, and Management," Disease-A-Month 57(2):74-101; Jackson, M. W., Gordon, T. P., and Waterman, S. A. 2004. "Disruption of Intestinal Motility by a Calcium Channel-stimulating Autoantibody in Type 1 Diabetes," Gastroenterology 126 (3): 819-828; Ejskjaer, N. T., Bradley, J. L., Buxton-Thomas, M. S., Edmonds, M. E., Howard, E. R., Purewal, T., Thomas, P. K., and Watkins, P. J. 1999. "Novel Surgical Treatment and Gastric Pathology in Diabetic Gastroparesis," Diabetic Medicine 16(6):488-495; Soulie, M. L., Cros, G., Serrano, J. J., and Bali, J. P. 1992. "Impairment of Contractile Response to Carbachol and Muscarinic Receptor Coupling in Gastric Antral Smooth Muscle Cells Isolated from Diabetic Streptozotocin-treated Rats and db/db Mice," Molecular and Cellular Biochemistry 109(2):185-188).

Where a different etiology would reasonably effect these 3 levels in a distinctively different way, existing electrostimulators such as sacral and gastric are limited to electrostimulation of the innervation; usually at a high enough level as to involve unintended end tissue. Electricity affects all 3 levels, but not necessarily to remedial effect, and not with distinction as to the effect on each according to the etiology, and not with the ability to detect and adjust the blood glucose level as an integral part of the treatment when the disorder is associated with diabetes, as is often the case. Conventionally, diabetes, which affects the entire body, is treated separately, whereas here, the systemic therapy is certainly provided but also locally coordinated with means to remediate the local consequences of the systemic disorder. Damage to the vagus nerve may be uninvolved in some gastroparesis, or may have resulted in other damage to the stomach, so that only to electrostimulate the nerve would never afford a cure. In fact, the condition is usually treated pharmacologically as well, but without the benefit of direct targeting.

Electrostimulation of the nerve or any of its branches, even though this might mask deeper pathology for a time, will not affect underlying damage to the cells of the gastric wall, which is likely to remain irreversible pending the development of stem cell technology (Farrugia, G. 2015. "Histologic Changes in Diabetic Gastroparesis," Gastroenterology Clinics of North America 44(1):31-38; Nguyen, L. A. and Snape, W. J. Jr. 2015. "Clinical Presentation and Pathophysiology of Gastroparesis," Gastroenterology Clinics of North America 44(1):21-30; Pasricha, P. J. and Parkman, H. P. 2015. "Gastroparesis: Definitions and Diagnosis," Gastroenterology Clinics of North America 44(1):1-7; Camilleri, M., Parkman, H. P., Shaft, M. A., Abell, T. L., Gerson, L. and the American College of Gastroenterology 2013. "Clinical Guideline: Management of Gastroparesis," American Journal of Gastroenterology 108(1):18-38; Khoo, J., Rayner, C. K., Jones, K. L., and Horowitz, M. 2009. "Pathophysiology and Management of Gastroparesis," Expert Review of Gastroenterology and Hepatology 3(2): 167-181).

The sustained high blood glucose in diabetic gastroparesis probably results in primary damage to the vagus, which electrostimulation can mask. The sustained mineral deficiency of zinc, sodium, and chloride can result in gastroparesis-associated hypochlorhydria. Autoimmune gastrointestinal dysmotility, for example, has been reported to respond to pyridostigmine supplemented by tegaserod, which " . . . suggests an immunopharmacologic rather than an inflammatory cytotoxic pathology." (Pasha, S. F., Lunsford, T. N., and Lennon, V. A. 2006. "Autoimmune Gastrointestinal Dysmotility Treated Successfully with Pyridostigmine," Gastroenterology 131(5):1592-1596). This often affords some relief but can be tailored to the patient only to the extent of the electrical discharge pattern applied, other therapy with drugs oral or by injection rather than accurately timed in coordination with the discharge.

By contrast, a nonjacketing side-entry connector or a number of these allow adjustment in the identity and concentration of medication or medications, as well as the electrical discharge pattern applied at each location. Preliminary testing allows the optimal combination of drugs and discharge pattern to be found for each location on the basis of empirical testing. This not only optimizes treatment in the least time, but may serve as diagnostic in revealing the cytological and histological basis or bases for the disorder and obviates the need for a detailed understanding or history of the condition presented. Keying a detailed therapeutic response to various expressions of a disorder such as gastroparesis therefore gains in refinement with each case reported. Empirical treatment is imposed by the number of variables known and unknown with any medical condition in any event, and has the added advantage of inherently fitting the therapy to the individual patient.

In most cases, the more detailed components of the condition will not be known; however, empirical adjustment to determine the optimal combination of electrostimulatory and pharmaceutical curative factors will not only serve to more effectively ameliorate the medical problem but help to explain its basis. In this process, the fact that the electrostimulation and drugs are precisely targeted eliminates the host of detractive factors contributed by exposure to extraneous tissues and organs. The pathophysiological analysis as to etiology and optimal treatment regimen for a given condition in a given patient are hindered by the number of variables, which is only further complicated when extraneous tissue is involved.

Gastroparesis can result from inflammation such as that seen in idiopathic gastroparesis (see, for example, Parkman, H. P. 2015. "Idiopathic Gastroparesis," Gastroenterology Clinics of North America 44(1):59-68; Chaudrey, K. H., Patel, R., Alam, M., Avashia, K., Khan, S. I., Titarenko, N., and Ihsan, M. 2013. "Idiopathic Gastroparesis: Case Report and Literature Review of Diagnostic and Treatment Modalities," American Journal of Therapeutics 20(1):111-117; Digestive Diseases and Sciences); may be autoimmune; postradiation; following gastric surgery, paraneoplastic; induced by antineoplastic chemotherapeutics or other drugs that affect motility; due to autonomic failure suspected to have followed a viral infection such as acquired and is associated with diabetes (gastroparesis diabeticorum), collagen vascular disorders, mitochondrial disease, Chagas' disease, Journal of the Society of Laparoendoscopic Surgeons[0066] [0067] [0068] Analogous application to dysmotility along the gut or urinary tract is intentional. Complicated conditions may necessitate a coordinated response that addresses collateral conditions elsewhere within the same or in other organ systems.

The satisfactory application of a therapeutic regimen which senses the need for and automatically actuates a coordinated response that includes directly targeted electrical discharges and/or drug delivery, as well as autonomic motor assist devices, requires and justifies the placement of a microcontroller, sensors, and other components necessary to provide such a coordinated response. Administered conventionally, proton pump inhibitors taken orally often fail to afford sufficient relief of acid reflux or of gastroparesis, and prokinetic, or promotility, drugs, such as erythromycin, domperidone, metoclopramide, (Camilleri, M., Parkman, H. P., Shafi, M. A., Abell, T. L., Gerson, L. and the American College of Gastroenterology 2013, Op cit.) which may be injected with an endoscope, have yielded unsatisfactory results for the long term relief of gastroesophageal reflux, as have hormonal and antinausea therapy.

A disease rarely if ever appears as completely unknown and without any experience at treatment. Diabetic gastroparesis, for example, is known with certainty to require control over the blood glucose level, intensification of stomach contractions, and relaxation of the puloric sphincter to expedite stomach emptying. A general procedure from electrical to pharmacological means provided below, the means for controlling blood glucose having been described in copending application Ser. No. 14/121,365, inotropic drugs to mobilize the stomach, some specified herein, and a relaxant such as botulinum toxin to open the pyloric sphincter are indicated.

Nonjacketing side-entry connectors used to deliver electrostimulation to the stomach wall through electrifiable anchoring needles and/or drugs through hollow anchoring needles are prepositioned for the delivery of drugs into the stomach wall. Provided these are already in use and the frequency of therapy or diagnosis warrants it, a catheter as side connector is added to allow the delivery of drugs directly into the stomach. Such can include radiopharmaceuticals essential for followup gastric emptying scintigraphy, single photon emission, or positron emission tomography.

In addition to the increased utility of drugs that must not be administered systemically at the required dose, automatically targeted delivery at intervals of a short duration drug such as botulinum toxin type A to a sphincter, for example, elevates it in utility from a temporary palliative, means of confirming a diagnosis, and possibly averting a surgical procedure to a sustainable source of relief (see, for example, Brisinda G, Sivestrini N, Bianco G, Maria G. 2015. "Treatment of Gastrointestinal Sphincters Spasms with Botulinum Toxin A," Toxins (Basel) 7(6):1882-1916; Uldeja, A., Tandon, K., Shah, K., and Alvarez, A. 2015. "Endoscopic Botox Injections in Therapy of Refractory Gastroparesis," World Journal of Gastrointestinal Endoscopy 7(8):790-798; Vittal, H. and Pasricha, P. F. 2006. "Botulinum Toxin for Gastrointestinal Disorders: Therapy and Mechanisms," Neurotoxicity Research 9(2-3):149-159). Using a side-entry connector or a number of these, antiemetic and antinausea drugs such as phenothiazines, prochlorperazine, mirtazapine, ondansetron, and diphenhydramine are targeted to the stomach in coordination with the direct delivery of prokinetics and electrostimulation as empirically determined through an automated process of self-optimization.

That the drug feedlines must be routed to preclude entanglement of viscera or strangulation of organs should be obvious (see, for example, Lederhuber, H., Axer, S., and Bile, C. 2015. "Case Report: Rare Case of Mechanical Bowel Obstruction Due to Strangulation by Gastric Stimulator Electrodes," BMC [BioMed Central] Surgery 15:35). To gain the advantage of uniformity, side-entry connectors of any given size include both electrical and fluid connections. Electrostimulation least complicated, most space-conserving, and contrary to the conventional sequence in therapy, which tries drugs before considering implantation of a neuromodulator, testing is initially electrical. In FIGS. 12A and 12C, electrostimulation requires only transdermal charging circuitry 50, microcontroller 53, battery 54, and transdermal battery charging secondary coil 64, thus avoiding the need for one or more portacaths 46 reservoir or reservoirs 47 and miniature reversible pump or pumps 49. Because it does not obstruct flow from the prostate, the bypass shown in FIG. 12C preserves fertility regardless of the cause for chronic obstructive uropathy at any point along the bypassed segment of the urethra.

However, in that electrified anchoring needles, 6 in the drawing figures, situated at the periphery, and an electrode in side connector 3—which can be made fine in gauge and tined or thicker and fixed to any angle and depth necessary—can each be made to discharge in any pattern relative to each of the others, electrical stimulation mediated by nonjacketing side-entry connectors is much more versatile than is electrostimulation of the gastric vagus using conventional leads. If after testing the most pertinent patterns of stimulation with the side-entry jacket, to include positioning an electrode to stimulate the gastric vagus, a satisfactory result is obtained, then testing is ended and the electrical means implemented. In diabetic gastroparesis, electrostimulation and treatment of the diabetes, conventional or unconventional, should prove ameliorative. Were this to cure the cytological and neurological consequences of the diabetes, more detailed treatment would not be necessary.

However, local treatment such as gastric electrostimulation always initiated with the patient already having been under treatment for the diabetes, that diabetic gastroparesis can arise and persist long after the initiation of systemic treatment indicates that, whether secondary to the diabetes or pleiotropic, (see, for example, Mazzone, A., Bernard, C. E., Strege, P. R., Beyder, A., Galietta, L. J., Pasricha, P. J., Rae, J. L., Parkman, H. P., and 5 others 2011. "Altered Expression of Ano1 Variants in Human Diabetic Gastroparesis," Journal of Biological Chemistry 286(15):13393-13403; Vittal, H., Farrugia, G., Pehlivanov, N. D., Lurken, M., Gomez, G., and Pasricha, P. J. 2006. "Neuropathological and Genomic Changes in the Stomach of Patients with Human Diabetic Gastroparesis," Digestive Disease Week; Forster, J., Damjanov, I., Lin, Z., Sarosiek, I., Wetzel, P., and McCallum, R. W. 2005. "Absence of Interstitial Cells of Cajal in Patients with Gastroparesis and Correlation with Clinical Findings." Journal of Gastrointestinal Surgery 9(1): 102-108; Jones, K. L., Russo, A., Berry, M. K., Stevens, J. E., Wishart, J. M., and Horowitz, M. 2002. "A Longitudinal Study of Gastric Emptying and Upper Gastrointestinal Symptoms in Patients with Diabetes Mellitus," American Journal of Medicine 113(6):449-455; Merio R, Festa A, Bergmann, H., Eder, T., Eibl, N., Stacher-Janotta, G., Weber, U., and 6 others 1997. "Slow Gastric Emptying in Type I Diabetes: Relation to Autonomic and Peripheral Neuropathy, Blood Glucose, and Glycemic Control," Diabetes Care 20(3):419-423, the detailed cytological and neuronal sequelae should be addressed directly.

And whether secondary or pleiotropic, irreversible cell damage (Iwasaki, H., Najimura, M., Osawa, S., Kanaoka, S., Furuta, T., Ikuma, M., and Hishida, A. 2006. "A Deficiency of Gastric Interstitial Cells of Cajal Accompanied by Decreased Expression of Neuronal Nitric Oxide Synthase and Substance P in Patients with Type 2 Diabetes Mellitus," Journal of Gastroenterology 41(11):1076-1087; He, C. L., Soffer, E. E., Ferris, C. D., Walsh, R. M., Szurszewski, J. H., and Farrugia, G. 2001. "Loss of Interstitial Cells of Cajal and Inhibitory Innervation in Insulin-dependent Diabetes," Gastroenterology 121(2):427-434 must await developments in stem cell research (see, for example, Vittal, H., Farrugia, G., Pehlivanov, N. D Lurken, M., Gomez, G., and Pasricha, P. J. 2006, Op cit.; Horvath, V. J., Vittal, H., Lorincz, A., Chen, H., Almeida-Porada, G., Redelman, D., and Ordog, T. 2006. "Reduced Stem Cell Factor Links Smooth Muscle Myopathy and Loss of Interstitial Cells of Cajal in Murine Diabetic Gastroparesis," Gastroenterology 130(3):759-770, with, however, the understanding that direct delivery means already in position to deliver conventional medication are available without another invasive procedure.

Thus, electrostimulation of the gastric vagus will ameliorate the slowness of emptying, and reducing the blood glucose level is likely to suppress the progress of cell degradation to lessen the more salient symptoms such as pain and nausea, but is unlikely to result in a cure at the cellular level (see, for example, Farrugia, G. 2015. "Histologic Changes in Diabetic Gastroparesis," Gastroenterology Clinics of North America 44(1):31-38, Op cit; Faussone-Pellegrini M S, Grover M, Pasricha P J, Bernard C E, Lurken M S, Smyrk T C, Parkman H P, Abell T L, and 83 others 2012. "Ultrastructural Differences between Diabetic and Idiopathic Gastroparesis," Journal of Cellular and Molecular Medicine 16(7):1573-1581; Grover, M., Bernard, C. E., Pasricha, P. J., Lurken, M. S., Faussone-Pellegrini, M. S., Smyrk, T. C., Parkman, H. P., Abell, T. L., and 73 others 2012. "Clinical-histological Associations in Gastroparesis: Results from the Gastroparesis Clinical Research Consortium," Neurogastroenterology and Motility 24(6):531-539, e249; Grover, M., Farrugia, G., Lurken, M. S., Bernard, C. E., Faussone-Pellegrini, M. S., Smyrk, T. C., Parkman, H. P., Abell, T. L, and 82 others 2011. "Cellular Changes in Diabetic and Idiopathic Gastroparesis," Gastroenterology 140(5):1575-1585.e8; Pasricha, P. J., Pehlivanov, N. D., Gomez, G., Vittal, H., Lurken, M. S., and Farrugia, G. 2008. "Changes in the Gastric Enteric Nervous System and Muscle: A Case Report on Two Patients with Diabetic Gastroparesis," BMC [BioMed Central] Gastroenterology 8:21; Horvath, V. J., Vittal, H., Lorincz, A., Chen, H., Almeida-Porada, G., Redelman, D., and Ordog, T. 2006. "Reduced Stem Cell Factor Links Smooth Myopathy and Loss of Interstitial Cells of Cajal in Murine Diabetic Gastroparesis," Gastroenterology 130(3):759-770).

It should be assumed that the need for drug feedlines will develop over time; especially if the insertion site is deep as will detain revision, fluid lines (drug feedlines, catheters) connected to the side-entry connector are routed to minimize the risk of organ strangulation. At least until the need therefor arises, these should be tunneled subdermally, so that the free proximal ends are prepositioned for connection to drug delivery components once these become necessary. Based upon the results obtained with the conventional delivery of medication for the relief of pain originating in the stomach wall, the direct injection of medication into the stomach wall through one or more nonjacketing side-entry connectors with injection anchoring needles such as shown in FIGS. 9 and 10B should go far to alleviate stomach wall pain (Alnahhas, M. F., Oxentenko, S. C., Locke, G. R. 3rd, Hansel, S., Schleck, C. D., Zinsmeister, A. R., Farrugia, G., and Grover, M. 2015. "Outcomes of Ultrasound-Guided Trigger Point Injection for Abdominal Wall Pain," Digestive Diseases and Sciences (pending publication) 2015 Aug. 30). This would appear to exclude opiates also used conventionally in the treatment of gastroparesis, usually idiopathic (Hasler, W. L., Wilson, L. A., Parkman, H. P., Koch, K. L., Abell, T. L., Nguyen, L., Pasricha, P. J., and 9 others 2013. "Factors Related to Abdominal Pain in Gastroparesis: Contrast to Patients with Predominant Nausea and Vomiting," Neurogastroenterology and Motility 25(5):427-438, e300-1).

Depending upon the individual patient and the number of drug delivery components likely to become necessary at a later date, a tissue expander is also placed in the pectoral region. The drug delivery components, which include a subdermal surface port, line from the port to a reservoir needed only when the volume of the drug necessitates, and a reversible pump, to be connected to the free end of the feedline that had been prepositioned, are generally pocketed subdermally in the pectoral region, making the addition of these less invasive. To assure its immediate sighting, the free proximal end of the catheter (line, feedline) is crimped with a magnetically susceptible ferrule marked with contrast, such as tantalum-based.

Electrostimulation of the gastric vagus with the aid of a nonjacketing side-entry connector used to fix an electrode as side connector in position substantially eliminates the risk of displacement. Nonjacketing side-entry connectors with electrified anchoring needles directly fastened to the outer surface of the stomach are able to deliver local stimulation at the stomach wall. For the reasons mentioned, while the relief initially afforded is likely to be considerable, over time, the result to be obtained using electrical stimulation alone will gradually subside to a level where it no longer serves as adequate. The same applies to the administration of systemic pharmaceuticals (see, for example, Pasricha, P. J., Yates, K. P., Nguyen, L., Clarke, J., Abell, T. L., Farrugia, G., Hasler, W. L., and 9 others 2015. "Outcomes and Factors Associated With Reduced Symptoms in Patients with Gastroparesis," Gastroenterology 149(7):1762-1774.e4). For this reason and to eliminate the need to reenter to any significant depth, the treatment of diabetic gastroparesis should include the placement of side-entry connectors at points about the outer surface of the stomach and pyloric sphincter with electrical and fluid delivery lines from the very start as explained above.

Conventionally, electrostimulation will not have constituted the sum of therapy but, in the form of a vagal modulator, represent the only implanted component thereof; the patient who later returns complaining of pain and nausea will thus present with an established systemic drug history as a starting point for initiating drug delivery by direct targeting. Often the insufficiency of systemic medication will have been the incentive to implant the electrostimulator (see, for example, Teich, S., Mousa, H. M., Punati, J., and Di Lorenzo, C. 2013. "Efficacy of Permanent Gastric Electrical Stimulation for the Treatment of Gastroparesis and Functional Dyspepsia in Children and Adolescents," Journal of Pediatric Surgery 48(1):178-183; Islam, S., Vick, L. R., Runnels, M. J., Gosche, J. R., and Abell, T. 2008. "Gastric Electrical Stimulation for Children with Intractable Nausea and Gastroparesis," Journal of Pediatric Surgery 43(3):437-442). Drug testing is by injection into a subdermal portacath. If necessary, a small number of these are positioned subdermally in the pectoral region.

If the number of drug target sites exceeds the number of subdermal ports acceptable, then a body surface type nonjacketing side-entry connector as described in copending application Ser. No. 14/121,365, entitled Ductus Side-entry Jackets and Prosthetic Disorder Response Systems is placed. Such a surface port can be placed temporarily during initial drug testing period. If the number of drug target sites is reduced, the external port connector is removed and replaced by portacaths. The need to continue with an external port connector is limited to comorbidity that poses numerous electrostimulation and/or drug target sites. Provided the systemic medication previously used provided some relief, the treatment commences with the same drugs, with, however, the dose adjusted for direct targeting, wherewith the exposure of unintended tissue ceases as a consideration. Small amounts of drugs are placed at the head of a column of water. The reversible pumps used allow drugs to be withdrawn, the line and reservoir if present flushed clean, and another drug introduced.

Directly targeted delivery on as frequent a basis as necessary with the aid of a nonjacketing side-entry connector could ameliorate such symptoms such as nausea and pain, especially in patients with normal peristalsis and taking a proton pump inhibitor which alone failed to afford relief (see, for example, Piche, T. and Galmiche, J. P. 2005, Op cit.; Tonini, M., De Giorgio, R., and De Ponti, F. 2004. "Progress with Novel Pharmacological Strategies for Gastro-oesophageal Reflux Disease," Drugs 64(4):347-361). Directly targeting gastric vagal tension receptor endings with gamma-aminobutyric acid type B (GABAB) receptor agonists and metabotropic glutamate type 5 receptor (mGluR5) antagonists appears promising (Blackshaw, L. A. 2008. "New Insights in the Neural Regulation of the Lower Oesophageal Sphincter," European Review for Medical and Pharmacological Sciences 12 Supplement 1:33-39).

For example, should a proton pump inhibitor prove inadequate, as is often the case, or its cessation induce rebound hyperacidity, then gastrin or pentagastrin, gastrin-releasing peptide, motilin, motilin with erythromycin (not preferred), octreotide, and/or secretin, are directly targeted to the sphincter, while urogastrone, bulbogastrone, somatostatin or its analogues octreotide or octreotate, prostaglandins, secretin, gastrin inhibitory peptide, for example, can be directly targeted to the antrum to suppress acid and stimulate mucin secretion (see, for example, Boron, W. F. and Boulpaep, E. L. 2012. "Acid Secretion," in Medical Physiology, Philadelphia, Pa.: Elsevier Saunders; Poitras, P. and Peeters, T. L. 2008. "Motilin," Current Opinion in Endocrinology, Diabetes and Obesity 15(1):54-57; Denef, C. 2008. "Paracrinicity: The Story of 30 Years of Cellular Pituitary Crosstalk, Journal of Neuroendocrinology 20(0:1-70; Hadley, M. E. and Levine, J. E. 2007. "Gastrointestinal Hormones," Chapter 10 in Endocrinology, Upper Saddle River, N.J.: Pearson Prentice Hall, pages 228-233; Hall, J. E. and Guyton, A. C. 2006. Textbook of Medical Physiology, St. Louis, Mo.:

Elsevier Saunders; Tonini, M., De Giorgio, R., and De Ponti, F. 2004, Op cit.; Ganong, W. F. 2003. "Regulation of Gastrointestinal Function," Chapter 26 in Review of Medical Physiology New York, N.Y.: McGraw-Hill; Itoh, Z. 1997. "Motilin and Clinical Application," Peptides 18(4): 593-608; Hoist, J., Orskov, C., and Seier-Poulsen, S. 1992. "Somatostatin is an Essential Paracrine Link in Acid Inhibition of Gastrin Secretion," Digestion 51(2): 95-102; Castell, D. O. 1978. "Gastrin and Lower Esophageal Sphincter Tone," Archives of Internal Medicine 138(2):196; Henderson, J. M., Lidgard, G., Osborne, D. H., Carter, D. C., and Heading, R. C. 1978. "Lower Oesophageal Sphincter Response to Gastrin—Pharmacological or Physiological?," Gut 19(2):99-102; Wormsley, K. G. 1971. "Reactions to Acid in the Intestine in Health and Disease," Gut 12(1):67-84) with no need to revise the initial procedure.

To treat achalasia would take the opposite tack to reduce sphincter pressure. At the same time, neurotransmitters, such as acetylcholine and tachykinins can be delivered for their inotropic effect, the potential points for electrostimulatory and neurohumoral neuromodulation known (Farre, R. and Sifrim, D. 2008. "Regulation of Basal Tone, Relaxation and Contraction of the Lower Oesophageal Sphincter. Relevance to Drug Discovery for Oesophageal Disorders," British Journal of Pharmacology 153(5):858-869) and securely joined with the aid of nonjacketing side-entry connectors. Electrostimulation is inotropically effective and involves the least complexity, so that it is tested first.

If the sphincter fails to attain normal pressure; electrostimulation is applied alone or in combination with a proton pump inhibitor and/or hormones. In this way, the placement of a connector with a drug delivery catheter as side connector and electrically conductive anchoring needles at the outset allows testing, optimizing, and instituting the optimal drug and/or electrical treatment regardless of whether one modality alone or a combination of these is indicated with the patient remaining closed. Exceptionally, when it appears that none of the foregoing would prove adequate, an electromechanical gastroesophageal sphincteric assist device with incorporated fluid delivery and electrical lines as described below in this section is placed.

The reason that such an assist device with electrical and fluid delivery capability is not placed at the outset is that to encircle the native sphincter requires an extent of dissection and use of suture to stabilize the surrounding tissue and avoid a paraesophageal giving the effect of sliding hiatal hernia. Primarily to prevent migration, autonomic motor assist devices such as an electromagnetic sphincter have suture pass-through loops such as those shown as part number 32 in the accompanying drawing figures. These loops, at several points toward the proximal and distal margins, allow connection of the implant to the surrounding tissue, here to the diaphragm, the sphincter and diaphragm therefore moving together. The use of an electromagnetic sphincteric assist device should be viewed as a last resort; in all but a small proportion of cases, the patient would never require mechanical assistance, so that the need for revision would almost always have been avoided. Native sphincters open by shortening upon contraction This action is best stimulated electrically, and next best through the direct application of inotropic drugs through a nonjacketing side-entry connector. An electromagnetic sphincteric assist device does not function thus but applies constrictive force entirely about the native sphincter. Because this mode of constriction is different than that to which the native sphincter is adapted (see, for example, Theodosiou, N. A. and Tabin, C. J. 2005. "Sox9 and Nkx2.5 Determine the Pyloric Sphincter Epithelium under the Control of BMP Signaling," Developmental Biology 279(2): 481-490; Moniot, B., Biau, S., Faure, S., Nielsen, C. M., Berta, P., Roberts, D. J., and de Santa Barbara, P. 2004. "SOX9 Specifies the Pyloric Sphincter Epithelium through Mesenchymal-epithelial Signals," Development (Cambridge, England) 131(15):3795-3804), an electromagnetic sphincteric assist device should always incorporate a fluid line for drug delivery to ameliorate any adverse sequelae of forcible constriction.

A potential disadvantage of conventional electrostimulation is that the stimulation is applied to a larger nerve which intercepted at too high a level is likely to include fibers that will eventually ramify to tissue other than that to be treated. In most instances, a side-entry connector is local to the target tissue, so that affecting unintended tissue is out of the question. Whereas electrostimulators have limited prescribed points of insertion, ductus side-entry jackets and nonjacketing side-entry connectors can be placed at any nervous or vascular level to deliver any combination of electrical discharge and/or medication. In the treatment of a sphincteric motor dysfunction, the resolution to be preferred is that simplest and most compact, beginning with electrostimulation through a nonjacketing side-entry connector with only an electrical wire, not a fluid drug delivery line or catheter. If inadequate, the addition of a fluid drug delivery line follows. If electrostimulation and direct drug targeting fail, then an electromechanical assist device is employed.

The longitudinal extent of a sphincter usually not affording sufficient space to position both a combination-form electromechanical sphincteric assist device with built in fluid and electrical capability and a nonjacketing side-entry connector, unless confidence in the side-entry connector is high, the nonjacketing side-entry connector should be placed first, just proximal to the sphincter, with the distal end of its catheter and/or electrode set to penetrate the sphincter proper. Then, if placed, the combination-form electromechanical sphincteric assist device will be drug and electrical discharge capable, allowing the side-entry connector to be removed. If the patient history indicates little probability that the side-entry connector will work to satisfaction, the combination-form electromechanical sphincteric assist device is placed ab initio. The larger sphincters of the digestive and urinary tracts consist of specialized adluminal muscle fibers continuous with the surrounding tissue.

In the case of the lower esophageal sphincter, the diaphragmatic sphincter anchored to the lower end of the esophagus by the phrenoesophageal ligament comprises the right and left crus of the diaphragm, which contribute closing force to the sphincter proper. Discontinuity between the lower esophageal sphincter proper and the diaphragm as results from a hiatal hernia allows transient relaxations and reflux often correctible by herniorrhaphy or sphincter pull down (see, for example, Stelzner, F. 2015. "Stretch Sphincter of the Esophagus: Paradoxical Sphincter with Angiomyoelastic Architecture," (in German with abstract at Pubmed) Chirurg 86(8):752-760; Mittal, R. K. and Goyal, R. K. 2006. "Sphincter Mechanisms at the Lower End of the Esophagus," GI Motility Online). However, when the sphincter is dystonic and/or dyssynergic, and not remediated by the direct delivery of electrical or pharmacological neuromodulation, justification to avoid dissection is lacking.

The electromechanical sphincteric assist device is placed to encircle the sphincter, the suture loops 32 such as those shown in FIG. 1 used to prevent unwanted mobility, in this case, equivalent to a sliding hiatal hernia. Provided to do so is not likely to result in erosions, ulceration, or fistulization of a sphincter lining such as that of the internal urinary sphincter which is unadapted to and intolerant of constant constriction, the electromagnetic sphincteric assist device type ductus jacket is placed just proximal to the native sphincter. The lining of the digestive tract much tougher and if not so intensely as a sphincter; routinely constrictive, when surrounding tissue or some peculiarity of the anatomy recommend, placement of cardiac, pyloric, and ileocecal electromagnetic sphincters are positioned just proximal or short of the native structure.

The surrounding tissue is dissected away if and only if the placement of an electromagnetic sphincteric assist device has been confirmed as necessary and not likely to cause injury that cannot be controlled through the delivery of medication through an accessory channel. Where separation from the surrounding tissue is disruptive, suture loops 32 in the accompanying drawing figures situated about the outer surface of the assist device are used to reattach the surrounding tissue. The ability to apply any drug, drugs, and/or electrostimulation in any pattern of pulsation with a nonjacketing side-entry connector such as that shown in FIG. 9 and the further ability to mechanically force the motility required with the aid of a combination-form sphincteric ductus side-entry jacket, by its spectrum of treatment modalities and results found empirically through adjustment outside the body, allows dispensing with much prediction and testing to offset the cost of treatment.

While it may be presumed that once forcible closure is instituted, electrical and chemical modulation might just as well be disposed of as superfluous, because forcible closure, especially where the tissue is not adapted for it, often injures the conduit lining. In this circumstance, the sphincteric assist device best includes the capability to forcibly contract the sphincter only once electrical and chemical neuromodulation have been unsuccessful. For this reason, a sphincteric assist device usually includes electrical and drug delivery means ab initio, allowing the use of force to be minimized through extracorporeal adjustment following closure, without the need for reentry or revision. Then, if neuromodulatiory means substantially close the sphincter so that only a final application of constrictive force is necessary to finally squelch acid reflux, the additional force is applied over the shortest interval following neuromodulation.

Thus, if the severity of the condition is recognized early, the placement of a sphincteric assist device with fluid and electrical delivery lines allows one time placement and the ability to adjust the therapy until that regimen most effective with the least treatment is determined. Then if medication and electrostimulation fail, the sphincter is forced shut. A comparable approach applies to the targeted delivery of digestive hormones, enzymes, and electrical neuromodulation to reverse gastric and/or intestinal hypo or hypermotility. The concurrent placement of sensors and control microcontroller allow the process of optimization and future adjustment as necessary to proceed automatically. When placed in conjunction with a robotically assisted procedure, use of a robotic or camera access port already present should be considered.

As to a LeVeen shunt, the ability to access the junction with the vein for delivery of drugs should substantially eliminate the complications of superior vena cava thrombosis, infection, variceal bleeding, and disseminated intravascular coagulopathy encountered with these devices. Ductus and nonjacketing side-entry connectors are intended to remain in place over a long period if not permanently, thus supporting the long term functionality of a fully implanted prosthetic disorder response system that uses inputs from implanted sensors to govern the targeted delivery of drugs to different treatment sites under automatic control. The elimination from the vena cava, internal jugular, or any other vein of an indwelling catheter provides a safety advantage.

Equally important as these conventional applications, the stable connections, long life, and direct to junction delivery of drugs that can treat the disease and maintain the catheteric line means that ductus and nonjacketing side-entry connectors are able to support, and in so doing, make possible, an automatic control system as addressed in copending application Ser. No. 14/121,365, entitled Ductus Side-entry Jackets and Prosthetic Disorder Response Systems, filed on 25 Aug. 2014. Such a system, conceived of as a prosthetic backup immune system able to treat comorbid disease, uses implanted sensors to signal the need to target medication in the appropriate doses to an organ, vessel, or a combination of these. Full implantation, automatic ambulatory operation, and system self maintenance have the potential to critically improve patient quality of life.

Where indwelling catheters limit free movement, require frequent examination, and cause progressive irritation and injury that limit duration, ductus side-entry jackets form secure catheteric junctions with ductus, and nonjacketing side-entry connectors the same with organs and tissues, to minimize if not eliminate growing trauma at the entry wound. An accessory channel to introduce catheter and target maintenance measures as needed is not accessed through a 'piggyback' port dangling out through a hole in the body wall but rather through a separate fully implanted or closed-skin portacath or secure port at the body surface, described in copending application Ser. No. 14/121,365. This allows apparatus such as nephrostomy tubes and central venous catheters previously limited to temporary use and the need for replacement if necessary to remain in place over a long term if not permanently.

Side-entry connectors are intended for long-term or permanent fastening of synthetic or tissue engineered ductus to or from native or transplanted organ or tissue, thus into the parenchyma. Ductus side-entry jackets allow secure connection to ductus, and so release, for example, drugs directly into the circulation rather than into the parenchyma. As such, both include secure fastening means, means for passing fluids and/or electrical currents through the junction, and an accessory channel to allow release into the line of medication to prevent the buildup of the clot, crystal accretion and biofilm as appropriate which have thwarted the long-term use of narrow catheter implants. Ordinarily, the line proximal to the outlet of the accessory channel does not convey biological but rather pharmaceutical materials, so that it is not susceptible to fouling or occlusive buildup.

Ductus and nonjacketing catheter-to-tissue and tissue-to-catheter fasteners that provide secure and leak-free attachment and can be accessed without invasive entry to deliver maintenance substances are indispensable for the implementation of ambulatory prosthetic disorder response systems. If necessary, counteracting agents, such as a solvent or antimicrobial can be included with the pharmaceutical at the inlet into the line. In addition to the growing irritation caused by movement at the tubing-tissue interface, synthetic tubing that is smaller in gauge placed in the vascular tree tends to be thrombogenic and subject to the formation of biofilm, and placed in the urinary tract, susceptible to crystal accretion, as seen in the need to periodically replace current ureteric stents. However, clot, biofilm, and crystallization eliminated, a synthetic tube can remain in place indefinitely, is not subject to stenosis, degradation, or infection, has no need for a blood supply, has no intrinsic physiology that is mismatched when resituated to a different location, and is not obtained at the cost of a preliminary procedure that harvests and renders normal tissue abnormal.

These factors have limited the time that catheters can be allowed to remain in place. Accordingly, side-entry connectors not only pass fluids as a primary object of placement, but incorporate an accessory line for self and catheter support. Such junctions can be used to extend the indwelling time of catheters in otherwise conventional practice, but are essential for the implementation of automatic ambulatory prosthetic disorder response control systems as described in copending nonprovisional application Ser. No. 14/121,365. Long term stability and ease of maintenance allow, for example, the placement of drug targeting means in a primigravida requiring a drug that would harm the fetus, where the unobtrusive apparatus placed early in pregnancy can remain in place over the balance of her reproductive if not entire life.

Provided a reversal agent is available, incomplete takeup within the target organ or tissue can be accomplished through a second ductus side-entry jacket on the outflow vein or veins to deliver that agent, thus preventing continued transport through the circulation, access to this second jacket as specified above for an accessory channel. Essential substances for which there is no reversal agent are prevented from further transport by introducing the medication in the form of a ferrofluid wherein the drug is bound to superparamagnetic nanoparticles drawn by magnets situated about the organ periphery from the point of entry into the surrounding tissue to draw the drug into the parenchyma or surrounding tissue. Nonjacketing side-entry connectors are of two types, those for internal use as described herein and those for placement at the surface of the body, described in copending application Ser. No. 14/121,365.

Reduction in the need for maintenance is advantageous for a patient of any age, but especially for those at the extremes of age and their caregivers. Whereas the object in forming a junction between a synthetic or tissue engineered tube and a native ductus, such as a vessel or a ureter, is to accomplish merging confluence with minimal shear stress, connection to solid or hollow organs and to fascia-invested muscle, for example, is usually to fixedly implant and if necessary, advance and retract a styloid or styliform, that is, a rod or needle-shaped device. Such include electrodes; ultrasonic, electrohydraulic, and laser probes; scopes; and/or hollow (injection/aspiration) needles, hypotubes, lasers; and/or heating elements. Those implanted for therapeutic neuromodulation can be chemical, electrical, such as leads placed for transcutaneous electrical nerve stimulation, or these inserted side by side.

Electrodes, for example, can be electroanalytic and/or electrotherapeutic, such as electroanalgesic, and different syloid or cabled devices can be positioned side by side. In an automated system, the energization of these, individually or in coaxial or disparate combinations to treat singular or comorbid conditions, can be a part of or coordinated with chemotherapy, radiotherapy, or chemoradiotherapy in adjuvant and/or ncoadvjuvant relation. That is, a connector for the immobile infixion to or within nontubular or nonductal anatomical structures must allow the connection as necessary of electrical lines and small caliber cabled devices or styliform components such as therapeutic and diagnostic electrodes or microelectrodes, lasers, or probes or microprobes in addition to fluid lines.

The ability to isolate or circumscribe an organ or region for treatment by pharmacotherapy, chemotherapy, radiotherapy (radiation therapy, radiation oncology), or chemoradiotherapy has the potential to eliminate much, perhaps all, of the adverse side effects, drug drug, and drug food interactions associated with these treatment modalities. Photon radiation as in brachytherapy involves the infixion of seeds, wires, or pellets that move with the substrate organ or tissue and are therefore positionally stable without the need for a means of positional fixation. Use of a remote afterloader, which has limited applicability, and must be withdrawn leaving no radioactive substance in the patient, denies the ability to terminate the treatment based upon reexamination at intervals without the need to repeat the procedure.

In general, the ability to circumscribe, or isolate, a native organ, blood supply territory, or an organ transplant by means of placing side-entry jackets on the arterial inflow, and if necessary, the venous outflow, allows the restriction of side effects, if any, to the organ or tissue circumscribed. The targeting of a lesion within an organ or tissue is by placing a nonjacketing side-entry connector mounting a styloid device such as a catheter or hollow needle at a fixed angle and depth within the organ or tissue. The use of both jackets and a side-entry connector to treat the same organ or tissue then serves to directly target the lesion while furnishing a background dose to the surrounding tissue as 'extension for prevention,' while containing exposure to the tissue intended.

All drugs have side effects, and the medical value and risk avoidance in targeting pertains to all drugs. Copending application Ser. No. 13/694,835 addresses the targeting of radiopharmaceuticals not on the basis of an inherent metabolic affinity of the target organ such that of the thyroid gland for iodine, but rather through the application of magnetic attractive force to superparamagnetic such as magnetite or maghemite drug carrier nanoparticles to which the radiopharmaceutical is bound within a ferrofluid introduced into the pre- or post-heapatic systemic circulation rather than delivered directly to the target (see, for example, Wilfried Andra, W. and Speer, T. 2010. Targeted Radionuclide Therapy, Lippincott Williams & Wilkins; Nowak, H. (eds.) 2006. Magnetism in Medicine: A Handbook, Hoboken, N.J.: John Wiley and Sons).

The same application describes radiation shielding with both short and longer half life radionuclides and other radioisotopes (see, for example, Murata, T., Miwa, K., Matsubayashi, F., Wagatsuma, K., Akimoto, K., and 5 others 2014. "Optimal Radiation Shielding for Beta and Bremsstrahlung Radiation Emitted by (89)Sr and (90)Y: Validation by Empirical Approach and Monte Carlo Simulations," Annals of Nuclear Medicine 28(7):617-622; Bhattacharyya, S. and Dixit, M. 2011. "Metallic Radionuclides in the Development of Diagnostic and Therapeutic Radiopharmaceuticals," Dalton Transactions 40(23):6112-6128; Yue, K., Luo, W., Dong, X., Wang, C., Wu, G., Jiang, M., and Zha, Y. 2009. "A New Lead-free Radiation Shielding Material for Radiotherapy," Radiation Protection Dosimetry 133(4):256-260; Amato, E. and Lizio, D. 2009. "Plastic Materials as a Radiation Shield for Beta-Sources: A Comparative Study through Monte Carlo Calculation," Journal of Radiological Protection 29(2):239-250; Jodal, L. 2009. "Beta Emitters and Radiation Protection," Acta Oncologica (Stockholm) 48(2):308-313; Papagiannis, P., Baltas, D., Granero, D., Perez-Calatayud, J., Gimeno, J., Ballester, F., and Venselaar, J. L. 2008. "Radiation Transmission Data for Radionuclides and Materials Relevant to Brachytherapy Facility Shielding," Medical Physics 35(11):4898-4906; Van Pelt, W. R. and Drzyzga, M. 2007. "Beta Radiation Shielding with Lead and Plastic: Effect on Bremsstrahlung Radiation when Switching the Shielding Order," Health Physics 92(2 Supplement):S13-S17).

When flushing through the line with water would not preclude the risk of injury, tungsten shielding offers the best combination of light weight and expense. Tungsten is toxic and must be encapsulated for chemical isolation, polyethylene terephthalate and related polyesters suitable materials therefore. Implants accurately prepositioned to work in conjunction with external pencil beam radiation or other means of excitation from outside the body at intervals, such as radiofrequency magnetic field alternators to warm the implants, can represent strike-target reactive or relay emitter devices, receiving antennas, or discharge tubes for substances used in radiopharmaceutical practice such as nuclides, any of which can be fixedly prepositioned in relation to the target for energization by the external source with the aid of a nonjacketing side-entry connector.

The nonjacketing connectors described herein are intended to achieve positioning as stable and durable as reversibility with relatively little trauma will allow. When placement is temporary, the needles are smooth surfaced and provided with a snare-grab to facilitate extraction. The fine needles must be of extreme strength, hence, made of graphene, titanium, or heat treated 17-4PH and 15-5 PH stainless steel, which martensitic however, are magnetic. If this will pose a problem, the needles are made of a cold worked austenitic stainless steel. The use of a nonjacketing side-entry connector assumes that positional stability is essential for a treatment to continue over a period long enough to work at all or to work to better effect.

Ductus and nonjacketing side entry connectors are drug delivery line distal target or insertion site connectors not intended for short term use in the clinic as does not justify implantation through an incision, but rather for long term use where patient mobility is to be unimpeded. For this reason, preference is always for fully, or closed skin, implantation, use of an external belt or shoulder suspended pump pack reserved for applications where multiple drugs in higher volume must be provided at a rate that would force excessive pocketing to position implant reservoirs, power source, and transdermal charging means. When implanted with pump assist, reservoir pocketing and the positioning of power source and transdermal charging components can be remote from the reservoir.

Individual anatomy and the variability of disease considerable, the placement of these various components must be determined on a patient by patient basis. Whenever possible, the implant system is entirely intracorporeal, with injectable portacath, reversible pump, charging electronics, and battery housed in a body cavity, surgically constructed pocket, or a combination of these. When an external pump or pumps are needed, the power source and controller are preferably located in the same belt-worn pump pack. Separate lines comprise independent channels that share no components other than a power source and transdermal charging implants.

Fully implanted digestive tract sphincteric and/or peristaltic, and/or cardiac electroactuated prostheses, graft-prostheses, and/or native organ assist devices not primarily intended for drug delivery per se but functionally bolstered with the aid of adjuvant drugs may be supported with system-integral drug delivery by these means. Urinary incontinence is not treated with an ectopically placed hydraulic pinch valve artificial sphincter that constantly constricts the urethra but rather with a ball check valve mechanism that eliminates compression of the urethra and therewith, the atrophy and erosion that typically presents at three to five years following placement. The relative merits of the ball check valve device and neuromodulation therapy are addressed below in the section entitled Targeted Electrical and/or Chemical Autonomic Motor Assistance. Existing artificial sphincters and neuromodulation therapy offer no means for the targeted delivery or drugs to the treatment site.

Moreover, the implantation of this device involves one, not three, separately located components, insertion of the one component less susceptible to the transection of small nerves and vessels, less traumatizing than it is to place any of the three components of the conventional device, and without moving parts or hydraulic joints, is unlikely to malfunction ever, so that once in place, the device may not require revisiting to the end of life. A more recent development is a more condensed artificial urinary sphincter, which still places a constricting cuff about the bulbar sphincter by perineal approach (Kandpal, D. K., Rawat, S. K., Kanwar, S., Baruha, A., and Chowdhary, S. K. 2013. "Single Piece Artificial Urinary Sphincter for Secondary Incontinence Following Successful Repair of Post Traumatic Urethral Injury," Journal of the Indian Association of Pediatric Surgeons 18(4):152-154).

Scheduled dosing with passive drug delivery necessitates patient or assistant compliance, whereas automated delivery does not. This factor becomes the more important as the number of drugs to be administered increases. A port with multiple openings fastened to the body surface is not considered an implant. Such a port, described in copending application Ser. No. 14/121,365, entitled Ductus Side-entry Jackets and Prosthetic Disorder Response Systems, can provide openings which are closed off to the exterior by injection bottle cap type elastomeric plugs or a lid that allows insertion of a line from an external pump. To admit a fiberscope or cabled device such as a fine excimer laser, for example, the plug is withdrawn from the port at the body surface.

Targeting comprehends two aspects-1. The direct delivery in concentrated form to a. Frank lesions whether localized as nidal or as the disseminated or metastasized expression of a systemic disorder and b. Affected segments of ductus and tracts such as the urinary and gastrointestinal of drugs other than the liver not dependent upon processing by the liver, and 2. The avoidance of organs and tissue not targeted. Both aspects, especially when combined with automated drug delivery responsive to physiological indicia reported by sensor implants, have far-reaching implications. Many drugs and many therapeutic situations make the ability to focus directly and sometimes confine drugs to lesioned tissue and avoid unintended tissue of fundamental advantage.

Drugs to treat some conditions are injurious to the liver or kidneys, for example, when healthy and especially when impaired. Drugs can be incompatible, and to treat different conditions in the same patient with the most effective drugs is often contraindicated due to the effects on unintended tissue, drug incompatibility, or these in the specific patient. The frankly lesioned areas directly targeted, disseminated and systemic disease is treated by systemic administration at a dosage level, usually of the same drug or drugs, which reduced, is less likely to induce adverse reactions, conflict with other drugs, food, or produce side effects.

The liver and/or kidneys bypassed, drugs ordinarily administered as prodrugs must be converted into the biotransformed (post-metabolized, post-hepatic, post-renal—and hypothetically, application to a fetus not yet practicable—post-placental) form exogenously before direct application at the treatment site (see, for example, Dreisbach, A. W. and Lertora, J. J. 2008. "The Effect of Chronic Renal Failure on Drug Metabolism and Transport," Expert Opinion on Drug Metabolism and Toxicology 4(8):1065-1074; Fagerholm, U. 2007. "Prediction of Human Pharmacokinetics—Renal Metabolic and Excretion Clearance," Journal of Pharmacy and Pharmacology 59(11):1463-1471; Pichette, V. and Leblond, F. A. 2003. "Drug Metabolism in Chronic Renal Failure," Current Drug Metabolism 4(2):91-103; Leblond, F. A., Giroux, L., Villeneuve, J. P., and Pichette, V. 2000. "Decreased in Vivo Metabolism of Drugs in Chronic Renal Failure," Drug Metabolism and Disposition 28(11):1317-1320; Lohr, J. W., Willsky, G. R., and Acara, M. A. 1998. "Renal Drug Metabolism," Pharmacological Reviews 50(1):107-141; Vree, T. B., Hekster, Y. A., and Anderson, P. G. 1992. "Contribution of the Human Kidney to the Metabolic Clearance of Drugs," Annals of Pharmacotherapy 26(11):1421-1428; Anders, M. W. 1980. "Metabolism of Drugs by the Kidney," Kidney International 18(5):636-647; Juchau, M. R. 1980. "Drug Biotransformation in the Placenta," Pharmacology and Therapeutics 8(3):501-524). Similarly, for direct application, conventional drugs must be adjusted in dose.

Using the means described herein, drugs such as lithium, which is neuroprotective (see, for example, Malhi, G. S., Tanious, M., Das, P., Coulston, C. M., and Berk, M. 2013. "Potential Mechanisms of Action of Lithium in Bipolar Disorder. Current Understanding," CNS Drugs 27(2):135-153; Soeiro-de-Souza, M. G., Dias, V. V., Figueira, M. L., Forlenza, O. V., Gattaz, W. F., Zarate, C. A. Jr., and Machado-Vieira, R. 2012. "Translating Neurotrophic and Cellular Plasticity: From Pathophysiology to Improved Therapeutics for Bipolar Disorder," Acta Psychiatrica Scandinavica 126(5):332-341), but a nephrotoxin, that poses the risk of significant gastrointestinal, diabetic, and thyroid, as well as renal complications (see, for example, Yu, A. S. I. and Brenner, B. M. 2005. "Tubulointerstitial Diseases of the Kidney," in Harrison's Principles of Internal Medicine, New York, N.Y.: McGraw-Hill, 16th Edition, pages 1703-1704) can be directly targeted to the treatment site, pre- or post-hepatically and/or pre- or post-renally.

That the immunosuppressant cyclosporine, also nephrotoxic (see, for example, Yu and Brenner, Op cit., pages 1703-1704), can be targeted to a non-kidney transplant, avoiding the kidney, is further addressed below in this section. With superparamagnetic iron oxide nanoparticles as drug carriers, one can selectively target diseased tissue within an organ or tissue while keeping the agent away from the healthy tissue surrounding the lesion. Such an application will be addressed in connection with FIGS. 6, 13A, and 13B. Ordinarily, the use of a reversal agent or counteractant is complicated by the possibility of unwanted reversal; however, the segregation implicit in targeting allows conjugation or chemical reaction between the therapeutic agent and reversal agent to be controlled. Delivery of the therapeutic agent, and if needed, the reversal agent, can be pulsed or continuous. Lithium, for example, to treat bipolar (manic depressive, mood) disorder, can be routed directly to the brain and substantially kept away from the kidneys, intestinal tract, and thyroid, for example.

Targeting to the brain of lithium or another drug, or to the eyes of an ophthalmic drug is by direct delivery into the carotids or internal carotids through ductus side-entry jackets. When directly delivered to the brain, the risk of drug-induced renal complications, especially if counteracted when continuing through the circulation, is substantially eradicated. The smaller dose needed when not dispersed throughout the pre- or post-systemic circulation should prove harmless, but if needed, a counteractant, neutralizing, or reversal agent is delivered directly into the jugulars or internal jugulars. In this way, acetaminophen can be kept away from the kidneys and nonsteroidal anti-inflammatory drugs from the gastrointestinal tract of a patient with chronic or migraine or cluster headache (see, for example, Raskin, N. M. 2005. "Headache," in Harrison's Principles of Internal Medicine, Op cit., pages 85-94).

The direct delivery to the brain of drugs averts metabolism by, and is limited to drugs that do not depend upon, conversion by the liver and kidneys, for example. Such drugs exercise the therapeutic effect locally at the site to which delivered, the brain exemplary in this regard. Where antecedent conversion of the drug is essential, administration of the drug through direct targeting must deliver the drug in its activated or effective post-metabolized form. For drugs with direct local action, dispersion in a relatively small and substantially isolated volume of blood conserves plasma concentration, minimizes the time to peak plasma concentration as a primary factor in clinical efficacy (Raskin, N. M. 2005, Op cit., page 91), avoids breakdown by nontargeted tissue, and minimizes loss through absorption which could induce adverse side effects.

This consideration, fundamentally important in the administration of chemotherapy, radiotherapy, chemoradiotherapy, and immunotherapy, all inducing severe side effects, is no less important in the administration of migraine medication, where the efficacy of the drug tends to vary in proportion to its toxicity. For example, when dispersed throughout the systemic circulation through injection or oral administration in systemic doses, sumatriptan, usually formulated to include naproxen, one of the most effective drugs for reducing the pain of migraine and one unlike a statin not in question as to its direct tissue contact efficacy, can induce serious side effects; to include ventricular dysrhythmias, coronary vasospasm, myocardial ischemia, and infarction. Less serious neurological side effects include altered sensation of temperature, pressure, pain, paresthesias, and sleep disturbances.

The release of serotonin 1B, 1D receptor agonists, antiemetics, analgesics (see, for example, Demaagd, G. 2008. "The Pharmacological Management of Migraine, Part 1: Overview and Abortive Therapy," PT [Pharmacy and Therapeutics] 33(7):404-416; Part 2: Preventative Therapy 33(8):480-487; The Merck Manual 18th edition, 2006, Section 216, Headache, page 1847; Ramadan, N. M., Schultz, L. L., and Gilkey, S. J. 1997. "Migraine Prophylactic Drugs: Proof of Efficacy, Utilization and Cost," Cephalalgia 17(2):73-80), amitriptyline (see, for example, Couch, J. R. 2011. "Amitriptyline in the Prophylactic Treatment of Migraine and Chronic Daily Headache," Headache 51(1):33-51), sumatriptan (Derry, C. J., Deny, S., and Moore, R. A. 2014. "Sumatriptan (All Routes of Administration) for Acute Migraine Attacks in Adults—Overview of Cochrane Reviews," Cochrane Database of Systematic Reviews 5:CD009108), zolmatiptan (Bird, S., Deny, S., and Moore, R. A. 2014. "Zolmitriptan for Acute Migraine Attacks in Adults," Cochrane Database of Systematic Reviews 5:CD008616), dihydroergotamine (see, for example, Silberstein, S. D. and Kori, S. H. 2013. "Dihydroergotamine: A Review of Formulation Approaches for the Acute Treatment of Migraine," CNS Drugs 27(5):385-394; Whyte, C. A., Stillman, M. J., and Tepper, S. J. 2010. "Dihydroergotamine and Its Use in Migraine with Posterior Fossa Symptoms," Headache (9):1419-1423), or ergotamine (Tfelt-Hansen, P., Saxena, P. R., Dahlof, C., Pascual, J., Lainez, M., and 5 others 2000. "Ergotamine in the Acute Treatment of Migraine: A Review and European Consensus," Brain 123(1 Part 1):9-18), for example, to suppress a migraine headache on inception depends upon the experience of an aura or prodrome by a competent patient able to control the drug delivery pump implant.

In patients who do not experience an aura, other sensible symptoms, such as paresthesia of a hand that progresses proximally up the arm signals onset (see, for example, The Merck Manual, page 1848). In an intellectually impaired patient or a young child, automatic release must be effected by a sensor implant which detects a physiological concomitant and experiential correlate to onset, signals the microcontroller to energize the pump, and provides the quantitative information for controlling the pump. Provided distention or vasoldilation of the extracerebral cranial arteries signals onset, a thin film strain gauge pressure type sensor implant can be used.

If for any reason, the action of the drug produces results outside the target range, further delivery is stopped upon receipt of pertinent sensor feedback. An unanticipated effect can be encountered during preliminary testing or at any time thereafter in which the patient experiences a primary change in metabolism, disease induced or otherwise. Then delivery of the drug is immediately stopped, and if available, a reversal agent (antidote, counteractant) is delivered. Drug delivery cessation and recovery are the reasons for requiring that all pumps be reversible.

A vascular basis for the prodromal experience not having been established with confidence (Dalkara, T., Nozari, A., and Moskowitz, M. A. 2010. "Migraine Aura Pathophysiology: The Role of Blood Vessels and Microembolisation," Lancet. Neurology 9(3):309-317; Theisler, C. W. 1990. Migraine Headache Disease: Diagnostic and Management Strategies, Gaithersburg, Md.: Aspen Publishers, Chapter 3, "Vascular Theories"), any alternative physicochemical concomitant to onset (see, for example, Tfelt-Hansen, P. C. 2010. "History of Migraine with Aura and Cortical Spreading Depression from 1941 and Onwards," Cephalalgia 30(7):780-792; Domitrz, I. 2007. "Current Views on the Pathogenesis of Migraine Aura," (in Polish with English abstract at Pubmed), Neurologia i Neurochirurgia Polska 41(1):70-75; Dalkara, T., Zervas, N. T., and Moskowitz, M. A. 2006. "From Spreading Depression to the Trigeminovascular System," Neurological Sciences 27 Supplement 2:S86-S90) is sensed.

Thus, alterations in blood chemistry and/or neuronal activity can be used to signal the microcontroller to energize and control the pump just as well. Generally, however remote or disseminated, symptoms that arise within anatomically or physiologically indissociable tissue from that circumscribed for drug targeting should also be suppressed without the need for direct treatment at the remote site or sites. Examples include the autonomic effects associated with migraine, such as nausea, emesis, pallor, blurred vision, vertigo, photophobia, sonophobia, osmophobia, confusion, weakness, ataxia (see, for example, Theisler, C. W. 1990, Op cit., Chapter 1, pages 1-23) and abdominal pain in children (see, for example; The Merck Manual, Op cit., page 1848), and tardive dyskinesia associated with neuroleptic or antipsychotic drugs.

Within the brain or other organ or tissue not divisible internally using mechanical means, isolation of the source tissue, if possible, must be accomplished pharmacologically in a manner analogous to a thalamic-limbic dissociative anesthetic agent such as ketamine, which at lower doses, achieves analgesia, sedation, and affects the state of consciousness, inducing a temporary state of catalepsy, while little if at all affecting respiratory function and increasing the heart rate (see, for example, Green, S. M., Roback, M. G., Kennedy, R. M., and Krauss, B. 2011. "Clinical Practice Guideline for Emergency Department Ketamine Dissociative Sedation," Annals of Emergency Medicine 57(5):449-461; Stoelting, R. K. and Dierdorf, S. F. 2002. Handbook for Anesthesia and Co-Existing Disease, Philadelphia, Pa.: Churchill Livingston/Elsevier, page 27; Rutter, T. W and Tremper, K. K. 1997. "Anesthesiology and Pain Management," Chapter 13 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven; pages 441-442).

If lithium is kept from the kidneys, the kidneys are unaffected. Lithium withheld form the systemic circulation, the thyroid gland remains unexposed, and anomalies of thyroid hormone production, whether primary or induced by lithium, cannot contribute to lithium nephrotoxicity (see, for example, Kraszewska, A., Abramowicz, M., Chlopocka-Wozniak, M., Sowi iski, J., and Rybakowski, J. 2014. "The Effect of Lithium on Thyroid Function in Patients with Bipolar Disorder," (in Polish with English abstract at Pubmed), Psychiatria Polska 48(3):417-428; Sato, Y., Taki, K., Honda, Y., Takahashi, S., and Yoshimura, A. 2013. "Lithium Toxicity Precipitated by Thyrotoxicosis Due to Silent Thyroiditis: Cardiac Arrest, Quadriplegia, and Coma," Thyroid 23(6):766-770; Kibirige, D., Luzinda, K., and Ssekitoleko, R. 2013. "Spectrum of Lithium Induced Thyroid Abnormalities: A Current Perspective," Thyroid Research 6(1):3). Lithium can also be a thyroid cytotoxin (see, for example, Kibirige, D., Luzinda, K., and Ssekitoleko, R. 2013, Op cit.; Lazarus, J. H. 2009. "Lithium and Thyroid," Best Practice and Research. Clinical Endocrinology and Metabolism 23(6):723-733; Phillips, B. D., Gopalakrishnan, G., Gohh, R., and Hennessey, J. V. 2008. "Lithium Toxicity Precipitated by Profound Hypothyroidism," Thyroid 18(6):651-654; Bocchetta, A and Loviselli, A. 2006. "Lithium Treatment and Thyroid Abnormalities," Clinical Practice and Epidemiology in Mental Health 2:23).

Administered thus, lithium in any amount that might accumulate in the gastrointestinal tract or pass to the kidneys is slight, eliminating the need for removal of the excess by gastric lavage or affecting excretion, for example. On exiting the brain, any residual lithium can be treated with sodium chloride (Hall, R. C., Perl, M., and Pfefferbaum, B. 1979). "Lithium Therapy and Toxicity," American Family Physician 19(4):133-139) and/or magnesium (Timmer, R. T. and Sands, J. M. 1999. "Lithium Intoxication," Journal of the American Society of Nephrology 10(3):666-674). These should provide sufficient reversal of any residue, even if small from a systemic perspective. Constrained to the brain but not within the brain, the adverse neuropsychiatric effects of lithium, which may be the result of long term and/or lithium overdose, may remain unaffected.

These effects include transient aphasia (Gordon, P. H., Hirsch, L. J., and Balmaceda, C. 1997. "Transient Aphasia Associated with Lithium Intoxication," Journal of Clinical Psychopharmacology 17(1):55-56; Fallgatter A. J. and Strik, W K. 1997. "Reversible Neuropsychiatric Side Effects of Lithium with Normal Serum Levels. A Case Report," (in German with English abstract in Pubmed), der Nervenarzt [Neurology] 68(7):586-590), delirium (Niethammer, R., Keller, A., and Weisbrod, M. 2000. "Delirium Syndrome as a Side-effect of Lithium in Normal Lithium Levels," (in German with English abstract in Pubmed), Psychiatrische Praxis [Psychiatric Practice] 27(6):296-297), chorea (Stemper, B., Thurauf, N., Neundorfer, B., and Heckmann, J. G. 2003. "Choreoathetosis Related to Lithium Intoxication," European Journal of Neurology 10(6):743-744; Wada, K., Sasaki, T., Yoshimura, Y., and Erabi, H. 2003. "Reversible Choreoathetosis Associated with Lithium Intoxication," (in Japanese with English abstract in Pubmed), Seishin Shinkeigaku Zasshi [Psychiatria et Neurologia Japonica] 105(9): 1206-1212; Podskalny, G. D. and Factor, S. A. 1996. "Chorea Caused by Lithium Intoxication: A Case. Report and Literature Review," Movement Disorders 11(6):733-737; Reed, S. M., Wise, M. G., and Timmerman, I. 1989. "Choreoathetosis: A Sign of Lithium Toxicity," Journal of Neuropsychiatry and Clinical Neurosciences 1(1):57-60), parkinsonism (Shen, H. C., Li, J. Y., and Lo, Y. K. 2007. "Lithium Intoxication-induced Acute Parkinsonism Complicated with Hyperparathyroidism and Nephrogenic Diabetes Insipidus: Report of a Case," Acta Neurologica Taiwanica 16(4):231-233), nephrogenic diabetes insipidus (Lam, S. S. and Kjellstrand, C. 1997. "Emergency Treatment of Lithium-induced Diabetes Insipidus with Nonsteroidal Antiinflammatory Drugs," Renal Failure 19(1):183-188; Posner, L. and Mokrzycki, M. H. 1996. "Transient Central Diabetes Insipidus in the Setting of Underlying Chronic Nephrogenic Diabetes Insipidus Associated with Lithium Use," American Journal of Nephrology 16(4):339-343; Martinez, E. J., Sinnott, J. T. 4th, Rodriguez-Paz, G., and Oehler, R. L. 1993. "Lithium-induced Nephrogenic Diabetes Insipidus Treated with Indomethacin," Southern Medical Journal 86(8):971-973; Allen, H. M., Jackson, R. L., Winchester, M. D., Deck, L. V., Allon, M. 1989. "Indomethacin in the Treatment of Lithium-induced Nephrogenic Diabetes Insipidus," Archives of Internal Medicine 149(5):1123-1126), and parkinsonism with diabetes (Shen, H. C., Li, J. Y., and Lo, Y. K. 2007, Op cit.), However, hepatic encephalopathy or coma as the result of ammonia of gastrointestinal origin would not occur, and the dose when directly targeted to the brain can be lowered so that adverse neuropsychiatric effects are unlikely to arise (Forester, B. P., Streeter, C. C., Berlow, Y. A., Tian, H., Wardrop, M., and 4 others 2009. "Brain Lithium Levels and Effects on Cognition and Mood in Geriatric Bipolar Disorder: A lithium-7 Magnetic Resonance Spectroscopy Study," American Journal of Geriatric Psychiatry 17(1):13-23; Shim, S. S. 2009. "Lower Serum Levels of Lithium May Produce Efficacy without Adverse Effects," American Journal of Geriatric Psychiatry 17(7):625-626), and the susceptible population is small.

Some bipolar patients experience renal impairment despite not having taken lithium. However, in that cohort of patients susceptible to renal degradation in response to lithium, preventing lithium from reaching the digestive tract and entering into the bloodstream, and thus the kidneys, should eliminate the risk of renal complications (see, for example, Rybakowski, J. K., Abramowitz, M., Szczepankiewicz, A., Michalak, M., Hauser, J., and Czekalski, S. 2013. "The Association of Glycogen Synthase Kinase-3beta (GSK-3.beta.) Gene Polymorphism with Kidney Function in Long-term Lithium-treated Bipolar Patients," International Journal of Bipolar Disorders 1:8; Grandjean, E. M. and Aubry, J. M. 2009. "Lithium: Updated Human Knowledge Using an Evidence-based Approach: "Part I: Clinical Efficacy in Bipolar Disorder," CNS Drugs 23(3):225-240; "Part II: Clinical Pharmacology and Therapeutic Monitoring," 23(4):331-349; "Part III: Clinical Safety," 23(5):397-418; Gitlin, M. 1999. "Lithium and the Kidney: An Updated Review," Drug Safety 20(3):231-243; Walker, R. G. 1993. "Lithium Nephrotoxicity," Kidney International. Supplement 42:S93-s98).

The same may be said for lithium associated hyperparathyroidism, which can necessitate parathyroidectomy that leads to multiple adverse sequelae (Albert, U., De Cor, i D., Aguglia, A., Barbaro, F., Lanfranco, F., Bogetto, F., and Maina, G. 2013. "Lithium-associated Hyperparathyroidism and Hypercalcaemia: A Case-Control Cross-Sectional Study," Journal of Affective Disorders 151(2):786-790; Ballehaninna, U.K., Nguyen, S. M., and Chamberlain, R. S. 2011. "Lithium Associated Hyperparathyroidism: An Evidence Based Surgical Approach," Surgical Science 2(10): 468-475; Saunders, B. D., Saunders, E. F., and Gauger, P. G. 2009. "Lithium Therapy and Hyperparathyroidism: An Evidence-based Assessment," World Journal of Surgery 33(11): 2314-2323; Rizwan, M. M. and Perrier, N. D. 2009. "Long-term Lithium Therapy Leading to Hyperparathyroidism: A Case Report," Perspectives in Psychiatric Care 45(1):62-65).

Questioned with respect to the direct healing of atherosclerotic plaque not produced by the lowering of low density lipoprotein (Pedersen, T. R. 2010. "Pleiotropic Effects of Statins: Evidence Against Benefits Beyond LDL-Cholesterol Lowering," American Journal of Cardiovascular Drugs 10 Supplement 1:10-17; Robinson, J. G., Smith, B., Maheshwari, N., and Schrott, H. 2005, "Pleiotropic Effects of Statins: Benefit Beyond Cholesterol Reduction? A Meta-Regression Analysis," Journal of the American College of Cardiology 46(10):1855-1862; Futterman, L. G. and Lemberg, L. 2004. "Statin Pleiotropy: Fact or Fiction?," American Journal of Critical Care 13(3):244-249), statins are far more generally accepted to have directly healing, or 'pleiotropic,' properties when directly applied to inflamed tissue, whether periodontal, neuronal, or atherosclerosed (see, for example, Estanislau, I. M., Terceiro, I. R., Lisboa, M. R., Teles Pde, B., Carvalho Rde, S., Martins, R. S., and Moreira, M. M. 2015. "Pleiotropic Effects of Statins on the Treatment of Chronic Periodontitis—A Systematic Review," British Journal of Clinical Pharmacology 79(6):877-885; Suresh, S., Narayana, S., Jayakumar, P., Sudhakar, U., and Pramod, V. 2013. "Evaluation of Anti-inflammatory Effect of Statins in Chronic Periodontitis," Indian Journal of Pharmacology 45(4):391-394; Ma, Y., Chen, Z., Zou, Y., and Ge, J. 2014. "Atorvastatin Represses the Angiotensin 2-induced Oxidative Stress and Inflammatory Response in Dendritic Cells via the PI3K/Akt/Nrf 2 Pathway," Oxidative Medicine and Cellular Longevity 2014:148798; Adam, O. and Laufs, U. 2008. "Antioxidative Effects of Statins," Archives of Toxicology 82(12):885-892), and have potency when directly applied to the affected or lesioned tissue.

The citation herein of specific drugs as to direct contact or nonsystemic healing value, whether as formulated in pre- or post-hepatic and/or post-renal form, is purely exemplary and based upon contemporaneous reports in the literature. Unconstrained to a circumscribed segment of an artery, statins can contraindicate the simultaneous administration of an antibiotic, antimycotic, antidepressant, immunosuppressant, or colchicine, and are known or suspected to damage myelin and induce myopathy and/or diabetes. The patient need not be advised to avoid grapefruit or grapefruit juice, which impede statin metabolism, resulting in higher plasma levels that can lead to muscle and/or liver damage, or advised to take coenzyme Q10, or ubiquinone, as a mitochondrial protectant.

Statins can be directly delivered to the site of the atherosclerotic lesion. When directly applied thus, any portion of the drug not taken up within the targeted segment will rarely if ever accede to medical significance given its dilution in the systemic circulation. Nevertheless, if necessary, the residue can be counteracted or neutralized by delivery of a counteractant or antagonist, usually a chemical solvent or enzyme for that applied therapeutically. The counteractant is delivered at the level for removal through the same means as the drug was to the level of inception. In the case of a statin, the counteractant might be only so much of the substrate, that is, the substance acted upon when the agent is or includes an enzyme, or reciprocal substance, 3-hydroxy-3-methylglutaryl-CoA) reductase, for example, as needed to neutralize or reverse the statin, for example.

In ascending order of elaboration, the applications of side-entry jackets comprise the following configurations. For simplicity, radiation shielding and dumb (uncontrollable) permanent magnets are omitted as equally applicable to any level. Once elaboration includes a controller, sensors, and closed loop control are present, electromagnets, telemetry, body area networks, remote diagnostics and adjustment, and reprogramming are equally applicable. For a frail patient and one requiring numerous components to treat comorbid disease, it is preferred to minimize the need for dissection.

In such a case, a port is placed at the body surface with dissection limited to the placement of the sensors and side connector catheters, or lines, leading to the side-entry connector needed. The balance of components are relegated to the external pump pack for which the need was evident ab initio. That is, once the need for an external pump pack is established, the tendency should be to keep as many system components within the pump pack as possible, thus minimizing the surgery to effect implantation. With a port at the body surface, only sensors and side connector lines must be implanted.

I. Fully (Closed Skin, Impedimenta-Free) Implanted:
a. Manually injected portacath with side-entry connector line connected line to the target ductus, organ, or tissue.
b. Separate manually injected portacaths, each with a side-entry connector line connected to its respective target ductus, organ, or tissue.
c. Manually injected Ommaya type reservoir or portacath-injected elastomeric storage bladder with release rate passively determined and sustained by gravity and/or elastomeric contraction, and side-entry connector line connected to the target ductus, organ, or tissue.
d. Separate manually injected Ommaya type reservoirs or portacaths leading to elastomeric storage bladders, with a side-entry connector line respective of each connected to its respective target ductus, organ, or tissue where the rate of release is passively determined and sustained by gravity and/or elastomeric contraction.
e. Manually injected Ommaya type reservoir or portacath leading to a reservoir with drug withdrawal or release through a side-entry connector line connected to its respective target ductus, organ, or tissue is by an implanted pump with transdermally charged power source under the control of an implanted microcontroller.
f. Separate manually injected Ommaya type reservoirs or portacaths leading to a reservoir with drug withdrawal or release by an implanted pump, with transdermally charged power source under the control of an implanted microcontroller through a. side-entry connector line, each connected to its respective target ductus, organ, or tissue.
II. Not Fully Implanted (Impedimenta Minimized):
a. External pump with power source and controller in a belt-worn pump pack, with drug delivery through a port at the body surface leading into a side connector line connected to the target ductus, organ, or tissue by a side-entry connector.
b. External pumps with shared power source, and controller in a belt-worn pump pack, with drug delivery through a port with an opening for each line at the body surface leading into side connector lines respective of each which connect to the target ductus, organ, or tissue with a side-entry connector.
c. External pump and power pack with drug delivery through a port at the body surface leading to a side connector line connected to the target ductus, organ, or tissue by a side-entry connector where control is by pump pack contained controller and implanted sensor feedback.
d. External pumps and power pack with drug delivery through a port at the body surface leading to side connector lines, each connected to its respective target ductus, organ, or tissue by a side-entry connector where control is by pump pack contained controller and implanted sensor feedback.

Drugs to be prevented from mixing with others and directly targeted, each according to a different dosing schedule, are passed through independent conduits from source to destination, to include the pump or injected portacath, reservoir if present, implant pump if present, and line leading to the side-entry connector. Delivery of either drug can be manual or by a microcontroller controlling the separate pumps. Those for the same target to be administered in a coordinated manner without mixing before reaching the destination are passed through either lumen of a double lumen catheter as side connector. In a ductus side-entry jacket placed about a native ductus with a catheter leading to another ductus side-entry jacket placed about a native ductus, the catheter is placed in the side connector, the water jacket as its distal terminus emptying into the catheter as the extension of the side connector.

At the junction of origin at the ductus side-entry jacket, the water jacket at this end of the line feeds into the catheter proximally (far removed from the target native ductus in the side connector of the receiving ductus side-entry jacket) and is thus positioned to treat the catheteric line itself or to add an adjuvant into the line as programmed. Such an arrangement is shown in FIGS. 21 and 22 of copending application Ser. No. 14/121,365, entitled Ductus Side-entry Jackets and Prosthetic Disorder Response Systems. In contrast to ductus side-entry jackets when positioned at the origin, nonjacketing side-entry jackets are far more frequently used at the terminal end so that the accessory channel outlets at the terminus of the catheter.

In FIG. 17, catheteric lines 34 and 35, representing the side connectors, hence, double part numbered 3, can be provided with adjuvant and maintenance substances through the accessory channels (service channels, sidelines of the ductus side-entry jackets. Moreover, these accessory channels are not limited to convergence with the mainline flow just before delivery into the tissue through the side connector: The anchoring needles if hollow can be connected to drug delivery lines. The manner in which 'trunk line' accessory channels running down through the side connector are connected each to its respective 'spur line' connected to a specific injection needle is shown in FIGS. 9 and 10B and is described below in the section entitled Description of the Preferred Embodiments of the Invention.

For this reason, a fluid substance used to maintain the catheter as side connector leading to a nonjacketing side-entry jacket is mixed in the fluid delivered, or the catheter provided with a side-entry accessory channel toward its origin. In this case, unless intracorporeal placement forces a degree of compactness that necessitates the use of a single pump and switching scheme and the maintenance substance should not be mixed into the drug, both accessory channels, meaning that used to maintain the catheter and that used to contribute an adjuvant at the terminus leading into the native ductus, as well as the ductus itself, are supplied from separately programmed pumps.

Other than that it empties into the mainline proximally, an accessory channel with the primary purpose of introducing substances into the mainline to keep it clear is the same as the more conventional accessory channels shown in FIGS. 1, 2, 5, 6, 13, and 14. FIG. 12A shows a singular channel from portacath 46 to the urinary bladder for the delivery of a drug, not blood or urine, for example, which are prone to foul the conduit through which these are conveyed. An antimicrobial-antibiofilm agent is presumed added to the medication without the need for the independent delivery of an adjuvant, for example. For this reason, a second channel from the portacath to support an accessory channel is not shown in FIG. 12A. Despite use to drain the bladder, so long as an anti-crystallization agent can be delivered through connector 61, the lower connector 62 in FIG. 12A also needs no accessory channel. Unlike connection to a blood vessel, connection to the bladder is by perforation without the need for a water jacket. Initial emptying is by temporary or bridging nephrostomy or suprapublic cystostomy as appropriate.

Such an accessory channel is no less separately controllable to deliver an adjuvant, for example, through the mainline. In conventional use for urinary diversion as shown toward the bottom of the bladder in FIG. 12A, the nonjacketing side-entry connector is positioned on the native structure at the catheter origin, so that citrate, for example, can be delivered through the accessory channel to prevent the formation of a crystal deposit on the inside of the catheter wall. When space constraints force the use of a nonjacketing side-entry connector on a vessel where a ductus side-entry connector would otherwise be used proximal emptying into the catheter might, for example, drip in heparin to prevent clot. The absolute volume of heparin used should not result in a heparin-induced thrombocytopenia or a heparin-induced thrombocytopenia and thrombosis.

If by some chance the accessory channel, or sideline, accumulates clot, a thrombolytic, excimer laser, or guide wire is passed through the line to dissolve or disperse it. When the catheter as side connector is used to convey a drug, drugs, or therapeutic solution, unless disallowed for some other reason, an adjuvant is mixed into the drug or solution at the source, eliminating the need for a second passageway. Primarily because an accessory channel negates the circularity essential for insertion with minimal trauma, and secondarily because extraction if needed to later service the side connector would cause needles trauma, emptying of an accessory channel, or sideline, into the mainline as side connector is kept proximal enough to remain outside the organ or tissue treated. This is so whether the sideline terminates with or without a water jacket.

When medical and control considerations do not disallow the nonexclusive delivery of drugs through independent lines as separate channels, a shared reservoir can be made larger in volume, an intracorporeal reservoir is used replenished by injection through a common portacath or Ommaya type reservoir. However, internally partitioning the reservoir allows preserving channel independence, which in a fully implanted system, allows unified, or centralized, as opposed to distributed pocketing. Depending upon the length of the catheters needed to reach each target, where the drugs need not be completely isolated from one another, a single pump is interposed between the pump incurrent and excurrent lines and switched from channel to channel.

Flushing through a line with water between drugs involving needles complexity and expense, where a line retains a preceding drug not to be combined with that next to pass, that line is provided with an independent pump. To minimize the internal space needed for such a system, when no more than four drugs to be kept separate are needed, well separated and easily distinguished portacaths are used. In an otherwise fully implanted multidrug and/or multi-target destination system, when a larger number of drugs or other substances must be used, a port with multiple entry orifices as described in copending application Ser. No. 14/121,365, each orifice clearly marked, is placed at the body surface.

In most instances, if made of materials presumed to be biologically compatible with a suitable surface, an implant will become surrounded by a non-necrotic avascular collagenous foreign body capsule through 'capsular contraction,' to produce a fibrous rim of connective tissue with a relatively quiescent implant site observed and further rejection subsided (see, for example, Sides, C. R. and Stenken, J. A. 2014. "Microdialysis Sampling Techniques Applied to Studies of the Foreign Body Reaction," European Journal of Pharmaceutical Sciences 57:74-86; Rujitanaroj, P. O., Jao, B., Yang, J., Wang, F., Anderson, J. M., Wang, J., and Chew, S. Y. 2013. "Controlling Fibrous Capsule Formation through Long-term Down-regulation of Collagen Type I (COL1A1) Expression by Nanofiber-mediated siRNA Gene Silencing," Acta Biomaterialia 9(1):4513-4524. Bryers, J. D., Giachelli, C. M., and Ratner, B. D. 2012. "Engineering Biomaterials to Integrate and Heal: The Biocompatibility Paradigm Shifts," Biotechnology and Bioengineering 109(8):1898-1911; Junge, K., Binnebosel, M., von Trotha, K. T., Rosch, R., Klinge, U., Neumann, U. P., and Lynen Jansen, P. 2012. "Mesh Biocompatibility: Effects of Cellular Inflammation and Tissue Remodelling," Langenbecks Archives of Surgery 397(2):255-270; Anderson, J. M., Rodriguez, A., and Chang, D. T. 2008. "Foreign Body Reaction to Biomaterials," Seminars in Immunology 20(2): 86-100; Stoncek, J. D. and Reichert, W. M. 2008. "Overview of Wound Healing in Different Tissue Types," in Reichert, W. M. (ed.), Indwelling Neural Implants: Strategies for Contending with the in Vivo Environment, Boca Raton, Fla.: Chemical Rubber Company Press, Chapter 1; Luttikhuizen, D. T., Dankers, P. Y., Harmsen, M. C., and van Luyn, M. J. 2007. "Material Dependent Differences in Inflammatory Gene Expression by Giant Cells during the Foreign Body Reaction," Journal of Biomedical Materials Research. Part A 83(3):879-886; Luttikhuizen, D. T., van Amerongen, M. J., de Feijter, P. C., Petersen, A. H., Harmsen, M. C., and van Luyn, M. J. 2006. "The Correlation between Difference in Foreign Body Reaction between Implant Locations and Cytokine and MMP [matrix metalloproteinase] Expression," Biomaterials 27(34):5763-5770; Luttikhuizen, D. T., Harmsen, M. C., and Van Luyn, M. J. 2006. "Cellular and Molecular Dynamics in the Foreign Body Reaction," Tissue Engineering 12(7): 1955-1970).

Where permanence is sought, the semicircular tissue retention needles 6 shown in FIGS. 1, 2, 7, 8, and 14, for example, used to engage the nonjacketing side-entry connector in the subjacent tissue, are surface-textured and through-etched, then coated to encourage tissue ingrowth, or infiltration. For example, depending upon the material of which they are made, the needles are etched entirely through, such as by means of deep reactive-ion etching, with pores to create a surface conformation aligned to a porous template outer scaffold capsule devised to forestall an adverse tissue reaction (see, for example, Bryers, J. D., Giachelli, C. M., and Ratner, B. D. 2012, cited below).

This can be combined with polydimethylsiloxane micropillar surfacing of the continuous surface of the needles suitably configured for the substrate tissue (see, for example, Zhang, H., Bian, C., Jackson, J. K., Khademolhosseini, F., Burt, H. M., and Chiao, M. 2014. "Fabrication of Robust Hydrogel Coatings on Polydimethylsiloxane Substrates Using Micropillar Anchor Structures with Chemical Surface Modification," ACS [American Chemical Society] Applied Materials and Interfaces 6(12):9126-9133. Gregory, C. W., Sellgren, K. L., Gilchrist, K. H., and Grego, S. 2013. "High yield Fabrication of Multilayer Polydimethylsiloxane Devices with Freestanding Micropillar Arrays," Biomicrofluidics 7(5):56503; Yang, J., Su, J., Owens, L., Ibraguimov, A., and Tang, L. 2013. "A Computational Model of Fibroblast and Macrophage Spatial/Temporal Dynamics in Foreign Body Reactions," Journal of Immunological Methods 397(1-2):37-46. Baker, D., Liu, X., Weng, H., Luo, C., and Tang, L. 2011. "Fibroblast/Fibrocyte: Surface Interaction Dictates Tissue Reactions," Biomacromolecules 12(4):997-1005).

Coatings, especially for implanted sensors in intimate contact with the surrounding tissue, may consist of substances such as hydrophilic, super hydrophobic, or zwitterionic polymers (Yang, R., Goktekin, E., Wang, M., and Gleason, K. K. 2014. "Molecular Fouling Resistance of Zwitterionic and Amphiphilic Initiated Chemically Vapor-deposited (iCVD) Thin Films," Journal of Biomaterials Science. Polymer Edition 25(14-15):1687-1702; Lin, P., Ding, L., Lin, C. W., and Gu, F. 2014. "Nonfouling Property of Zwitterionic Cysteine Surface," Langmuir 30(22):6497-6507; Schlenoff, J. B. 2014. "Zwitteration: Coating Surfaces with Zwitterionic Functionality to Reduce Nonspecific Adsorption," Langmuir 30(32):9625-9636; Lin, P., Lin, C. W., Mansour, R., and Gu, F. 2013. "Improving Biocompatibility by Surface Modification Techniques on Implantable Bioelectronics," Biosensors and Bioelectronics 47:451-460), an interleukin 17A counteractant (Bian, Z., Guo, Y., Ha, B., Zen, K., and Liu, Y. 2012. "Regulation of the Inflammatory Response: Enhancing Neutrophil Infiltration under Chronic Inflammatory Conditions," Journal of Immunology (Baltimore) 188(2):844-853), anti-adhesive proteins (Pliyev, B. K. 2013. "Anti-adhesive Proteins and Resolution of Neutrophil-mediated Inflammation," Immunobiology 218 (8):1085-1092), a dexamethazone, phosphorylcholine, and/or a positively charged polymer surface modified by treatment with oriented osteopontine (Liu, L., Chen, G., Chao, T., Ratner, B. D., Sage, E. H., and Jiang, S. 2008. "Reduced Foreign Body Reaction to Implanted Biomaterials by Surface Treatment with Oriented Osteopontin," Journal of Biomaterials Science. Polymer Edition 19(6):821-835; Anderson, J. M. and Jones, J. A. 2007. "Phenotypic Dichotomies in the Foreign Body Reaction," Biomaterials 28(34):5114-5120; Iwasaki, Y. and Ishihara, K. 2005. "Phosphorylcholine-containing Polymers for Biomedical Applications, Analytical and Bioanalytical Chemistry 381(3):534-546; Whelan, D. M., van der Giessen, W. J., Krabbendam, S. C., van Vliet, E. A., Verdouw, P. D., Serruys, P. W., and van Beusekom, H. M. 2000. "Biocompatibility of Phosphorylcholine Coated Stents in Normal Porcine Coronary Arteries," Heart 83(3):338-345), methylprednisolone (Huang, Y., Liu, X., Wang, L., Verbeken, E., Li, S., and De Scheerder, I. 2003. "Local Methylprednisolone Delivery Using a Biodi-vYsio Phosphorylcholine-coated Drug-Delivery Stent Reduces Inflammation and Neointimal Hyperplasia in a Porcine Coronary Stent Model," International Journal of Cardiovascular Interventions 5(3):166-171), cytochalasin D (Salu, K. J., Huang, Y., Bosmans, J. M., Liu, X., Li, S., and 5 others 2003. "Addition of Cytochalasin D to a Biocompatible Oil Stent Coating Inhibits Intimal Hyperplasia in a Porcine Coronary Model," Coronary Artery Disease 14(8):545-555), and/or dexamethasone poly(lactic-co-glycolic) acid microsphere/poly(vinyl alcohol)/hydrogel composite (references below), for example, to ward off a foreign body response induced adverse tissue reaction.

Ascertaining the incidence of adverse, or material sensitivity, reaction is first through clinical trials to identify materials undesirable for most patients. Solid implant surface materials to include outer coatings and microsurfacing are tested. These measures will eliminate statistically high incidence of foreign body reaction materials and substances. However, when the patient has been determined to heal well without it and the implant not to incur degraded performance by its omission, the added expense of special implant treatments is avoided.

These precautions notwithstanding, some patients will invariably present inconsistent or idiopathic adverse tissue reactions to commonly accepted materials such as the monosodium glutamate in vaccine (Chiu, Y. K., Huang, C. C., Jeng, J., Shiea, J., and Chen, W. J. 2006. "Foreign Body Granuloma Caused by Monosodium Glutamate after BCG [Bacille Calmette-Guerin to prevent tuberculosis] Vaccination," Journal of the American Academy of Dermatology 55(2 Supplement):S1-S5), suture (Koktener, A., Akin, K., Kosehan, D., Cakir, B., and Haltas, H. 2012. "Two Foreign Body Reactions Caused by Suture Materials: Mammograms Mimic Cancer as a Spiculated Lesion," JBR-BTR Journal Beige de Radiologie—Belgisch Tijdschrift voor Rad [Journal of the [Royal] Radiological Society of Belgium) 95(1):20-21; Postlethwait, R. W., Willigan, D. A., and Ulin, A. W. 1975. "Human Tissue Reaction to Sutures," Annals of Surgery 181(2):144-150), other skin closure materials such as staples (Slade Shantz, J. A., Vernon, J., Morshed, S., Leiter, J., and Stranges, G. 2013. "Sutures Versus Staples for Wound Closure in Orthopaedic Surgery: A Pilot Randomized Controlled Trial," Patient Safety in Surgery 7(1):6; Slade Shantz, J. A., Vernon, J., Leiter, J., Morshed, S., and Stranges, G. 2012. "Sutures Versus Staples for Wound Closure in Orthopaedic Surgery: A Randomized Controlled Trial," BioMed Central Musculoskeletal Disorders 13:89); poly-L-lactic acid suture anchors (Schrumpf, M. A., Lee, A. T., and Weiland, A. J. 2011. "Foreign-body Reaction and Osteolysis Induced by an Intraosseous Poly-L-lactic Acid Suture Anchor in the Wrist: Case Report," Journal of Hand Surgery 36(11):1769-1773), hyaluronic acid (Cecchi, R., Spota, A., Frati, P., and Muciaccia, B. 2014. "Migrating Granulomatous Chronic Reaction from Hyaluronic Acid Skin Filler (Restylane): Review and Histopathological Study with Histochemical Stainings," Dermatology 228(1):14-17; Yang, J. H., Lee, S. M., Won, C. H., Chang, S. E., Lee, M. W., Choi, J. H., and Moon, K. C. 2012. "Foreign Body Granuloma Caused by Hyaluronic Acid/Dextranomer Microsphere Filler Injection," International Journal of Dermatology 51(12):1517-1518), benign melanocytic naevi (Knox, W. F., McWilliam, L. J., Benbow, E. W., McMahon, R. F., Wilkinson, N., and Bonshek, R. 1993. "Foreign Body Giant Cell Reactions and Ossification Associated with Benign Melanocytic Naevi," Journal of Clinical Pathology 46(1):72-74), and surgical cements (Cardillo, G., Carleo, F., Carbone, L., De Massimi, A. R., Lococo, A., Santini, P. F., Janni, A., and Gonfiotti, A. 2012. "Adverse Effects of Fibrin Sealants in Thoracic Surgery: The Safety of a New Fibrin Sealant: Multicentre, Randomized, Controlled, Clinical Trial," European Journal of Cardiothoracic Surgery 41(3): 657-662; Dragu, A., Unglaub, F., Schwarz, S., Beier, J. P., Kneser, U., Bach, A. D., and Horch, R. E. 2009. "Foreign Body Reaction after Usage of Tissue Adhesives for Skin Closure: A Case Report and Review of the Literature," Archives of Orthopaedic and Trauma Surgery 129(2):167-169; Yoo, J., Chandarana, S., and Cosby, R. 2008. "Clinical Application of Tissue Adhesives in Soft-Tissue Surgery of the Head and Neck," Current Opinion in Otolaryngology and Head and Neck Surgery 16(4):312-317), so that for any internal application, the patient should be pretested.

Even pretesting and experience may not allow the predictability with confidence of an adverse tissue reaction that will not subside within a reasonable interval. In that circumstance, a line (conduit) to wet the implant with an adverse reaction counteractant such as phosphorylcholine and/or dexamethasone, is provided. Direct manual delivery of the counteractant is by injection into a subcutaneous portacath. Sustained automated delivery is by initial injection into a portacath with storage reservoir. An implanted pump draws off the counteractant under the control of an implanted microcontroller. When the volume or number of drugs to be administered makes full implantation with transdermal pump charging impracticable, a belt-worn pump pack is used. Once this need is identified, components that would otherwise have been implanted are relegated to the pump pack with delivery through a port at the body surface.

A drip line to automatically dispense a therapeutic solution to wet the entry wound of a catheter is shown as part number 34 in FIG. 21 as the external view of the embodiment shown in FIG. 20. Such a line can also be used to wet the foam cushion lining a ductus side-entry jacket or nonjacketing side-entry connector, as well as other type jackets described in copending application Ser. No. 13/694,835. Asymptomatic encapsulation can affect any implant, but is obstructive when direct communication with the surrounding tissue is necessary as applies in the case of numerous sensor implants (Lin, P., Ding, L., Lin, C. W., and Gu, F. 2014. "Nonfouling Property of Zwitterionic Cysteine Surface," Op cit.; Lin, P., Lin, C. W., Mansour, R., and Gu, F. 2013. "Improving Biocompatibility by Surface Modification Techniques on Implantable Bioelectronics," Op cit.). For an automatic disorder response system, this pertains to the feedback sensors used to signal the need for a certain site or sites to be sent an adverse reaction remediating drug.

Nonsensor and sensor implants not requiring direct and undistorted communication with the tissue at the site of implantation typically induce local inflammation that leads to fibrous encapsulation; however, in this instance, the reaction does not cause complications. Unless completely encapsulated by a refractory foreign body granuloma, the surface treatment encourages tissue integration with a coating and surface texture eventually supplanted by tissue ingrowth (see, for example, Wang, Y., Vaddiraju, S., Qiang, L., Xu, X., Papadimitrakopoulos, F., and Burgess, D. J. 2012. "Effect of Dexamethasone-loaded Poly(lactic-co-glycolic Acid) Microsphere/Poly(vinyl Alcohol) Hydrogel Composite Coatings on the Basic Characteristics of Implantable Glucose Sensors," Journal of Diabetes Science and Technology 6(6):1445-1453; Bhardwaj, U., Sura, R., Papadimitrakopoulos, F., and Burgess D. J. 2007. "Controlling Acute Inflammation with Fast Releasing Dexamethasone-PLGA Microsphere/PVA Hydrogel Composites for Implantable Devices," Journal of Diabetes Science and Technology 1(1):8-17).

Along the digestive tract, sensors implanted to signal bolus transit are pressure sensors that lose no function when contained in a fibrous capsule. With sensor implants such as these, which do not require direct contact with the surrounding tissue, to interfere with the process that starts with minor inflammation and leads to fibrotic encapsulation is counterproductive. If the intrinsic material of the sensor provokes a more adverse response, then an outer coating of polyethylene terephthalate will usually prevent this. By contrast, chemical sensors along the digestive tract must not be cut off from the immediate tissue or blood by a fibrous capsule.

To preserve direct contact with the blood that would otherwise be cut off by clot, metabolic sensors such as those used to detect the blood glucose level are fixed to the wall surrounding the bloodstream to be suspended in it, the accessory channel of the ductus side-entry jacket or the nonjacketing side-entry connector used to position the sensor used as an anticoagulant drip, such as heparin or warfarin. Suspension within the heart of a chemical sensor, for example, is indicative of the value in the secure means for fixation thus afforded by ductus side-entry jackets and nonjacketing side-entry connectors.

For sensors implanted within solid tissue and must remain in contact with the tissue, antifibrotic drugs (see, for example, Schaefer, C. J., Ruhrmund, D. W., Pan, L., Seiwert, S. D., and Kossen, K. 2011. "Antifibrotic Activities of Pirfenidone in Animal Models," European Respiratory Review 20(120):85-97; Cho, M. E. and Kopp, J. B. 2010. "Pirfenidone: An Anti-fibrotic Therapy for Progressive Kidney Disease," Expert Opinion on Investigational Drugs 19(2):275-283; Di Sario, A., Bendia, E., Macarri, G., Candelaresi, C., Taffetani, S., Marzioni, M., and 4 others 2004. "The Anti-fibrotic Effect of Pirfenidone in Rat Liver Fibrosis is Mediated by Downregulation of Procollagen Alpha1(I), TIMP-1 and MMP-2," Digestive and Liver Disease 36(11): 744-751) are delivered the same way.

While called into question (see, for example, Xaubet, A., Serrano-Mollar, A., and Ancochea, J. 2014. "Pirfenidone for the Treatment of Idiopathic Pulmonary Fibrosis," Expert Opinion on Pharmacotherapy 15(2):275-281), whether a shortcoming of pirfenidone for the treatment of pulmonary fibrosis (see, for example, Poletti, V, Ravaglia, C., and Tomassetti, S. 2014. "Pirfenidone for the Treatment of Idiopathic Pulmonary Fibrosis," Expert Review of Respiratory Medicine 8(5):539-545; Prescrire International 2013. "Pirfenidone. First, Do No Harm," Prescrire International 22(138):117-119; Carter, N.J. 2011. "Pirfenidone: In Idiopathic Pulmonary Fibrosis," Drugs 71(13):1721-1732) applies to its use to suppress fibrosis in implant encapsulation using minute quantities of the drug released at the implant requires study; pulmonary fibrosis demands entering the drug into the circulation. Similarly, whether antifibrotic drugs that prove carcinogenic in other contexts would exert the same effect when used in minute local amounts to suppress the fibrotic encapsulation of sensor implants (see, for example, Andrade, S. G., Grimaud, J. A., Tabone, E., Banal, and Netto, M. B. 1981. "Malignant Transformation of a Rat Fibroma by the Treatment with an Anti-fibrosing Drug: CY-168F (Plastenan)," Memorias do Instituto Oswaldo Cruz 76(3):259-268).

When an adverse tissue or foreign body reaction commences following depletion or weakening of the initial outer coating, such as a dexamethasone-loaded poly(lactic-co-glycolic acid) microsphere/poly(vinyl alcohol) hydrogel composite coating, (see, for example, Zhang, H., Bian, C., Jackson, J. K., Khademolhosseini, F., Burt, H. M., and Chiao, M. 2014, Op cit.; Avula, M. N., Rao, A. N., McGill, L. D., Grainger, D. W., and Solzbacher, F. 2013. "Modulation of the Foreign Body Response to Implanted Sensor Models through Device-based Delivery of the Tyrosine Kinase Inhibitor, Masitinib," Biomaterials 34(38):9737-9746; Wang, Y., Papadimitrakopoulos, F., and Burgess, D. J. 2013. "Polymeric "Smart" Coatings to Prevent Foreign Body Response to Implantable Biosensors," Journal of Controlled Release 169(3):341-347; Zhang, L., Cao, Z., Bai, T., Carr, L., Ella-Menye, J. R., Irvin, C., Ratner, B. D., and Jiang, S. 2013. "Zwitterionic Hydrogels Implanted in Mice Resist the Foreign-body Reaction," Nature Biotechnology 31(6):553-556; Wang, Y., Vaddiraju, S., Qiang, L., Xu, X., Papadimitrakopoulos, F., and Burgess, D. J. 2012. "Effect of Dexamethasone-loaded Poly(lactic-co-glycolic Acid) Microsphere/Poly(Vinyl Alcohol) Hydrogel Composite Coatings on the Basic Characteristics of Implantable Glucose Sensors," Journal of Diabetes Science and Technology 6(6):1445-1453; Koh, A., Nichols, S. P., and Schoenfisch, M. H. 2011. "Glucose Sensor Membranes for Mitigating the Foreign Body Response," Journal of Diabetes Science and Technology 5(5):1052-1059; Morais, J. M., Papadimitrakopoulos, F., and Burgess, D. J. 2010. "Biomaterials/Tissue Interactions: Possible Solutions to Overcome Foreign Body Response," AAPS [American Association of Pharmaceutical Scientists] Journal 12(2):188-196; Bhardwaj, U., Sura, R., Papadimitrakopoulos, F., and Burgess, D. J. 2010. "PLGA/PVA Hydrogel Composites for Long-term Inflammation Control following S.C. Implantation," International Journal of Pharmaceutics 384(1-2):78-86), systemic allopurinol (see, for example, de Barros Silveira, L. K., de Oliveira, F. L., Alves Tde, B., Rambaldi, M. L., de Andrade, F. C., Kelmer Sde, C., and Barbosa, F. C. 2012. "The Therapeutic Benefit of Allopurinol in the Treatment of Foreign Body Granulomas Caused by Polymethylmethacrylate Microspheres," Case Reports in Dermatological Medicine; 2012: 945205, section 3, paragraph 3) or a line led from a pump in the power, control, and pump pack can replenish the adverse reaction counteractant. The implant not coated but wetted, the duration of protection is less.

The ability imparted by nonjacketing side-entry connectors to rigidly fix the point of treatment allows systemic disease and dispersed expressions of autoimmune disease to be treated at the primary site and/or at the distributed lesions without exposing unaffected tissue. The complications associated with the systemic circulation of substances that would best be accurately directed to frank lesions and primary culprit sites can leave the patient little less vulnerable or uncomfortable than does the disease. Use of the term 'connector' without qualification refers to a nonjacketing side-entry connector as a whole; a stem extending at right angles from the connector used to attach a device such as a catheter, hollow (injection/aspiration) needle, or warming rod seen as part number 3 in FIG. 1, for example, is qualified as a 'side connector' or stem.' In the drawing figures, part number 3 denotes the rod-shaped object inserted into the side-entry connector for positional fixation. The context will specify whether this object is a side stem connector for a catheter or a hollow needle, for example.

A central time-limiting factor for the duration of indwelling lines inserted into or through tissue is that the catheter or needle and tissue can move in relation to one another rather than as one with, moreover, the point of treatment accurately fixed. In an ambulatory patient, even slight relative movement will eventually cause irritation and lesioning, perhaps most familiar from the growing irritation caused by an intravenous line in the basilic vein. Another is an antixenic or an immune adverse tissue reaction, which personalized medicine (patient-specific therapeutic diagnostics, theranostic, or personalized medicine, pharmacogenomics, precision medicine) with respect to individual sensitivities, is determined before placement using test samples or patches of different implant materials, comprising a large number of polymers, titanium, stainless steel, alloys of these, and gold, among others.

The type of tissue fastener described allows not only catheters and needles but numerous different styliform (rod-shaped, styloid) devices to be fixed in position relative to tissue to be treated or diagnosed. The means to be described are intended for the treatment primarily of pre-critical chronic disease, which allows sufficient time for the pretesting of materials. When the implant is intended to remain in place indefinitely, the wetting of implants upon insertion with phosphorylcholine, dexamethasone, an anti-inflammatory steroid, or curcumin, for example, is not preferred as temporary, usually requiring replenishment, and exceptionally reserved for implants that allow reapplication without reentry. To minimize the risk of infection and irritation, electrical and fluid lines passed through the integumentary and internal entry wounds for long term use must be joined positively and securely to the tissue lining and bounding the wounds with adverse reactions kept to the minimum.

A urinary catheter will eventually cause irritation, then lesioning, and an indwelling catheter of the central line or central venous type disallows free movement and is limited to limited term use in the clinic. However, were the junction between catheteric and native lumina fixed, secure, and made of materials least likely to induce an adverse tissue response, then such lines could remain in place indefinitely with the patient free to move about. Such a secure line could, moreover, be used by an automatic ambulatory system to target drugs, draw test samples, or monitor blood pressure, for example, on an intermittent or continuous basis in even a young and active patient. When not systemic such as infectious, drugs delivered by the means to be described target the primary cause of disease. Drug targeting allows any disease or disorder that can be treated to be treated far more safely and effectively.

Combined with automatic drug delivery, such a system powered by transdermal or transcutaneous energy transfer at a distance by resonance recharging and entirely implanted can effect remedial action to fundamentally improve the quality of life while scarcely noticed even by the patient. When the rate of the drug or drugs required exceeds that deliverable as an internal drip requiring occasional replenishment through a subcutaneous, subfascial, or submuscular port, an external belt-worn pack and port diagrammatically shown in FIG. 17 as part number 39 for the electrical and fluid lines that must course into and out of the body are needed. These components allow anchoring needles 6 to inject drugs and deliver electrical discharges. Transcutaneous energy transfer and body-generated energy used to energize any function other than continuous, to include the discretionary activation through sensor input to an automatic control system is used to store the energy in a battery, not power the implant device or devices directly.

Recent advances in transdermal energy transfer seek to increase the tolerance for axial misalignment of the extracorporeal and intracorporeal energy transfer coils, thus allowing recharging while the patient is lying down in bed, for example. Also sought is battery-free operation through the use of energy intrinsically generated within or by the body, such as body heat or mechanical action of the foot, to directly power the device, thus eliminating the need for a battery altogether, or with a battery used, to recharge the battery (see, for example, Hannan, M. A., Mutashar, S., Samad, S. A., and Hussain, A. 2014. "Energy Harvesting for the Implantable Biomedical Devices: Issues and Challenges," Biomedical Engineering Online 13:79; Yang, Y., Guo, W., Pradel, K. C., Zhu, G., Zhou, Y., and 4 others 2012. "Pyroelectric Nanogenerators for Harvesting Thermoelectric Energy," Nano Letters 12(6):2833-2838; Bhatia, D., Bairagi, S., Goel, S., and Jangra, M. 2010. "Pacemakers Charging Using Body Energy," Journal of Pharmacy and Bioallied Sciences 2(1):51-54; Lay-Ekuakille, A., Vendramin, G., Trotta, A., and Mazzotta, G. 2009. "Thermoelectric Generator Design Based on Power from Body Heat for Biomedical Autonomous Devices," in Proceedings of the 2009 IEEE International Workshop on Medical Measurements and Applications, Cetraro, Italy, 29-30 May 2009, pages 1-4).

The organ or tissue side-connector for the fixed placement of catheters, hypofibrosal or hypocapsular hollow injection/aspiration needles, hypotubes, lasers, electrodes, and probes, for example, to be described is intended to further endoscopic medical surgery, or minimally invasive surgery for the purpose of positioning implants that will steer drugs directly and restrictedly to the treatment site or sites along with applying any necessary collateral therapeutic measures, and an access port at the body surface without the need for reentry. This prepositioning of drug delivering elements makes possible the application of an automatic ambulatory control system programmed to respond to data received from minute sensor implants.

Means for the stable infixion within an organ or tissue of miniature styloid devices such as hollow needles for injection or aspiration, hypotubes, ultrasound probes, lasers, diagnostic microelectrodes, and other physical and chemical property diagnostic probes are of fundamental importance to the realization of the functional potential in these to continue functioning with the patient free to move about (see, for example, Birngruber, T., Ghosh, A., Hochmeister, S., Asslaber, M., Kroath, T., Pieber, T. R., and Sinner, F. 2014. "Long-term Implanted cOFM Probe Causes Minimal Tissue Reaction in the Brain," PLoS [Public Library of Science (online)] One 9(3):e90221; Birngruber, T., Ghosh, A., Perez-Yarza, V., Kroath, T., Ratzer, M., Pieber, T. R., and Sinner, F. 2013. "Cerebral Open Flow Microperfusion: A New in Vivo Technique for Continuous Measurement of Substance Transport across the Intact Blood-brain Barrier," Clinical and Experimental Pharmacology and Physiology 40(12): 864-871).

With reference to FIGS. 13A and 13B, this functionality would be further expanded were a motorized nonjacketing side-entry connector used to move the probe, microelectrode, or laser along its long central axis, and further still were the drug delivery catheter made responsive to feedback from the styloid probe sensor to the controller while both moved alongside one another (see, for example, Birngruber, T., Raml, R., Gladdines, W., Gatschelhofer, C., Gander, E., and 5 others 2014. "Enhanced Doxorubicin Delivery to the Brain Administered through Glutathione PEGylated Liposomal Doxorubicin (2B3-101) as Compared with Generic Caelyx, (®)/Doxil (®)—a Cerebral Open Flow Microperfusion Pilot Study," Journal of Pharmaceutical Sciences 103(7):1945-1948). The potential applications to the liver and kidneys, for example, are no less considerable than those pertaining to the brain, cited here as exemplary.

The sensors signal out of range values to their organ system control node, whereupon a higher-order controller programmed to coordinate the action of the nodes issues the commands to achieve the most efficacious overall response. The application of such a system is generally reserved for chronic conditions where an automatic system not only effects remedial action immediately to interdict progression but serves to dispel a central condition that detracts from the quality of life. Such an automatic ambulatory system, operating barely if at all noticed, has the potential to forestall if not prevent the inducement by a chronic systemic disease of a terminal condition. For example, if left untreated, diabetes, hypertension, atherosclerosis, or the metabolic syndrome will eventually induce chronic, then end-stage kidney disease.

That will necessitate dialysis or a kidney transplant and the use of immunosuppressive drugs that will leave the patient immunocompromised and highly susceptible to infection that could prove fatal. Without targeting and thus limiting the immunosuppressant and potent nephrotoxin cyclosporine to a non-kidney transplant, the dose must be severely limited, and this is especially the case when the transplant is a kidney (see, for example, Yu, A. S. I. and Brenner, B. M. 2005. "Tubulointerstitial Diseases of the Kidney," Op cit., pages 1703-1704). The cyclosporine or other immunosuppressant is delivered into the parenchyma of the transplant organ through a nonjacketing side-entry connector, and/or through the blood supply by means of a ductus side-entry jacket on the main supply artery.

transplant organ that passes biological contents has a ductus side-entry jacket attached to the inlet remnant or stump prior to transplantation. The same isolation of chemotherapeutics allows the severe side effects of cancer therapy to be averted. If radionuclides are used, the radiation shielded embodiments shown in FIGS. 10A and 10B, where that in FIG. 10A is nondisintegrating for long term use and that shown in FIG. 10B is disintegrating for short term use. Because the dose is significantly smaller and targeted to the transplant, the fraction not taken up within the transplant poses little if any immunosuppressive risk for the patient. Whenever this is not so, a second jacket is fastened to the outlet stump to allow the delivery of a reversal agent, or counteractant.

Because the system functions automatically on the basis of physicochemical indicia sensors set by the diagnostician and programmer before symptoms appear, and targets drugs to the disease origins or nides sparing exposure of other tissue, it is able to prevent the progression of a premonitory to a fatal condition. However, a collection of indwelling catheters that deliver medication into the pre- or post-systemic circulation disallow drug dosage at the optimal concentration, and would never allow the implementation of an ambulatory system. Targeting also allows treating and diagnosing the problem at or as close upstream to the source or nidus as can safely be done.

For example, urolithiasis resistant to change in diet and systemic medication is best intercepted as close to the origin, the calyces and pelvis, as possible—in this case, by releasing the stone dissolving substance prescribed for the type stone in a higher than systemic dose through a prerenal jacket, that is, a ductus side-entry jacket placed along the renal artery, where it can be used to deliver medication to treat any prerenal or renal intrinsic condition primary or secondary. Stone preventive medication targeted directly to the pelvis is discussed below in conjunction with FIGS. 11 and 12. Any level along the ductal portions of the urinary tract can be directly accessed, that is, entered, exited, or using multiluminal tubing, both, with a ductus side-entry jacket, nonjacketing side-entry connectors used to accomplish the same with a kidney or the bladder.

Ductus side-entry jackets are described in copending application Ser. No. 14/121,365, entitled Ductus Side-entry Jackets and Prosthetic Disorder Response Systems, filed on 25 Aug. 2014. The importance of lining such jackets with viscoelastic polyurethane foam, usually high density open cell, to allow periodic saturation through a direct side-tube such as shown as part number 34 in FIG. 21 is typified in a prerenal jacket, where the renal plexus runs along the outside of the renal arteries and would otherwise be subject to compression. While the generally 0.8 percent per year breakdown of polyurethane, which is compensated for in manufacture, should be too slight to pose a toxicity issue, such a side tube 34, shown in FIG. 21 where it is used instead to drip anesthetic and anti-inflammatory about the catheteric entry wound with a doubly anchored connector, can also be run into the open cell foam to suffuse it and flush away any 2,4-toluenediamine, thus diluting it to a trace amount.

Such a side tube is generally fed by injection of antiinflammatory, antimicrobial, or other medication into a subcutaneously, subfascially, or submuscularly positioned portacath conventially positioned in the pectoral region. The foam lining serves several purposes, to include protecting small vessels and nerves that enter the substrate tissue from compression, the tissue surface from abrasion, the accommodating of irregularities in the outer surface of the substrate tissue and changes in tissue contour due to intrinsic and voluntary movement, and providing the interface between the bottom surface of baseplate 1 and foam 2 in FIG. 1, for example, with a cushioned and isolated location for a sensor, such as a foil strain gauge.

The toxicity associated with the gradual release of breakdown products into the surrounding tissue is related to larger volumes of 2,4-toluenediamine (2,4-Diaminotoluene, TDA) administered both intravenously and subcutaneously in breast implants with a surface area considerably larger than that of the lining cushions described herein, and the testing of workers involved in the manufacture of polyurethane foam (see, for example, Shanmugam, K., Subrahmanyam, S., Tarakad, S. V., Kodandapani, N., and Stanly, D. F. 2001. "2,4-Toluene Diamines—Their Carcinogenicity, Biodegradation, Analytical Techniques and an Approach towards Development of Biosensors," Analytical Sciences 17(12): 1369-1374; Hester, T. R. Jr., Ford, N. F., Gale, P. J., Hammett, J. L., Raymond, R., Turnbull, D., Frankos, V. H., and Cohen, M. B. 1997. "Measurement of 2,4-toluenediamine in Urine and Serum Samples from Women with M me or Replicon Breast Implants," Plastic and Reconstructive Surgery 100(5):1291-1298).

The subject is discussed in copending application Ser. No. 13/694,835 entitled Integrated System for the Ballistic and Nonballistic Infixion and Retrieval of Implants with or without Drug Targeting. In such small quantity, minute compared to the amount of polyurethane in breast implants, the foam, thoroughly cleaned of polymerization residues, does not pose a meaningful toxicity problem and is too small in the amount of 2,4-toluenediamine (2,4-Diaminotoluene, TDA) released to act as a carcinogen (see, for example, Kulig, K. 1998. "Lifetime Risk from Polyurethane Covered Breast Implants," Environmental Health Perspectives 106 (11):A526 with response by Luu, H-M. D. 106(11):-A527). At a presumptive rate of 0.8 percent degradation annually, reduction in half (compensated for ab initio) would take 62.5 years.

Intervention at the most proximal or upstream level prevents ureterolithiasis, cystolithiasis, or urethrolithiasis, for example. For targeting a ferrofluid-borne superparamagnetic nanoparticle drug carrier-bound radionuclide into the kidney from a fluid line or lines passed through a transcutaneous or transintegumentary port at the body surface, the line or lines to the prerenal jacket are radiation shielded with clasp-permanent or electromagnets attached to the renal cortex to draw the radionuclide centrifugally into the lesion or lesions as appropriate. Ductus side-entry jackets and fluid delivery lines absorbably and nonabsorbably radiation shielded are addressed in the aforestated copending application Ser. No. 14/121,365.

Using this approach, it is only when a localized (defined, circumscribed) lesion or nidus within the kidney not responsive to drugs delivered upstream and not requiring removal of the kidney that the kidney is entered. However, done conventionally, the site of insertion, or entry wound, into the renal cortex is not fully immobilized, especially when due to fascial deficiency, the kidney is not well stabilized. Prerenal and postrenal ductus side-entry jackets self stabilizing, a hypotube, hollow needle, or catheter driven into the kidney to remain in an ambulatory patient after discharge is anchored with a nonjacketing side-entry connector.

Postrenal ductus side-entry jackets are either ureteric or renal venous. If necessary, the suppression of adverse tissue reactions on a continued basis is accomplished by configuring the surface of the foam cushion to include small furrows. Bleeder holes through the side of the side connector each aligned to its respective furrow then drips rejectionsuppressive agents or counteractants such as a steroid hormone and/or dexamethasone, for example, into the entries of to run down through the furrows. These agents are added into the incurrent fluid whether medicinal or blood according to the rate dictated by the spontaneous adverse reaction. This eliminates the need for a costly dedicated line from a separate pump to deliver these agents to the foam-tissue interface.

Because these agents are targeted to the interface, the concentration can be higher than would be allowed to enter the general circulation. At the same time, the concentration within incurrent fluid context is negligible and should not induce complications for the target tissue. The incurrent fluid can include anticlotting or anticrystallization to prevent the furrows from becoming obstructed. A circumscribed lesion, to include a tumor, within the kidney other than malignant as to necessitate a nephrectomy is targeted through the insertion of a fine catheter, hypotube, or needles into the kidney. A nephrostomy seeks to gain drainage during obstruction or some other cause of functional impairment along the distal tract not remediable or readily remedied through alternative treatment.

Such causes vary widely in curability and the time to achieve a cure. Obstruction of the renal pelvis by stones (nephroliths, renal calculi) requires short term drainage to prevent hydronephros and kidney damage, and is appropriately responded to by placement of a conventional temporary nephrostomy tube, or pigtail catheter, and collection bag for drainage and for drawing diagnostic test samples. Nephrostomy as addressed herein seeks to achieve long term diversion. By contrast, resection for a urothelial tumor, or transitional cell carcinoma, for example, warrants life long kidney-ureteric bypass. Lesions within the renal parenchyma require entry with a fine catheter, hollow needle, microelectrode, microprobe, or other syliform device, as shown in FIGS. 6, 11, and 13.

Accidental or surgical trauma such as following the resection of a tumor or a pelvic exenteration (pelvic evisceration, see, for example, Chen, M. and Pan, L. 2014. "Current Status and Outcomes of Pelvic Exenteration for Recurrent Cervical Cancer: A Systematic Review," (in Chinese; English abstract at Pubmed) Zhonghua Fu Chan Ke Za Zhi [Chinese Journal of Obstetrics and Gynecology] 49(6):

460-465; Andikyan V, Khoury-Collado F, Gerst S R, Talukdar S, Bochner B H, and 5 others 2012. "Anterior Pelvic Exenteration with Total Vaginectomy for Recurrent or Persistent Genitourinary Malignancies: Review of Surgical Technique, Complications, and Outcome," Gynecologic Oncology 126(3):346-350; Kim, J. 2012. "Pelvic Exenteration: Surgical Approaches," Journal of the Korean Society of Coloproctology 28(6):286-293; Schmidt, A. M., Imesch, P., Fink, D., and Egger, H. 2012. "Indications and Long-term Clinical Outcomes in 282 Patients with Pelvic Exenteration for Advanced or Recurrent Cervical Cancer," Gynecologic Oncology 125(3):604-609; Baiocchi, G., Guimaraes, G. C., Rosa Oliveira, R. A., Kumagai, L. Y., Faloppa, C. C., and 4 others 2012. "Prognostic Factors in Pelvic Exenteration for Gynecological Malignancies," European Journal of Surgical Oncology 38(10):948-954; Kaur, M., Joniau, S., D'Hoore, A., Van Caister, B., Van Limbergen, E., and 5 others 2012. "Pelvic Exenterations for Gynecological Malignancies: A Study of 36 Cases," International Journal of Gynecological Cancer 22(5):889-896; Domes, T. S., Colquhoun, P. H., Taylor, B., Izawa, J. I., House, A. A., Luke, P. P., and Izawa, J. I. 2011. "Total Pelvic Exenteration for Rectal Cancer: Outcomes and Prognostic Factors," Canadian Journal of Surgery 54(6):387-393. Ferenschild, F. T., Vermaas, M., Verhoef, C., Ansink, A. C., Kirkels, W. J., Eggermont, A. M., and de Wilt, J. H. 2009. "Total Pelvic Exenteration for Primary and Recurrent Malignancies," World Journal of Surgery 33(7):1502-1508; Nishio, M., Sakakura, C., Nagata, T., Miyashita, A., Hamada, T., Ikoma, H., Kubota, T., and 12 others 2009. "Outcomes of Total Pelvic Exenteration for Colorectal Cancer," Hepato-gastroenterology 56(96):1637-1641; Berman, L., Aversa, J., Abir, F., and Longo, W. E. 2005. "Management of Disorders of the Posterior Pelvic Floor," Yale Journal of Biology and Medicine 78(4):211-221; Jimenez, R. E., Shoup, M., Cohen, A. M., Paty, P. B., Guillem, J., and Wong, W. D. 2003. "Contemporary Outcomes of Total Pelvic Exenteration in the Treatment of Colorectal Cancer," Diseases of the Colon and Rectum 46(12):1619-1625; Schoenberg, M., Hortopan, S., Schlossberg, L., and Marshall, F. F. 1999. "Anatomical Anterior Exenteration with Urethral and Vaginal Preservation: Illustrated Surgical Method," Journal of Urology 161(2):569-572; Wheeless, C. R. Jr. and Roenneburg, M. L. Undated. "Anterior Exenteration," [gynecologic] atlasofpelvicsurgery.com/10 MalignantDisease/16AnteriorExenteration/cha10sec16.html; Wheeless, C. R. Jr. and Roenneburg, M. L. Undated."Posterior Exenteration," [gynecologic] atlasofpelvicsurgery.com/10MalignantDisease/17 PosteriorExenteration/cha10sec17html; Wheeless, C. R. Jr. and Roenneburg, M. L. Undated. "Total Exenteration," [gynecologic] atlasofpelvicsurgery.com/10MalignantDisease/18TotalPelvicExenteration/cha10sec18html), or due to congenital malformation or dysplasia warrants nephrostomy that is fully contained within the body, and except when placed in a neonate or an infant, has the potential to remain functional to the end of life.

Using the means described herein, all requiring the stability and direct drug delivery support made possible by nonjacketing side-entry connectors and ductus side-entry jackets, the considerable postoperative complications associated with an exenteration, often severe or fatal, to include hydronephrosis, urinary tract infection, renal failure, and bladder dysfunction (Tanaka, S., Nagase, S., Kaiho-Sakuma, M., Nagai, T., Kurosawa, H., Toyoshima, M., Tokunaga, H., and 6 others 2014. "Clinical Outcome of Pelvic Exenteration in Patients with Advanced or Recurrent Uterine Cervical Cancer," International Journal of Clinical Oncology 19(1): 133-138; Jager, L., Nilsson, P. J., and Radestad, A. F. 2013. "Pelvic Exenteration for Recurrent Gynecologic Malignancy: A Study of 28 Consecutive Patients at a Single Institution," International Journal of Gynecolological Cancer 23(4):755-762; Wydra, D., Emerich, J., Sawicki, S., Ciach, K., and Marciniak, A. 2006. "Major Complications following Exenteration in Cases of Pelvic Malignancy: A 10-year Experience," World Journal of Gastroenterology 12(7):1115-1119) should be significantly reduced if not eliminated.

Using the configurations shown in FIG. 6, 11, 13A, or 13B, wherein the side-entry connector is shown positioned so that entry is through the flank and relatively avascular coronal or bloodless plane of Brodel, access is through a keyhole incision in the flank, continued between the end-arterial vessels of the anterior and posterior branches of the renal artery, through the cortex, medulla, thence to the depth within the kidney that provides the best aim at the target lesion. FIG. 6 shows a side view of a nonjacketing side-entry connector as shown in FIG. 1, less the radiation shielding shown in FIGS. 10A and 10B for use with radionuclides.

Also omitted are fibrosally fastened clasp-electromagnets as shown in FIG. 13B to magnetically vector radionuclide or nonradioactive superparamagnetic nanoparticle carrier-bound drugs, in use to 1. Fix a stationary styliform device, such as a drug delivery catheter, as shown in FIG. 5, or a hypotube, hollow needle, and/or electrode, scope, or probe, at a fixed depth within tissue, here the renal medulla, and 2 Inclination, here posterolaterally, or behind, the adrenal gland, to treat a TNM (Tumor-[lymph] Node-Metastasis) Stage TIb adenocarcinoma or a renal cell carcinoma (tumor less than 7 centimeters across) 41. Use thus supports treatment such as the targeting of drugs directly at the lesion through a fluid line injected through a portacath or passed from a pump through a port at the body surface.

FIGS. 13A and 13B show an overall view of the nonjacketing side-entry connector detailed in FIGS. 14 thru 16 without permanent radiation shielding as shown in FIG. 10A or disintegrating radiation shielding as shown in FIG. 10B for use with radionuclides, but with fibrosally fastened clasp-electromagnets to magnetically vector superparamagnetic nanoparticle carrier-bound drugs, in use to stabilize a precision stepper piezomotor-driven hollow needle to allow adjustable depth, close proximity fine needle therapy, such as Auger therapy, with or without external beam radiation, or adjuvant, transfective, or conventional therapy, where the side-entry connector has been positioned posterolaterally to (behind) the adrenal gland to treat a TNM (Tumor-Node-Metastasis) Stage TIb adenocarcinoma, renal cell carcinoma (tumor less than 7 centimeters across or a nephroblastoma (Wilms tumor, adenomyosarcoma), 41 by means of non-radionuclide drug carrier bound chemotherapy not requiring radiation shielding. Metastasis can be suppressed by the direct targeting of chemotherapeutics into the kidney through a ductus side-entry jacket on the renal artery with suppression of spread from a nidus within the kidney by placement about the capsule of a nonjacketing side-entry connector or connectors with injection at intervals and at increments of needle travel as addressed below.

The arrangements shown in FIGS. 13A and 13B using a motorized nonjacketing side-entry connector as detailed in FIGS. 14 thru 16 allows the destruction of a small tumor with the least damage to the tissue investing or surrounding and in intimate contact with the tumor, systemic chemotherapy still administered to kill any malignant cells that may have been shed. The ability to target the tumor as distinct from the tissue surrounding it is important when to preserve parenchyma is essential, as in incipient pancreatic cancer. The capsular fibrosa reached, a pocket to hold the typically 2 by 1 centimeter side-entry connector baseplate is cleared in the perirenal fat, the connector placed on the renal capsule, the anchoring round needles set, access incision closed fluid and electrical lines led out by subfascial or submuscular tunneling up to the port at body surface usually overlying the pectoralis major.

Clasp-magnets are shown in FIGS. 25 and 26 and described in copending application 2014/0163664 and expanded in application to include electromagnets as well as permanent magnets in copending application Ser. No. 14/121,365. Between FIGS. 13A and 13B, shown only in FIG. 13B, and otherwise in FIGS. 12B and 12D, clasp- or patch-electromagnets are no less applicable to the configuration shown in FIG. 6, wherein the side connector 3 is fixed at the depth and inclination applied when placed, rather than motorized for advancement or retraction as shown in FIGS. 13A and 13B after the patient has been closed. In FIG. 13B, the positions of the electromagnets have been limited to the plane of the drawing for visual clarity. Because the kidneys are retroperitoneal and highly vascular, the placement of magnets significantly aside from the relatively 'bloodless' plane of Brodel is best reserved for long term use.

When attached to the fibrosal or adventitial surface of an organ where small vessels and nerves would be compressed eventually resulting in morbidity, clasp-magnets or electromagnets are cushioned beneath with a layer of viscoelastic polyurethane foam, which tends to envelop or invest. In FIGS. 6 and 13A, the suprarenal, or adrenal, gland has been omitted along with other extraneous tissue; the nonjacketing side-entry connectors positioned posterolaterally that is, behind, these. To show the relative positions of three claspelectromagnets 40 and the adrenal when restricted to the plane of the drawing figure, these are included in FIG. 3B. Clasp-magnets are described and illustrated in copending application 2014/0163664. Clasp-electromagnets are of like mounting. The angle of a device mounted with a clasp is adjusted by bending the mounting platform and inserting viscoelastic polyurethane foam beneath the mounting.

The value of the means shown in FIGS. 6, 13A, and 13B when used to eradicate a tumor 41, for example, in preserving more of the organ—in this case, a kidney—than any alternative method, is addressed below in the section entitled Description of the Preferred Embodiments of the Invention. The configurations shown in FIGS. 13A and 13B offer the capability to selectively target and eradicate a tumor 41 within an organ or tissue that is resistant to antineoplastics in the circulation and only place other tissue at risk, while conserving as much of the organ or tissue as possible, and with less intrusion or trauma than any alternative method. In FIGS. 6, 13A, and 13B, side connector 3 can be an electrode, laser, injection needle, or a combination of these in adjacent relation.

An accessory channel not required to assist in side connector insertion need not connect to a water jacket 31 within the side connector 3 as shown in FIG. 5 but can simply empty into the side connector or run alongside it to empty at their common terminus. While the accessory channel 13 in the application of FIG. 6 does include a water jacket, unseen in FIG. 6 but shown in FIG. 5, that shown in FIGS. 13A and 13B need not; the availability of an accessory channel or sideline, as opposed to the distal termination of this channel in the form of a water jacket depends upon whether a water jacket is needed for or would expedite insertion. A needle pointed device such as that shown as side connector in FIGS. 13A and 13B does not require an accessory channel for this purpose. Prone to accumulate debris during insertion, a water jacket allows flushing through the trepan front edge side connectors shown in FIGS. 6, and 11.

If not needed to expedite insertion, an accessory channel is usually provided for another purpose, such as to allow the direct targeting of adjuvant medication into the mainline lumen or to convey an electrical lead or laser, for example. This is usually so even when the line is a drain such as that shown toward the bottom of the bladder in FIG. 12A that in a stone former, would be more likely to accrete crystalline debris over the internal surface of the lumen wall were not an accessory channel available to deliver a solvent. Direct delivery of a solvent that spares exposure to tissue as opposed to one allowed into the systemic circulation fundamentally expands the zone of solvents that can be used. Thus, except when the styloid device connected, or side connector, is a needle, fine gauged trocar, or has a closed distal end, entry into a vascular bed is with the aid of a water jacket.

Of the various applications for nonjacketing side-entry connectors shown, those in FIGS. 13A, 13B, and 17 thru 19 do have an accessory channel but not a water jacket. While remaining as the distal segment of an accessory channel, a water jacket as shown in FIGS. 1, 2, 5, 7 thru 10B, 20, and 21 is needed to assist in the insertion of wider catheters with cut off front end. This need is greater when a crosshair cutter 22, best seen in FIGS. 1, 2, and 5, would accumulate clot or accrete a crystalline deposit. Moving through thicker or harder tissue, the water jacket expedites the removal of crosshair cutter gratings, while moving through heavily vascularized tissue, it is used to restrain bleeding. To insert a larger caliber drainage catheter as shown in FIG. 11, a crosshair cutter and aspirator are used. The outer surface of the catheter is wetted with a hemostatic, and once inserted, the open tip of the catheter is positioned in a substantially blood free location.

In FIG. 11, provided insertion is with the aid of a fine gauge trocar and cannula, an accessory channel without water jacket at the distal segment can be omitted, drug targeting to the kidney usually through a ductus side-entry jacket on the renal artery. An accessory channel is thus included in FIG. 6 but omitted in FIG. 11. The applications shown in FIGS. 13A, 13B, and 17 do not require a water jacket but to allow targeting medication through the hollow styloid device to the treatment site are provided with an accessory channel. In FIG. 13B, patch-, or clasp-, electromagnets 40 are shown about the margin of the organ, here a kidney.

When used with extended half life and high dose rate radionuclides, the delivery line, reservoir and assist pump if used, side connector, or mainline, and accessory channel, or sideline in FIG. 13B are radiation shielded permanently as shown in FIG. 10A or nonpermanently as shown in FIG. 10B. With respect to the motorized side connector shown in FIGS. 13A, 13B, and 14, when shielded, housing 24 is of like constitution as caps 71 in FIGS. 10A and 10B as appropriate. To clear away radioactive matter, the subdermal portacath or port at the body surface is scrubbed. For continued use and where the half life makes it necessary, the permanent shielding shown in FIG. 10A is applied all along the delivery catheter. For temporary treatment with weakly radioactive or short half life radionuclides, the disintegrable radiation shielding described in copending application Ser. No. 14/121,365, entitled Ductus Side-entry Jackets and Prosthetic Disorder Response Systems, and shown in FIG. 10B is used.

Since in the clinic, an external (extracorporeal) magnet can be used, the absence of clasp-electromagnets in FIG. 13A need not indicate that a superparamagnetic iron oxide nanoparticle (SPION) carrier-bound drug or drugs are not in use. The clasp-electromagnets shown in FIG. 13B might steer the SPIONs or assist steering through fine vector multidirectional adjustment. FIG. 13B should not suggest that the area though which the SPION carrier-bound drug can be drawn is two dimensional; generally, at least one of the electromagnets will lie outside the section plane of the figure to define a three dimensional volume within which the drug can be stereotactically steered by means of magnetic vectoring. Other components are positioned in a pocket or pockets away from the kidney. The side-entry connector is thus deep to the skin, several layers of fascia, muscle, and fat intervening. Special circumstances may require alternate access, such as through the anterior surface of the kidney.

Application of the configurations depicted in FIGS. 13A and 13B for direct chemotherapeutic and/or Auger therapy pertain to small tumors, to include those malignant where the need for resection or transplantation may be discounted. In the liver, for example, reference is to a small hepatocarcinoma, usually discovered as an 'incidentaloma,' whether an hepatoblastoma (malignant teratoma, or dermoid cyst), hepatocellular carcinoma, or other malignant hepatoma, especially in a patient with inadequate healthy liver tissue to allow a wider resection and regeneration but who would avoid a transplant were little more tissue than the tumor itself removed. Rarely, it may be necessary to first dissect out and stabilize the kidney by nephropexy, or positional fixation. With a nephrostomy, stone formation is prevented by delivering the solvent for the type stone through a prerenal jacket, or ductus side-entry jacket on the renal artery.

Postrenal disease is treated through the delivery of medication through a ductus side-entry jacket placed along the renal vein. Means will be described herein which allow urinary diversion under any circumstance save a patient too mentally impaired to go to and use the bathroom. Ureterostomy previously reconstructive, the severed end of the ureter connected to the gut or to an ostium created at the body surface to allow catheterization or drainage to the bladder or bulbar urethra as appropriate or if unavoidable or the patient near death, to an extracorporeal collection bag, the use of a ductus side-entry jacket allows a permanent nonreconstructive and minimally invasive ureterostomy made entirely of synthetic materials. Urine can be diverted to an extracorporeal bag through a catheter led from the ductus side-entry jacket placed along the upper ureter with the distal tract pinched closed with a narrow cross-clamp or embolized to divert the urine.

However, as experience with the first artificial urethral sphincter invented by Foley in 1947 with an improved model in 1949 made clear, the compression of the urothelial lining of the urethra at a location other than sphincterohotopically, or at the level of the native sphincter, leads to erosions, pressure necrosis, infection, fistulization, and other serious sequelae (Trost, L. and Elliott, D. S. 2012. "Male Stress Urinary Incontinence: A Review of Surgical Treatment Options and Outcomes," Advanced Urology 2012: 287489; Diokno, A. C. and Peters, K. M. 2002. "Artificial Urinary Sphincter for Treatment of Male Urinary Incontinence," in Carson, C. C. III, Urologic Prostheses: The Complete Practical Guide to Devices, Their Implantation, and Patient Follow Up, Chapter 17, page 264, New York, N.Y.: Springer; Debruyne, F. M. J. and van Kerrebroeck, P. E. V. A. 1986. Practical Aspects of Urinary Incontinence, Dordrecht, Holland: Martinus Nijhoff).

Hydraulic prostheses originated prior to the advent of transdermal charging, miniature high capacity rechargeable storage batteries, and the microcircuitry that makes possible full, or closed-skin, implantation. It was then improved over the years as a technology apart from contemporary advancements in and now remains incompatible with electronics. This experience notwithstanding, a fixation on compression of the urethra as a suitable approach for treating urinary incontinence has led to the perpetuation of these poorly conceived devices rather than the development of a noncompressive device that eliminates atrophy, erosion, and the need for revision.

This fixation results from the fact that 1. The hydraulic internal sphincter is a pinch valve that applies compression where the tissue is not adapted to withstand it, 2. The mistaken presupposition that given adequate time, the urothelium would adapt, allowing long term function as a pinch valve, and 3. A 70 year financial commitment and unwillingness to abandon the established product. Not only is the concept wrong, but its implementation in the form of an ectopic multi-component implant requires far more dissection than does placing a simple ball check valve drawn down the neck by gravity and retracted by a small electromagnet fastened at the superior surface of the bladder by a highly flexible nonjacketing side-entry connector that does not interfere with contraction of the detrusor.

To avoid interfering with contraction of the detrusor and irritation of the bladder serosa and fibrosa, nonjacketing side-entry connectors applied to the urinary bladder have a baseplate that is highly flexible, thicker foam, and are oriented to bend with the muscle during contraction. This conceptually and surgically simpler noncompressive means for the reinstatement of urinary continence is addressed below in the section entitled Urethra-noncompressive Reinstatement of Urinary Continence. This is critical when the semicircular, or half round, needles are used to deliver electrical discharges into the detrusor to effect contraction when the muscle is atonic or ataxic, as addressed below in the section entitled Targeted Electrical and/or Chemical Autonomic Motor Assistance.

By comparison, the hydraulic compression cuff makes revision inevitable—a fact only reduced in incidence because the patients are often advanced in age and die before reoperation becomes necessary. A Mitrofanoff flap valve allows continent drainage through an intromitted catheter and therefore, dispensing with the need for a collection bag. If the distal tract recovers, compression necrosis beneath the clamp requires excision and end to end anastomosis. Notwithstanding the padded lining of the jacket, to least interfere with the intrinsic peristalsis initiated at the pelvis, the jacket is placed as far down along the ureter as possible. Unless left in place for no longer than a brief period, takeoff high on the ureter with the caudal ureter clamped or emobolized risks atrophy of the lower tract, which access to the renal pelvis through the relatively avascular coronal or bloodless plane of Brodel does not.

The segment by segment specialization of the epithelial lining along any bodily conduit also militates against the use of gut for surgical constructions to replace portions of the urinary tract. The gut is segment by segment differentially adapted for the absorption of different nutrients and is unsuited to contact with urine. Conventional access combined with a novel method of shunting to bypass a diseased or missing segment of the ureter with drainage through the lower tract, eliminating an external collection bag fed through a surface wound and port is addressed below. Passive, or incontinent, outflow with a need for a collection bag is eliminated by capping the distal end of the excurrent line with a pressure responsive flap or slit valve, which allows excurrent self closure with the buildup of bladder content and the forced entry into the excurrent line of a catheter.

The port at the body surface which is used is described in copending application Ser. No. 14/121,365, entitled Ductus Side-entry Jackets and Prosthetic Disorder Response Systems. Such a port is a nonjacketing side-entry connector specialized for the passage of multiple fluid, electrical, and fiberoptic lines through the body wall Placed in less time than is needed to create an ileal, or Bricker, conduit and ostium, for example, the port eliminates the need to divert native tissue as a preliminary procedure itself subject to complications and sequelae.

The remedies described herein are for long term or lifetime conditions not remediable, for example, by excision of an affected segment of ureter that is short enough to allow pull up with or without a downward nephropexy and end to end anastomosis without the introduction of synthetic materials other than suture, and similar procedures now routine (see, for example, Hoyt, D. B., Potenza, B. M., Cryer, H. G., Larmon, B., Davis, J. W., Chesnut, R. M., Orloff, L. A., and 13 others 1997. "Trauma," Chapter 11 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven; pages 358-361).

Conventional short term nephrostomy using synthetics with needle and plastic collection bag external to the body for urinary diversion to bypass an obstruction or discontinuity in the tract distal to the obstruction. The approach is through the flank, the kidney, and into the pelvis, with drainage through a catheter to the collection bag, and is unsuited to long term treatment. This procedure is suitable for the emergency relief of pressure that threatens to engorge the upper tract causing extremely painful ureteric distension and hydronephros that if not relieved promptly will case kidney damage. Incisional entry avoided, the ureter is not closed off with suture.

Surgical nephrostomy for longer use pending restoration to normal voiding function is through a cutaneous vesicostomy (cystostomy) or a button vesicostomy, possibly using a gastostomy button, and due to long term complications, is recommended for short- to medium-term use (Bradshaw, C. J., Gray, R., Downer, A., and Hitchcock, R. J. 2014. "Button Vesicostomy: 13 Years of Experience," Journal of Pediatric Urology 10(1):80-87; Hitchcock, R. J. and Sadiq, M. J. 2007. "Button Vesicostomy: A Continent Urinary Stoma," Journal of Pediatric Urology 3(2):104-108). Long term diversion when the distal tract is obstructed is directly to a rosebud stoma or by bypass of the obstruction to the vesicostomized or cystostomized bladder through an ileal conduit with bladder outlet configured to spontaneously press closed as the bladder fills.

Ductus side-entry jackets allow anastomosis free junctions with minimal shear stress of synthetic tubing to native ductus, while nonjacketing side-entry connectors allow styliform and miniature cabled devices to be stably and durably aligned along an axis into an organs or other tissue. For singular applications and including an accessory path for maintenance substances if necessary, these provide junctions less prone to complications than alternative means. The fuller realization of these is achieved with a second type of nonjacketing side-entry connector, placed at the body surface. This port-connector provides a number of entry openings for the injection or pumping of therapeutic substances in response to feedback from sensor implants used to detect deviations from normal levels in the relevant health maintenance indica.

The system microcontroller is programmed to dispense medication as needed to treat different organs, glands, and/or other tissue in comorbid disease. Such a system is conceived of as a prosthetic backup immune system and is referred to as an automatic disorder response system. A synthetic port for placement at the body surface and such automatic response systems are described in copending application Ser. No. 14/121,365, entitled Ductus Side-entry Jackets and Prosthetic Disorder Response Systems. A stoma for the single purpose of allowing the diversion of waste appropriates normal tissue, necessitating far more dissection and creating the risk of adverse sequelae and infection at both donor and recipient sites (Kreder, K. J. and Stone, A. R. 2005. Urinary Diversion: Scientific Foundations and Clinical Practice, Abingdon-on-Thames, England: Taylor and Francis).

More importantly, its functionality compared to a synthetic port in affording little if any compatibility with the application of electronics and integration into a prosthetic disorder response system is minimal. In that a synthetic port 1. Can provide multiple inlets to separate channels for the delivery of drugs to different treatment sites, as well as 2. A pathway for the evacuation of native luminal contents; 3. Involves no diversion of normal tissue; 4. Is impermeable, not subject to erosion from acidity or cleaning agents, and is easily sterilized; 5. Requires far less dissection to place; and 6. Provides inlets which are exact and nondeformable in dimensions, allowing leakproof connection to incoming and outgoing lines and the precise fitting of electronic components; it is critically superior to a surgically constructed stoma.

A surgically constructed stoma represents an abnormal reconformation of functionally distinct tissue moved to an alien milieu that opens the way for complications at both donor and recipient sites, to include dermal (see, for example, Szymanski, K. M., St-Cyr, D., Alam, T., and Kassouf, W. 2010. "External Stoma and Peristomal Complications following Radical Cystectomy and Real Conduit Diversion: A Systematic Review," Ostomy/Wound Management 56(1):28-35). By contrast, a synthetic outlet and/or entry port eschews these deterrents, is made to a high degree of precision, is therefore amenable to the fitting of electronic elements, and is not susceptible to infection, necrosis, fistulization, or deformation over time. Synthetic materials as such are intrinsically invulnerable to microbial attack and irradiation, and means such as accessory channels or sidelines and quick access are provided to facilitate sterilization and the application of drugs such as anti-inflammatories.

To correct changes in surgical reconstructions that result in leakage or incontinence requires revision (reoperation) or the application of synthetics (see, for example, Roth, C. C., Donovan, B. O, Tonkin, J. B., Klein, J. C., Frimberger, D., and Kropp, B. P. 2009. "Endoscopic Injection of Submucosal Bulking Agents for the Management of Incontinent Catheterizable Channels," Journal of Pediatric Urology 5(4): 265-268; Matthiessen, P., Hallbook, O., Rutegard, J., Simert, G., and Sjodahl, R. 2007. "Defunctioning Stoma Reduces Symptomatic Anastomotic Leakage after Low Anterior Resection of the Rectum for Cancer: A Randomized Multicenter Trial," Annals of Surgery 246(2):207-214; Prieto, J. C., Perez-Brayfield, M., Kirsch, A. J., and Koyle, M. A. 2006. "The Treatment of Catheterizable Stomal Incontinence with Endoscopic Implantation of Dextranomer/Hyaluronic Acid," Journal of Urology 175(2):709-711; Halachmi, S., Farhat, W., Metcalfe, P., Bagli, D. J., McLorie, G. A., and Khoury, A. E. 2004. "Efficacy of Polydimethylsiloxane Injection to the Bladder Neck and Leaking Diverting Stoma for Urinary Continence," Journal of Urology 171(3):1287-1290).

For this reason, a synthetic cystostomy is far less susceptible to leaks, much less in the short term. Provided synthetics are made to avoid infection, the formation of a biofilm, and adverse tissue reactions, the use of these materials is plainly preferable to reconfiguring normal tissue. With urinary diversion proximal, the ureter is usually closed off with suture. If the self-closing entry into the excurrent shunt allows leakage, the patient must periodically insert a catheter to draw off the bladder contents. For a patient unable to do so, this necessitates frequent attention by a trained technician.

The addition of flexible flaps at the entry into the lower of the two nonjacketing side-entry connectors shown in FIG. 12A to provide urinary drainage provides the same self-closing or automatic cutoff function which is less susceptible to leakage than one surgically constructed. The upper connector shown in FIG. 12A is used to insert a fiberscope or laser down to any point along the lower urinary tract as an alternative to transurethral passage, which may be impossible, and to target drugs to the urinary tract without concern for adverse interactions with drugs intended for other parts of the body.

For the targeted treatment of interstitial cystitis, such drugs include amitriptyline (see, for example, Generali, J. A. and Cada, D. J. 2014. "Amitriptyline: Interstitial Cystitis (Painful Bladder Syndrome)," Hospital Pharmacy 49(9): 809-810; Hsieh, C. H.; Chang, W. C.; Huang, M. C.; Su, T. H., Li, Y. T., and Chiang, H. S. 2012. "Treatment of Interstitial Cystitis in Women," Taiwan Journal of Obstetrics and Gynecology 51(4):526-532; van Ophoven, A., Pokupic, S., Heinecke, A., and Hertle, L. 2004. "A Prospective, Randomized, Placebo Controlled, Double-blind Study of Amitriptyline for the Treatment of Interstitial Cystitis," Journal of Urology 172(2):533-536; Hanno, P. M. 1994. "Amitriptyline in the Treatment of Interstitial Cystitis," Urologic Clinics of North America 21(1):89-91), cimetidine, hydroxyzine, or pentosan hydrochloride, which ordinarily taken orally, hence, systemically, must be converted into liquid form to be pumped directly into the bladder. Intravesical heparin appears effective in a subset of patients (Generali, J. A. and Cada, D. J. 2013. "Intravesical Heparin: Interstitial Cystitis (Painful Bladder Syndrome)," Hospital Pharmacy 48(10):822-824). Other drugs prepared as fluids used to treat interstitial cystitis include dimethylsulfoxide and lidocaine.

In FIG. 12A, in addition to providing a path for the direct targeting of drugs into the bladder and fulguration, or electrodessication of recurrent tumors if necessary, the upper line provides a prepositioned passage for the periodic insertion of a fiberscope to view or biopsy the bladder (see, for example, Anastasiadis, A. and, de Reijke, T. M. 2012. "Best Practice in the Treatment of Nonmuscle Invasive Bladder Cancer," Therapeutic Advances in Urology 4(1):13-32; Nielsen, M. E., Smith, A. B., Pruthi, R. S., Guzzo, T. J., Amiel, G., Shore, N., and Lotan, Y. 2012. "Reported Use of Intravesical Therapy for Non-muscle-invasive Bladder Cancer (NMIBC): Results from the Bladder Cancer Advocacy Network (BCAN) Survey," British Journal of Urology International 110(7):967-972; The Merck Manual 18th edition, 2006, page 1938).

For biopsy, an anticoagulant is delivered through the same line. Because passage of the catheter or other device through the line is never in contact with tissue, the need for anesthesia is eliminated and that for an antibiotic reduced if not eliminated. When the condition recommends periodic reexamination of the bladder interior, the one-time minor surgery required to place the line more than compensates for the irritation, and greater risk of patient resistance and complications of repeated conventional cystoscopy. Patients may also object to the repeated radiation exposure of chest x-rays and sense of confinement with computed tomography, the low radiation exposure of recent equipment notwithstanding.

For viewing, biopsy, and treatment, entry through the upper line in FIG. 12A represents an alternative to urethral access for the entire post cystic urinary tract, whereas the pelvic urinary diversion or nephrostomy line shown in FIG. 11 affords access to the entire post renal urinary tract. Repeated examination is essential in the treatment of bladder cancer, where tumors recur in more than 40 percent of patients, carcinoma in situ tends to recur, and bladder cancer not in situ tends to be highly metastatic (see, for example, The Merck Manual 18th edition, 2006, page 2048). Drugs can be delivered, into either ureter through a ductus side-entry jacket; however, the nonjacketing side-entry connector is more versatile in allowing passage of cabled devices, such as scopes, lasers, and/or a biopsy device.

Negative urine cytology and no evidence of recurrence of carcinoma in situ following a course of *Bacillus* Calmette-Guerin on cystoscopy usually allows dispensing with biopsy (see, for example, Smith, P. J., Lotan, Y., Raj, G. V., Sagalowsky, A. I., and Margulis, V. 2014. "Assessing Treatment Response after Induction *Bacillus* Calmette-Guerin for Carcinoma in Situ of the Urinary Bladder: Can Post-induction Random Bladder Biopsies be Avoided?," Cytopathology 25(2):108-111; Swietek, N., Waldert, M., Rom, M., Schatzl, G., Wiener, H. G., Susani, M., and Kiatte, T. 2012. "The Value of Transurethral Bladder Biopsy after Intravesical *Bacillus* Calmette-Guerin Instillation Therapy for Non-muscle Invasive Bladder Cancer: A Retrospective, Single Center Study and Cumulative Analysis of the Literature," Journal of Urology 188(3):748-753; See, W. A. 2013. "Commentary on Swietek N, Waldert M, et al. 2012, ibid, Urologic Oncology 31(5):715-716).

In FIG. 12A, near-apical side-entry connector 61 and ventral side-entry connector 62 used to connect catheters to the urinary bladder can be implanted and used individually or implanted and used simultaneously, either independently or in coordination. Where repeated examination will be needed and urethral passage of a cystoscope is not possible or the use thereof contraindicated, the catheter connected toward the apex, usually single lumen and without an accessory channel, can be used to deliver antispasmodic, antimicrobial, antineoplastic, and/or anti-inflammatory drugs to treat the bladder itself, that draining down through the ureters treating the lower tract. When not to be avoided (see, for example, The Merck Manual, Op cit. page 1938, which specifies: bleeding diatheses, solitary kidney, uncooperative patient, acute tuberculous cystitis), the upper line can be used to insert an endoscope, here a flexible cystoscope, or laser, for biopsy, or these in combination.

A double lumen catheter allows the manual or automated delivery of drugs independently or in coordination, or the viewing or use of a laser, for example, concurrently with the delivery of drugs or testing solutions. Access thus, especially since it is intended for repeated use, avoids the risks of urethral and/or bladder trauma (incisions, perforation), and sequelary stricture. A double lumen line to the lower connector allows the delivery of drugs to treat the lower tract concurrent with urinary diversion where alternative access is not possible. Unless the bladder is itself infected, when used for urinary diversion, the lower line provides urinalysis test samples substantially free of microbiota and cellular detritus associated with infection of the lower tract.

In coordinated use the upper of the two lines, where the incurrent line is usually placed, and at the level of the trigone, where the excurrent line is placed, allows irrigation and lavage in either direction with water or any therapeutic or diagnostic solution, to include a solvent to wash away any organic and/or crystalline coating on the internal surface of the bladder, whether the bladder is native, tissue engineered, synthetic, or surgically constructed. For a child or the mentally impaired, lavage is automated as programmed, the means therefor addressed in copending application Ser. No. 14/121,365, entitled Ductus Side-entry Jackets and Prosthetic Disorder Response Systems.

While side-entry connections can be singular, the configurations depicted in FIGS. 6, 11, 12A thru 12D, 13A, and 14, for example, should not be conceived of in a limiting sense as either singular or isolated: any side-entry connected line can be used in combination with any other or others, any can be incurrent or excurrent, and such combinations can pertain to one organ system or across organ systems. For example, in the urinary tract, an obstructed ureter can be bypassed by urinary diversion from the pelvic tap in FIG. 11 to the upper connector in FIG. 12A. In comorbid disease, treatment, pharmacological and/or electrostimulatory, is meted out adaptively on the basis of implanted sensor inputs to the different organ systems affected by an implanted microcontroller and associated components in accordance with a prescription program.

The application to such a system of hierarchical control and intracorporeal and extracorporeal communications networks was delineated in copending application Ser. No. 14/121,365, entitled Ductus Side-entry Jackets and Prosthetic Disorder Response Systems, Cross-system connections can be direct or literal, through lines side-entry connected at either end or implicit, without literal connection, in dependence upon the intrinsically related function and flow of the systems. Such an arrangement can replace or facilitate normal function or intentionally create alternative channels of cross-system communication. With different organs, tissues, drugs, devices incurrent, excurrent, or both, such as a hollow needle usable for aspiration and injection, the combinations and permutations among these variables are limitless.

If necessary, a neobladder, one surgically constructed, or 'donor gut,' (see, for example, The Merck Manual 18th edition, 2006, page 2048), or preferably, one tissue engineered (see, for example, Yoo, J. J., Olson, J., Atala, A., and Kim, B. 2011. "Regenerative Medicine Strategies for Treating Neurogenic Bladder," International Neurourology Journal 15(3):109-119; Soler, R., Fullhase, C., and Atala, A. 2009. "Regenerative Medicine Strategies for Treatment of Neurogenic Bladder," Therapy 6(2):177-184; Atala, A., Bauer, S. B., Soker, S., Yoo, J. J., and Retik, A. B. 2006. "Tissue-engineered Autologous Bladders for Patients Needing Cystoplasty," The Lancet 367(9518):1241-1246) is provided. Nonjacketing side-entry connectors are usable with either.

A synthetic bladder developed to prevent kidney damage and infection from the reflux and retention of urine and coating of the lumen wall by crystallization was described in 1992 (O'Sullivan, D. C. and Barrett, D. M. 1994. "Prosthetic Bladder: in Vivo Studies on an Active Negative-pressure-Driven Device," Journal of Urology 151(3):776-780; Barrett, D. M., O'Sullivan, D. C., Parulkar, B. G., and Donovan, M. G. 1992. "Artificial Bladder Replacement: A New Design Concept," Mayo Clinic Proceedings 67(3)215-220). A prosthetic bladder avoids complications associated with anticancer radiation (see, for example, Leissner, J., Black, P., Fisch, M., Hockel, M., and Hohenfellner, R. 2000. "Colon Pouch (Mainz Pouch III) for Continent Urinary Diversion after Pelvic Irradiation," Urology 56(5):798-802).

Unlike surgically constructed neobladders such a the Kock type, a tissue engineered bladder is best situated orthotopically, not apposite the body wall where it is susceptible to cutaneous fistulization. The lower line in FIG. 12A with a port at the body surface favorably replaces an ileal conduit to a stoma in any context, whether entered directly by the ureters or to a pouch reservoir, or neobladder, interposed between the ureters and stoma. Where the ureters are missing or obstructed, flow can be passed from a nephrostomy from the pelvis as shown in FIG. 11 directly to the bladder or neobladder in FIG. 12A to allow continent urethral flow, or if the lower tract is missing, the line in FIG. 11 can flow directly through surface port 58 into collection bag 59. Only considerable deformity or trauma disallows the creation of a neobladder and the application of one or more of the embodiments depicted herein to return the patient to urethral voiding without the need for an external bag.

The superiority over conventional treatment to divert urine over a long term of lower line 51 in FIG. 12A subsumes at least five factors: 1. The appropriation of healthy ileum or colon to construct the conduit, with risk now extended from the recipient conduit to the harvesting or donor site as the source of its tissue; 2. The availability of the accessory channel of the line shown in FIG. 11 to deliver drugs to assure sterility and freedom from eventual clogging by crystal accretion, and 3. The upper line in FIG. 12A if necessary to allow the direct targeting of drugs to a tissue engineered or constructed bladder, or neobladder, from portacath 46; and 4. The substantial elimination of the numerous complications such as infection associated with a stoma enumerated above, and 5. The nonstandard dimensions and other factors that militate against the fitting of electronic elements. Some complications associated with a tissue engineered bladder without integral drainage line and constructed neobladders are addressed below in this section.

Due to the adverse sequelae associated with displaced, hence, physiologically misplaced, native tissue in surgical reconstructions, preference is given to synthetic materials with means for the direct delivery of maintenance medication as necessary. This does not include the bladder itself, best tissue engineered. When drainage cannot be shunted to a point along the urinary tract distal to the obstruction, drainage through the body wall is through a surgically constructed rosebud stoma which is more susceptible to complications than a 'cosmetically, surgically, more quickly placed, and cleaner,' entirely synthetic and nonobtrusive port introduced in copending application Ser. No. 14/121,365, which is conformed to avert and withstand head-on and sidewise impacts.

Intracorporeal storage bladder reservoirs along the lines leading from such a surface port to the destination side-entry connector is easily recharged with antimicrobials and anti-inflammatories as necessary. Until regenerative medicine can produce missing anatomy, surgical reconstruction with maintainable synthetic, rather than surgically constructed conduit not requiring intrinsic motility will remain necessary for long term use and during the period required for regeneration. With respect to the urinary tract, ileal, or Bricker, conduits should be replaced by synthetic tubing, a bladder or reservoir if needed obtained through surgical construction only until one regenerated over a considerable interval can be provided.

Continence and nonrefluxing function attainable using synthetic materials, the detubularization of ileum and colon to construct a conduit to stoma as in an ileal or Bricker conduit, or a bladder pouch as in a Mainz type, Indiana, Studer, or Kock procedure is necessitated by the need to anastomose the conduit produced to native tissue. As gastrostomy, or stomach tubes, Foley catheters, and suprapubic cystostomy and nephrostomy tubes make it plain, where ureteroenteric anastomosis is not essential, synthetics are preferable. The nonanastomotic connection of synthetic material to native tissue is precisely a central object in ductus and nonjacketing side-entry connectors. Eventually, tissue engineering will replace the ductus as well. However, anatomy which replaced will, or is likely to, require support best achieved by direct targeting, and where bridging pending regeneration is necessary will continue a need for synthetics.

Urinary diversion to the bulbar urethra by means of a bypass—which if necessary to regain urinary continence, includes a prosthetic sphincter or pinch valve that compresses a synthetic length of tubing rather than the urethra to dispense with the need for an external collection bag—is addressed below in this section. Also addressed is the reinstatement of continence by means of a nondiversionary stopper ball check valve with or without obstruction of the proximal urethra as to necessitate bypass, diversion to the distal colon, and the remediation of colon and/or anal sphincter motor dysfunction if necessary. Yet another application of nonjacketing side-entry connectors is autonomic motor support through electrical discharge and/or drug induced neuromoduation. In this, connectors fastened to the outside of the dysfunctional sphincter or segment of a peristaltic tract, using electrified anchoring needles, discharge electrical stimulation pulses, and those with hollow needles can additionally be used to inject drugs.

As to capability rather than actual need for treating a real condition, any nonjacketing side-entry connector can deliver drugs through a catheter and electrical discharges through an electrode ensheathed within the same conduit as side connector. The same may be said for the anchoring half round needles when hollow with drug feedline attached and electrified by connection to a conductor under the control of the microcontroller for the delivery of pulsed discharges. Electrical discharge from the needles and the electrode can be combined in any pattern, as can drug release through the side connector and each of the needles. Moreover, the electrical stimulation can be coordinated with drug delivery in any pattern, the same pertaining to connectors regardless of configuration, and thus with anchoring needle arrangement such as those shown in FIGS. 1, 4, 17, and 20, for example.

As to its electrical and positional pattern, the electrical discharge can be controlled in detail and coordinated with the chemical components of the treatment to provide peristaltic and/or sphincteric support. Diversion to a preserved but dysfunctional distal colon or rectum even with an incompetent anal sphincter, can thus be treated by peristaltic and/or sphincteric stimulation. In contrast to a single channel surgical stoma, the multiple channel port is additionally able to provide service channels to the internal components and/or the anatomical structures these components connect. A fine fiberscope can be passed down through any line, or with a dedicated endoscopic opening at the center of the port, view each line. Where the line enters tissue, the fine fiberscope can, if necessary, be passed alongside the line to examine the side-entry jacket or nonjacketing side-entry connector at the distal end of the line.

Providing both the inlet and port with slit or flap valves equivalent to a self-closing surgically constructed inlet with gastric button at the outlet, makes subsequent leaking unlikely. Whenever a permanent nephrostomy can avoid emergence through the body wall, not only is the risk of infection reduced, but irritation at the surface entry wound is eliminated. Entirely intracorporeal or fully implanted closed-skin placement using synthetics has the advantages of leaving uninvolved tissue unaffected. If medication must be injected into any one line, a portacath allows the system to remain closed skin. If the volume of medication necessitates targeting to any point along the catheteric line or the anatomical structures the catheteric line is used to connect, then, an internal reservoir can be constructed of bovine pericardium, for example, with the electronic components housed within a separate pocket.

Complications appurtenant of diverting a healthy internal thoracic artery, or fabricating an ileal, or Bricker, conduit, or an Indiana pouch are mentioned below. If a volume of multiple drugs must be targeted to one or more points along a number of catheteric lines or the anatomical structures these connect at a rate in excess of what the foregoing configuration can accommodate, then a belt-worn pump pack and synthetic port placed at the body surface as described in copending application Ser. No. 14/121,365, with clearly marked destination entry holes can deliver the drugs automatically. That used thus, synthetics can remain in place indefinitely is due to the stability of the connection interfaces and the ability to deliver medication directly into the synthetic line or lines.

In this case, the control electronics and power source can be included in the pump pack or implanted within an internal pocket. With the present approach, the need for an ileal conduit, for example, led to a rosebud stoma at the body surface and the additional surgery this requires can always be avoided, even if drainage to an extracorporeal collection bag is necessary because the patient is too impaired to go to or to use the bathroom. If drainage thus is necessary, a body surface port as described in copending application Ser. No. 14/121,365, entitled Ductus Side-entry Jackets and Prosthetic Disorder Response Systems less susceptible to infection and requiring little dissection compared to the convention allows passage through the body wall.

Moreover, unlike a surgically constructed conduit and stoma, the synthetic conduit can pass through as many independent channels as necessary to allow not only excurrent passage for urinary drainage or lavage, for example, but incurrent access to any implanted line or connector whether applied to the vascular tree, urinary tract, or any other bodily system or combination of systems. In mentally competent patients, the use of such a port at the body surface is not for urinary diversion but reserved for continuous or frequent processes such as ambulatory apheresis where reservoir volume is too large to be implanted. Otherwise, incontinence is treated with the arrangement shown in FIG. 12B or that in FIG. 12C, wherein, as will be explained, rather than applying a Foley type pinch sphincter to the urethra where complications are inevitable, an artificial pinch sphincter 60 is relegated to bypass line 52 from the bladder to the bulbar urethra, so that the patient voids normally through the urethral meatus.

Whether pending a prostatectomy, the arrangement shown in FIG. 12C, with or without the in-line sphincter, can be used to bypass the prostate. Rather than to run the excurrent (outflow or takeoff) catheter to the exterior, drainage from the renal pelvis of a normal kidney is through a catheter tunneled retroperitoneocaudally to a ductus side-entry jacket on the ipsilateral ureter distad the problem segment (nonanastomotic ureteropyeloneostomy, nephroureterostomy), or if necessary, to the contralateral ureter (nonanastomotic ureterotranspyeloneostomy, nephrotransuterostomy), or directly to the bladder (nonanastomotic nephrocystostomy). Not involving tissue not otherwise involved a central object, diversion to the contralateral ureter when otherwise unaffected is to be avoided as risking peristaltic impairment on the one good side.

In advanced benign prostatic hyperplasia where alpha blockers would reduce or eliminate the ejaculate, 5.alpha.-reductase inhibitors reduce libido, and sildenafil citrate in the absence of erectile dysfunction are otherwise inadequate to alleviate the blockage so that to transurethral resection, photoselective vaporization, or holmium laser enucleation of the prostate remain as the only remedies, for example, the configuration depicted in FIG. 12C without in-line diversion or bypass pinch valve 60 can be used to preserve sterility. Where incontinence is also present, in-line diversion or bypass pinch valve 60 is then included. With respect to any combination of applications depicted among the configurations shown in FIGS. 12A thru 12D, unless fluid drug feedlines and/or a probe or electrode, for example, must be mounted alongside the magnet, a clasp-electromagnet is used.

To avert nephrolithiasis, for example, anti-crystallization medication is delivered to the kidney, usually through a ductus side-entry jacket about the ipsilateral renal artery. In a stone former and/or a patient required to take a crystallization-inducing drug or drugs such as ceftriaxone, additional protection against the long term accretion of crystal along the internal surfaces of synthetic lines such as bypass drain line 52 in FIG. 12C is by delivery of one or more alkaline anti-crystallization solvents or acidity level adjustment agents through nonjacketing side-entry connector 61 or its accessory channel (not shown in FIG. 12C but shown in FIGS. 1, 2, 5 thru 10A, 10B, 13A, 13B, and 14.

Referring now to FIGS. 12B and 12D, electromagnets 66 in FIG. 12B and 69 and 70 in FIG. 12 have wide diameter, high permeability permalloy or, iron-silicon crystal cores, while draw-plates, or lifing disks, 67 and 68 in FIG. 12D, polymerically encapsulated for chemical isolation, contain high susceptibility iron-silicon crystal. These elements can be mounted as clasp-electromagnets described and shown in FIGS. 25 and 26 of copending application Ser. No. 14/121, 365, FIG. 23 therein showing the perforations in each clasp to allow tissue ingrowth. When the arrangements depicted in FIGS. 12B and 12D are combined, at least one of the electromagnets positioned on the superior surface of the bladder is eliminated. Ordinarily, as shown in FIG. 12B, clasp-electromagnets and encapsulated iron draw-disks such as 67 and 68 in FIG. 12D are mounted separately from nonjacketing side-entry jackets such as that shown as 61 in FIG. 12B. To compensate for the low ratio of tractive force to mass of the electromagnets at the roof of the bladder that would compel the use of larger magnets, the draw-plates beneath the bladder are made of silicon-iron magnetized to respond to a lesser attractive force.

This is equally applicable when a nonjacketing side-entry connector is used to furnish pharmaceutical or electrostimulatory therapy in conjunction with the arrangement shown in FIG. 12D. Separate mounting, especially where fluid drug and/or electrical delivery is not required, is best reserved for heavier or passive elements, such as magnets and the iron disk draw-plates 67 and 68 in FIG. 12D. Not only are the nonjacketing side-entry connectors and clasp-electromagnets shown in FIGS. 12A and 12B used together in whatever combination is necessary, but any may be retrofitted as the ensuing medical condition warrants. This prevents the concentration of weight at a single point of attachment and affords the advantage of varying the angle between these.

Where a later need for supplementary therapeutic means cannot be ruled out, side-entry connectors, preferably with injection and electrically conductive anchoring needles, should be placed at the outset. So that the leads thereof will be located immediately, the fluid and electrical delivery lines or leads are brought subdermally along a route that rules out organ strangulation and sutured, the proximal ends thereof bent about to prevent incisions and contrast coated as with tantalum for immediate access when the need arises. While many drugs intended to treat the urogenital tract can be taken orally, where the need for several drugs might lead to errors in compliance; such a line can be used to target these and other drugs to the bladder.

Moreover, the same applies to other bodily organs, such as the gallbladder, where directly targeted drugs would alleviate biliary sludge, crystalline or cholesterol concretion, for example, thereby reversing complications often encountered with hormonal contraceptives or xanthogranulomatous cholecystitis. The bypass configuration depicted in FIG. 12C with the addition of magnets 69 and 70 shown in FIG. 12D will additionally alleviate a neurogenic, dyssynergic (ataxic), or atonic bladder. As when a ductus side-entry jacket is used to shunt blood into a blood vessel, a side connector when used to divert urine to the urethra is angled to minimize shear stress on the urothelium along the segment of merging confluence. Ductus side-entry jackets angled thus may be seen in copending application Ser. No. 14/121,365, entitled Ductus Side-entry Jackets and Prosthetic Disorder Response Systems, filed on 25 Aug. 2014, FIG. 22, for example. The operator gently presses down on the trepan edged connector with crosshair cutter and twists it to cut through the lumen wall.

As shown in FIG. 11, diversion is through a tube or drain catheter as side connector. As depicted, the drain tube has been inserted with the aid of a trocar as the cannula thereof. Otherwise, insertion is either with a side connector as shown in FIG. 5 or a hollow injection and aspiration needle inserted through the flank into the lateral margin of the kidney and plane of Brodel into the renal pelvis. Tunneling down through the retroperitoneum is practicable (see, for example, Bae, S. U., Park, J. S., Choi, Y. J., Lee, M. K., Cho, B. S., Kang, Y. J., Park, J. S., and Kim, C. N. 2014. "The Role of Hand-assisted Laparoscopic Surgery in a Right Hemicolectomy for Right-sided Colon Cancer," Annals of Coloproctology 30(1):11-17; Kuzuya, A., Fujimoto, K., Iyomasa, S., and Matsuda, M. 2006. "Extra-anatomical Aortobifemoral Bypass for Juxtarenal Aortic Occlusion," EJVES Extra [European Journal of Vascular and Endovascular Surgery (online)] 11(1):10-12; Dion, Y. M., Chin, A. K., and Thompson, T. A. 1995. "Experimental Laparoscopic Aortobifemoral Bypass," Surgical Endoscopy 9(8):894-897).

When too great a length of the ureter has been resected or rendered irremediably damaged to allow direct end to end anastomosis of the free ends, then rather than to autotransplant the kidney or perform a downward nephropexy (see, for example, Knight, R. B., Hudak, S. J., and Morey, A. F. 2013. "Strategies for Open Reconstruction of Upper Ureteral Strictures," Urologic Clinics of North America 40(3): 351-361), which is more complex and risk laden, the continuous catheter or the catheter continuous with the needle is tunneled retroperitoneocaudally to a nonjacketing side-entry connector used to fasten the catheter directly to the bladder, the ureterovesical junction aperture having been sutured closed. Due to cell death and collagen atrophy, a free or nonpedicled native conduit used as a graft to bridge a gap resulting from surgical removal or injury to a segment of ureter that is too long for direct anastomosis is subject to gradual deterioration and necrosis.

A tube made of ligamentous or fascial tissue performs well only so long as its collagen remains sufficiently intact. When the kidney is itself normal, a missing segment of ureter too long to allow anastomosis is bridged by a catheter between ductus side-entry jackets about the upper and lower ureteral remnants, or stumps. The ureters supplied by no less than nine branches from larger arteries at intervals throughout their length (see, for example, Delacroix, S. E. Jr., and Winters, J. C. 2010. "Urinary Tract Injures: Recognition and Management," Clinics in Colon and Rectal Surgery 23(2): 104-112), such a nonanastomotic ureteroureterostomy mediated by ductus side-entry jackets properly selected and applied should not result in ischemia. Innervation similarly multiple, the effect on contractile and sensory function should approximate the impact of anastomosis with the interposition of any nonureteric tissue or material. The delivery of medication is by incurrent catheter or hollow needle fixed in position by means of a nonjacketing side-entry jacket as shown in FIG. 11.

If diversion is also needed at the renal pelvis, then adjacent catheters or a double lumen catheter is used. It is also possible to use a side connection tube configured as shown in FIG. 5 the water jacket/accessory channel thereof used to flush out debris during insertion and thereafter allow delivery into the pelvis of medication. Medication to be provided solely to the urinary tract is injected into a portacath in the pectoral region, while drainage is to a ductus side-entry jacket along the ureter or through a nonjacketing side-entry connector on the bladder. Drugs to treat the synthetic segment are injected into a portacath for emission through the accessory or service channel of the upper or proximal ductus side-entry jacket. Drugs to treat the tract distad the prosthetic segment are injected into a portacath for emission through the ductus side-entry jacket at the proximal end of the distal segment. The addition along any of these lines of a reservoir, transcutaneously recharged battery, and small assist pump allows an implant timer or microprocessor to govern the periodic delivery of medication.

The urinary tract cited in an exemplary sense, the use of more than one portacath allows analogous delivery of mediation to another bodily system. Rather than to employ a portacath with an internal switching mechanism to redirect the outflow among a number of catheters connected to different destinations, a more complex situation is responded to with a belt worn or shoulder suspended power, drug reservoir, and pump pack containing separate pumps and lines that prevent mixing among drugs moved through different lines. Fluid and electrical lines from the belt worn or shoulder suspended power and pump pack pass as independent channels through a multientrant port body wall affixed to the outer surface of the body, generally in the pectoral region.

Such a port, devised to avert skin breakdown, infection, and an adverse tissue response is described in copending application Ser. No. 14/121,365, entitled Ductus Side-entry Jackets and Prosthetic Disorder Response Systems. The outer layering of implants with sterile plasticizer-free polymers such as polyester usually results in fibrotic (collagenous) encapsulation without complications, eliminating or significantly reducing the need to deliver adverse reaction counteractive medication. Such medication should be reserved for instances where the initial adverse reaction fails to subside within the time expected. Otherwise, integral to the process leading to fibrous encapsulation, to interfere with the initial reaction actually hinders if not prevents acceptance.

More versatile drug delivery through a single port is A primary advantage in the interposition of a synthetic segment is avoidance of the need to harvest autologous ileum (Wolters, H. H., Palmes, D., Krieglstein, C. F., Suwelack, B., Hertle, L., Senninger, N., and Brinkmann, O. 2006. "Reconstruction of Ureteral Necrosis in Kidney Transplantation Using an Ileum Interposition," Transplantation Proceedings 38(3):691-692; Ghoneim, M. A. 2005. "Replacement of Ureter by Ileum," Current Opinion in Urology 15(6):391-392; Matlaga, B. R., Shah, O. D., Hart, L. J., and Assimos, D. G. 2003. "Ileal Ureter Substitution: A Contemporary Series," Urology 62(6):998-1001) or vermiform, or cecal, appendix (Yoon, B. I., Hong, C. G., Kim, S., Ha, U.S., Chung, J. H., Kim, S. W., Cho, Y. H., and Sohn, D. W. 2014. "Ureteral Substitution Using Appendix for a Ureteral Defect Caused by a Retroperitoneal Rhabdomyosarcoma in a Child," Korean Journal of Urology 55(1):77-79; Deyl, R. T., Averbeck, M. A., Almeida, G. L., Pioner, G. T., and Souto, C. A. 2009. "Appendix Interposition for Total Left Ureteral Reconstruction," Journal of Pediatric Urology 5(3):237-239; Estevao-Costa, J. 1999. "Autotransplantation of the Vermiform Appendix for Ureteral Substitution," Journal of Pediatric Surgery 34(10):1521-1523), for example, in a preliminary procedure which itself poses potential risks; avoidance of direct catheter to native ureteric tissue anastomosis with its complications; and the avoidance of anastomosis entirely, the foam jacket lining suffusable if necessary with anti-inflammatory or adverse tissue reaction-countering medication, to include phosphorylcholine or dexamethasone, for example.

That both proximal and distal segments remain vascularized means immune function should be little affected. After 60 years of experimentation, arteries remain poor candidates for ureteric grafting (Schein, C. J, Sanders, A. R., and Hurwitt, E. S. 1955. "The Fate of Fresh Autogenous Arterial Grafts Embedded in Submucosal Intestinal Tunnels as Applied to the Bridging of Ureteral Defects," Annals of Surgery 142(2):266-273; Sewell, W. H. 1955. "Failure of Freeze-dried Homologous Arteries Used as Ureteral Grafts," Journal of Urology 74(5):600-602), and veins have seldom shown the ability to adapt (Engel, O., de Petriconi, R., Vollmer, B. G., Gust, K. M., Mani, J., Haferkamp, A., Hautmann, R. E., and Bartsch, G. 2014. "The Feasibility of Ureteral Tissue Engineering Using Autologous Veins: An Orthotopic Animal Model with Long Term Results," Journal of Negative Results in Biomedicine 13:17; Wolters, H. H., Heistermann, H. P., Stoppeler, S., Hierlemann, H., Spiegel, H. U., and Palmes, D. 2010. "A New Technique for Ureteral Defect Lesion Reconstruction Using an Autologous Vein Graft and a Biodegradable Endoluminal Stent," Journal of Urology 184(3):1197-1203).

When the pelvis and ureter continuous with it are resected or irremediably damaged, a pyeloplasty to close off the pelvis and drain the urine according to the length of ureter lost involves less risk and complexity than a pyeloureterostomy with interposition of the appendix (see, for example, Jang, T. L., Matschke, H. M., Rubenstein, J. N., and Gonzalez, C. M. 2002. "Pyeloureterostomy with Interposition of the Appendix," Journal of Urology 168(5):2106-2107; Mesrobian, H. G. and Azizkhan, R. G. 1989. "Pyeloureterostomy with Appendiceal Interposition," Journal of Urology 142(5): 1288-1289. Due to advances in tissue engineering, a replacement length of ureter amenable to anastomosis should supplant such measures, and one that sustains peristaltic function should become available some time thereafter.

Where the kidney is unaffected and the need for drainage sought and a smaller segment of ureter is missing following resection or injury, the catheter or the catheter continuous with the needle depicted in FIG. 11 is run to a ductus side-entry jacket at the top of the ureteral remnant following transverse sectioning and uretetoplasty. Ureteric peristalsis is lost whether the problem segment is resected with the free ends sutured closed or not. In this situation, ceca (culs de sac, blind pouches) for bacteria to accumulate are reduced by placing the jacket coterminously with the free ends, and if necessary, an antimicrobial is delivered through the accessory channel, or sideline. Because the jacket side connectors incorporate accessory channels which can be use to run through antimicrobials and other drugs through such bypasses, these diversionary passages can remain in place indefinitely.

As shown in FIGS. 6, 13A, and 13B, intrarenal pathology which does not respond to medication delivered through a prerenal ductus side-entry jacket, that is, a drug delivery jacket placed along the renal artery, or where only a limited region within the parenchyma is to be the focus, may be targeted by intromission of a catheter, hollow injection and aspiration needle, hypotube, electrode, ultrasonic, electrohydraulic, or laser probe, scope, or any other kind of miniature styliform device. Complications associated with standard percutaneous nephrostomies tend to be few but serious (see, for example, Radecka, E and Magnusson, A. 2004. "Complications Associated with Percutaneous Nephrostomies. A Retrospective Study," Acta Radiologica (Stockholm) 45(2):184-188; Wah, T. M., Weston, M. J., and Irving, H. C. 2004. "Percutaneous Nephrostomy Insertion: Outcome Data from a Prospective Multi-operator Study at a UK Training Centre." Clinical Radiology 59(3):255-261).

In FIG. 11, the side connection tube 3 used as the nephrostomy drain fixed in position by a nonjacketing side-entry connector can be used to bypass an obstruction anywhere along the remaining (downsteam, distal) urinary tract thus averting hydronephrosis (uretohydronephrosis, nephrohydrosis, nephrydosis). Such a drain can be used to divert urine to a ductus side-entry jacket at any level along either ureter. If the ipsilateral ureter is obstructed or missing, the drain can divert to the contralateral ureter, or bypass the ureter and insert into the bladder through a nonjacketing side-entry connector such as 61 in FIG. 12B, or bypass the ureter and bladder by drainage through a ductus side-entry jacket positioned as would the urethral compression cuff of an artificial urinary sphincter about the urethra as shown in FIG. 12C. When connector 61 in FIG. 12B is used as in FIG. 12A to allow the inflow of a drug or drugs from pump 49, it either connects two separate lines or catheter 48 is dual luminal with flow through either lumen opposing that through the other. Assisted evacuation of the bladder is needed when the intrinsic function is abolished, whether at a higher level as in neurogenic bladder consequent to a wider paralysis or locally, as cystoparesis, or cystoplegia.

The urinary tract is here cited in an exemplary and not a limiting sense; any organ can be accessed at the blood supply to treat the organ as a whole, within the organ to treat a discrete lesion within it, or at the draining veins to treat blood as it departs from the organ. Using conventional means, irritation at the insertion into the kidney limits the time the line can be left without maintenance. A normal kidney is not immobile, some exhibit exceptional mobility (hypermobility, renal ptosis, nephroptosis, 'floating' kidney') and a kidney already diseased and left to rub against neighboring tissue may be the more susceptible to abrasive erosion. Such a kidney must be securely nephropexied before placement of a side-entry connector can even be considered.

With anti-infection measures included, a nonjacketing side-entry connector that allows a hollow needle, catheter, electrode, or combination of these to be stabilized in position within tissue at the entry wound into the organ or tissue and at the lesion or nidus to be targeted eliminates the circumstance that necessitates replacement of the catheter at relatively brief intervals. In this, permanent implantation using components previously limited to temporary use to treat permanent or chronic conditions in lieu of reconstructive surgery is intended. The other entry wound—that through the body wall into the body—suffers from the same shortcoming, and was addressed in copending application Ser. No. 14/121,365, entitled Ductus Side-entry Jackets and Prosthetic Disorder Response Systems, filed on 25 Aug. 2014. Firm and dependable connectors are imperative for the use of an automatic ambulatory control system to perform deliver treatment on the basis of diagnostics with no dependency upon the patient or a medical worker.

Prerequisite for the implementation of such a system are 1. A type fastener that will allow the rigid joining of a catheter to a native ductus so that the confluent luminae form a continuous passageway, and if in the vascular tree, then at an angle as to achieve the minimal shear stress; 2. A type fastener that will allow the rigid infixion of therapeutic and/or diagnostic catheters or electrodes, for example, within tissue, vascular beds, or solid organs so that the tip thereof is rigidly held at the required depth; and 3. An especially infection and leak resistant port for placement at the body surface that will allow transit of the integument by fluid and electrical lines that requires little maintenance. Copending application Ser. No. 14/121,365, entitled Ductus Side-entry Jackets and Prosthetic Disorder Response Systems, filed on 25 Aug. 2014 addressed the first two of these; the third is addressed below.

Where ductus side-entry connectors as described in copending application Ser. No. 14/121,365 are for joining catheteric to tubular anatomical structures to channel fluids such as drugs or blood from or to a vessel, nonjacketing side-entry connectors can be used to fasten catheters, electrodes, heating rods, angioscopes, sensors, different types of probes, or lasers, for example, so that the distal tips of these are fixed at a certain depth in an organ or vascular bed, for example, and will remain positioned thus indefinitely. The electrode can be singular or multiple point. Nonjacketing side-entry connectors for intracranial or spinal application are very small, stabilized with multiple knife switch-configured snap-clasps as will be described to securely grasp the outer meninges, and generally require placement with the aid of magnification.

Therapeutic electrodes adaptable thus, to include intracranial and cardiac applications, include active, dispersive or indifferent, gas absorbing, point or spark-ball, iontophoretic for delivering ionic medication, radiofrequency radiating; electrodessicative; electrocatalytic; electrocauterizing; electrocoagulative or electrohemostatic; electrocontracting; electroanalgesic; electroanesthetic; electrosleep; bone, muscle, or nerve electrostimulative; electrotherapeutic types direct or unidirectional current monophasic, alternating current biphasic, and pulsed polyphasic; simulating the action potential of the underlying muscle and/or fine nerves into which the needles penetrate, fulgurating; and warming. Sustained stimulation to treat gastroparesis, for example, might require single or multichannel high-energy long-pulse electrical stimulation (Kashyap, P. and Farrugia, G. 2010. "Diabetic Gastroparesis: What We Have Learned and Had to Unlearn in the Past 5 Years," Gut 59(12):1716-1726). The potential value of electroporation in this context remains to be determined. Some implanted electrodes can be focused more tightly when provided with an aiming disk implanted, or if outside the organ, then placed behind the target. Separately wired needles and electrodes can discharge independently or in any combination.

When the prospective range of treatment to be anticipated is unclear, a ductus, or jacketing, or nonjacketing side-entry connector can include separately electrifiable half round anchoring needles, an electrode, an electromagnet, and catheter at little additional cost. Rather than to risk the need to reenter, the type connectors indicated are placed from the outset for utilization as the need arises. Diagnostic electrodes adaptable for holding in place as sensors include those electroanalytic (chemical); electrodiagnostic (electrical); electrographic, such as electromyographic, erlectrocardiographic, electroencephalographic or electrocorticographic; calomel type to measure pH; gas-sending to measure gas partial pressure; ion-selective to sense the concentration of a given ion; and electrothermometric. With a nonjacketing side-entry connector providing the number of side connectors needed, any of these can be used in combination for any number of therapeutic and diagnostic purposes under the coordinated control of the master microcontroller.

In most instances, placement of a catheter to deliver a drug or blood, for example, or a discharge electrode, for example, is to treat a chronic condition or lesion under the control of a prosthetic disorder response system programmed to respond to sensors that input relevant physiological data; however, such means have application in accelerating the healing of transient conditions such as follow a surgical procedure. The tip of the catheter or electrode is additionally configured to achieve uniform dispersion or aimed delivery. A single fine catheter, and/or rod or pin configured electrode to be positioned with its tip fixed at a precise depth within an organ or tissue can be designed to deliver current or heat at its tip or along its entire length, and can be combined with other cable type device functions, such as a coaxial laser or a sensor to confirm the energy delivered and/or provide diagnostic data.

A coaxial probe incorporating the elements required can heat, discharge current, and with a dual lumen and mixing or educator nozzle, allow the mixing of two-part and other substances best combined upon emission. Using the scheme shown in FIG. 13A, side by side mounted devices can include a diagnostic sensing probe or detector and a therapeutic microelectrode, laser, hollow needle, or laser, for example, where drug delivery by or energization of the therapeutic device is modulated by a microcontroller The various drug and electrical components might fall under the control of a single node, which in a situation of comorbidity will be assigned to a specific organ system, but more often under different nodes whose actions are coordinated by the master controller.

While waist belt-mounted insulin pumps with a subcutaneously implanted hypodermic needle for the injection of insulin, for example, can be adapted to respond to blood glucose sensor implants with adaptive or learning capability, such an arrangement is not intended for and is not capable of drug targeting a circumscribed arterial supply territory or an organ with little if any entry or spillover into the systemic circulation. However, targeting thus is essential for avoiding adverse side effects as well as drug drug, and drug food interactions. In the treatment of localized chronic comorbidities, especially where the standard of care drug regimen appurtenant of one condition would conflict with that of another, the ability to isolate treatment sites can be critical.

A suitable circumstance where comorbid disease may be best controlled with automatic monitoring by sensor implants and the delivery of insulin and drugs to treat concurrent hypertension with an angiotensin converting enzyme inhibitor and angiotensin receptor blocker, or atherosclerosis with a statin, is diabetic nephropathy. By impeding progression to end-stage renal disease, which necessitates precise diagnosis and correctly measured treatment, survival is extended (see, for example, The Merck Manual 18th edition, 2006, page 2008). The automatic system functions continuously, and can do so in a mentally impaired patient.

Secure means for connecting lines that target circumscribed regions or organs makes possible automatic ambulatory prosthetic disorder response control systems which are able to treat comorbid conditions (see, for example, Hines, R. L. and Marschall, A. E. 2012. Stoelting's Anesthesia and Co-Existing Disease, Philadelphia, Pa.: Elservier Health Sciences) independently while monitoring, overseeing, and responding to any alteration in homeostasis or interactions between treatment sites. Intended for temporary use in the clinic, a central line, or central venous catheter is little exposed to the risks of accidental falls or collisions, and ambulatory indwelling catheters must limit activity, movement between the catheter and the tissue in contact with it eventually injuring the tissue. To avoid infection, catheters also require frequent changing and are unsuitable for permanent or even temporary placement without the activity of the patient considerably curtailed.

While this is true for an individual catheter, the implementation of an ambulatory prosthetic disorder response system hinges on the ability to place multiple catheters with little if any risk of infection or injury. Secure connectors to allow converging and diverging junctions to be made with anatomical lumina and secure junctions to be made with nontubular tissue such as at the surface of an organ are a prerequisite for the implementation of automatic ambulatory prosthetic disorder response systems. Such a system can include multiple channels or axes of control where each axis is applied, for example, to the treatment of an organ system or a portion thereof. Treatment in each such axis is governed by a control node in response to inputs from implanted sensors, and each control node in turn is subject to the coordinating and synchronizing control of a master microcontroller.

The use of such junctions is not limited to specialized systems but can also lessen the annoyance of ambulatory patients with catheters allowed to remain in place for a few days at a time. Urethral catheters such as a Foley are highly susceptible to "recurrent urinary tract infection, and in men, a high risk of urethritis, periurethritis, prostatic abscesses, and urethral fistulas" (The Merck Manual 18th edition, 2006, page 1961; see also, for example, Stafford, P. and Prybys, K. M. 2014. "Pyocystis and Prostate Abscess in a Hemodialysis Patient in the Emergency Department," Western Journal of Emergency Medicine 15(6):655-658; Leuck, A. M., Wright, D., Ellingson, L., Kraemer, L., Kuskowski, M. A., and Johnson, J. R. 2012. "Complications of Foley Catheters—Is Infection the Greatest Risk?," Journal of Urology 187(5):1662-1666; Zaouter, C., Kaneva, P., and Carli, F. 2009. "Less Urinary Tract Infection by Earlier Removal of Bladder Catheter in Surgical Patients Receiving Thoracic Epidural Analgesia," Regional Anesthesia and Pain Medicine 34(6):542-548).

Nonjacketing side-entry connectors are part of a drug targeting, diagnostic sampling, and measurement access technology introduced in copending application Ser. No. 13/694,835, which addressed the use of permanent magnets that copending application Ser. No. 14/121,365 extended to electromagnetic means and fluid piping. The barriers to the long term use of catheters to deliver drugs is the formation of biofilm, to transmit blood, biofilm and clot, and lines to divert crystallureic urine, the deposition and accretion along the internal walls of oxalate, urate, carbonate, or sulfate crystal. Ductus side-entry connectors and ductus side-entry jacket achieve long life by providing accessory channels to allow the targeted delivery into the connected lines of anticoagulants, antimicrobials, anti-inflammatories, and alkaline solvents, for example.

The infection rate of catheters generally and urethral catheters in particular is in part a result of the lack of a service or accessory source pump which can be used to introduce antimicrobials into the catheter without exposing the rest of the body and thereby prevent the formation of a biofilm (see, for example, Rasamiravaka, T., Labtani, Q., Duez, P., and El Jaziri, M. 2015. "The Formation of Biofilms by *Pseudomonas aeruginosa*: A Review of the Natural and Synthetic Compounds Interfering with Control Mechanisms," Biomed Research International; 2015:759348; Asai, K., Yamada, K., Yagi, T., Baba, H., Kawamura, I., and Ohta, M. 2014. "Effect of Incubation Atmosphere on the Production and Composition of Staphylococcal Biofilms," Journal of Infection and Chemotherapy pii: S1341-321X(14)00353-00355; Amalaradjou, M. A. and Venkitanarayanan, K. 2014. "Antibiofilm Effect of Octenidine Hydrochloride on *Staphylococcus aureus*, MRSA [methicillin-resistant *Staphylococcus aureus*] and VRSA [vancomycin-resistant *Staphylococcus aureus*]," Pathogens (Basel) 3(2):404-416; Lawi iski, M., Majewska, K., Gradowski, L., Foltyn, I., and Singer, P. 2014. "A Comparison of Two Methods of Treatment for Catheter-related Bloodstream Infections in Patients on Home Parenteral Nutrition," Clinical Nutrition (Edinburgh). pii: S0261-5614(14)00241-00246; Vuotto, C., Longo, F., Balice, M. P., Donelli, G., and Varaldo, P. E. 2014. "Antibiotic Resistance Related to Biofilm Formation in *Klebsiella Pneumoniae*," Pathogens (Basel) 3(3):743-758; Nicolle, L. E. 2005. "Catheter-related Urinary Tract Infection," Drugs and Aging 22(8):627-639).

Such a service or accessory pump can add any fluid state adjuvant substance, and when the catheter is used to move blood, an anticoagulant. To remain in place indefinitely, contact between the outer surface of fluid and electrical lines and the tissue lining and bounding the wounds through which the lines are passed, first, through the body wall and then, where these enter into tissue, must be connected as to disallow relative movement while least interfering with intrinsic movement, and induce no adverse tissue reaction that lasts for more than a brief interval, as well as seal off the wounds from pathogens. Long term use also necessitates means for preventing the accumulation of a biofilm or accretions whether due to crystallization, agglutination, or clotting. Even slight relative movement results in irritation.

Fixed and secure connection would not just allow extended use of otherwise conventional suprapubic cystostomy or nephrostomy lines but is an absolute essential for the implementation of an automatic ambulatory prosthetic disorder response system. The ability to provide secure junctions between prosthetic materials and native tissue is a prerequisite upon which the entire technology depends. While its various components must be described seriatim, the drug steering or targeting system contemplates numerous potential uses for these devices in combination. When comorbid conditions, for example, necessitate a tightly coordinated as well as targeted delivery of drugs, the automatic ambulatory delivery of drugs is placed under the synchronizing control of a master microcontroller.

The term 'nephrostomy' conventionally denotes the introduction of a catheter retained in the renal pelvis by a curled distal segment, or 'pigtail,' which is connected to an extracorporeal collection bag to provide drainage and/or draw diagnostic test samples. The line does not enter directly into the pelvis from outside the body but rather punctures entirely through the renal cortex and medulla, usually through the relatively avascular plane of Brodel. By contrast, to effect drainage or draw urinalysis samples where the tract distal to the pelvis is obstructed, a ductus side-entry jacket high up on the ureter and run to a ductus side-entry jacket placed as would the cuff of an artificial urinal sphincter to allow emission through the urethra and avoid the need for an external collection bag results in a much improved quality of life. Unlike the compression cuff, a ductus side-entry jacket is nonconstictive and therefore does not risk atrophy and erosion of the urethra.

Using the means described herein, except when the renal pelvis cannot be cleared, the parenchyma is perforated only to directly target a lesion within the kidney. A line to divert urine directly from the renal pelvis is shown in FIG. 11. Similarly here, the kidney is perfused to treat prerenal or intrinsic disease with a drug by delivery through a side-entry jacket placed on the renal artery. The drugs used are typically antimicrobial, urolith preventive, and anti-inflammatory. When a circumscribed lesion within the kidney and not the entire parenchyma is to be targeted, a hypotube, hollow (injection/aspiration) needle, or catheter is moved through the cortex and medulla to the depth desired. The position of the discharge end is fixed by a nonjacketing side-entry connector, and may be adjusted by a direct drive dc stepper micromotor with local microcircuit controller.

Since the distinct majority of drugs are not radioactive, FIGS. 13A and 13B are shown without radiation shielding, which is shown in FIGS. 10A and 10B. For precisely targeted Auger or Auger as adjuvant therapy, the motorized nonjacketing side-entry connector stabilizes and advances a hollow needle or fine catheter through the lesion. The radionuclide, delivered in a ferrofluid wherein it is bound to a superparamagnetic nanoparticle drug carrier, is drawn radially outward from the tip of injection needle as side connector 3 toward the outer surface of the renal tumor 41 in FIG. 13B by clasp-electromagnets 40 fastened about the fibrosal outer layer or Gerota capsule of the kidney. The same ferrofluid can also deliver a bound chemotherapeutic, for example. That the clasp mounting in clasp-magnets and clasp-electromagnets such as 40 in FIG. 13A might be replaced by more costly snap-clasps 5 in FIGS. 1 thru 4, 7, and 14, described in detail below in the section entitled Description of the Preferred Embodiments of the Invention, is considered obvious.

Where advancement of the needle or catheter as side connector 3 is essential, a nanometer-range normally locked spindle bidirectional piezoelectric direct-drive rotary stepper motor, for example (see, for example, Jou, J. M. 2014. "A Study on the Multiple Composite Piezoelectric Motor," Open Journal of Acoustics 4(2):55-69; Shieh, Y-J., Ting, Y., and Yeh, C-C. 2012. "High Speed Piezoelectric Motor," Proceedings of the Joint IEEE European International Symposium on Ferroelectrics and Polar Dielectrics, Aveiro, Portugal [ISBN 978-1-4673-2668-1], pages 1-3; Koc, B., Cagatay, S., and Uchino, K. 2002. "A Piezoelectric Motor Using Two Orthogonal Bending Modes of a Hollow Cylinder," IEEE Transactions on Ultrasonics, Ferroelectrics, and Frequency Control (4):495-500) or bidirectional ultrasonic direct-drive rotary stepper motor with circumferentially and axially-poled piezoelectric elements, for example (see, for example, Nishimura, Y., Tanaka, K., Wakasa, Y., and Nakamura, H. 2011. "Robust Angle Regulation for Ultrasonic Motor Using CLF-based Controller," 37th Annual Conference of the IEEE Industrial Electronics Society, Melbourne, Australia [978-1-61284-969-0] pages 716-721; Spanner, K. 2006. "Survey of the Various Operating Principles of Ultrasonic Piezomotors," White paper for the 10th International Conference on New Actuators and 4th International Exhibition on Smart Actuators and Drive Systems, Bremen, Germany; Chang, K-T., and Ouyang, M. 2006. "Rotary Ultrasonic Motor Driven by a Disk-shaped Ultrasonic Actuator," IEEE [Institute of Electrical and Electronics Engineers] Transactions on Industrial Electronics 53(3):831-837; Hagwood, N. W. and McFarland, A. J. 1995. "Modeling of a Piezoelectric Rotary Ultrasonic Motor," IEEE Transactions on Ultrasonics, Ferroelectrics, and Frequency Control 42(2):210-224) is preferred. The term 'direct-drive' denotes the direct, hence, backlash, or 'play'-free connection of the motor shaft to the biconcave driver roller shown in FIGS. 15 and 16. Patch-electromagnets, usually three, fastened at points to reciprocally subtend the target lesion are used to vector the adjuvant substance or radionuclide into tumor 41, shown in FIGS. 13A and 13B, radiation shielding as seen in FIGS. 10A and 10B omitted as exceptional and for visual clarity.

Pending reliable gene therapy, intrarenal Auger therapy, if facilitated, can be used, for example, to treat a malignant tumor, renal oncocytoma, or angiomyolipoma neoplasms, for example, within the kidney without radiation spillover. If detected as an incidentaloma with treatment begun upon discovery, metastasis and further progression to a more distributed lymphangioleiomyomatosis, to include a pneumothorax, for example, may be interdicted and impeded if not averted (see, for example, Jain, V. V., Gupta, O. P., Jajoo, S. and Khiangate, B. 2014. "Recurrent Pneumothorax in a Young Female with Pulmonary Lymphangiomyomatosis: A Case Report and Overview of Literature," Journal of Family Medicine and Primary Care 3(1):86-88; Gilbert, E. R., Eby, J. M., Hammer, A. M., Klarquist, J., Christensen, D. G., Barfuss, A. J., and 5 others 2013. "Positioning Ganglioside D3 as an Immunotherapeutic Target in Lymphangioleiomyomatosis," American Journal of Pathology 183(1):226-234; Bujalance-Cabrera, C., Vaquero-Barrios, J. M., Redel-Montero, J., Caballero-Ballesteros, L., Requejo-Jimenez, A., and Santos-Luna, F. 2012. "Reduction in Size of Renal Angiomyolipoma after Treatment with Everolimus in Lung Transplantation Due to Lymphangioleiomyomatosis," (bilingual English Spanish) Archivos de bronconeumologia 48(12): 479-481; Dilling, D. F., Gilbert, E. R., Picken, M. M., Eby, J. M., Love, R. B., and Le Poole, I. C. 2012. "A Current Viewpoint of Lymphangioleiomyomatosis Supporting Immunotherapeutic Treatment Options," American Journal of Respiratory Cell and Molecular Biology 46(1):1-5; Kim, D., Lee, S. N., Lee, S. K., and Lee, J. 2012. "Lymphangiomyomatosis Discovered by Massive Hemoptysis during General Anesthesia—A Case Report," Korean Journal of Anesthesiology 62(4):371-374) or as symptomatic or tuberous sclerosis complex (see, for example, Peng, Z. F., Yang, L., Wang, T. T. Han, P., Liu, Z. H., and Wei, Q. 2014. "Efficacy and Safety of Sirolimus for Renal Angiomyolipoma in Patients with Tuberous Sclerosis Complex or Sporadic Lymphangioleiomyomatosis: A Systematic Review," Journal of Urology 192(5):1424-1430; Bissler, J. J., Kingswood, J. C., Radzikowska, E., Zonnenberg, B. A, Frost, M., Belousova, E., Sauter, M., and 10 others 2013. "Everolimus for Angiomyolipoma Associated with Tuberous Sclerosis Complex or Sporadic Lymphangioleiomyomatosis (EXIST-2): A Multicentre, Randomised, Double-blind, Placebo-controlled Trial," Lancet 381(9869):817-824; Davies, D. M., de Vries, P. J., Johnson, S. R., McCartney, D. L., Cox, J. A., Serra, A. L., Watson, P. C., and 7 others 2011. "Sirolimus Therapy for Angiomyolipoma in Tuberous Sclerosis and Sporadic Lymphangioleiomyomatosis: A Phase 2 Trial," Clinical Cancer Research 17(12):4071-4081).

Except for some malignancies, with endoscopic placement on the anterior renal fascia, the procedure is safer than a less discriminating use of drugs, direct embolization of the renal artery, invasive wedge resection, partial nephrectomy or radical nephrectomy (see, for example, Urciuoli, P., D'Orazi, V., Livadoti, G., Foresi, E., Panunzi, A., Anichini, S., Cialini, M., and 5 others 2013. "Treatment of Renal Angiomyolipoma: Surgery versus Angioembolization," Giornale di chirurgia 34(11-12):326-331; Sivalingam, S., and Nakada, S. Y. 2013. "Contemporary Minimally Invasive Treatment Options for Renal Angiomyolipomas," Current Urology Reports 14(2):147-153).

The configurations diagrammatically depicted in FIGS. 6, 13A, and 13B are suitable for the direct injection into the renal parenchyma of sirolimus (rapamycin), for example. The addition of electromagnets fastened to the fibrosa or capsule allows the drug to be magnetically vectored stereotactically from the needle tip to the locus within the kidney or other organ. Where a radioactive component is included that cannot be flushed through and scrubbed at the surface, nondisingegrating permanent shielding as shown in FIG. 10A or temporary shielding as shown in FIG. 10B must be used. Broadly, the configuration shown in FIG. 6, with hollow needle or fine catheter fixed at depth once the patient is closed, is used for less precise targeting than is the piezomotor driven rigid hypotube or very fine hollow needle to allow advancement and retraction in literally nanometric increments depicted in FIG. 13B.

FIG. 13B shows that positioning patch-electromagnets 40 about the fibrosa also allows magnetic vectoring for Auger therapy, transfection, and other treatment that demand extreme precision. Patch-electromagnets 40 may be used with or without assistance from an extracorporeal magnet. A diffuse condition throughout a discrete organ or circumscribed blood supply territory is treated by placement of a ductus side-entry jacket on the supply artery. Connection to a discrete organ or tissue of a catheter or styliform device is with a nonjacketing side-entry connector. To treat a gradient-defined lesion or chemical imbalance within an organ or tissue, a driver and controls are incorporated into the side-entry connector. The gradual advancement through a pre-lesioned area or frank lesion of penetrable hardness to accomplish gradient responsive treatment in fine increments, such as by Auger therapy, transfection, or chemotherapy, is accomplished with the aid of a precision driver.

Research into the characterization of lesions according to contour and gradient and the diagnostic use of a gradient in the properties of tissue as it transitions from normal to and through a lesion, is not new and continues (see, for example, Lemercier, P., Paz Maya, S., Patrie, J. T., Flors, L., and Leiva-Salinas, C. 2014. "Gradient of Apparent Diffusion Coefficient Values in Peritumoral Edema Helps in Differentiation of Glioblastoma from Solitary Metastatic Lesions," American Journal of Roentgenology 203(1):163-169; Liu, Z., Sun, J., Smith, L., Smith, M., and Warr, R. 2012. "Distribution Quantification on Dermoscopy Images for Computer-assisted Diagnosis of Cutaneous Melanomas," Medical and Biological Engineering and Computing 50(5): 503-513; Erkol, B., Moss, R. H., Stanley, R. J., Stoecker, W. V., and Hvatum, E. 2005. "Automatic Lesion Boundary Detection in Dermoscopy Images Using Gradient Vector Flow Snakes," Skin Research and Technology 11(1):17-26; Wolfla, C. E., Luerssen, T. G., and Bowman, R. M. 1997. "Regional Brain Tissue Pressure Gradients Created by Expanding Extradural Temporal Mass Lesion," Journal of Neurosurgery 86(3):505-510; Wolfla, C. E., Luerssen, T. G., Bowman, R. M., and Putty, T. K. 1996. "Brain Tissue Pressure Gradients Created by Expanding Frontal Epidural Mass Lesion" Journal of Neurosurgery 84(4):642-647; van der Zwet, P. M. and Reiber, J. H. 1994. "A New Approach for the Quantification of Complex Lesion Morphology: The Gradient Field Transform; Basic Principles and Validation Results," Journal of the American College of Cardiology 24(1):216-224).

The gradual advancement of a stylus containing a sensing microelectrode probe mounted alongside a drug injection needle or electrode, for example, allows feedback from the sensor to be applied by a microcontroller to modulate the rate of drug delivery or application of the electrode emission over a tightly circumscribed region, for example. The controller with a nonstepper dc motor is provided with a negative feedback loop. At the same time, the delivery of adjuvant medication delivered through a supply artery through a ductus side-entry jacket, likewise under the coordinated control of the microcontroller regulating the pump, or through an injection needle such as shown in FIG. 6 at another angle selected for atrumatic access as well as efficacy can facilitate this action.

Telemetric readout provided, such a scheme can be made to function as fully implanted and semiautonomous. The conformation of a nonjacketing side-entry connector with nanometer range piezomotor, for example, incorporated, is indicated in FIGS. 13A thru 16. In FIG. 14, a drug delivery injection needle as side connector 3 can be made as long as necessary for the needle or other stylus tip to reach to the opposite boundary of the lesion. This requires that the needle tail or line outside housing 24 be soft as not to irritate, that junction 23 be brought sufficiently proximal so that it will not reach to the line entry aperture in the top of housing 24. If necessary, passage of the extended needle line through housing 24 is aligned by a sleeve. Radiation shielding of the motorized nonjacketing side-entry connector shown in FIG. 14 is analogous to that shown in FIGS. 13A and 13B.

Where the injectant is a ferrofluid, patch-electromagnets are positioned about the periphery of the organ so as to describe the zone or volume subtended for targeting. Depending upon the specific drug, the configurations shown in FIGS. 6, 13A, and 13B may allow healthy tissue to the rear of the needle tip to be spared from exposure to the drug. Such a compound or doublet styloid can deliver an antiangiogenic drug, such as bevacizumab or thalidomide, and/or a chemotherapeutic drug, such as doxorubicin or mitomycin C, or gas, and provided the lines and nonjacketing side-entry connector is radiation shielded, radionuclide. When the therapeutic fluid substance is magnetically drug carried into a discrete organ, electromagnets fastened about the organ can draw the drug radially outward from the end of a catheter or tip of an injection needle.

While the disorganized vasculature of a solid tumor results in reduced and sluggish blood flow that impedes penetration by a systemically introduced antineoplastic drug (see, for example, Rohwer, N. and Cramer, T. 2011. "Hypoxia-mediated Drug Resistance: Novel Insights on the Functional Interaction of HIFs [hypoxia-inducible transcription factors] and Cell Death Pathways," Drug Resistance Updates 14(3):191-201; Huang, L., Ao, Q., Zhang, Q., Yang, X., Xing, H., Li, F., Chen, G., and 6 others 2010. "Hypoxia Induced Paclitaxel Resistance in Human Ovarian Cancers via Hypoxia-inducible Factor 1 alpha, Journal of Cancer Research and Clinical Oncology 136(3):447-456; Ruan, K., Song, G., and Ouyang, G. 2009. "Role of Hypoxia in the Hallmarks of Human Cancer," Journal of Cellular Biochemistry 107(6):1053-1062; Huang, L. E. 2008. "Carrot and Stick: HIF [hypoxia-inducible transcription factor]-alpha Engages c-Myc in Hypoxic Adaptation," Cell Death and Differentiation 15(4):672-677; Yasuda, H. 2008. "Solid Tumor Physiology and Hypoxia-induced Chemo/Radio-resistance: Novel Strategy for Cancer Therapy: Nitric Oxide Donor as a Therapeutic Enhancer," Nitric Oxide 19(2):205-216; Brown, J. M. and Giaccia, A. J. 1998. "The Unique Physiology of Solid Tumors: Opportunities (and Problems) for Cancer Therapy," Cancer Research 58(7):1408-1416), repeated injection of the drug directly into the tumor in conjunction with disruption of blood flow altogether can be used to destroy the tumor. Taking the reverse approach, the scheme shown in FIG. 13B allows injecting the tumor with a nitrate such as nitroglycerin to facilitate systemic therapy.

Nidus targeting by mechanical routing is not dependent upon an intrinsic affinity for a certain tissue of an agent, as in the relation of the thyroid gland to iodine or the preparation of peptides and drug carrier nanoparticles, for example, for takeup by certain cells or organelles within the cells (see, for example, Biswas, S. and Torchilin, V. P. 2014. "Nanopreparations for Organelle-specific Delivery in Cancer," Advanced Drug Delivery Reviews 66:26-41; Ubah, O. C. and Wallace, H. M. 2014. "Cancer Therapy: Targeting Mitochondria and Other Sub-cellular Organelles," Current Pharmaceutical Design 20(2):201-222; Sakhrani, N. M. and Padh, H. 2013. "Organelle Targeting: Third Level of Drug Targeting," Drug Design, Development, and Therapy 7:585-599; Gao, W., Xiang, B., Meng, T. T., Liu, F., and Qi, X. R. 2013. "Chemotherapeutic Drug Delivery to Cancer Cells Using a Combination of Folate Targeting and Tumor Microenvironment-sensitive Polypeptides," Biomaterials 34(16):4137-4149).

However, agents that take advantage of formulation devised to target specific cells or organelles within the cells are still administered systemically. Directly piping the agent to the target fundamentally improves this approach. By combining intrinsic chemical targeting with direct piping bypasses unintended tissue, and delivers the agent quickly to the target at a higher pre- or post-hepatic concentration than might be introduced into the general circulation. In this combination, the piping targets the organ in a mass load, and the agent targets the tumor cells within the tumor or the intended organelles within the tumor cells. The alteration of the environment surrounding a hard tumor is also addressed below in connection with the combined uses of Auger, and external beam radiation and/or chemotherapy in the section entitled Auger Therapy.

Significantly, the agent can be formulated to pass through if not dispel the disordered region surrounding a hard tumor which serves it as a self protective barrier (see, for example, Khawar, I. A., Kim, J. H., and Kuh, H. J. 2015. "Improving Drug Delivery to Solid Tumors: Priming the Tumor Microenvironment," Journal of Controlled Release 201:78-89; Gao, W., Meng, T., Shi, N., Zhuang, H., Yang, Z, and Qi, X. 2015. "Targeting and Microenvironment-responsive Lipid Nanocarrier for the Enhancement of Tumor Cell Recognition and Therapeutic Efficiency," Advanced Healthcare Materials 4(5):748-759; Yang, Y., Yang, Y., Xie, X., Cai, X., and Mei, X. 2014. "Preparation and Characterization of Photo-responsive Cell-penetrating Peptide-mediated Nanostructured Lipid Carrier," Journal of Drug Targeting 22(10):891-900; Ishida, T. and Kiwada, H. 2013. "Alteration of Tumor Microenvironment for Improved Delivery and Intratumor Distribution of Nanocarriers," Biological and Pharmaceutical Bulletin; 36(5):692-697).

If the tumor, small notwithstanding, already shed daughter cells, then direct high dose more potent targeting of the tumor per se allows a reduction in the systemic or background chemotherapeutic drug dose compared to that needed to treat the tumor, substantially lessening severe adverse side effects (see, for example, Jones, R. G. A. and Martino, A. 2015. "Targeted Localized Use of Therapeutic Antibodies: A Review of Non-systemic, Topical and Oral Applications," [Online] Critical Reviews in Biotechnology January 20:1-15; Sakhrani, N. M. and Padh, H. 2013, Op cit.; Chen, X., Soma, L. A., and Fromm, J. R. 2013. "Targeted Therapy for Hodgkin Lymphoma and Systemic Anaplastic Large Cell Lymphoma: Focus on Brentuximab Vedotin," Onco Targets and Therapy 7:45-56; Phillips, M. A., Gran, M. L., and Peppas, N. A. 2010. "Targeted Nanodelivery of Drugs and Diagnostics," Nano Today 5(2):143-159; Viens, P., Tarpin, C., Roche, H., and Bertucci, F. 2010. "Systemic Therapy of Inflammatory Breast Cancer from High-dose Chemotherapy to Targeted Therapies: The French Experience," Cancer 116(11 Supplement):2829-2836; Robbins, K. T., Pelliteri, P. K., Vicario, D., Kerber, C. W., Robertson, J. H., Hanchett, C., and Howell, S. B. 1996. "Targeted Infusions of Supradose Cisplatin with Systemic Neutralization for Carcinomas Invading the Temporal Bone," Skull Base Surgery 6(2):69-76).

The application of this approach to Auger therapy allows the nidus of disease to be eradicated with less trauma than alternative methods of treatment to allow the organ to be spared from radical resection. In a patient with bilateral tumors, impaired kidney function, or only one kidney, preservation can avert the need for transplantation (see, for example, Grossman, H. B., Belville, W. D., Faerber, G. J., Konnak, J. W, and Ohl, D. A. 1997. "Genitourinary System," Chapter 109 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven; page 2209). If transplantation is needed, ductus and/or nonjacketing side-entry connectors make it possible to target the immunosuppressive medication to the transplant automatically. Auger therapy is addressed below in the section of like title.

The configuration shown in FIG. 6 with patch- or clasp-electromagnets added as shown in FIG. 13B allows a supraparamagnetic nanoparticle bound drug such as sirolimus, or rapamycin, to be magnetically steered into the tumor (see, example, El-Dakdouki, M. H., Pure, E., and Huang, X. 2013. "Development of Drug Loaded Nanoparticles for Tumor Targeting. Part 1: Synthesis, Characterization, and Biological Evaluation in 2D Cell Cultures," Nanoscale 5(9):3895-3903; Dakdouki, M. H., Pure, E., and Huang, X. 2013. "Development of Drug Loaded Nanoparticles for Tumor Targeting. Part 2: Enhancement of Tumor Penetration through Receptor Mediated Transcytosis in 3D Tumor Models," Nanoscale 5(9):3904-3911. Release thus in immediate proximity to the lesion minimizes the drug side effects, even as would affect adjacent renal tissue. Precise targeting reduces acute short term nephrotoxicity of unaffected or otherwise compromised tissue within the kidney.

In addition to short term nephrotoxicity, the potential side effects of sirolimus and everolimus include ototoxicity, neurotoxicity, and numerous others (see, for example, Ravaud, A. 2011. "Treatment-associated Adverse Event Management in the Advanced Renal Cell Carcinoma Patient Treated with Targeted Therapies," Oncologist 16 Supplement 2:32-44; Flechon, A., Boyle, H., and Negrier, S. 2010. "Management of Side effects Associated with Antiangiogenic Treatment in Renal Cell Carcinoma," (in French, English abstract at Pubmed) Bulletin du cancer 97:73-82; Cho, M. E., Hurley, J. K., and Kopp, J. B. 2007. "Sirolimus Therapy of Focal Segmental Glomerulosclerosis is Associated with Nephrotoxicity," American Journal of Kidney Diseases 49(2):310-317; Tumlin, J. A., Miller, D., Near, M., Selvaraj, S., Hennigar, R., and Guasch, A. 2006. A Prospective, Open-label Trial of Sirolimus in the Treatment of Focal Segmental Glomerulosclerosis," Clinical Journal of the American Society of Nephrology 1(1):109-116; Fervenza, F. C., Fitzpatrick, P. M., Mertz, J., Erickson, S. B., Liggett, S., and 7 others 2004. "Acute Rapamycin Nephrotoxicity in Native Kidneys of Patients with Chronic Glomerulopathies," Nephrology, Dialysis, Transplantation 19(5):1288-1292).

Key objects of nonjacketing side-entry connectors are to achieve the stable and entry enclosed connection of a catheter or hollow needle at the entry into an organ or other tissue. Degrees in increased relative movement with recession from the treatment site is addressed below in the section entitled Stereotactic Drug Steering by Magnetic Vectoring. Delivery into the parenchyma by puncture bypasses the vascular tree; for targeted vascular delivery, the renal artery is encircled by a ductus side-entry jacket. If injected as shown in FIG. 6, targeting in detail within the parenchyma is by stereotactic or magnetic steering obtained with patch-electromagnets positioned at points about the renal capsule to subtend the target, the drug then carried by superparamagnetic nanoparticles. Such a configuration, albeit confined to the plane of the drawing, is shown in FIG. 13B.

Analogous configurations apply equally to other organs and drugs, such as the direct delivery to the liver of a statin into the parenchyma or by release into the portal vein through a ductus side-entry jacket, for example. As shown in FIGS. 10A and 10B, when the radioactive therapeutic substance is not scrubbed much less easily flushed away, the delivery line is radiation shielded. For therapeutic modalities that use magnetic fields, such as the use of superparamagnetic nanoparticles to include superparamagnetic drug carrier assisted Auger therapy, and the intentional warming of implants by placing the patient in a radiofrequency alternated magnetic field, the nonsusceptibility to magnetic fields of these motors is a fundamental advantage. The use of multiple indwelling catheters indicated would preclude such treatment entirely.

Impasse jackets are described in copending application US 2014/0163664 filed on 9 Jan. 2013. The placement of permanent magnet impasse jackets along the ureters, for example, should be apprehended as implicit. The impetus for devising such means is the indispensability of safe and secure tissue connections for use in an automatic ambulatory prosthetic disorder response system as described in copending application Ser. No. 14/121,365 entitled Ductus Side-entry Jackets and Prosthetic Disorder Response Systems. However, the means for securing lines to be described as these pass through surgical wounds are applicable to the long term placement of prosthetic fluid and electrical conduits connecting an entry point at the surface of the body to an internal organ generally and especially as regards indwelling catheters.

Whereas magnetized ductus side-entry jackets may be viewed as combining a nonjacketing side-entry connector and an impasse jacket, separating these allows placing multiple impasse-jackets alongside lesions at numerous levels downstream, thus eliminating the need for piping to each and reducing the space taken up by the distributed implant as a whole. That the operation of digestive and urinary assist devices and prostheses is infrequent means that power consumption falls well within the ability of transcutaneous energy transfer to support. Unless a fluid line must connect to an external pump pack, this allows the elimination of a port at the body surface to pass electrical conductors through the body wall. The implant positioned and the entry wound healed, placement thus yields a fully implanted, closed-skin placement that eliminates the risk of infection by microbial incursion along lines that must traverse the integument.

Such power requirements can be satisfied by transcutaneous energy transfer at a distance by resonance recharging (see, for example, Wang, J. X., Smith, J. R., and Bonde, P. 2014. "Energy Transmission and Power Sources for Mechanical Circulatory Support Devices to Achieve Total Implantability," Annals of Thoracic Surgery 97(4):1467-1474; Waters, B. H, Sample, A. P, Bonde, P. and Smith, J. R 2012. "Powering a Ventricular Assist Device (VAD) with the Free-Range Resonant Electrical Energy Delivery (FREE-D) System," Proceedings of the Institute of Electrical and Electronics Engineers 100(1):138-149; Wang, B., Hu, A. P., and Budgett, D. 2012. "Power Flow Control Based Solely on Slow Feedback Loop for Heart Pump Applications," IEEE Transactions on Biomedical Circuits and Systems 6(3):279-286; Waters, B. H, Sample, A. P, Smith, J. R, and Bonde, P. 2011. "Toward Total Implantahility Using Free-range Resonant Electrical Energy Delivery System: Achieving Untethered Ventricular Assist Device Operation Over Large Distances," Cardiology Clinics 29(4):609-625; Roy, S., Jandhyala, V., Smith, J. R., Wetherall, D. J., Otis, B. P., Chakraborty, R., Buettner, M., Yeager, D. J., Ko, Y.-C., and Sample, A. P. 2010. "RFID: From Supply Chains to Sensor Nets," Proceedings of the Institute of Electrical and Electronics Engineers 98(9): 1583-1592; Dissanayake, T., 2010. An Effective Transcutaneous Energy Transfer (TET) System for Artificial Hearts, Doctoral 'Dissertation, University of Auckland, Auckland, New Zealand; Dissanayake, T., Budgett, D., Hu, A. P., Malpas, S., and Bennet, L. 2009. "Transcutaneous Energy Transfer System for Powering Implantable Biomedical Devices," in Lin, C. T. and Goh, J. C. H. (eds.), 13th International Conference on Biomedical Engineering, New York, N.Y.: Springer; pages 235-239; Bossetti, C. A. 2009. Design and Evaluation of a Transcutaneous Energy Transfer System, Dissertation, Department of Biomedical Engineering, Duke University, Durham, N.C.; Mussivand, T., Hum, A., Diguer, M., Holmes, K. S., Vecchio, G., Masters, R. G., Hendry, P. J., and Keon, W. J. 1995. "A Transcutaneous Energy and Information Transfer System for Implanted Medical Devices," American Society for Artificial Internal Organs (ASAIO) Journal 41(3):M253-M258; Miller, J. A. 1994. Transcutaneous Energy Transfer Device, U.S. Pat. No. 5,350,413; Mussivand, T., Miller, J. A., Santerre, P. J., Belanger, G., Rajagopalan, K. C., Hendry, P. J., Masters, R. G, and 5 others. 1993. "Transcutaneous Energy Transfer System Performance Evaluation," American Society for Artificial Internal Organs (ASAIO) Journal 17(10:940-947; Miller, J. A., Belanger, G., and Mussivand, T. 1993. "Development of an Autotuned Transcutaneous Energy Transfer System," American Society for Artificial Internal Organs Journal 39(3):M706-M710).

Resonance recharging systems are available, for example, from WiTricity, Inc., Watertown, Mass. and 3DVOX Technology, Huizhou, Huizhou, Guangdong, China. In addition, significant improvements in rechargeable batteries, such as the use of a stir-lengthened ultralong cross-linked-titanium dioxide/sodium hydroxide-based nanotube gel to provide increased power density, and therewith, faster charging rates, and much improved life expectancy, considerably increase the functionality of fully implanted, or closed-skin, power and therewith, any prosthesis that uses electrical energy (Tang, Y., Zhang, Y., Deng, J., Wei, J., Tam, H. L., Chandran, B. K., Dong, Z., Chen, Z., and Chen, X. 2014. "Nanotubes: Mechanical Force-driven Growth of Elongated Bending $TiO_2$-based Nanotubular Materials for Ultrafast Rechargeable Lithium Ion Batteries," Advanced Materials 26(35):6046; Chao, D., Xia, X., Liu, J., Fan, Z., Ng, C. F., Lin, J., Zhang, H., Shen, Z. X., and Fan, H. J. 2014. "Lithium-Ion Batteries: A V205/Conductive-Polymer Core/Shell Nanobelt Array on Three-Dimensional Graphite Foam: A High-Rate, Ultrastable, and Freestanding Cathode for Lithium-Ion Batteries," Advanced Materials 26(33): 5733; Tang, C., Zhang, Q., Zhao, M.-Q., Huang, J.-Q., Cheng, X.-B., Tian, G.-L., Peng, H. J., and Wei, F. 2014. "Lithium-Sulfur Batteries: Nitrogen-Doped Aligned Carbon Nanotube/Graphene Sandwiches: Facile Catalytic Growth on Bifunctional Natural Catalysts and their Applications as Scaffolds for High-Rate Lithium-Sulfur Batteries," Advanced Materials 26(35): 6199).

Whether for implementation independently under the control of dedicated fully implanted controller or as a module and channel or axis of control of an automatic ambulatory disorder response system, permanent synthetic, or catheteric, tubing for urinary diversion as described herein or for infusion as described in application Ser. No. 14/121,365, is devised to avoid the pitfalls of implantation which have prevented such use for decades. These consist of susceptibility to the formation of a biofilm lining, typically caused by *Staphylococcus aureus, Staphylococcus epidermidis*, or coagulase negative staphylococci (see, for example, The Merck Manual 18th edition, 2006, page 1388), and where blood is conveyed, occlusion due to clot. For application in prosthetic vascular grafts, for example, occlusion results from adhesion to the internal surface of the catheter and the coagulation of blood passing through, while occlusion in urogenital shunts or bypasses results from crystallization and accretion.

Through the use of catheters made of a hydrophilic materials having a smooth internal surface, usually a fluoropolymer such as polytetrafluoroethylene tubing used in accordance with the guidelines set forth in the foregoing and in this application thwarts the two factors that have prevented the use of synthetic tubing in the body—the formation of a biofilm and clot. Additionally, along the vascular tree, an accessory channel (service channel, sideline) attached to the primary or mainline is always provided to allow the targeted and tightly metered addition of an anti-coagulant, antiseptic, and/or anti-inflammatory as well as any other fluid medication into the blood or therapeutic fluid passing through the mainline. By substantially avoiding the systemic circulation, the targeted delivery of medication allows use of the drugs at higher concentrations for restricted site specific local application.

When necessary and available, a reversal agent or counteractant is delivered at the terminus or outer boundary of the tissue intended for exposure. Critically, targeting allows not only more concentrated dosing but the avoidance of adverse side effects, drug drug, and drug food interactions, and thus makes possible the use of existing drugs in concentrations not previously allowable. By projecting a jet of water or other therapeutic fluid to undercut and thus assist in extracting a plug of tissue cut by a cannula-like stem, or side-entry connector, for connection of the mainline catheter, with trepan (trephine) front edge as it is inserted, the sideline initially serves as an aid to connection of the mainline along the vascular tree or to a thicker wall of tissue such as the body wall.

Narrow trocars, hollow needles, and other fine gauge devices self incising, a trepan leading edge with crosshair tissue cutter, or crosshair cutter, such as shown in FIG. 5 is needed only when the rod-shaped device to be stably infixed in the subjacent tissue is a tube and inflow or outflow at the tube-tissue interface is to preserve the luminal cross sectional area of the tube. Trepan edge 21 is usually applied by connecting the mainline to an aspirator. A side connector or side stem, with trepan forward edge can be combined with a crosshair cutter with slight set back from the forward edge and a water jacket proper 31 as shown in FIGS. 1, 2, 5, 7, and 8. A water jacket is usually incorporated within the side connector 3 when a catheter as shown in the foregoing drawing figures, but not incorporated into a hypotube, electrode, heating element, or a hollow needle such as shown in FIGS. 13A and 13B.

As depicted in FIG. 14, a sideline used to deliver adjuvant medication into a hollow needle is connected to feed into the needle lumen through a side hole in the nonmetal catheter or tubing proximal to the junction with the needle proper. By the same token, when the catheter shown in FIG. 6 is replaced with a hollow needle, hypotube, electrode, or heating element, the water jacket is usually omitted as nonessential for insertion when the styloid device is made to penetrate tissue. Where an accessory channel is desired to supply adjuvant medication, for example, the accessory is run alongside the hollow needle or electrode, for example, from a subcutaneously, subrascially, or submuscularly place portacath, usually positioned pectorally. In FIG. 6, for example, access into the water jacket is outside the outer fibrous coat, or renal capsule. When the operator loosens locking collar or lock nut 20 used to secure the side connector 3 in position, the side connector can be rotated, withdrawn, or retracted.

On entering a blood vessel, water-jacket 31, with supply line 13 and inlet 23 serves to pressure flush the opening or ostium introduced into the vessel side, preventing the extravasation of blood. The same action serves to prevent the leakage of septic contents when entering the digestive tract, for example. Once placed, filling the side connector with medication or a plug prevent extravasation or leaking, and the water jacket serves as an accessory channel, or sideline, for the delivery of medication to the junction of the side-entry connector with the tissue entered. The water jacket/sideline must therefore be just short of coextensive with side connector or mainline 3. That is, it must extend distally to just short of the trepan leading edge 21 at the distal end of side connector 3 to the proximal origin of the line.

This may be a port at the body surface, where paired entry holes allow access to the mainline and its respective sideline, or accessory channel, or an implanted pump preceded or not by a reservoir. In either case, the pump or pumps are actuated automatically by a microcontroller, itself implanted. To minimize tissue disruption by shifting or abrading, power and control components may be positioned in a separate pocket readily accessed through a small incision. With a surface port, the introduction of medication is from outside the body, either manually, or automatically by a pump or pumps within a belt-worn pump, power, and control pack. Such a port at the body surface can provide a central opening for insertion of a fine fiberoptic endoscope or angioscope.

The entry holes respective of each line can also serve to allow an endoscope to be passed down to the treatment site. Turning now to FIG. 5, which shows the leading edge of side connector 3 with water jacket/accessory channel consisting of part numbers 13, 23, and 31, when a ductus side-entry jacket is placed about a blood vessel, crosshair cutting wires 22 is omitted as thrombophylic. The vessel wall relatively thin, aspiration through the mainline with trepan edge 21 flush against the outside of the vessel drives the trepan through the vessel wall, extravasation minimized by water ejected from the water jacket, which is aspirated away through the mainline.

The flush water ordinarily includes an antimicrobial, an anti-inflammatory, and an anticoagulant, the volume of which is far too small to induce an adverse platelet reaction, or thrombocytopenia. When entering the gut, for example, except that the side connector used includes the fine titanium crosshair cutter, the use thereof is by reciprocal rotation by hand, and the anticoagulant is omitted, the same process is used to prevent the spillage of septic contents. Once placed, mainline and sideline can be coordinated in different ways. Either or both can be used feed forward or aspirate a liquid or gas. The use of either is coordinated with the use of the other, usually by contributing supportive medication and/or fluid flow.

Subcutaneous tunneling is conventional, as with a portacath. Deep tunneling through tissue is to be avoided in favor of the least traumatizing route from the implanted pump or extracorporeal pump pack as origin to the point of entry as destination. An examination of FIG. 5 will make it apparent that the water jacket, which unlike the irrigation line in a high speed dental drill, or hand piece, must deliver flush water in a circular pattern, and its supply line consisting of parts 13 and 23 cannot be kept stationary by means of a swivel at the same time that the proximal end of the side connector is inserted within the chuck of a rotary tool.

For this reason, if conditions necessitate tunneling through tissue, either a separate catheter without a water jacket but with a trepan leading edge and crosswire cutter is used with sufficient aspirative force to draw the cutting edge through the tissue without rotation. The tissue gratings cut by the crosshair cutting wires are then not aspirated out through the side connector as it rotates but rather allowed to accumulate in the line to be flushed out afterward. Another approach, which has the advantage that the lumen is patent for flow in either direction and therefore allows aspiration through the catheter lumen, is the use of such a catheter having a rotary joint and external planetary epicyclic gear train where the catheter as side connector is encircled with a sun gear and the handpiece serves as carrier.

Yet another approach, one which blocks the lumen and omits the water jacket, is to attach a rotary tool to the proximal end of the catheteric side connector with cutting end for use as a high speed 'drill.' Once the treatment site is reach, such a tunneling side connector is withdrawn and replaced with one having a water jacket. Because it is essential to constrain penetration to that path calculated to least disrupt the anatomy, deep tunneling disallows the use of a catheter more than slightly flexible. Alternative tunneling tools such as mechanical and fine-cable lasers available, the choice among these depends upon the anatomical particulars, such as the proximity of ganglia and whether anticoagulants were used. The use of suitable imaging equipment must be presumed.

For less tenacious tissue, the trepan with water jacket without crosshair cutter is adequate to undercut and expel the tissue plug out through the line. The side connector may be either integral to as the distal segment of the supply (incurrent) or outflow (excurrent) line as supplied or a separate side-stem associated with the nonjacketing side-entry connector made as part of the line. The side connector extends abductally or away from the ductus to be served only so far as is necessary to place the nonjacketing side-entry connector, and the line connected to it sufficiently flexible to least encroach upon or abrade against neighboring tissue. Provided the line is properly routed, flexible, and is given sufficient slack, flexion or bending at its junction with the baseplate is not a problem. If a tight placement makes flexibility at the junction necessary, tubing flexible due to intrinsic elasticity or convoluted geometry is used.

A motorized side connector such as shown in FIGS. 13A thru 16 is reserved for precise advancement and retraction of the side connector in such applications as numerically controlled extreme proximity electron radiation, and is not needed for gross anatomical surgery, for example. The motor can move the hypotube, hollow (injection/aspiration) needle, catheter, or electrode the nonjacketing side-entry connector is used to fix in position in linear or longitudinal reciprocation but not oscillatory rotation. Should the plug 'hang,' an aspiration (vacuum, suction) line or guidewire with hooked tip is passed down the catheter to extract the plug. Because the water jacket remains as an accessory line allowing the delivery of drugs into the side connector, few side connectors should lack this feature. To prevent the unintentional avulsion of adjoining tissue or clogging of the water jacket, connection of a powerful suction pump to the water jacket to draw away tissue debris is to be avoided.

Manual side to side reciprocating rotation of the trepan with crosshair cutter cuts through any but hard connective tissue, and the expelling force of the water jacket and vacuum force through the catheter or mainline connected to the side connector (side stem, side line) will extract that tissue. Provided a crosshair cutter will not pose a problem with accretion or clot following placement, the ability to slice out the tissue as the trepan is advanced rather than to extract it in the form of an intact plug facilitates removal. The water jacket is used to flush the removed tissue out through the catheter, an aspiration line not normally needed. The trepan is usually applied by connecting the mainline to a suction pump. Connection of the mainline to a tubular anatomical structure, or ductus, is by means of an encircling jacket, whereas connection to nonductal tissue is by means of the type connector further to be described herein.

For entry into solid tissue, the trepan can be rotated when the lock nut is loosened. If the trepan and water jet fail to extract the plug, then a finer catheter connected to a more powerful vacuum is passed down the mainline to the face of the plug to pull it out of the line. Along the urinary tract, crystallization is prevented by targeting a drip of a counteractant or solvent keyed to the type crystal at the highest level along the tract providing the best combination of simplicity to apply and efficacy. With respect to FIG. 11, citrate and/or bicarbonate (Pinheiro, V. B., Baxmann, A. C., Tiselius, H. G., and Heilberg, I. P. 2013. "The Effect of Sodium Bicarbonate upon Urinary Citrate Excretion in Calcium Stone Formers," Urology 2013 82(1):33-37), for example, can be delivered through one lumen of a double lumen nephrostomy catheter, the other lumen used for drainage to a point farther down the tract. If this is the only catheter involved, the catheter is connected directly to a portacath such as 46 in FIGS. 12A and 12C.

For ease and economy of manufacture, baseplate aperture 4 is made circular in certain standardized diameters, thus averting the need for differently configured central apertures. So long as mainline or side connector 3 is not radiation shielded, accessory or service channels that enter mainline or side connector 3 to deliver an adjuvant into mainline 3 above the level of aperture 4 can run alongside mainline as side connector 3. As shown in FIGS. 10A and 10B, to preserve the circularity of baseplate aperture 4, when side connector 3 as mainline is shielded, accessory channels (service channels, sidelines), to include water jacket feed line 13, are run down through the inside of side connector 3.

The value in preserving circularity also greater when shielding is used, because mainline 3 must pass through a central aperture in the roof of the portion of radiation shield 71, or radiation shield cap, used to cover over the side-entry connector. Generally then, accessory channels or sidelines which deliver water or one or more adjuvants, for example, into the mainline just before the mainline passes down through aperture 4—primarily water jacket feed line 13—because these do not run down through aperture 4 unless shielding is necessary, can run alongside the mainline as side connector 3.

The methods and apparatus described herein are not intended to compete with or to supplant devices used for short-term placement as relates to the removal or calculi or to treat temporary obstruction, inflammation, or infection but rather to treat conditions which are chronic and/or incurable. Neither are established procedures that achieve good results with equal or less trauma than the placement of an implant, such as a retropubic cystourethropexy. With respect to FIG. 12A, of the two lines, the citrate and/or bicarbonate, for example, is delivered through upper line 48. In progressively distal order, drainage from the renal pelvis as shown in FIG. 11 can empty into:

a. A ductus side-entry jacket placed along the ipsilateral or the contralateral ureter, the drainage catheter routed to bypass the obstruction.

b. A nonjacketing side-entry connector placed to empty into the bladder as the upper line in FIG. 12A. If medication is to be delivered into the bladder, a second nonjacketing side-entry connector with catheter routed to the portacath or other port at the body surface is used, or separate catheters, one for drug delivery, the other for drainage, are routed to the same connector.

c. The urethra. With either of two means for imparting urinary continence described below, the need for an external collection urostomy bag is eliminated. This improvement in the quality of life is discounted only when placement of a urethral ductus side-entry jacket is inadvisable.

d. An external urostomy bag. Such is reserved for situations where to introduce either of two means for achieving urethra-noncompressive continence described below must be discounted.

If the urethra is obstructed, precluding application of either the electromagnetic check ball device shown in FIG. 12B or the diversion catheter without an in-line pinch valve bypass sphincter shown in FIG. 12C, a bypass sphincter is included in the bypass 52. If urethral obstruction or trauma disallows bypassing to the bulbar urethra, then and only then is a drainage catheter as shown in FIG. 12A led to an external urostomy bag through a surface port type nonjacketing side-entry connector described in copending application Ser. No. 14/121,365 entitled Ductus Side-entry Jackets and Prosthetic Disorder Response Systems.

1. When the bladder outlet, or neck, and/or the urethra of an incontinent patient is unobstructed, the check valve shown in FIG. 12B is placed. An ataxic, dystonic, or dyssynergic detrusor is also shocked by electrical discharge from the semicircular, or half round, anchoring needles 6 and/or medicated if the needles are hollow or an injection needle or hypotube is inserted through baseplate aperture 4. Additional connectors are fastened about the surface of the bladder as necessary.

2. When the patient would be continent but the bladder outlet, or neck, and/or the proximal urethra is obstructed or missing, a bypass line without in-line pinch valve diverting to the bulbar urethra through a ductus side-entry jacket as shown in FIG. 12C is placed.

3. Should the patient with incontinence already corrected by placement of a check valve as shown in FIG. 12B later experience a bladder outlet or urethral obstruction or resection, a bypass line diverting to the bulbar urethra through a ductus side-entry jacket as shown in FIG. 12C is added. With incontinence already resolved, the bypass omits an in-line pinch valve, instead relying on the existing check valve shown in FIG. 12B.

4. Should the patient with the bypass shown in FIG. 12C without bypass in-line pinch valve become incontinent, then depending upon which approach is least traumatic, either the check valve shown in FIG. 12B is added or a pinch valve inserted in the existing bypass.

5. When the patient would be incontinent and the bladder outlet or proximal urethra obstructed at the outset, the bypass shown in FIG. 12C with bypass in-line pinch valve is placed.

6. When the bladder is atonic or ataxic, the devices shown in FIG. 12B for the treatment of incontinence and FIG. 12C for the treatment of bladder outlet obstruction without a sphincter in the bypass and outlet obstruction with incontinence with the addition of the sphincter can be supplemented with nonjacketing side-entry connectors fastened about the surface of the bladder. Control of detrusor contraction thus is addressed below in the section entitled Targeted Electrical and/or Chemical Autonomic Motor Assistance.

7. As shown in FIG. 12D, if bladder contraction effected by electrical stimulation lacks sufficient strength to adequately empty the bladder, clasp-electromagnets as described in copending application US 2014/0163664, or if adjuvant drug or electrical support is needed, nonjacketing side-entry connectors mounting electromagnets, are fastened to the superior surface of the bladder in opposing relation to [iron] disks 67 and 68.

Disks 67 and 68 are polymerically encapsulated for chemical isolation and inserted subserously on the inferolateral surface toward the bladder neck so that the patient with intact trigonal pressure sensation is able to press a switch causing the bladder to contract. To minimize any abnormal sensation, the magnets are selected to secure the least abrupt action using the least effective field strength, and care is taken to position the magnets to simulate intrinsic contraction. The light weight and support of the median and lateral umbilical ligaments make it possible to eliminate electrical wires, the negligible weight added by remote radio control and transcutaneous or transdermal energy transfer in lieu of wiring well tolerated. Placement at points about a cystoparetic (cystoplegic) bladder of nonjacketing side-entry connectors with electrified needles under the control of a microcontroller implanted within a pectoral pocket is less likely to cause pain than is a neuromodulatory pulse generator implanted in the pelvis.

Much the same may be said for a dystonic or ataxic gall bladder or gastroparetic (gastroplegic, gastoparalytic) stomach likewise electrostimulated by connectors attached at points about the organ surface. Moreover, a microcontroller with nonjacketing side-entry connectors can coordinate treatment using prokinetic drugs and various electrical discharge pulse patterns in one or plural organs until that regimen optimal for the patient has been found empirically through electrogastrography and patient reaction. The foregoing applications of nonjacketing side-entry connectors that include delivery or draining fluid and/or electrical lines or clasp-electromagnets which do not, and ductus side-entry jackets, as depicted in FIGS. 12A thru 12D, have been separated for clarity; patients often present incontinence, obstruction, atony, or ataxia in combination. For example, for a patient with both an obstructed outlet and a dystonic bladder, the solutions depicted for either condition in FIGS. 12B and 12D respectively can be combined.

For this reason, the arrangements depicted should be understood as usable in the combination appropriate for the patient. Thus, provided electromagnets are properly adjusted in field strength and if necessary, in position, the check valve iron-silicon crystal-lined stopper ball 65 with overhead electromagnet 66 in FIG. 12B and the iron-silicon crystal-filled lifing plates 67 and 68 with overhead electromagnets 69 and 70 can be merged to omit the overhead magnet 66 in FIG. 12B. While preferably located as shown in FIG. 12D, should deviation from the normal anatomy dictate, the clasp-electromagnets 68 and 69 and iron lifing plates 67 and 68 can be positioned elsewhere about the outside surface of the bladder. By the same token, by adjusting the current, magnets 69 and 70 in FIG. 12D can be adjusted in field strength and if necessary, in position, to lift check valve ball 65 in FIG. 12B. To later change the field strength of any magnet by increasing the current is accomplished remotely. However, to change the position of these requires reentry.

In every instance, the position and field strength of these components, to include the addition, omission, or repositioning of any is thoroughly tested and optimized before closing the patient. Neither should cross sectional views impart an understanding limited to the planar: in shape, a variably mixed spherical/scaphoid volume, the normal bladder is markedly variable in conformation. This circumstance is considered in the actual placement of the connectors and magnets, which are placed at the angle and anteroposterior position along the superior and inferolateral surfaces of the bladder to best simulate normal function. These remedies avert the need for the harvesting, reconstruction, and misplacement of gut or other uninvolved tissue much less the need for catheters or an external collection bag, which necessitating a breach in the body wall, leaves the patient with a stoma susceptible to irritation and infection as well as degrades the quality of life.

Equally important, surgical reconstructions and artificial urinary sphincters are not configured for integration into a wider homeostasis maintenance or backup prosthetic 'immune' system, for drug targeting with built in channels and channel accessory channels that make possible the life long maintenance of synthetic materials. For example, with respect to FIG. 12B, nonjacketing side-entry connector 61 fastened alongside the superior surface of the urinary bladder aside from clasp-electromagnet 66 and stopper ball 65, which constitute the urinary check valve, includes aperture 4 through baseplate 1, best seen in FIG. 1 for connection of a catheter as side connector 48, led to a portacath to deliver medication during and following placement.

This mainline will include a service channel for the delivery of line maintenance and therapeutic drugs and solutions. If the patient already suffers from interstitial cystitis, or bladder pain syndrome, the portacath with line is placed ab initio. The side-entry connector can thus deliver hydroxyzine, pentosan polysulfate, amitryptiline, or cimetidine from the outset. Furthermore, the anchoring half round needles if hollow can be used to inject botulinum toxin A or deliver neurostimulation electrotherapy, or neuromodulation, at the treatment site, rather than at a higher level at the sacral root or pudendal nerve where the pertinent fibers may not be affected while impertinent fibers are. Current sacral neuromodulators are not equipped to deliver drugs, much less coordinate such delivery with the electrical discharge.

Initial placement of a connector or connectors having separately wired conductive anchoring half round needles 6, allows the use of individual or grouped needles, in opposing pairs for example, as an anode and cathode. Discharges can conform to any monophasic, biphasic, or multiphasic sequence and/or spatial pattern. This can be extended by adding connectors or through the use of a more expansive connector such as those shown in FIGS. 4 and 20. While the synchronization of the heart necessitates relatively large anode and cathode paddles, the delivery of current through the half round needles is not percutaneous with the resistance of the integument and skeletal muscles intervening, the needles are embedded within the target tissue, unless the heart itself, the muscle mass addressed is much less, and the neurological dysfunction to be corrected is not a complex arrhythmia but a relatively simple atony or ataxia.

Sufficient miniaturization of remote implants so that these function without connection by fluid and/or electrical lines to a centralized implanted power and control center requires that these incorporate transcutaneous energy transfer, inmate power source, and radio remote control receiver. This is not practicable for the foreseeable future; the release of drugs by the half round needles is through fluid and electrical discharge into the substrate tissue through electrical connection to a central power source with transcutaneous energy transfer receiving, remote radio signal transmitting, drug reservoir if needed, and controls implanted in its own pocket or pockets.

The routing of fluid and electrical lines decided on the bases of proximity and nonencroachment upon tissue, the pocket is placed subdermally in the pectoral region near the portacath or body surface type nonjacketing side-entry connector as described in copending application Ser. No. 14/121,365 when required, or placed within the parietal cavity. Initial positioning of the control center is not on the basis of the initial diagnosis alone but rather the probable need to add channels to other organ systems. When, as the result of trauma or surgical resection, the higher level nerve is gone, direct stimulation at the target thus is still practicable as well as more effective. If the portacath is unnecessary at the time of placement, it can be added laparoscopically through keyhole incisions as conditions warrant.

With reference to FIGS. 12A and 12D, where paralysis with neurogenic bladder or dementia exist so that external bag 59 is necessary and would not represent as significant an impediment, the use of a synthetic conduit or catheter with origin at a ureter through a ductus side-entry jacket or a nonjacketing side-entry connector such as 62 at the level of the trigone shown as catheter 51 leading to a body surface type nonjacketing side-entry connector as described in copending application Ser. No. 14/121,365, entitled Ductus Side-entry Jackets and Prosthetic Disorder Response Systems, is placed. If the patient is a stone former, a simple portacath connected to an accessory channel of connector 62 allows an anticrystallization agent to be injected. If the implanted arrangement includes microcontroller 53, administration of the agent is automatic. In this and most practical systems, other components associated with microcontroller 53, such as those to allow transdermal charging, are omitted.

Unlike an ileal conduit with rosebud stoma surgically fabricated of tissue not lined with urothelium but to the contrary, with tissue adapted for absorption, susceptible to infection, and irritation, a conduit, and if unavoidable, a port made entirely of synthetic materials do not appropriate and divert healthy tissue from its inherent and orthotopic to a vulnerable and ectopic location and function. While it is a least preferred option reserved for the patient unable to accept a ball check or diversion catheter pinch valve to allow urethral emission, with an accessory channel to prevent the formation of a biofilm and periodically wet the lumen with an antimicrobial, a synthetic line and terminus port is still less susceptible to infection and tissue degradation than is a conduit or stoma made of living tissue. An antimicrobial can also be delivered into the renal artery through a ductus side-entry jacket.

In FIG. 12A, lower nonjacketing side-entry connector 62 provides the diversionary drainage outlet, and upper nonjacketing side-entry connector 61 provides a portal for the targeted delivery to the bladder of drugs. For the most part used independently, these connectors can be used together to flush through or lavage the bladder with a medicated solution, for example. Within the context of a hierarchical adaptive ambulatory prosthetic disorder response system, the delivery of drugs through upper connector 61 in FIG. 12A is controlled by a separate urinary tract axis or channel of control, other control nodes directed to the treatment of other organs or organ systems. In FIG. 12A, drainage is passive and continuous as is essential when, for example, trigonal sensation is impaired so that urgency is not felt.

Referring now both to FIGS. 12A and 12B, provided the patient is mentally competent, continuous passive drainage with the need for catheter 51 and external bag 59 is eliminated. A strain gauge sensor positioned at the trigone, for example, is used to generate a tactile signal for the patient to go to the bathroom where a subcutaneously implanted keyless entry type radio control switch is used to energize electromagnet 66, lifting check valve stopper ball 65 away from the bladder outlet. If additionally the bladder outlet and/or the urethral tract is obstructed, a bypass as shown in FIG. 12C and described below is used. Where the neurological deficit is more extensive, the native external sphincter can be synchronously released by electrostimulation, a small electrode positioned with a nonjacketing side-entry connector used.

With reference to the hierarchical control program of the microcontroller, a dedicated urinary tract control node can also deal with problems of bladder atony in a number of ways. When a marketed sacral neuromodulator or conventional technique (see, for example, Sakas, D., Simpson, B., and Krames, E. S. (eds.) 2007. Operative Neuromodulation, Volume 1: Functional Neuroprosthetic Surgery. An Introduction, Vienna, Austria: Springer) is not preferred or incompatible with the disorder response system microcontroller, nonjacketing side-entry connectors can fix electrode side connectors for sacral or pudendal nerve stimulation. The current can be delivered thus and/or through the half round anchoring needles. The electrical source can be an implanted battery under the control of an implanted microcontroller with battery charged by transcutaneous (transdermal) energy transfer. If needed infrequently, body-generated energy can be direct or stored. If the atony is intermittent, a thin film strain gauge type sensor implanted within the detrusor is used to report a complete or partial failure to contract.

Having been designed for styliform and cabled device interchangeability, the nonjacketing side-entry connector attaching and guiding the side connector, or side stem, to which the catheter is connected allows relatively quick endoscopic side connector exchange. In this, the approach is much closer in degree of trauma, complexity, and the risk of complications to the direct percutaneous needle-and-catheter access of a suprapubic cystostomy than to open surgical construction of an ileal conduit and stoma, for example. Where conventional practice necessitates much intricate dissection, that required to place the means to be described is less extensive or predisposing to iatrogenic injury.

As attested to by the literature cited below, compared to the placement of a conventional hydraulic forcible constriction or pinch-type artificial sphincter, which necessitates access to each of three separate sites for insertion of the components, access to implant the noncompressive device shown in FIG. 12B can be accomplished with relatively negligible trauma and risk of complications, and that shown in FIG. 12C little more trauma than is caused by placing the ductus side-entry connector seen as cuff 63 alone. In this, it warrants emphasis that placement of an hydraulic artificial sphincter, especially when accompanied by a prosthesis to impart erectile function, imposes more trauma. The check valve device for reinstating urinary continence shown in FIG. 12B and described below, for example, calls for laparoscopic entry into the pelvic cavity to place a single component through the superior surface of the urinary bladder. To do so requires two small entry wounds, the first through the body wall, the other through the superior surface of the bladder.

By contrast, to place a conventional hydraulic sphincter involves the separate placement of three components in far more intricate locations. The first noncompressive continence reinstatement device to be described an electromagnet and susceptible stopper ball in a check valve arrangement, is held in position by a nonjacketing side-entry connector in the superior surface of the bladder. The other, using an electromagnetic sphincter as a pinch valve along a catheteric drainage line—not the urethra—is held in position by a nonjacketing side-entry connector placed toward the bottom of the bladder. Both are fully, or closed-skin, implanted, with no port or collection bag either outside or inside the body wall.

Instead, the battery is energized by means of transdermal charging that will eventually recharging generated by movement of the body itself. Moreover, the size of the components required is small enough that discomfort following healing should be avoidable in almost every case. Since neither of the continence devices to be described maintain the urethra in a constant state of constriction at a level not adapted to this condition until flow is allowed, both avoid the urethral atrophy and erosion that—unless the patient dies before it becomes necessary—are likely to ensue, necessitating an even more intricate and complication prone revision.

Conventional approaches to the bulbar urethra in order to place the compression cuff of an hydraulic artificial urinary sphincter are detailed in the literature (see, for example, Wiedemann, L., Cornu, J. N., Haab, E., Peyrat, L., Beley, S., Cathelineau, X., and Haab, F. 2013. "Transcorporal Artificial Urinary Sphincter Implantation as a Salvage Surgical Procedure for Challenging Cases of Male Stress Urinary Incontinence: Surgical Technique and Functional Outcomes in a Contemporary Series," BJU [British Journal of Urology] International 112(8):1163-1168; Kandpal, D. K., Rawat, S. K., Kanwar, S., Baruha, A., and Chowdhary, S. K. 2013. "Single Piece Artificial Urinary Sphincter for Secondary Incontinence Following Successful Repair of Post Traumatic Urethral Injury," Journal of the Indian Association of Pediatric Surgeons 18(4):152-154; Segal, R. L., Cabrini, M. R., Harris, E. D., Mostwin, J. L., Bivalacqua, T. J., and Burnett, A. L. 2013. "Combined Inflatable Penile Prosthesis-artificial Urinary Sphincter Implantation: No Increased Risk of Adverse Events Compared to Single or Staged Device Implantation," Journal of Urology 2013 190(6):2183-2188; Amend, B., Toomey, P., and Sievert, K. D. 2013. "Artificial sphincter," Current Opinion in Urology 23(6):520-527; Roupr t, M., Misrai, V., Vaessen, C., Cardot, V., Cour, F., Richard, F., and Chartier-Kastler, E. 2010. "Laparoscopic Approach for Artificial Urinary Sphincter Implantation in Women with Intrinsic Sphincter Deficiency Incontinence: A Single-centre Preliminary Experience," European Urology 57(3):499-504; Wilson, S. K., Aliotta, P. J., Salem, E. A., and Mulcahy, J. J. 2010. "New Enhancements of the Scrotal One-incision Technique for Placement of Artificial Urinary Sphincter Allow Proximal Cuff Placement," Journal of Sexual Medicine 7(10):3510-3515; Mandron, E., Bryckaert, P. E., and Papatsoris, A. G. 2010. "Laparoscopic Artificial Urinary Sphincter Implantation for Female Genuine Stress Urinary Incontinence: Technique and 4-year Experience in 25 Patients," BJU [British Journal of Urology] International 106(8):1194-1198; Singh, S. K., Pawar, D. S., Khandelwal, A. K., Jagmohan, P. 2010. "Transperineal Bulboprostatic Anastomotic Repair of Pelvic Fracture Urethral Distraction Defect and Role of Ancillary Maneuver: A Retrospective Study in 172 Patients," Urology Annals 2(2):53-57; Lane, B. R., Abouassaly, R., Angermeier, K. W., and Montague, D. K. 2007. "Three-piece Inflatable Penile Prostheses Can Be Safely Implanted after Radical Prostatectomy through a Transverse Scrotal Incision," Urology 70(3):539-542; van der Horst, C., Naumann, C. M., Wilson, S. K., Wefer, B., Braun, P. M., and Junemann, K. P. 2007. "Dysfunctions of Artificial Urinary Sphincters (AMS 800) and Their Management via a Transscrotal Access. Optimum Procedure Illustrated by Reference to Clinical Examples," (in German, abstract at Pubmed) Urologe A. (12):1704-1709; Roth, C. C., and Winters, J. C. 2006. "Insertion of Artificial Urinary Sphincter with Preservation of Bulbospongiosus Muscle in Patients at Risk for Sphincter Erosion: An Assessment of Patient Satisfaction," Ochsner Journal 6(2):54-58; Wilson, S. K and Delk, J. R. 2nd. 2005. "Ectopic Placement of AMS 800 Urinary Control System Pressure-regulating Balloon," Urology 65(1):167-170; Wilson, S. K., Delk. J. R. 2nd, Henry, G. D., and Siegel, A. L. 2003. "New Surgical Technique for Sphincter Urinary Control System Using Upper Transverse Scrotal Incision," Journal of Urology 169(1):261-264; Guralnick, M. L., Miller, E., Toh, K. L., and Webster, G. D. 2002. "Transcorporal Artificial Urinary Sphincter Cuff Placement in Cases Requiring Revision for Erosion and Urethral Atrophy," Journal of Urology 167(5): 2075-2079).

Moreover, such a cuff, usually a component in an artificial urinary sphincter as a single purpose or independent device needed to suppress urinary incontinence, often appears in a more complicated context, such as conjoint placement with a urinary diversion system, double cuff arrangements, and/or an erectile prosthesis (see, for example, Segal, R. L., Cabrini, M. R., Harris, E. D., Mostwin, J. L., Bivalacqua, T. J., and Burnett, A. L., 2013, Op cit., section above entitled Background of the Invention; Rolle, L., Ceruti, C., Sedigh, O., Timpano, M., Destefanis, P, and 6 others 2012. "Surgical Implantation of Artificial Urinary Device and Penile Prosthesis through Transscrotal Incision for Postprostatectomy Urinary Incontinence and Erectile Dysfunction: Synchronous or Delayed Procedure?," Urology 80(5):1046-1050). Incontinence and erectile dysfunction often follow a radical prostatectomy, for example, which might also necessitate diversion.

The recent use of an antibiotic coating notwithstanding (Amend, B., Toomey, P., and Sievert, K. D. 2013, Op cit.), infection is the primary short term cause of artificial urinary sphincter failure, and cuff compression and atrophy of the urethra the secondary, longer term cause (see, for example, Isiah, M. A. R., Cho, S. Y., and Son, H. 2013. "The Current Role of the Artificial Urinary Sphincter in Male and Female Urinary Incontinence," World Journal of Mens Health 31(1): 21-30; Montague, D. K. 2012. "Artificial Urinary Sphincter: Long-Term Results and Patient Satisfaction," Advances in Urology (online) 2012:835290; Guralnick, M. L., Miller, E., Toh, K. L., and Webster, G. D. 2002, Op cit.). Such cuffs may be single or double (see, for example, O'Connor, R. C., Lyon, M. B., Guralnick, M. L., and Bales, G. T. 2008. "Long-term Follow-up of Single Versus Double Cuff Artificial Urinary Sphincter Insertion for the Treatment of Severe Postprostatectomy Stress Urinary Incontinence," Urology 71(1):90-93; O'Connor, R. C., Gerber, G. S., Avila, D., Chen, A. A., and Bales, G. T. 2003. "Comparison of Outcomes after Single or DOUBLE-CUFF Artificial Urinary Sphincter Insertion," Urology 62(4):723-726).

Performance of a conventional hydraulic artificial urinary sphincter is considered satisfactory when no more than a single absorption pad is needed per day (Montague, D. K. 2012, Op cit.). Revision with a conventional hydraulic artificial urinary sphincter poses greater risk for damaging small nerves and vessels than does the original procedure, tandem cuff arrangements and combined placement with an erectile prosthesis, for example, unlikely to prove satisfactory over a period of more than a few years. With fewer parts and nonhydraulic operation, the devices shown in FIGS. 12B and 12C are less susceptible to leaks or malfunctions. For example, were ball stopper 65 in FIG. 12B to become lodged in the bladder outlet, or neck, merely increasing the current to direct current (dc) electromagnet 66 until ball stopper 65 is retracted quickly remedies the problem without the prospect of reentry even poorer odds for long term success.

While unlikely, a failure or electromagnet 66 to become energized, preventing drainage is easily avoided through redundancy, the electrical line and light weight magnet doubled. While ordinarily only one of the magnets would be used, this makes it possible to surge the current to both magnets, thus doubling the field strength to retract a stopper ball that had become lodged in the neck. By comparison, the hydraulic device appropriates much more space, is positioned in more intricate anatomy, and is not amenable to redundancy. Separating two electromagnets connected to the superior surface not only allows combining their tractive field strengths to retract the stopper ball along the joint path of traction, or resultant, of the two vectors, but allows either to pull at the ball alone, or both to be alternated, thus nudging the ball from side to side until it dislodges, which eventuality is emphasized, is highly improbable.

Less necessary still is the need to implant both the device shown in FIG. 12B and that shown in FIG. 12C to have either as a backup drainage route should the other malfunction. Unless a preexisting condition prompts it, such an arrangement should never be necessary. Where the problem is incontinence, such as following a prostatectomy, the stopper ball, or check valve, device shown in FIG. 12B is preferred for use alone, the pinch valve flow controlled drainage line reserved for situations where the condition of the bladder, such as a benign tumor at the superior surface, prohibits placement of the electromagnet. The bladder a scaphoid volume of which the superior surface describes a more or less acute triangle, only a tumor of considerable anteroposterior extension would eliminate a position to place the magnet or separately positioned magnets. In that case, the device shown in FIG. 12C is used.

The post prostatectomy patient will often experience erectile dysfunction, and unlike an hydraulic artificial urinary sphincter, the application of the check valve device shown in FIG. 12B is well removed from the sites for implantation of a penile prosthesis. Hypothetically, since it is highly improbable, with the arrangements shown in FIGS. 12B and 12C combined, should electromagnet 66 shown as singular in FIG. 12B or as doubled fail to energize, pinch valve 60 along drainage line 52 to the distal urethra through ductus side entry jacket 63 shown in FIG. 12C serves as a backup drainage route from lower connector 62 into the distal urethra through ductus side-entry jacket 63, thus averting the need for an emergency suprapubic cystostomy and an external collection bag. In the diagrammatic rather than anatomical depiction of FIG. 12C, side-entry jacket 63 is shown at an interval distal to the prostate if circumstances necessitated additional space to place line 52 and external sphincter 60.

In FIG. 12A, part number 58 is a body surface port type nonjacketing side-entry connector of the kind described in copending application Ser. No. 14/121,365, entitled Ductus Side-entry Jackets and Prosthetic Disorder Response Systems, and part number 59 is an external collection bag used when the magnetic pinch valve type electromagnetic artificial sphincter 60 for achieving continence next to be described cannot be placed. The use of such a bag is least preferred, and admitted when neither the device shown in FIG. 12B nor 12C is applicable, as following a pelvic exenteration, or evisceration when diversion to the distal colon is not possible, or when death is near. In that case, continent drainage is to an external collection bag through a body surface port type nonjacketing side-entry connector at the body surface described in copending application Ser. No. 14/121,365, entitled Ductus Side-entry Jackets and Prosthetic Disorder Response Systems.

When the bladder outlet or neck is obstructed or missing, or the internal and/or external urinary sphincter is functionally impaired or missing, a diversion path to include a prosthetic sphincter, for distal reconvergence with the bulbar or membranous urethra through a ductus side-entry jacket, as shown in FIG. 12C is placed. Such a bypass uses an electromagnetic pinch valve as a prosthetic sphincter. The patient remotely controls the sphincter with a radio keyless entry type switch (not shown), thus eliminating the need for an external collection bag 59 in FIG. 12A. When continence remains intact despite an obstruction or stricture of the proximal urethra, or a segment of the urethra has been resected, the impasse is bypassed with urinary diversion line 52 shown in FIG. 12C, electromagnetic in-line pinch valve prosthetic sphincter 60 then omitted.

Otherwise, the devices of FIGS. 12B and 12C are not used together, check valve stopper ball 65 incontinence remediation device shown in FIG. 12B used to impart continence. In FIG. 12C, diversion line 52 drains through ductus side-entry jacket 63 which has a side connector that passes through the extraurethral tissue to converge with the urethra at an angle to minimize shear stress. In a male, ductus side entry jacket 63 is placed as would the cuff of an hydraulic artificial urinary sphincter. In a prostatectomized male or a female, jacket 63 is placed along the intracorporeal urethra. A ductus side-entry jacket differs from the cuff of an hydraulic incontinence prosthesis in that it is noncompressive, has no moving parts, and is unaccompanied by two other components that must also be implanted in a region containing numerous small nerves and vessels.

Such a drainage line has a segment of a nonallergenic polymeric rubbery tubing with a polymeric biodegradation-proof encapsulated thin elemental iron disk along one side of the lumen and a small neodymium iron boron permanent magnet encapsulated to isolate the toxic magnet on the opposite side. The permanent magnet holds the iron disk, compressing the tube between disk and magnet so that urine cannot pass. An electromagnet positioned diametrically across the lumen from the permanent magnet when energized with the radio switch overpowers the permanent magnet, forcing the disk away from the permanent magnet, opening the lumen. The bladder outlet remains unstopped until the patient presses the switch, worn as a watchband or subcutaneously implanted on the inside of the wrist a second time, whereupon electromagnetic check valve stopper ball 65 drops back down to drop into, thus obturating the bladder outlet. Dissection of the lower esophageal sphincter to encircle it within such an electromechanical sphincter requires suturing the adjacent diaphragm to prevent the effect of a sliding hiatal hernia.

Alternatively, when the stopper ball check valve continence device shown in FIG. 12B is not used, in-line pinch valve sphincter 60 in FIG. 12C and described above provides continent control, bypass line 52 along which pinch valve 60 is positioned affording diversion to the urethra. Other parts in FIG. 12C are defined in the section below entitled Description of the Preferred Embodiments of the Invention. In FIG. 12A, upper connector 61 and lower connector 62 are shown longitudinally disposed relative to the plane of the section for visual clarity; in actuality, either or both connectors can be oriented perpendicular or off-perpendicular to the plane of the drawing, the upper to avoid encroaching upon the ureters if closely positioned, the lower to allow closer proximity to the bladder outlet, or neck, in a nonprostatectomized male as represented in FIG. 12C.

Thus, the arrangement shown in FIG. 12B allows continent urinary function with considerably less trauma to place than does an hydraulic artificial sphincter, and that shown in FIG. 12C not only imparts continence but bypasses an obstruction, whether prostatic or due to a traumatically destroyed segment of the distal urethra between the bladder and the bulbar urethra, for example, to allow voiding through the urethra in a manner externally indistinguishable from that normal, an external collection bag eliminated. In a patient with incipient dementia, diversion line 51 is placed ab initio. If the advancement of the dementia appears to be rapidly progressive, body surface type nonjacketing side entry connector 58 is also placed. If mental deterioration is projected to take years, then a suprapubic cystostomy is performed to relieve the pressure and the threat of hydronephros, for example, and connector 58 and external collection bag 59 placed. Voluntary control lost, urinary diversion to bag 59 is continuous through connector 62.

Electrification of the half round needles in the nonjacketing side-entry connector atop the bladder in FIG. 12B and toward the bladder neck in FIG. 12C, which can be supplemented by a lead or electrode running parallel to the fluid delivery side connector, allows neuromodulation secondary and supportive of these primary functions (see, for example, McGee, M. J., Amundsen, C. L., and Grill, W. M. 2015. "Electrical Stimulation for the Treatment of Lower Urinary Tract Dysfunction after Spinal Cord Injury," Journal of Spinal Cord Medicine. (2):135-146; van Kerrebroeck, P. E., van Voskuilen, A. C., Heesakkers, J. P., Lycklama a Nijholt, A. A., Siegel, S., Jonas, U., and 10 others 2007. "Results of Sacral Neuromodulation Therapy for Urinary Voiding Dysfunction: Outcomes of a Prospective, Worldwide Clinical Study," Journal of Urology 178(5):2029-2034). In neurogenic bladder dysfunction, to include spinal cord injured patients, bladder neuromodulation increases bladder capacity by more than 100 milliliters (Persu, C., Braschi, E., and Lavelle, J. 2014. "A Review of Prospective Clinical Trials for Neurogenic Bladder: The Place of Surgery, Experimental Techniques and Devices," Central European Journal of Urology 67(3): 270-276; Radziszewski, K. 2013. "Outcomes of Electrical Stimulation of the Neurogenic Bladder: Results of a Two-year Follow-up Study," NeuroRehabilitation 32(4):867-873). Electrical stimulation may thus eliminate the need for an augmentation cystoplasty.

At the same time, augmentation cystoplasty accompanied by conduit construction that takes gut and reforms it into a continent stoma requiring catheterization (Khavari, R., Fletcher, S. G., Liu, J., and Boone, T. B. 2012. "A Modification to Augmentation Cystoplasty with Catheterizable Stoma for Neurogenic Patients: Technique and Long-term Results," Urology 80(2):460-464) is eliminated by placement of a bypass sphincter, diverting urine to the bulbar urethra. Eliminated thus are the augmentation cystoplasty, the appropriation, reconformation, and misplacement of gut, diversion from the urethra to a stoma, and the need to catheterize the stoma with loss in the ability to void through the urethra.

That is, in a nonprostatectomized male, the connector is positioned horizontally just above the prostate gland, whereas in a proctatectomized male or a female, the connector is positioned at the level of the bladder neck, or outlet. The use of an external collection bag least preferred, other configurations can use a nonjacketing side-entry connector fastened toward the neck for drainage through a second nonjacketing side-entry connector fastened by means of a nonjacketing side-entry connector to empty into the distal colon. The rectum will sometimes afford a collection cistern with anal continence. If the distal colon and or rectum are also dysfunctional, then two options are to fasten nonjacketing side-entry connectors with electrified half round needles as pulse electrodes to the distal colon and/or rectum, or to divert the urine to the bulbar urethra.

When the internal sphincter is to be preserved, this is ectopically through a bypass electromagnetic pinch valve sphincter that runs in parallel to the urinary tract as shown in FIG. 12C, from a onductus side-connector at the bladder neck to a ductus side-entry jacket at the bulbar urethra. When the sphincter must be excised, the electromagnetic pinch valve sphincter is positioned orthotopically to replace the native sphincter. If neither route for voiding through the meatus is possible, a surface port type nonjacketing side-entry connector as described in copending application Ser. No. 14/121,365, entitled Ductus Side-entry Jackets and Prosthetic Disorder Response Systems, with external bag is used.

To the extent that the actual condition of the patient dictates the best response, certain generalizations can be made concerning the placement of sphincters as orthotopic, or inserted to replace a portion of the tract, or nearby but ectopic to bypass the native sphincter. As shown in FIG. 12C, because the urinary tract is nonabsorptive and without distinctions in function along its length, the placement of a bypass sphincter to replace a dysfunctional native internal urinary sphincter arouses little concern compared to an analogous treatment along the gut. If circumstances recommend or necessitate a more circuitous routing or tunneling of a urethral bypass, the patient will readily adapt to the time lag and momentary loss of sensation over the bypassed segment prior to voiding at the meatus.

Along the gut, however, distinctions in digestive function from segment to segment recommend an in-line graft over a bypass and as short a prosthetic segment as possible. Impairment in peristalsis across the prosthesis is compensated for by electrical stimulation. While the in-line graft is end to end anastomosed, nonjacketing side-entry connectors placed to supply drugs or electrical stimulation as necessary, the bypass is joined craniad and caudad by ductus side-entry jackets able to provide the same support. If left well vascularized, the bypassed segment should undergo some disuse atrophy but not be resorbed, allowing reversal in a young patient with an impairment that for which an etiological remedy becomes available.

A bypass sphincter along the nonabsorptive and relatively passive urinary tract of a patient with intact urge sensation will rarely necessitate more control than that afforded by a remotely controlled radio switch on a wristband or implanted subdermally. By contrast, a sphincter along the fully involuntary and metabolically differentiated digestive tract, however, necessitates deglutition and segmental metabolic sensors, as well as peristaltic support leads or electrodes. These modulate the delivery of enzymes and hormones as necessary, and may be fixed in position or included in ductus side-entry jackets and nonjacketing side-entry connectors used to position drug delivery lines.

Control of these sensors, electrodes, and drug delivery lines is by an implanted microcontroller, with power preferably replenished by transdermal charging. Preservation of the native sphincter always preferable; consideration is given to the use of an assist device only when more conservative medical and/or surgical treatment has proven ineffective, and to the placement of a prosthesis when dysfunction or loss due to trauma or following the resection of malignant tissue leaves no other recourse. In almost every case, a hypertrophic pyloric stenosis or a chronically spasmic pyloric sphincter, for example, is treated by longitudinal pyloromyotomy through laparoscopic access, leaving intact the muscosa and inner, or adaxial, layers of the lumen.

An atonic sphincter which has not responded favorably to electrical and/or pharmaceutical neuromodulation or surgery is encircled within a sphincteric assist device, which is an electromagnetic pinch valve placed to encircle the native sphincter. By contrast, an artificial or prosthetic sphincter, or graft prosthesis, differs from an assist device in including a synthetic or tissue engineered replacement tract wall. To least disrupt the digestive process, when the native sphincter must be excised, the segment including the prosthetic sphincter is kept as short as possible, a nonjacketing side-entry connector placed just past the distal anastomosis to trigger peristalsis and deliver medication as necessary. The use of graft prostheses should become less objectionable the more tissue engineered ductus approximate normal function.

The use of a surface port type nonjacketing side-entry connector in this way constitutes a new vesicorectomy (cystoproctostomy, cystorectostomy, vesicoproctostomy, vesicorectostomy) not subject to the sequelae encountered with earlier surgical connections between these structures (Webster, G. D. and Peterson, A. C. 2005. "History of Urinary Diversion Techniques," in Kreder, K. J. and Stone, A. R., Urinary Diversion: Scientific Foundations and Clinical Practice, Abingdon-on-Thames, England: Taylor and Francis). Drainage into the sigmoid colon placed in apposition to the bladder, or a cystosigmoidostomy, or vesicocolostomy, is not preferred; of these urine diversion routes, that led to the urethra is preferred as not directing urine through digestive conduit adapted to absorb rather than urothelium lined conduit adapted to resist the potentially corrosive effects of frequent exposure to urine.

Incontinence whether due to an incompetent internal urinary sphincter or any other cause is dealt with by means of a ball check valve that seals the bladder neck, eliminates both compression of the urethra and the need for an external collection bag, and is implanted with substantially less dissection and in a fraction of the time compared to the artificial sphincters now marketed. Diversion past an obstruction in the upper urinary tract is from a takeoff ductus side-entry jacket or nonjacketing side-entry connector through a catheter with accompanying accessory channel to an outlet ductus side-entry jacket or nonjacketing side-entry connector. Such differs from past applications of synthetic tubing in that both connectors have accessory channels that allow drugs or therapeutic solutions to be delivered into the line and receiving portion of the urinary tract.

The accessory channel of the takeoff connector is supplied by injection into a portacath, the substance then flowing into the drainage catheter. This allows the catheter and distal tract to be protected against the formation of a biofilm, accretion of crystalline deposits along the lumen wall, and an anticholinergic drug or drugs such as darifenacin, oxybutynin, fesoterodine, and others to be used to treat an overactive bladder, for example. Significantly, in that it might justify delivery thus in itself, drugs delivered thus are targeted, so that common side effects of anticholinergics, such as fatigue, accelerated heart rate, double vision, incoordination, and photophobia, among others are avoided. The accessory channel of the outlet connector allows the same treatment at and distad the level at which the tract is rejoined.

Continent diversion from any level along the urinary tract to the distal colon which eliminates the need for an external collection bag, is accomplished by means of an entry level (origin, takeoff) nonjacketing side-entry connector or ductus side-entry jacket connected to a catheteric line that leads to through a side-entry connector into the distal colon. Provided the distal colon provides continence and signals that it is filled, a reservoir with strain gauges to signal the patient the need to void by switching the remote radio switch to actuate the pinch valve sphincter described above is not necessary. That is, because a direct line to the distal colon is simple, direct, can eliminate the need for a bladder with intact urge sensation or a reservoir with sensors to signal when it is full, it is likely to be applicable following an anterior pelvic exenteration.

If urinary diversion to the distal colon would not provide continence by the anal sphincter and/or signal the need to void, then using the means described herein, diversion remains to the distal colon, except with the interpositioning of storage and continence imparting components. The condition is treated as would an anterior or total pelvic exenteration, by placement of a synthetic bladder, or reservoir, with outline line in-line electromagnetic pinch valve sphincter to serve as an artificial urinary sphincter through compression of a catheter, not urothelium. Without side-entry connectors or jackets equipped with accessory channels to directly target drugs or maintenance solutions to the junction and outlet or drainage line, routing thus, essentially no different than the earliest diversion path used (Webster, G. D. and Peterson, A. C. 2005, Op cit.), is not dependable over the long term.

Continent diversion from the upper urinary tract directly to the bulbar urethra, eliminating the need for an external collection bag, is accomplished with an implant reservoir of which the outlet line includes an bypass pinch valve sphincter as addressed above. Such a disposition follows an anterior or total pelvic exenteration, for example. If the ureters remain, the origin of diversion is through ductus side-entry jackets about these; otherwise, the origin can be through a nephrostomy catheter fixed in position by a nonjacketing side-entry connector as shown in FIG. 11. In order to open the lumen or passageway, the wearer depresses a radio remote keyless entry type control switch to energize a dc electromagnet opposite the permanent magnet, thereby overpowering the permanent magnet.

To avoid encroachment upon neighboring tissue, the core of the electromagnet is bent around, or folded. Using this mechanism, the patient can be reinstated to urinary continence even if the bladder is missing, the takeoff then from a ureter through such a line as just described and a ductus side-entry jacket with side connector giving access to the bulbar urethra. Except for procedure avoidance in the feeble and the patient unable to use the implant system, leaving these as the only justifications for the continued use of an external collection bag, the means described herein can achieve continent diversion in any patient.

While ductus side-entry jacket 63 in FIG. 12C is positioned about the urethra as is the compression cuff of an hydraulic prosthesis, unlike a single or double sphincter cuff, which compressive, can induce urethral atrophy or erosions, a ductus side-entry jacket is not compressive and does not require as much dissection as does the placement of a constriction cuff pinch valve type artificial sphincter. Dissection and anastomosis in this area can cause much injury to include urethral stricture, incontinence, impotence, and retrograde ejaculation (see, for example, Kandpal, D. K., Rawat, S. K., Kanwar, S., Baruha, A., and Chowdhary, S. K. 2013, Op cit.), and the junction created can be directly accessed for the delivery of drugs or solutions introduced through the upper side-entry connector in FIG. 12A or through the accessory channel of the urethral side-entry jacket. In this way, ductus side-entry jackets make possible procedures that eliminate the need for an external collection bag.

A ductus side-entry jacket applied to a ureter or the urethra is noncompressive and is not susceptible to the ecompression necrosis that resulted with Foley's original artificial urinary sphincter of 1949 (see, for example, Trost, L. and Elliott, D. S. 2012. "Male Stress Urinary Incontinence: A Review of Surgical Treatment Options and Outcomes," Advanced Urology 2012:287489). While more recent artificial urinary sphincters are much improved in this regard, compressive degradation of the urethra remains the single most problematic sequela, often necessitating revision that requires remedial surgery as well as the removal and replacement or resituation of the cuff (see, for example, Rahman, N. U., Minor, T. X., Deng, D., and Lue, T. F. 2005. "Combined External Urethral Bulking and Artificial Urinary Sphincter for Urethral Atrophy and Stress Urinary Incontinence," BJU [British Journal of Urology] International 95(6):824-826; DiMarco, D. S. and Elliott, D. S. 2003. "Tandem Cuff Artificial Urinary Sphincter as a Salvage Procedure following Failed Primary Sphincter Placement for the Treatment of Post-prostatectomy Incontinence," Journal of Urology 170(4 Part 1):1252-1254; Guralnick, M. L., Miller, E., Toh, K. L., and Webster, G. D. 2002, Op cit.).

The experience of Foley and subsequent developers of artificial sphincters positioned along the bulbar urethra made it clear that unless an artificial sphincter, in this case urinary, could be positioned to encircle the native sphincter with its epithelial lining adapted to withstand forcible closure, sustained compression would eventually, probably inevitably, result in urethral atrophy and erosion. The epithelial linings of bodily conduits are all genetically adapted in structure and function for the segment lined, those along the gastrointestinal tract adapted to absorb certain type nutrients, those lining the blood vessels to admit bloodborne constituents such as the emigration of leukocytes, and those lining sphincters to withstand compression.

A temporary cystostomy is incapable of long term durability, and the reconstructive surgery far more traumatic and susceptible to complications. Neither is compatible with the fitting of an automatic ambulatory prosthetic disorder response system. This factor makes it possible to provide long term remedial therapy to patients lacking the stability to withstand a more traumatic procedure. Such a system is intended for the long term if not life-long automatic ambulatory treatment of a chronic condition or combination of conditions and not for supplanting short term clinical measures such as a conventional percutaneous suprapubic cystostomy, nephrostomy, or infusion, for example. One object in the use of such a system is precisely to make possible a permanent implant that provides fluid and electrical communication with an internal organ, for example, with the need to change catheters and dressings eliminated.

For example, existing means for urinary diversion, whether temporary, using prosthetic or catheteric means as in a suprapubic cystostomy or a nephrostomy, or permanent, through surgical reconstruction using gut to create a channel for the insertion of catheters in a urostomy (vesicostomy, surgical cystostomy, epicystostomy) and/or construct a bladder in an enterocystoplasty or ileocystoplasty, for example, demand constant attention. Synthetic or surgical, diligent maintenance notwithstanding, the treatment almost always gives rise to complications of irritation if not infection that add annoyance to what has been an unwanted focus of attention in the first place, significantly degrading the quality of life. Moreover, a stoma of the kind constructed for the discharge of solid excreta, or colostomy—not itself addressed here but only cited as a surgical technique—is irregularly configured and unsuited for use in an electrical control system or as a channel leading into an organ or tissue where sepsis or irritation at the catheter-tissue interface is intolerable.

Neither can either kind of conduit provide the security, structural integrity, or standardization in conformation and material composition essential for incorporation into an automatic ambulatory control system. These factors clearly delineate an object in devising synthetic means requiring minimal surgery to place that will remain in place indefinitely with few if any complications. The endoscopic placement of a permanent prosthesis for excurrent drainage or to draw diagnostic test samples, or incurrent use for drug delivery, for example, will supplant the need for surgical construction which achieves permanence at the expense of more significant trauma and extension of the risk of infection and complications such as anastomotic stricture, to what had been healthy tissue.

Aside from the relative complexity of surgically constructing the channel—which in itself promotes complications—the complications associated with stomal catheteric channels unrelated to early or late infection include retraction, prolapse, parastomal herniation, mucocutaneous separation, necrosis, stenosis, peristomal complications superficial and deep, such as dermal ulceration, and high susceptibility to accidental injury (see, for example, Sheetz, K. H., Waits, S. A., Krell, R. W., Morris, A. M., Englesbe, M. J., Mullard, A., Campbell, D. A., and Hendren, S. 2014. "Complication Rates of Ostomy Surgery are High and Vary Significantly between Hospitals," Diseases of the Colon and Rectum 57(5):632-637; Kwiatt, M. and Kawata, M. 2013. "Avoidance and Management of Stomal Complications," Clinics in Colon and Rectal Surgery 26(2):112-121; Bafford, A. C. and Irani, J. L. 2013. "Management and Complications of Stomas," Surgical Clinics of North America 93(1):145-166; Jordan, R. S. and Burns, J. L. 2013. "Understanding Stoma Complications," Wound Care Advisor at http://woundcareadvisor.com/understanding-stoma-complications_vol2-no4/; Schleicher, C., Senninger, N., Vowinkel, T., and Anthoni, C. 2010. "Stoma Prolapse and Stoma Retraction [in German with English abstract at Pubmed," Chirurg 81(11):978-981; Kann, B. R. 2008. "Early Stomal Complications," Clinics in Colon and Rectal Surgery 21(1):23-30; Husain, S. G. and Cataldo, T. E. 2008. "Late Stomal Complications," Clinics in Colon and Rectal Surgery 21(1):31-40; Salvadalena, G. 2008. "Incidence of Complications of the Stoma and Peristomal Skin among Individuals with Colostomy, Ileostomy, and Urostomy: A Systematic Review," Journal of Wound, Ostomy, and Continence Nursing 35(6):596-607; Dugas, J. P., Oves, S. D., Sajo, E., Matthews, K. L. 2nd, Ham, K., and Hogstrom, K. R. 2008. "Monochromatic Beam Characterization for Auger Electron Dosimetry and Radiotherapy," European Journal of Radiology 68(3 Supplement):S137-S141; Kim, J. T., and Kumar, R. R. 2006. "Reoperation for Stoma-related Complications," Clinics in Colon and Rectal Surgery 19(4):207-212), which taken together, are common.

Surgical reconstruction is substantially limited to urinary and fecal waste diversion and unsuited to the creation of a permanent passageway from the body surface into the medulla or medulla or parenchyma of an internal organ such as the spleen, gall bladder, kidney, prostate, uterus, and so on. However, the means described herein are not limited to the urological but pertain to the creation of a secure junction to and from an organ in any organ system. Illustration in urological terms as applied to a temporary catheteric suprapubic cystostomy or to a surgical urostomy, for example, should not be interpreted in a limiting sense as only relevant to the urinary tract but rather descriptive of a general approach that includes the bladder as but exemplary of any organ to which communication from the body surface must be established.

The surgical construction of a passageway as in a urostomy, which extends trauma and the risk of complications to uninvolved tissue, has been limited to relatively few organs and tissues. The appropriation of uninvolved tissue to construct a diversionary channel to a stoma at the body surface and the diversion of an unaffected artery, usually the internal thoracic, to ameliorate hypoxia, or arterial and/or venous insufficiency obstructing runoff, attests to the incompetence of synthetic catheters, which have a propensity for accumulating clot, and void of immune function, a biofilm. By providing the entry into the synthetic catheter through a ductus side-entry jacket as described in patent application Ser. No. 14/121,365 with a subsidiary side-entry or service channel, a path is created for the metered delivery into the catheter lumen of anticoagulant or thrombolytic and antimicrobial drugs.

Complications of an ileal, or Bricker, conduit without pouch or reservoir as a replacement bladder, or neobladder—which the lower of the two lines shown in FIG. 12A, connected with a side-entry connector with accessory channel, and described herein replace with a catheter and port at the body surface, rather than by diverted gut or colon with stoma—are numerous (see, for example, Khalil, el-S. A. 2010. "Long Term Complications following Ileal Conduit Urinary Diversion after Radical Cystectomy," Journal of the Egyptian National Cancer Institute 22(1):13-18; Yang, W. J., Cho, K. S., Rha, K. H., Lee, H. Y., Chung, B. H., Hong, S. J., Yang, S. C., and Choi, Y. D. 2006. "Long-term Effects of Ileal Conduit Urinary Diversion on Upper Urinary Tract in Bladder Cancer," Urology 68(2):324-327; Hetet, J. F., Rigaud, J., Karam, G., Glemain, P., Le Normand, L., Bouchot, O., Le Neel; J. C., and Buzelin, J. M. 2005. "Complications of Bricker Ileal Conduit Urinary Diversion: Analysis of a Series of 246 Patients," (in French, English abstract at Pubmed) Progres en Urologie 15(1):23-29; Wood, D. N., Allen, S. E., Hussain, M., Greenwell, T. J., and Shah, P. J. 2004. "Stomal Complications of Ileal Conduits are Significantly Higher when Formed in Women with Intractable Urinary Incontinence," Journal of Urology 172(6 Part 1):2300-2303; Madersbacher, S., Schmidt, J., Eberle, J. M., Thoeny, H. C., Burkhard, F., Hochreiter, W., and Studer, U. E. 2003. "Long-term Outcome of Ileal Conduit Diversion," Journal of Urology 169(3):985-990).

A line such as that upper in FIG. 12A advantageously replaces an ileal conduit, a surface port as described in copending application Ser. No. 14/121,365 advantageously replaces a rosebud stoma for drainage, and these combined are superior to surgically diverted and reconfigured healthy tissue in any context. When formed as the drain of a constructed pouch or neobladder interposed between the ureters and conduit, replacement of the ileal conduit by a line such as that lower in FIG. 12A allows use of the upper line shown in FIG. 12A, its accessory channel, and the accessory channel of the lower drainage line to target medication to the pouch.

This ameliorates the complications to which surgically constructed, or fabricated pouches or neobladders such as the Kock, hemi-Kock, Indiana, Florida, Miami, Mainz I, Mainz II, Mainz III, Hautmann, Studer, Mansoura, Lundiana, and Penn, among others (see, for example, Monn, M. F., Kaimakliotis, H. Z., Cary, K. C., Pedrosa, J. A., Flack, C. K., Koch, M. O., and Bihrle, R. 2014. "Short-term Morbidity and Mortality of Indiana Pouch, Meal Conduit, and Neobladder Urinary Diversion following Radical Cystectomy," Urologic Oncology 32(8):1151-1157; Moon, A., Vasdev, N., and Thorpe, A. C. 2013. "Continent Urinary Diversion," Indian Journal of Urology 29(4):303-309; Salom, E. M., Mendez, L. E, Schey, D., Lambrou, N., Kassira, N., Gomez-Marn, O., Averette, H., and Penalver, M. 2004. "Continent Ileocolonic Urinary Reservoir (Miami Pouch): the University of Miami Experience over 15 Years," American Journal of Obstetrics and Gynecology 190(4):994-1003) are ordinarily susceptible (see, for example, Moon, A., Vasdev, N., and Thorpe, A. C. 2013, ibid.; Hadzi-Djokic, J. B. and Basic, D. T. 2006. "A Modified Sigma-rectum Pouch (Mainz Pouch II) Technique: Analysis of Outcomes and Complications on 220 Patients," British Journal of Urology International 97(3):587-591; Nam, J. K., Kim, T. N., Park, S. W., Lee, S. D., and Chung, M. K. 2013. "The Studer Orthotopic Neobladder: Long-term (More than 10 Years) Functional Outcomes, Urodynamic Features, and Complications," Yonsei Medical Journal 54(3):690-695; Wyczolkowski, M., Juszczak, K., Rzepecki, M., Drewniak, T., and Klima, W. 2010. "Studer Orthotopic Ileal Bladder Substitute Construction—Surgical Technique and Complication Management: One-center and 12-year Experience," Advances in Medical Sciences 55(2):146-152. Hadzi-Djokic, J. B. and Basic, D. T. 2006. "A Modified Sigma-rectum Pouch (Mainz Pouch II) Technique: Analysis of Outcomes and Complications on 220 Patients," British Journal of Urology International 97(3): 587-591; Wilkin, M., Horwitz, G., Seetharam, A., Hartenbach, E., Schink, J. C., Bruskewitz, R., and Jarrard, D. F. 2005. "Long-term Complications Associated with the Indiana Pouch Urinary Diversion in Patients with Recurrent Gynecologic Cancers after High-dose Radiation," Urologic Oncology 23(1):12-15; Mirhashemi, R., Lamrbou, N., Hus, N., Salom, E., Penalver, M. A., and Averette, H. E. 2004. "The Gastrointestinal Complications of the Miami Pouch: A Review of 77 Cases," Gynecologic Oncology 92(1):220-224; Wilson, T. G., Moreno, J. G., Weinberg, A., and Ahlering, T. E. 1994. "Late Complications of the Modified Indiana Pouch," Journal of Urology 151(2):331-334).

Reports of complications in the literature tend to consist of self-appraisals that concentrate on urinary function and not the digestive tract as tissue source. These may include partial shutdown of the digestive system, fecal incontinence, and loss in the sense of urinary urgency. An orthotopic sigmoid neobladder is claimed to fare somewhat better, although the evaluation is provided at a meantime following surgery of only 48 months by the team that devised the 'detacnial' technique for construction of an orthotopic neobladder (Xu, K., Liu, C. X., Zheng, S. B., Li, H. L., and 4 others 2013. "Orthotopic Detaenial Sigmoid Neobladder after Radical Cystectomy: Technical Considerations, Complications and Functional Outcomes," Journal of Urology 190(3):928-934).

Where complications are due to negligent maintenance, an automatic drug delivery system with a drainage line as shown in FIG. 12A to with accessory channel to replace an ileal conduit can dispense medication on a programmed basis between clinic visits (see, for example, Ignjatovic, I. and Basic, D. 2007. "Modified Mainz Pouch II (Sigma Rectum Pouch) Urinary Diversion: 12 Years Experience," Acta Chirurgica Iugoslavica 54(4):73-77) This factor considerably expands the zone of patients for which a high maintenance reconstruction can be applied (see, for example, Obek, C., Kural, A. R., Ataus, S., Cokuner, E., Demirkesen, O., Citci, A., Onder, A. U., and Solok, V. 2001. "Complications of the Mainz pouch II (Sgma Rectum Pouch)," European Urology 39(2):204-211).

A parallel set of advantages in the availability of permanent catheteric implants is elimination of the need to extend trauma and the risk of complications to an uninvolved vessel that would otherwise have to be diverted as the blood supply for a shunt. The diversion of the internal thoracic (previously, the internal mammary), for example, can result in grave consequences (see, for example, Bintoudi, A., Malkotsi, T., Goutsaridou, F., Emmanoullidou, M., and Tsitouridis, I. 2011. "Breast Necrosis Following Coronary Artery Bypass Grafting," Breast Journal 17(1):83-86; Cathenis, K., Goossens, D., Vertriest, R., Coppens, M., and Hamerlijnck, R. 2011. "Breast Infarction Due to Calciphylaxis After Coronary Artery Bypass Grafting, Annals of Thoracic. Surgery 91(5):1603-1606; Wong, M. S., Kim, J., Yeung, C., and Williams, S. H. 2008. "Breast Necrosis Following Left Internal Mammary Artery Harvest: A Case Series and a Comprehensive Review of the Literature," Annals of Plastic Surgery 61(4):368-374; Rosato, F. Jr., Schaner, P., Chojnacki, K., and Rosato, E. L. 2006. "Left Breast Necrosis Following Cardiac Bypass Surgery," Breast Journal 12(5): 485-487; Gonyon, D. L. Jr., Zenn, M. R., Milano, C. A., and Levin, L. S. 2005. "Breast Necrosis Following Use of the Internal Mammary Artery for Coronary Artery Bypass," Annals of Plastic Surgery 54(1):88-91; Hata, M., Raman, J., Seevanayagam, S., Hare, D., and Buxton, B. F. 2002. "Post Radial Artery Harvest Hand Perception: Postoperative 12-month Follow-up Results," Circulation Journal 66(9): 816-818).

Broadly, the appropriation of any vessel of larger caliber is likely to result in adverse consequences for its supply territory (see, for example, Zhu, Y. Y., Hayward, P. A., Hadinata, I. E., Matalanis, G., Buxton, B. F., Stewart, A. G., and Hare, D. L. 2013. "Long-term Impact of Radial Artery Harvest on Forearm Function and Symptoms: A Comparison with Leg Vein," Journal of Thoracic and Cardiovascular Surgery 145(2):412-419; Dick, F., Hristic, A., Roost-Krahenbuhl, E., Aymard, T., Weber, A., Tevaearai, H. T., and Carrel, T. P. 2011. "Persistent Sensitivity Disorders at the Radial Artery and Saphenous Vein Graft Harvest Sites: A Neglected Side Effect of Coronary Artery Bypass Grafting Procedures," European Journal of Cardiothoracic Surgery 40(1):221-226; Aziz, O., Athanasiou, T., and Darzi, A. 2006. "Minimally Invasive Conduit Harvesting: A Systematic Review," European Journal of Cardiothoracic Surgery 29(3):324-333; Hata, M., Shiono, M., Sezai, A., Iida, M., Saitoh, A., and 5 others 2005. "Comparative Study of Harvest-Site Complications Following Coronary Artery Bypass Grafting between the Radial Artery and the Saphenous Vein in Identical Patients," Surgery Today 35(9):711-713).

Rather than to divert an artery away from its normal supply territory or a vein from its drainage area with the usual risks of surgical trauma, hypoxia, and infection, the use of a ductus side-entry jacket confers the ability to tap into and divert a portion of the vessel flow, and, moreover, introduce drugs into the flow-diversion catheter. If tapping into one artery results in an inadequate volumetric flow rate, then a second artery can be tapped, the line therefrom led to the same ductus side-entry connector on the native supply artery, or a nonjacketing side-entry connector if that artery is diseased or missing. The selection of a supply vessel need not be on the basis of proximity or relative ease to anastomose.

Harvesting of the saphenous vein can result in donor leg saphenous neuropathy, ischemia, and recurrent cellulitis (Abbaszadeh, M., Arabnia, M. K., Rabbani, A., Mandegar, M. H., and Vahedi, S. 2008. "The Risk Factors Affecting the Complications of Saphenous Vein Graft Harvesting in Aortocoronary Bypass Surgery," Revista Brasileira de Cirurgia Cardiovascular/Brazilian Journal of Cardiovascular Surgery 23(3):317-322; Lavee, J., Schneiderman, J., Yorav, S., Shewach-Millet, M., and Adar, R. 1989. "Complications of Saphenous Vein Harvesting Following Coronary Artery Bypass Surgery," Journal of Cardiovascular Surgery (Turin) 30(6):989-991).

Instead, the takeoff can be relatively remote from the treatment site, such as upstream, to an artery larger in caliber, thus allowing the placement of a shunt where the vasculature would not afford a suitable source. A single takeoff ductus side-entry jacket with multiple side-connectors can supply several shunts to different sites. Provided the risks of clotting and formation of a biofilm have been eliminated, a catheteric shunt can be any length and have a wall of whatever toughness is needed to remain patent even if encroached upon by bone. It is easier to channel or tunnel from one point to another and can be placed beginning at the origin or destination. Arteriovenous bridging between vessels at any relative levels within their respective trees diverts neither and imposes relatively little trauma.

An automatic ambulatory prosthetic disorder response system with direct and targetable access to multiple sites of internal disease must coordinate the automatic treatment of these in a synchronized manner while the patient engages in normal activity. Even one, much less a collection of indwelling catheters would disallow this. The central need for and the lack of safe and secure tissue perforating wound connectors is an obstruction to the implementation of such systems. Already described in application Ser. No. 14/121,365 are body surface ports and ductus side-entry jackets for connection to tubular anatomical structures, or ductus, to meet the immediate requirement for such connection in an automatic ambulatory prosthetic disorder response control system.

However, regardless of application thus, such means overcome the need to detain an otherwise ambulatory patient in the clinic merely because a catheter, infusion line, the tape securing it, or the solution used to promote antisepsis require frequent examination and changing or because more radical surgery necessitates more time to heal. Described here is a prosthetic disorder response system-compatible fluid and electrical line connector for fastening one or a number of catheters to nontubular internal surfaces and organs, such as the kidneys, the urinary or the gall bladder, the spleen, prostate gland, uterus, and any location along a serous membrane-lined internal surface. Surface ports secure the wound at the body surface, ductus side-entry jackets where connection is made to a tubular anatomical structure, and the internal surface connector described herein is used to attach a catheter to any surface which nontubular, is not articulable by means of encirclement.

The nondurability and in particular, the impermanence of a catheteric suprapubic cystostomy or a nephrostomy is due not only to contamination or the accretion of crystalline matter but to irritation and the risk of infection at the body wall and at the renal and urinary bladder or urocystic puncture wounds. To overcome such vulnerability, means for enclosing, sealing, and immobilizing these breaches are provided, allowing the catheter to remain in place indefinitely. Compared to surgical procedures that appropriate healthy tissue to construct a urinary conduit, the reduction in trauma allows application to preterm neonates, the elderly, and the severely ill requiring extended or life-long diversion but unable to withstand significant trauma. The use of special tubing allows accommodation for growth. While drainage is passive, therapeutic substance delivery can be implemented independently or as one in a plurality of control axes in an automatic ambulatory prosthetic disorder response system, as described in copending patent application Ser. No. 14/121,365, entitled Ductus Side-entry Jackets and Prosthetic Disorder Response Systems, filed on 25 Aug. 2014.

Urinary tract infections the most common complication in urinary catheterization, therapeutic substance delivery will periodically include antimicrobials. If mineralization is a problem, then a counteractant, usually citrate, is added. Application to cystostomy and nephrostomy is illustrative and not to be interpreted in a limiting way. The delivery of drugs into the kidney is usually through a ductus side-entry jacket also described in application Ser. No. 14/121,365, entitled Ductus Side-entry Jackets and Prosthetic Disorder Response Systems, placed along the renal artery with another placed along the renal vein to release a reversal agent to counteract or neutralize any residue to be kept from the systemic circulation. In reality, collaterals will deliver some negligible amount into the circulation, which, however, can be discounted or reversed with systemic medication.

Precise delivery directly into the medulla or parenchyma to target a lesion or structural feature therein is by direct penetration with a fine catheter, needle, or electrode to the site, the depth and inclination of the catheter tip figidly fixed by a nonjacketing side-entry connector such as shown in FIGS. 6 and 13A, and 13B. Release of the drug may be from the distal tip, a side-hole or side-slit, or a running slit along a side of a catheter. Because the nonjacketing side-entry connectors hold these rigidly in the focus position, more than one catheter or needle, for example, can be used. Not restricted to fixing the entry of a catheter to the outer cortex, fibrosa, or adventitia so that the tip will be held at a certain depth, a nonjacketing side-entry connector can also position thus a discharge electrode or any other tubular or cable configured device wherein the various components such as laser or heating element, for example, can be combined in any coaxial or concentric arrangement.

Whether pertaining to drug delivery or the application of heat or an electrical current, therapeutic targeting is distinguished as applied to a discrete organ or region, treated by delivering medication into the supply artery or arteries with one or more ductus side-entry jackets, or as site-specific within the organ, region, or territory, treated with one or more parenchymal or tissue-inserted or intromission-type styliform devices, such as a catheter, electrode, which can be singular or a coaxially and/or separately arranged combination of these. In most instances, tissue-inserted or intromission-type styliform devices, such as catheters, hypotubes, and electrodes are little more than capillary tube in caliber. These modalities are not exclusive but to be coordinated, so that a focal point of disease within an organ, region, or territory is directly targeted at a higher dose, while the organ or region as a whole is provided with a background dose to prevent spreading of the disease whether infectious or metastatic, for example.

For example, diffuse brain disease is treated with ductus side-entry jackets placed on the internal carotids with an agent such as mannitol added to allow passage through the blood brain barrier, as addressed in copending application Ser. No. 13/694,835, whereas focal lesions within the brain are directly targeted through the meninges and barrier by means of insertion or intromission-type catheters and/or electrodes. Referring now to FIG. 6, shown is a nondiversionary nephrostomy using synthetic materials where the attitude of the catheter here shown as side connector must be durable. A hollow catheter or needle is statically fixed in position within the kidney. Here tissue irritation at the tissue interface is the initial factor limiting the duration of placement. The nonjacketing side-entry connector makes it possible to position the tip of a catheter, hypotube, hollow needle, or electrode precisely for targeting drugs to a lesion within the renal medulla or parenchyma.

Prerenal and postrenal kidney disease and a tumor within the kidney can be treated or additionally treated with a drug delivering ductus side-entry jacket placed on the renal artery. The nonjacketing side-entry connector with accessory or service channel to deliver adjuvant substances such as an antimicrobial or anti-inflammatory, rigidly stabilizes the implant forestalling irritation at the tissue interface. It is also possible to steer the injectant away from the stationary point of the needle. When the substance delivered is a ferrofluid containing a superparamagnetic nanoparticle carrier-bound drug, clasp-electromagnets as described in copending application Ser. No. 14/121,365, entitled Ductus Side-entry Jackets and Prosthetic Disorder Response Systems, are positioned about the organ, here the kidney, to magnetically vector the drug under the control of a microcontroller.

Whether the microcontroller, power source, and transdermal charging components are implanted depends upon the absolute field strength required of the electromagnets and the prospective indwelling time. The current delivered to each magnet, hence, the relative field strength of these is controlled by a microcontroller which may or may not be collocated with the injection and/or biopsy sample taking implant, power source, and transdermal charging components. When the need for treatment is expected to be brief, surgical pocketing is avoided, these components then belt-carried in a power and pump pack with drug delivery through a port positioned at the body surface as described in copending application Ser. No. 14/121,365, entitled Ductus Side-entry Jackets and Prosthetic Disorder Response Systems.

When the battery is recharged by transdermal energy transfer, and a portacath or Ommaya-type reservoir is used to supply the drug injected through the skin, into this subdermal port, implantation is fully intracorporeal, or closed-skin. In the pectoral region, such a reservoir can hold a large volume of a therapeutic substance or combination thereof. To steer the injectant from the stationary tip of the needle, two clasp-electromagnets allow the carrier to be stereotactically drawn into any direction within the triangular sector defined by the tip of the needle and the two magnets, and in any direction through the three-sided pyramidal sector defined by the addition of a third magnet, and so on. Whereas the tip of the drug delivering catheter shown in FIG. 6 is rigidly fixed in position, that shown in FIGS. 13A and 13B allow a microneedle or hypotube, for example, to be advanced and withdrawn in minute increments.

The needle or microneedle is advanced by nanometer-range precision piezoelectric or ultrasonic stepper motor 25 in FIG. 15 (references above), with a resolution that makes possible the support of processes that require targeting at the cellular level. As may be seen in FIG. 17, when separate channels are essential to deliver drugs into different lines or channels, a port at the body surface with multiple entries or (not shown) more than one portacath can be used. Where patient competency to self inject is involved, or where more than a couple lines are needed, it is best to place a special port at the body surface with clearly marked injection points or if pumped, insertion holes for access to each destination is used. Such a port is described in copending application Ser. No. 14/121,365, entitled Ductus Side-entry Jackets and Prosthetic Disorder Response Systems, filed on 25 Aug. 2014.

The fine control afforded by a piezo motor can be applied, for example, to Auger therapy (references below in the section entitled Novel Applications) and transfection, to include magnetic transfection (see, for example, Schwerdt, J. I., Goya, G. F., Calatayud, M. P., Heren, C. B., Reggiani, P. C., and Goya, R. G. 2012. "Magnetic Field-assisted Gene Delivery: Achievements and Therapeutic Potential," Current Gene Therapy 12(2):116-126; Vainauska, D., Kozireva, S., Karpovs, A., {hacek over (C)}istjakovs, M., and Bari{hacek over (s)}evs, M. 2012. "A Novel Approach for Nucleic Acid Delivery into Cancer Cells," Medicina (Kaunas, Lithuania) 48(6):324-329; Laurentt, N., Sapet, C., Le Gourrierec, L., Bertosio, E., and Zelphati, O. 2011. "Nucleic Acid Delivery Using Magnetic Nanoparticles: The Magnetofection Technology," Therapeutic Delivery 2(4):471-482; Scherer, F., Anton M., Schillinger, U., Henke, J., Bergemann, C., and 3 others 2002. "Magnetofection: Enhancing and Targeting Gene Delivery by Magnetic Force in Vitro and in Vivo," Gene Therapy 9(2):102-109).

When emission of an antineoplastic drug is local from the fine needle stabilized by a catheteric, hollow needle, or electrode nonjacketing side-entry connector as shown in FIGS. 6, 13a, and 13b with no external beam involved, the three-dimensional coordinate system frame is applied to the organ, such as the kidney or spleen, so that even if the organ as a whole is not fully stabilized, the targeting frame moves as one with the kidney, independently of the surrounding anatomy. FIG. 6 shows a fine caliber tube or catheter and FIG. 13A an injection and aspiration hollow needle as side connector. Fixation in position of the device by the connector is to direct the distal or outlet end of the side connector toward the lesion, shown as tumor 41. In FIG. 6, the side connector is not motorized as it is in FIGS. 13A and 13B, so that to deliver a conventional fluid or semifluid drug such as chemotherapeutic requires that the drug be put under sufficient pressure to wet tumor 41.

In FIGS. 13A and 13B, the motor driven hollow needle is forcibly projected at a controlled rate into the tumor. This allows the drug to be injected in and about the trajectory of the needle side connector. FIG. 13B adds patch-electromagnets for magnetically vectoring and by this means steering susceptible superparamagnetic nanoparticle carrier-bound drugs toward, into, and through the lesion and throughout the tumor without the need for the drug in ferrofluid form to be delivered under pressure. The pressure of emission from the delivery device is thus not required to propel the drug to the lesion or any locus within the lesion. Application to a tumor within a kidney should be understood as exemplary: this arrangement allows any locus within any tissue or organ to be targeted for perfused application of the drug. Clasp-electromagnets can similarly be added to the configuration depicted in FIG. 6, which can then be applied to a soft tumor.

The addition of patch-electromagnets about the kidney shown in FIG. 13A thus allows steering the drug from the point of emission toward and entirely through the lesion. FIGS. 14 thru 16 show the mechanism for advancing and retracting the hollow injection/aspiration needle to change the point of emission of the drug. The configuration shown in FIG. 13A is generally reserved for precise drug targeting as is essential for Auger therapy and transfection, for example. Whereas the arrangement shown in FIG. 6 can function open loop, or without negative feedback, as to the instantaneous focus of the nanoparticles steered, the precision contemplated for the application of the arrangement shown in FIG. 13A necessitates servomechanical control. The comments herein pertaining to Auger therapy refer to the configuration shown in FIGS. 13A and 13B, wherein the radionuclide or preradionuclide is precisely released through the tissue treated, this precision facilitated by the stability lent by the nonjacketing side-entry connector and use of a nanometer range stepper motor.

Magnetically administered stereotactic therapy, whereby the relative energization of the magnets arranged according to Carterian or polar coordinates, can be conceived of as realized at any of three levels, all focusing upon the instantaneous position of the ferrofluid, released in minute amounts, as target. The apportionment of current delivery or level of energization of each of the two patch-electromagnets used for 2-dimensional steering, or three for 3-dimensional steering is determined empirically, not by computation, after the magnets have been placed. This approach is the more beneficial as expediting magnet placement, which need only straddle or stand in subtending relation to the target without the need for accuracy that might slow down treatment and/or conflict by indicating a need to incise connective tissue best not cut as serving a stabilizing function, for example.

Preliminary tomography, for example, is used to establish the rate of nanoparticle-carried drug advancement through the healthy or partially diseased leading up to the frankly lesioned tissue and then into the lesioned tissue at sample angles at the test apportionments. Auger therapy has the potential to achieve extremely precise targeting, far beyond that of current means of external beam radiation. Moreover, were a form of external beam radiation having nanometer range resolution to become available, there is no reason to suppose that this would function in combination with, gain any advantage from, or contribute improved performance to Auger therapy. The positional control imparted by a nonirritating stable fastener and nanometer range mover allows the precise release of drugs, radionuclides, or precursors thereof for stereotactic magnetic vectoring, apart from or in conjunction with pencil beam tracking.

Neither should the potential in the ability to cause external pencil beams to track drugs bound to superparamagnetic nanoparticles be conceived of as necessarily associated with Auger therapy. Under a pencil beam at a certain energy level, a drug, drugs, predrug, predrugs, radionuclides, normal tissue, and diseased tissue interact such that any one or more can affect any one or more of the others. Conversion of cholesterol into vitamin D in sunlight and its biological activation through enzymatic hydroxylation in the liver and kidneys and the darkening and increased production of melanin in tanning are instances of the interaction between incident radiation and living tissue. "Very recently, gene therapy techniques have been developed which should enhance the clinical efficacy of both external beam radiation and targeted radiotherapy." (Wheldon, T. E. 2000. "Radiation Physics and Genetic Targeting: New Directions for Radiotherapy. The Douglas Lea Lecture 1999," Physics in Medicine and Biology 45(7):R77-R95).

Whether in conjunction or apart from Auger therapy, noncytocidal neoadjuvant or concomitant adjuvant radiation has the potential to facilitate the penetration into diseased cells of magnetic carrier-bound nuclides or antineoplastic drugs and/or increase the susceptibility of diseased cells to radiation (see, for example, Calugaru, V., Magne, N., Herault, J., Bonvalot, S., Le Tourneau, C., and Thariat, J. 2015. "Nanoparticles and Radiation Therapy," (in French, English abstract at Pubmed) Bulletin du cancer 102(1):83-91; Alvarez, D., Hogstrom, K. R., Brown, T. A., Ii, K. L., Dugas, J. P., Ham, K., and Varves, M. E. 2014. "Impact of IUdR on Rat 9L Glioma Cell Survival for 25-35 keV Photon-activated Auger Electron Therapy," Radiation Research 182(6): 607-617; Morgenroth, A., Vogg, A. T., Ermert, K., Zlatopolskiy, B., and Mottaghy, F. M. 2014. "Hedgehog Signaling Sensitizes Glioma Stem Cells to Endogenous Nano-irradiation," Oncotarget 5(14):5483-5493; Morgenroth, A., Vogg, A. T., Zlatopolskiy, B. D., Siluschek, M., Oedekoven, C., and Mottaghy, F. M. 2014. "Breaking the Invulnerability of Cancer Stem Cells: Two-step Strategy to Kill the Stem-like Cell Subpopulation of Multiple Myeloma," Molecular Cancer Therapeutics 13(1):144-153; Barth, R. F., Vicente, M. G., Harling, O. K., Kiger, W. S. 3rd, Riley, K. J., Binns, P. J., Wagner, F. M., and 4 others 2012. "Current Status of Boron Neutron Capture Therapy of High Grade Gliomas and Recurrent Head and Neck Cancer," Radiation Oncology 7:146; Tanaka, Y., Tatewaki, N., Nishida, H., Eitsuka, T., Ikekawa, N., and Nakayama, J. 2012. "Non-thermal DNA Damage of Cancer Cells Using Near-infrared Irradiation," Cancer Science 103(8):1467-1473; Hossain, M. and Su, M. 2012. "Nanoparticle Location and Material Dependent Dose Enhancement in X-ray Radiation Therapy," Journal of Physical Chemistry. C. Nanomaterials and Interfaces 116 (43):23047-23052; Kassis, A. I. 2011. "Molecular and Cellular Radiobiological Effects of Auger Emitting Radionuclides. Radiation Protected Dosimetry 143(2-4):241-247; Tabuchi, S., Ozawa, S., Koyanagi, K., Shigematsu, N., Kubo, A., Ueda, M., Kitagawa, Y., and Kitajima, M. 2011. "Radiation-sensitizing Effect of Low-concentration Docetaxel on Human Esophageal Squamous Cell Carcinoma Cell Lines," Experimental and Therapeutic Medicine 2(4): 601-606; Van den Heuvel, F., Locquet, J. P., and Nuyts, S. 2010. "Beam Energy Considerations for Gold Nano-particle Enhanced Radiation Treatment," Physics in Medicine and Biology 55(16):4509-4520; Suen, A. W., Galoforo, S., Marples, B., McGonagle, M., Downing, L., Martinez, A. A., Robertson, J. M., and Wilson, G. D. 2010. "Sorafenib and Radiation: A Promising Combination in Colorectal Cancer," International Journal of Radiation Oncology, Biology, and Physics 78(1):213-220; Cerullo, N., Bufalino, D., and Daquino, G. 2009. "Progress in the Use of Gadolinium for NCT," Applied Radiation and Isotopes 67(7-8 Supplement): 5157-160; Boyd, M., Sorensen, A., McCluskey, A. G., and Mairs, R. J. 2008. "Radiation Quality-dependent Bystander Effects Elicited by Targeted Radionuclides," Journal of Pharmacy and Pharmacology 60(8):951-958; Boyd, M., Ross, S. C., Dorrens, J., Fullerton, N. E., Tan, K. W., Zalutsky, M. R., and Mairs, R. J. 2006. "Radiation-induced Biologic Bystander Effect Elicited in Vitro by Targeted Radiopharmaceuticals Labeled with Alpha-, Beta-, and Auger Electron-emitting Radionuclides," Journal of Nuclear Medicine 47(6):1007-1015; Barth, R. F., Grecula, J. C., Yang, W., Rotaru, J. H., Nawrocky, M., Gupta, N., Albertson, B. J., and 4 others 2004. "Combination of Boron Neutron Capture Therapy and External Beam Radiotherapy for Brain Tumors," International Journal of Radiation Oncology, Biology, and Physics 58(1):267-277; Boyd, M., Mairs, R. J., Keith, W. N., Ross, S. C., Welsh, P., Akabani, G., Owens, J., and 4 others 2004. "An Efficient Targeted Radiotherapy/Gene Therapy Strategy Utilising Human Telomerase Promoters and Radioastatine and Harnessing Radiation-mediated Bystander Effects," Journal of Gene Medicine 6(8):937-947; Wheldon, T. E. 2000, Op cit.; Laster, B. H., Thomlinson, W. C., and Fairchild, R. G. 1993. "Photon Activation of Iododeoxyuridine: Biological Efficacy of Auger Electrons," Radiation Research 133(2):219-224; Wheldon, T. E. 1994. "Targeting Radiation to Tumours," International Journal of Radiation Biology 65(1):109-116).

Fine tracking pencil beam proton therapy, for example, also has potential with respect to the dual chemotherapeutic and radiation use of a platin (see, for example, Porcel, E., Liehn, S., Remita, H., Usami, N., Kobayashi, K., Furusawa, Y., Le Sech, C., and Lacombe, S. 2010. "Platinum Nanoparticles: A Promising Material for Future Cancer Therapy?," Nanotechnology 21(8):85103; Rousseau, J., Barth, R. F., Fernandez, M., Adam, J. F., Balosso, J., Esteve, F., and Elleaume, H. 2010. "Efficacy of Intracerebral Delivery of Cisplatin in Combination with Photon Irradiation for Treatment of Brain Tumors," Journal of Neurooncology 98(3):

287-95; Scalliet, P., De Pooter, C., Hellemans, P. W., De Bruijn, E. A., and Van Oosterom, A. T. 1999. "Interactions of Carboplatin, Cisplatin, and Ionizing Radiation on a Human Cell Line of Ovarian Cancer," (in French, English abstract at Pubmed) Cancer radiotherapie 3(1):30-38; Gorodetsky, R., Levy-Agababa, F., Mou, X., and Vexler, A. M. 1998. "Combination of Cisplatin and Radiation in Cell Culture: Effect of Duration of Exposure to Drug and Timing of Irradiation," International Journal of Cancer 75(4):635-642; Groen, H. J., Sleijfer, S., Meijer, C., Kampinga, H. H., Konings, A. W., De Vries, E. G., and Mulder, N. H. 1995. "Carboplatin- and Cisplatin-induced Potentiation of Moderate-dose Radiation Cytotoxicity in Human Lung Cancer Cell Lines," British Journal of Cancer 72(6):1406-1411).

The use of magnetic vectoring as depicted in FIG. 13A so contains magnetic carrier-bound gadolinium, for example, even renal when the gadolinium is targeted to a tumor within the kidney, essentially eliminates side effects elsewhere in the body and, significantly reduces the odds for any within the kidney itself. In this example, where gadolinium subserves imagining to allow the process to be monitored, the sequelae when gadolinium is administered systemically comprise nephrogenic systemic fibrosis and other forms of nephropathy (see, for example, Stefan{hacek over (c)}ikova, L., Porcel, E., Eustache, P., Li, S., Salado, D., and 6 others 2014. "Cell Localisation of Gadolinium-based Nanoparticles and Related Radiosensitizing Efficacy in Glioblastoma Cells," Cancer Nanotechnology 5(l):6). For these reasons, the facilitation of Auger therapy through the bonding of the radionuclide used with a superparamagnetic carrier and using electromagnets to steer these is probably closer to practical implementation than is any concept that would involve some combination of external beam and Auger therapy.

References to eventual combination of the two should be understood as hypothetical. The first of these levels, without the need to instantly adapt to physiological or pathophysiological movement in the surrounding tissue or to adjust the aim of externally beamed radiation, uses surrounding magnets endoscopically fastened onto the organ so that relative movement between the ferrofluid head and controlling magnets other the movement of the ferrofluid controlled is uninvolved. The second and third, which necessitate compensation for movement between the susceptible particles and lesion, constitute forms of stereotactic body therapy, or if external radiation beams are used, then stereotactic body radiotherapy.

The second, using more powerful magnets fastened about the treatment site at the body surface, requires the instantaneous reapportionment among the magnets of current to compensate for displacements in relation to the magnets of the treatment site as the result of normal or pathophysiological movement with negative feedback used to instantly correct the instantaneous set point.

The third necessitates instantaneous adjustment in the focus of externally beamed radiation as well as apportionment of tractive force among the magnets. Fixation of the point of drug emission and advancement by a nonjacketing side-entry jacket enables the first of these, and by substantially eliminating motion at the point of emission due to inadequacy of positional stabilization, as an additional variable, leaves displacements outside the organ or tissue as an additional variable, reducing the complexity of the latter two. Since no fixed mechanical coordinate frame or manually controlled instruments other than the magnets are used to reapportion the relative energization among the magnets, or if used, the externally beamed radiation, the process is noninertial, instantaneous, and without manual involvement by the operator.

The focus of steering control set by the distances between each magnet and ferrofluid drug or nuclide carriers controlled as a unit servomechanism, movement outside the organ or tissue treated need not be distinguished as to intra or extracorporeal. Auger therapy aside, the ability to track superparamagnetic nanoparticles with an external beam offers certain prospects. The means for achieving instantaneous effective control of external radiation beams, such as the use of respiratory gating in the thorax, 3D-conformal radiation therapy (3D-CRT), intensity modulated radiation therapy (IMRT), stereotactic radiation surgery (SRS) and stereotactic radiation therapy, must be related to different techniques, each of which involves numerous variants and combinations, introduces additional control variables (SRT) (see, for example, Henni, M., Fabre, E., Abane, R., and Housset, M. 2014. "New Techniques in Thoracic Radiation Therapy," (in French, English abstract at Pubmed), Revue de pneumologie clinique 70(1-2):63-68; Abbas, A. S., Moseley, D., Kassam, Z., Kim, S. M., and Cho, C. 2013. "Volumetric-modulated Arc Therapy for the Treatment of a Large Planning Target Volume in Thoracic Esophageal Cancer," Journal of Applied Clinical Medical Physics 14(3):4269. Li, R and Xing, L. 2011. "Bridging the Gap between IMRT and VMAT: Dense Angularly Sampled and Sparse Intensity Modulated Radiation Therapy," Medical Physics 38(9): 4912-4919; Andreassen, B., Straat, S. J., Holmberg, R., Nafstadius, P., and Brahme, A. 2011 "Fast IMRT with Narrow High Energy Sanned Photon Beams," Medical Physics 38(8):4774-4784; Purdy, J. A. 2008. "Dose to Normal Tissues Outside the Radiation Therapy Patient's Treated Volume: A Review of Different Radiation Therapy Techniques," Health Physics 95(5):666-676; Fenwick, J. D., Riley, S. W., and Scott, A. J. 2008. "Advances in Intensity-modulated Radiotherapy Delivery," Cancer Treatment and Research 139:193-214; Svensson, R., Larsson, S., Gudowska, I., Holmberg, R., and Brahme, A. 2007. "Design of a Fast Multileaf Collimator for Radiobiological Optimized IMRT with Scanned Beams of Photons, Electrons, and Light Ions," Medical Physics 34(3):877-888; Maebayashi, K., Nasu, S., Seki, K., Kiyoduka, M., Hashimoto, Y., and Mitsuhashi, N. 2006. "Intensity Modulated Radiation Therapy (IMRT)," (in Japanese, English abstract at Pubmed), Gan To Kagaku Ryoho [Cancer and Chemotherapy] 33(4):436-443; Brahme, A. "Recent Advances in Light Ion Radiation Therapy," International Journal of Radiation Oncology, Biology, Physics 58(2):603-616), and must be elaborated upon elsewhere.

Magnetic vector steering of drugs can be used to support the selection and timing of drug release and incorporated into the program prescription governing the microcontroller or node subordinate thereto when disease elsewhere in the body is simultaneously treated. Stabilization at the point of drug emission when the substrate or tissue to be connected is motile is made further tenacious through use of nonjacketing side-entry connectors of the kind shown in FIGS. 4 and 20 with or without the aid of fixation by putting suture through suture loops 32. The connector shown in FIG. 4, for example, extends the area and doubles the number of anchoring needles into the subjacent tissue. The motorized side connector shown in FIG. 14 is mounted to the quadruple snap-clasp baseplace shown in FIG. 4 at the center, aperture 4 smaller but gauged to allow freedom of aligned reciprocal movement therethrough of an injection needle as side connector, for example.

The nonjacketing side-entry connector shown in FIG. 20, where two of the connectors shown in FIG. 4 are joined by a span which holds the hollow needle or catheter between the two at the center, not only doubles the stabilization base and the number of securing needles, but minimizes the extent to which an impact from either side can be transmitted across the span to displace the connector at the other side. To accomplish this, compression springs inside either telescoping arm of the span act as shock absorbers. Within the force of impact set by the springs, the connector to the rear, or on the side opposite the central hollow needle or catheter, thus continues to fix the position of the hollow needle or catheter as the connector on the side of the impact absorbs the kinetic energy.

In a double baseplate embodiment as shown in FIG. 20 but without the shock absorption feature afforded by the compression springs inside crossover bar 33, the motorized side connector housing shown in FIG. 14 is mounted on a flat platform that spans the baseplate to either side. Such a spanning platform might connect any number of paired baseplates to either side along a line of unlimited length, and that crosswise spans might be inserted between each successive pair along the line, for example. The combination of the motorized side connector shown in FIG. 14 with preservation of the shock absorption capability in FIG. 20 and as further described below in the section entitled Description of the Preferred Embodiments of the Invention is accomplished by fastening the motor housing to the stationary central segment of internal spring stops connector 90.

Stereotactic body radiotherapy makes use of means and methods for stabilizing the tissue under treatment in relation to the external radiation beam or beams, necessitating stabilization of the treatment site in relation to exterior space (see, for example, Gaya, A. and Mahadevan, A. 2015. Stereotactic Body Radiotherapy: A Practical Guide, New York, N.Y.: Springer; Serpa, M., Baier, K., Cremers, F., Guckenberger, M., and Meyer, J. 2014. "Suitability of Markerless EPID Tracking for Tumor Position Verification in Gated Radiotherapy," Medical Physics 41(3):031702; Ranck, M. C., Golden, D. W., Corbin, K. S., Hasselle, M. D., Liauw, S. L., and 4 others 2013. "Stereotactic Body Radiotherapy for the Treatment of Oligometastatic Renal Cell Carcinoma," American Journal of Clinical Oncology 36(6): 589-595; Siva, S., Pham, D., Gill, S., Corcoran, N. M., and Foroudi, F. 2012. "A Systematic Review of Stereotactic Radiotherapy Ablation for Primary Renal Cell Carcinoma," British Journal of Urology International 110(11 Part B):E737-E743; Tao, C. and Yang, L. X. 2012. "Improved Radiotherapy for Primary and Secondary Liver Cancer: Stereotactic Body Radiation Therapy," Anticancer Research 32(2):649-655; Kavanagh, B. D., Scheftera, T. E., and Wersall, P. J. 2007. "Liver, Renal, and Retroperitoneal Tumors: Stereotactic Radiotherapy," Frontiers of Radiation Therapy and Oncology 40:415-426). Current procedure is to obtain a four dimensional planning computed tomogram to evaluate the movement of the lesion or tumor due to physiological movement.

The stability and precision imparted by the nonjacketing side-entry connector shown in FIG. 6 with piezomotorized side connector and clasp-electromagnets as shown in FIG. 13B, supported by suture as necessary, makes possible the stereotactic magnetic steering of superparamagnetic nanoparticle-bound drugs at the very fine level required for Auger therapy and transfection, for example. Including a contrast agent other than gadolinium-based additionally eschews the risk of nephrogenic systemic fibrosis and other nephropathy (see, for example, Manjunath, V. and Perazella, M. A. 2011. "Imaging Patients with Kidney Disease in the Era of NSF: Can it Be Done Safely?," Clinical Nephrology 75(4):279-285; Abu-Alfa, A. K. 2011. "Nephrogenic Systemic Fibrosis and Gadolinium-based Contrast Agents," Advances in Chronic Kidney Disease 18(3):188-198; Neuwelt, E. A., Hamilton, B. E., Varallyay, C. G., Rooney, W. R., Edelman, R. D., Jacobs, P. M., and Watnick, S. G. 2009. "Ultrasmall Superparamagnetic Iron Oxides (US-PIOs): A Future Alternative Magnetic Resonance (MR) Contrast Agent for Patients at Risk for Nephrogenic Systemic Fibrosis (NSF)?," Kidney International 75(5):465-474).

The advantage in direct targeting of a contrast agent other than gadolinium-based is all the more pertinent for the example cited, wherein the kidney is represented as already diseased (see, for example, Perazella, M. A. 2009. "Advanced Kidney Disease, Gadolinium and Nephrogenic Systemic Fibrosis: The Perfect Storm, Current Opinion in Nephrology and Hypertension 18(6):519-525). Perazella, M. A. 2009. "Current Status of Gadolinium Toxicity in Patients with Kidney Disease," Clinical Journal of the American Society of Nephrology 4(2):461-469; Abu-Alfa, A. 2008. "The Impact of NSF on the Care of Patients with Kidney Disease," Journal of the American College of Radiology 5(1):45-52; Perazella, M. A. 2008. "Gadolinium-contrast Toxicity in Patients with Kidney Disease: Nephrotoxicity and Nephrogenic Systemic Fibrosis," Current Drug Safety 3(1):67-75).

The use instead of superparamagnetic iron oxide (SPIO) (see, for example, Saraswathy, A., Nazeer, S. S., Nimi, N., Arumugam, S., Shenoy, S. J., and Jayasree, R. S. 2014. "Synthesis and Characterization of Dextran Stabilized Superparamagnetic Iron Oxide Nanoparticles for in Vivo MR Imaging of Liver Fibrosis," Carbohydrate Polymers 101:760-768; Lam, T., Pouliot, P., Avti, P. K., Lesage, F., and Kakkar, A. K. 2013. "Superparamagnetic Iron Oxide based Nanoprobes for Imaging and Theranostics," Advances in Colloid and Interface Science 199-200:95-113; Yoffe, S, Leshuk, T., Everett, P., and Gu, F. 2013. "Superparamagnetic Iron Oxide Nanoparticles (SPIONs): Synthesis and Surface Modification Techniques for Use with MRI and Other Biomedical Applications," Current Pharmaceutical Design 19(3):493-509; Lartigue, L., Hugounenq, P., Alloyeau, D., Clarke, S. P., Levy, M., and 5 others 2012. "Cooperative Organization in Iron Oxide Multi-core Nanoparticles Potentiates Their Efficiency as Heating Mediators and MM Contrast Agents," ACS [American Chemical Society] Nano 6(12):10935-10949; Wahajuddin and Arora, S. 2012. "Superparamagnetic Iron Oxide Nanoparticles: Magnetic Nanoplatforms as Drug Carriers," International Journal of Nanomedicine 7:3445-3471; Wang, Y. X. 2011. "Superparamagnetic Iron Oxide based MRI Contrast Agents: Current Status of Clinical Application," Quantitative Imaging in Medicine and Surgery 1(1):35-40; Islam, T. and Josephson, L. 2009. "Current State and Future Applications of Active Targeting in Malignancies Using. Superparamagnetic Iron Oxide Nanoparticles," Disease Biomarkers. Cancer Biomarkers 5(2):99-107) makes it possible to impart imaging contrast, magnetic steerability, and thermotherapeutic, or electromagnetic hyperthermia, capabilities in the same ferrofluid and the same nanoparticles.

Ultrasmall superparamagnetic iron oxide (USPIO) nanoparticles (see, for example, Zhao, X., Zhao, H., Chen, Z., and Lan, M. 2014. "Ultrasmall Superparamagnetic Iron Oxide Nanoparticles for Magnetic Resonance Imaging Contrast Agent," Journal of Nanoscience and Nanotechnology 14(1):210-220; Shanehsazzadeh, S., Oghabian, M. A., Allen, B. J., Amanlou, M., Masoudi A., and Daha, F. J. 2013. "Evaluating the Effect of Ultrasmall Superparamagnetic Iron Oxide Nanoparticles for a Long-term Magnetic Cell Labeling." Journal of Medical Physics 38(1):34-40; Hong, G. B., Zhou, J. X., and Yuan, R. X. 2012. "Folate-targeted Polymeric Micelles Loaded with Ultrasmall Superparamagnetic Iron Oxide: Combined Small Size and High MRI Sensitivity," International Journal of Nanomedicine 7:2863-2872; Frascione, D., Diwoky, C., Almer, G., Opriessnig, P., Vonach, C., and 5 others 2012. "Ultrasmall Superparamagnetic Iron Oxide (USPIO)-based Liposomes as Magnetic Resonance Imaging Probes," International Journal of Nanomedicine 7:2349-2359; Neuwelt, E. A., Hamilton, B. E., Varallyay, C. G., Rooney, W. R., Edelman, R. D., Jacobs, P. M., and Watnick, S. G. 2009, Op cit.; Di Marco, M., Sadun, C., Port, M., Guilbert, I., Couvreur, P., and Dubernet, C. 2007. "Physicochemical Characterization of Ultrasmall Superparamagnetic Iron Oxide Particles (USPIO) for Biomedical Application as MRI Contrast Agents," International Journal of Nanomedicine 2(4):609-622; Neuwelt, E. A., Hamilton, B. E., et al. 2000, Op cit.), serve both for magnetic susceptibility and as a contrast agent.

Superparamagnetic iron platinum particles are likewise multifunctional and considered superior to iron oxide (see, for example, Taylor, R. M., Huber, D. L., Monson, T. C., Esch, V., and Sillerud, L. O. 2012. "Structural and Magnetic Characterization of Superparamagnetic lion Platinum Nanoparticle Contrast Agents for Magnetic Resonance Imaging," Journal of Vacuum Science and Technology. B. Nanotechnology and Microelectronics 30(2):2C101-2C1016). Drugs, stem cells, and radionuclides delivered by carriers containing platinum can be formulated to provide not only antineoplastic function but contrast, thermotherapy, and the magnetic susceptibility needed for precise stereotactic drug targeting.

Binding stem cells alone or in combination with a drug or drugs to such multifunctional carrier nanoparticles allows these to be steered and tracked (see, for example, Sykova, E. and Jendelova, P. 2007. "In Vivo Tracking of Stem Cells in Brain and Spinal Cord Injury," Progress in Brain Research. 161:367-383; Jin, X. H., Yang, L., Duan, X. J., Xie, B., Li, Z., and Tan, H. B. 2007. "In Vivo MR [magnetic resonance] Imaging Tracking of Supermagnetic Iron-oxide Nanoparticle-labeled Bone Marrow Mesenchymal Stem Cells Injected into Intra-articular Space of Knee Joints: Experiment with Rabbit," (in Chinese; English abstract at Pubmed) Zhonghua Yi Xue Za Zhi [Chinese Medical Journal] 87(45): 3213-3218).

Drug targeting as depicted in FIGS. 13A and 13B can thus be viewed as obtained in stages. The first consists of positioning the motorized nonjacketing side-entry connector, the second of moving the tip of the injection microneedle to the location wanted, the third in controlling the release of the drug or drugs. within the organ or tissue parenchyma. When used for motorized fine needle magnetic vector steering in solid tumor Auger therapy, for example, the next stage consists of using the microcontroller to coordinate the proportional energization between two, but more often among three or more clasp-electromagnets for 3-dimensional control, to stereotactically direct the superparamagnetic nanoparticle drug carrier-bound drug or drugs in the ferrofluid released by the microneedle to be steered into any direction, here toward a solid tumor.

Representation in terms of the kidney of these various embodiments simple and combined or compound is exemplary, ductus side-entry jackets and tissue-inserted or intromission-type catheters, electrodes, and other styliform devices positioned with nonjacketing side-entry connectors equally applicable to any organ or tissue. While placement to deliver an antibiotic and other drugs to a site of poor penetration such as the cerebrospinal fluid or the prostate will usually be temporary, the use of an intromission-type catheter rigidly fixed in position by means of a nonjacketing side-entry connector can be used to avoid the need for increased parenteral or poorly targeted local dose over a longer time (see, for example, Archer, G. L. and Polk, R. E. 2005. "Treatment and Prophylaxis of Bacterial Infections," in Harrison's Principles of Internal Medicine, New York, N.Y.: McGraw-Hill, 16th Edition, page 795), contributing to bacterial resistance, and reducing gut microbiota to provide *Clostridium difficile*, an opportunity to gain prevalence.

If radioactive, then baseplate, side connector, and catheter, hollow needle, hypotube, or other rod-shaped device 3 is radiation shielded as described below and in copending application Ser. No. 14/121,365. When radiation shielded, locking collar 20 must be embedded within the shielding. Then, to release the side connector so that it can be rotated and moved back and forth, the segment with the collar embedded is made separately rotatable or is included at the proximal end of the proximal segment of the side connector. In either case, when the collar is loosened, the side connector is moved with the segment distal to the segment containing the collar.

Dispersion of the drug throughout the kidney as opposed to direct targeting in detail within the medulla or parenchyma as a whole is by means of a side-entry jacket on the renal artery with another on the ipsilateral renal vein if and only if a reversal agent must be used to prevent a residue from circulating. In some instances, a persistent disorder to be treated may have arisen as sequelary to a self limiting condition. The means described herein, which involve an invasive component to place and remove, can be recommended for temporary use only when the speed of recovery to be obtained from direct targeting outweighs the intrusive factor.

A more tenacious glomerulonephritis as may occur following an upper respiratory tract infection due to certain strains of streptococci, subacute bacterial endocarditis, systemic lupus erythematosis, cryoglobulinemia, vasculitis such as polyarteritis nodosa, Henoch-Schonlein purpura, or Wegener's granulomatosis, for example, is likewise treated with immunosuppressive anti-inflammatory drugs such as cyclophosphamide, corticosteroids, and/or azathioprine delivered through ductus side-entry jackets on the renal arteries. In some instances, recurrent and refractory lesions may be treatable without the need for resection.

An antibiotic or antimicrobial, for example, to treat a circumscribed lesion such as a localized or defined abscess within the medulla or parenchyma within an organ or in tissue is addressed with an intromission or insertion type catheter, hollow needle, or other styloid device fixed in position as shown in FIGS. 6, 13A, and 13B. The distribution and diameter of the emission aperture or apertures at the tip 21 of needle or catheter 3, here depicted as applied to the kidney, determine the volumetric distribution and dispersal pattern of the drug or other agent as sharply focused, or dispersed to allow 'extension for prevention.' To minimize the antimicrobial, the prevention of infection from spreading through the circulation is by placement of a ductus side-entry connector on the primary venous outlet, and in this example, spreading to the lower urinary tract, by placement high on the ureter, to release the antimicrobial in high concentration.

If during recirculation the systemic level is inadequate, the difference to the systemic dose needed is administered orally, or if the patient is incompetent, then by manual injection through a portacath or automatic delivery from a pump-pack, as described in copending application Ser. No. 14/121,365. To maximize the targeted dose while achieving protection against spreading, both an intromission-type catheter and ductus side-entry jacket on the primary artery can be used without concern for needles exposure to unaffected tissue as might contribute to bacterial resistance and reduce gut microbiota, giving *Clostridium difficile*, for example, an opportunity to gain prevalence. Citrate to prevent crystallization and the formation of calculi is delivered directly into the renal pelvis.

Analogously, diffuse (spread out, scattered, disseminated, infiltrated, distributed) disease within the liver is isolated for drug targeting by placing ductus side-entry jackets on the hepatic artery and/or portal vein, with a reversal agent or agents if necessary delivered through a jacket on the hepatic vein, whereas a discrete (localized, circumscribed) lesion such as a tumor within the liver is targeted through a fixedly positioned styloid device or devices such as a tissue-inserted or intromitted catheter, hollow (injection/aspiration) needle, electrode, or these in coaxial adjacency mounted through the same nonjacketing side-entry connector or separately through a separate nonjacketing side-entry connector.

Concurrent delivery through directly lesion-targeted antineoplastic, anti-inflammatory, antimicrobial, and/or immunosuppressive medication through a radiation shielded catheter such as the side connectors 3 shown in FIGS. 10A and 10B held in position by a nonjacketing side-entry connector with a background dose suffused through the hepatic vasculature through ductus side-entry jackets allows apportionment of the medication to prevent the spread of the disease from the primary nidus lesion directly targeted. Such means constrain this medication to the target organ and lesion therein, substantially eliminating drug interactions outside the target organ.

Permanent clasp-magnets for placement at the surface of an organ such as the kidney, spleen, or liver, to draw a ferrofluid containing superparamagnetic nanoparticle drug carrier bound pharmaceutical from the blood supply through the medulla or parenchyma toward the outer cortex, fibrosa, or adventitia as appropriate, or for placement alongside a vessel to steer the drug into a desired branch, for example, were described in copending application Ser. No. 13/694,835 entitled Integrated System for the Ballistic and Nonballistic Infixion and Retrieval of Implants with or without Drug Targeting, as were impasse-jackets for targeting drugs such as immunosuppressive, radioactive, ribonucleic acid interfering, or antimicrobial, to a native or transplant organ, region, or supply territory without exposing the rest of the body.

Clasp-electromagnets, which can be coordinated in field strength, preferably under the control of a microcontroller with program and negative feedback as to the instantaneous nanoparticle trajectory, are described in copending application Ser. No. 14/121,365 entitled Ductus Side-entry Jackets and Prosthetic Disorder Response Systems. While avoiding the risk of rejection and the need for lifelong immunosuppressive medication, surgery that harvests and reconfigures healthy autologous tissue to support a different function, one for which the tissue is not adapted and ill suited, extends trauma and involves a loss of normal function at the donor site. To involve otherwise unaffected tissue begs adverse sequelae to include the risk of infection at both harvesting and graft sites. Using the wound or tissue perforation fastener with side-entry connector feed of an antiseptic described herein, a suprapubic cystostomy or nephrostomy for voiding dysfunction or for the targeted delivery of drugs to the urinary tract through a separate line avoids the formation of a biofilm or irritation at the entry wound.

Placed endoscopically with trauma intermediate between a temporary suprapubic cystostomy and diversion through surgical reconstruction, typically an ileal conduit, the catheter should remain in place without complications for years. The belief that patients will always opt for a noninvasive procedure over one that is minimal and provides optimal results has been dispelled with the experience of laparoscopic cholecystectomy (see, for example, The Merck Manual 18th edition, 2006, page 242; Giurgiu, D. I. N. and Roslyn, J. J. 1997. "Calculous Biliary Disease," Chapter 41 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven, page 1045).

Surgical procedures to accomplish urinary diversion at the bladder include the Monti, spriral Monti, Yang-Monti, and Young-Monti methods for creating an ileal conduit (see, for example, Kamat, N. N. and Khandelwal, P. 2007. "Laparoscopy-assisted Reconstruction of a Long-segment Ureteral Stricture Using Reconfigured Ileal Segment: Application of the Yang Monti Principle," Journal of Endourology 21(12): 1455-1460; Castellan, M. and Gosalbez, R. 2006. "Ureteral Replacement Using the Yang-Monti Principle: Long-term Follow-up," Urology 67(3):476-479), and the Mitrofanoff appendicovesicostomy, all showing good durability without risk of rejection, but procedurally and anesthetically more lengthy, coopting normal tissue, complex, sometimes postoperatively painful due to trauma (Lazica, D. A., Ubrig, B., Brandt, A. S., von Rundstedt, F. C., and Roth, S. 2012. "Ureteral Substitution with Reconfigured Colon: Long-term Followup," Journal of Urology 187(2):542-548) and exceptionally, subject to stricture (Castellan, M. A., Gosalbez, R. Jr., Labbie, A., and Monti, P. R. 1999. "Clinical Applications of the Monti Procedure as a Continent Catheterizable Stoma," Urology 54(1):152-156), or fistulization (Ordorica, R., Wiegand, L. R., Webster, J. C., and Lockhart, J. L. 2014. "Ureteral Replacement and Onlay Repair with Reconfigured Intestinal Segments," Journal of Urology 191(5):1301-1306).

A central object in seeking life long durability using synthetics is to eliminate the need to divert normal tissue, which preliminary step risks the complications of a separate procedure and places the source system and diverted tissue at jeopardy. By contrast, urinary diversion using currently available synthetic, or alloplastic components, such as a catheter and hollow needle in a patient with a long term if not life long need for urinary diversion avoids significant trauma and the appropriation of healthy tissue but does so at the expense of durability, complications that develop over time, necessitating periodic catheter replacement. Essentially, the durability and freedom from complications of urinary diversion are greatest when the greatest trauma is involved and least when the least trauma is involved.

For the highly vulnerable patient requiring extended diversion and unable to tolerate much trauma, extended general anesthesia, the risk of complications, or a life-long need to replace catheters, this relationship must be overcome. For such a patient, an endoscopic procedure involving minimal surgery to place a permanent device little susceptible to complications is plainly beneficial. Due to the susceptibility to complications at the integumentary and internal structure entry wounds of conventional means such as intravenous needles and indwelling catheters for establishing connections inside the body, these are unsuited to use in a long term or life long automatic ambulatory prosthetic disorder response system. For such use, these connections must be positive, secure, and compatible with the control system.

Congenital deformities of the gastrointestinal tract are often the result of ischemia during development, and when the loss due to accidental trauma, mesentery will have been destroyed as well. Therefore, to become fully integrated, a tissue engineered gut must include vessels, preferably mesentery, that will anastomose with remaining mesentery or native vessels. Even though as living, a tissue engineered gut will be susceptible to disease, ischemia, postprocedural spasm, and stricture as would no prosthesis, provided nervous, vascular, and immune function are present, it grows in a child, and will anastomose with native vessels to become fully integrated, a tissue engineered ductus is to be preferred. Tissue engineered gut under development should therefore include mesentery which the operator can trim as necessary.

The prevention of short gut syndrome where the length of gut is significant will most likely be accomplished through tissue engineering and less likely through allograft with drug targeting to spare tissue outside the treatment site from immunocompromise. By contrast, a sufficient prosthesis must not simply replace a missing segment of gut to the extent of motile or extrusive function but compensate for missing digestive function to include hormonal, enzymatic, and secretory. It need not, however, include mesentery or living vessels. Rather than to become integrated as living tissue, connection to living tissue is by means of long available end to end anastomotic connectors and ductus and nonjacketing side-entry connectors. For this reason, prosthetic gut must for a time be limited to short segments where the chime need only be propelled from one intact segment to the next.

Another benefit in avoiding the appropriation of otherwise uninvolved tissue is that the reduction in trauma allows intervention in a patient such as a preterm neonate that should not undergo more elaborate reconfigurative or radical surgery, whether as a bridge until a different procedure can be performed. Procedures that appropriate healthy tissue are numerous, traumatizing, destructive of function, physiologically disruptive, and expose healthy tissue to the risk of infection. Not included is the surgical construction of a stoma as in a colostomy where unaffected tissue is appropriated and distal portions of the structure and often related structures must be removed as well. Ultimately, any foreign object placed inside the body will arouse an adverse reaction in some patient; however, the use of appropriate adverse reaction suppressive substances, materials, and coatings keeps such reactions to a minimum.

However, existing means for accomplishing urinary diversion which use synthetic materials cannot be placed and then left unattended. Instead, to reduce the risk of infection, the catheter from the body surface must periodically be replaced. Essentially, the means for urinary diversion to be described seeks to combine the speed and convenience of a temporary suprapubic cystostomy with the permanence of a Mitrofanoff appendicovesicostomy, Monti, Young-Monti, or Yang-Monti ileovesicostomy (see, for example, Dolat, M. T., Wade, G., Grob, B. M., Hampton, L. J., and Klausner, A. P. 2014. "Completely Intracorporeal Robotic-Assisted Laparoscopic Ileovesicostomy," Case Reports in Urology 2014:823813; Sarin, Y. K. 2011. "Yang-Monti Continent Ileovesicostomy: Experience with Three Cases," Association of Paediatric Surgeons of Pakistan Journal of Case Reports 2(2):15, available at http://www.apspjcaserep.com/documents/2011-2/pdf/ajcr-2011-2-23.pdf; Leslie, J. A., Dussinger, A. M., and Meldrum, K. K. 2007. "Creation of Continence Mechanisms (Mitrofanoff) without Appendix: The Monti and Spiral Monti Procedures," Urologic Oncology 25(2):148-153), for example, without the procedural duration, complexity, pain, or risk of infection.

It has already been stated that the gut is segment by segment differentially adapted for the absorption of different nutrients and its lining unsuited for contact with much less the regular transport of urine. Thus, aside from the risk to both donor and recipient systems of much additional dissection and prolonged anesthesia to cover not one but two procedures, even if perfectly executed for catheters to be inserted through a stoma, an ileal conduit or gut-derived neobladder will remain vulnerable to sequelae from frequent contact with urine. Provided drainage using synthetic materials can be made equally if not more durable and less subject to sequelae, it is clearly to be preferred.

A key consideration in the connection of a catheteric line to an organ such as the kidney or spleen is the point of entry. For example, when the renal pelvic outlet is obliterated or the ureter must be bypassed necessitating a nephrostomy for urinary diversion, the intrinsic motility or peristalsis that would normally drive flow into and through the ureter is disabled. Thus, if diversion must be permanent, connection is made directly to the renal pelvis. If peristaltic function is disrupted due to distal obstruction of the ureter so that a later remedy would allow its reinstatement, the takeoff is positioned just proximal to the obstruction. In some instances, peristaltic pacemaker function can be excited by placing leads much as with a prosthetic cardiac pacemaker/defibrillator.

By contrast, where drainage is adequate but drugs would best be delivered into the kidney, connection must not disrupt peristalsis (see, for example, Pruitt, M. E., Knepper, M. A., Graves, B., and Schmidt-Nielsen, B. 2006. "Effect of Peristaltic Contractions of the Renal Pelvic wall on Solute Concentrations of the Renal Inner Medulla in the Hamster," American Journal of Physiology. Renal Physiology 290(4): F892-F896; Schmidt-Nielsen, B. and Schmidt-Nielsen, B. 2011. "On the Function of the Mammalian Renal Papilla and the Peristalsis of the Surrounding Pelvis," Acta Physiologica (Oxford) 202(3):379-385. Kiil, F. 1973. "Urinary Flow and Ureteral Peristalsis," in W. Lutzeyer, W. and Melchior, H. (eds.), Urodynamics: Upper and Lower Urinary Tract, Berlin, Germany: Springer-Verlag, pages 57-70).

Usually, the kidney is targeted for the delivery of drugs through placement of a ductus side-entry jacket on the renal artery, with a reversal or neutralizing agent if needed, accomplished through the placement of a second jacket on the renal vein. With the distal tip of the side-entry connector stereotactically guided to the desired point with the aid of three dimensional fluoroscopy and computed tomography (see, for example, Sommer, C. M., Huber, J., Radeleff, B. A., Hosch, W, Stampfl, U., and 5 others 2011. "Combined CT- and Fluoroscopy-Guided Nephrostomy in Patients with Non-obstructive Uropathy Due to Urine Leaks in Cases of Failed Ultrasound-guided Procedures," European Journal of Radiology 80(3):686-691; Soria, F., Delgado, M. I., Sanchez, F. M., Allona, A., Jimenez Cruz, J. F., Morell, E., and Uson, J. 2009. "Effectiveness of Three-dimensional Fluoroscopy in Percutaneous Nephrostomy: An Animal Model Study," Urology 73(3):649-654) a drug can be precisely targeted within the renal cortex or medulla.

If delivered in the form of a ferrofluid wherein the drug is bound to a superparamagnetic nanoparticle drug carrier, one or more, most often three, clasp-magnets attached at a point or points about the outer cortex can draw the drug toward those locations from the point of entry or steer the drug so that it passes through an intervening region. Moreover, when the clasp-magnets are clasp-electromagnets as described in copending application Ser. No. 14/121,365, this steering can be actively controlled. The connector fitting to be described can be connected directly to the renal pelvis for diversion but can also be placed along the outer cortex with the distal tip brought to the depth at the angle needed. Conventional nephrostomy catheters anchor by means of an expansion within a calyx or the renal pelvis, which can be a pigtail curl, balloon, or a spreading apart of the sides of the catheter at its distal segment.

It is clear that this disallows positioning of the tip anywhere but within the pelvis or a calyx. This will serve for urinary diversion and to pass through a calculus retrieval basket, forceps, or scope, but does not allow positioning the distal tip of the catheter within the cortex or medulla. Conventional nephrostomy catheters can deliver drugs to the pelvis or a calyx but are unintended for and incapable of the directly targeted delivery of drugs to a lesion or region within the renal medulla and/or cortex. None are connected at the body surface or at the point of entry into the kidney as would allow the device to remain in place more than 4 weeks, and no surgical reconstruction can yield a permanent passage that would allow the functionality sought herein.

It is best to place a urinary drainage line at a point where the urinary tract is not inflamed. Placement of a ductus side-entry jacket along the ureter is to be preferred as least traumatic. Using nonjacketing and ductus side-entry connectors, takeoff at any level along the urinary tract to bypass an obstruction and empty at any suitable ipsilateral or contralateral point downstream is expedited; unless the pelvis and/or the ureter is obstructed or missing, a nephrostomy to tap off the urine at the renal pelvis as shown in FIG. 11 is not to be preferred to the placement of a jacket on the ureter. Urinary diversion takeoff lines are applicable upstream to a diseased or missing bladder either by nephrostomy from the renal pelvis or by placement of a ductus side-entry jacket on the ureter.

It is noteworthy that standard practice is to penetrate through the kidney in order to position the pigtail distal end of a catheter in the renal pelvis. Long term if not permanent placement of a urinary drain at a point where the urinary tract is not inflamed is accomplished by bypassing the affected tissue. The use of nonjacketing and ductus side-entry connectors allows diversion from the drain as shown in FIG. 11 to any level downstream along the urinary tract. Diversion into the ipsilateral or contralateral ureter is through a ductus side-entry jacket. So long as any portion of either ureter remains intact, to apply a nonjacketing side-entry connector to the bladder when the wall of the bladder is swollen due to an infectious or crystallization cystitis, cystitis cystica, for example, is unnecessary. Takeoff from the ureter also avoids the need for perforation entirely through the kidney.

Diversion to the bladder, or a long term or permanent drainage cystostomy, is through connector 61 through a catheter separate from line 48 or through a second connector used to convey medication from portacath 46 injection-replenished reservoir 47 by pump 49 in FIG. 12A. In stressing the durability of these connections, it should be understood that the impermanence of relatively small caliber synthetic tubing was due to the lack of an ability to maintain these lines and junctions through an accessory channel. Placing a ductus side-entry jacket on the ipsilateral ureter and emptying through either connector 61 or 62 in FIG. 12A, a drainage cystostomy can divert past diseased or missing intervening tissue.

The volume of urine emptied into the bladder increased as the height above the level of the trigone, diversion is best through connector 61 or a separate connector high on the bladder. Shown here in an exemplary sense as intravesical to treat bladder cancer, the delivery of radioactive chemotherapeutics will usually require that the line and side connector to which it is connected to baseplate 1 in FIGS. 1, 2, 4, 6 thru 12C, 13A, thru 14, 16, 18, and 20 be shielded as shown in FIGS. 9 and 10, the distal segment of the side connector in FIG. 10A shown with permanent, and that in FIG. 10B with disintegrating radiation shielding.

To avert the life-ruining prognosis of congenital irregularities in kidney function such as antenatal Bartter's syndrome, provided a conclusive diagnosis has been made, ductus side-entry jackets are placed antenatally on the renal arteries to initiate the targeted delivery of remedial medication (see, for example, The Merck Manual 18th edition, 2006, page 2024; Harrison's Principles of Internal Medicine, 16th Edition, 2005, page 1698) to the kidneys while minimizing if not eliminating other tissue from exposure. Using a nonjacketing side-entry connector as well be described, any obstacle to normal voiding can be averted through a nephrostomy as shown in FIG. 11 or a cystostomy, as shown in FIG. 12A, any inflow or outflow connections to a ureter, or in a female or prostatectomized male, the urethra, accomplished with a ductus side-entry connector. Other than in neonates and young children, a urinary prosthesis using the means to be described is meant to be permanent.

At the same time, the nonjacketing side-entry connector is endoscopically removable upon late remission and replaceable with a larger diversion set to allow for years of growth with little trauma. This durability is achieved through the use of optimally tissue compatible materials, by stabilizing the prosthesis-tissue interfaces, and by drip feeding an antibiotic into the lines to prevent infection and the formation of a biofilm By placing ductus side-entry jackets on the renal arteries, the kidneys can also be circumscribed for targeted drug delivery. If a reversal agent is available and it is necessary to avert the takeup of the drugs used by other tissue, the renal veins are jacketed to release the reversal agent or agents. Growth is accommodated through the use of a telescoping catheter. The use of a conventional gastrostomy tube averts the considerable number of complications that increase in probability and severity over time with the use of nasogastric and orogastric tubes.

However, in a conventional gastrostomy, the lack of a junction securely fastened to the tissue surrounding the small gastric entry wound risks distal retention-balloon migration and gastric obstruction, which can lead to vomiting, hematemesis, and aspiration pneumonia (see, for example, Than, M. M., Witherspoon, J., Tudor, G., and Saklani, A. 2012. "Gastric Outlet Obstruction Secondary to Percutaneous Endoscopic Gastrostomy Tube Placement," Endoscopy 44 Supplement 2 UCTN [Unusual Cases and Technical Notes]:E269-E270; Akashi, T., Takahashi, S., Yodoe, K., Yamada, M., Yoshimura, D., and 3 others 2012. "Gastric Outlet Obstruction Caused by Gastrostomy Tube Balloon in 3 Cases," (in Japanese; English abstract at http://www.ncbi.nlm.nih.gov/pubmed/22481261), Nihon Shokakibyo Gakkai Zasshi [Japanese Journal of Gastroenterology] 109(4):600-605; Chong, V. H. 2004. "Gastric Outlet Obstruction Caused by Gastrostomy Tube Balloon,"

Indian Journal of Gastroenterology 23(2):80; Shellito, P. C. and Malt, R. A. 1985. "Tube Gastrostomy. Techniques and Complications," Annals of Surgery 201(2):180-185).

Retrograde jejunoduodenal intussusceptions due to gastrostomy tube or Foley catheter balloon migration appears more common than is often supposed (see, for example, Jamil, Y., Idris, M., Kashif, N., Alam, T., Idris, S., and Memon, W. A. 2012. "Jejunoduodenogastric Intussusception Secondary to Percutaneous Gastrostomy Tube in an Adult Patient," Japanese Journal of Radiology 30(3):277-280; Ibegbu, E., Relan, M., and Vega, K. J. 2007. "Retrograde Jejunoduodenogastric Intussusception Due to a Replacement Percutaneous Gastrostomy Tube Presenting as Upper Gastrointestinal Bleeding," World Journal of Gastroenterology 13(39):5282-5284; Hui, G. C., Gerstle, J. T., Weinstein, M., and Connolly, B. 2004. "Small-bowel Intussusception around a Gastrojejunostomy Tube Resulting in Ischemic Necrosis of the Intestine," Pediatric Radiology 34(11):916-918; Ragunath, K., Roberts, A., Senapati, S., and Clark, G. 2004. "Retrograde Jejunoduodenal Intussusception Caused by a Migrated Percutaneous Endoscopic Gastrostomy Tube," Digestive Diseases and Sciences 49(11-12):1815-1817; Fisher, D. and Hadas-Halpern, I. 2001, "Jejunoduodenogastric Intussusception—A Rare Complication of Gastrostomy Tube Migration," Pediatric Radiology 31(6):455; Gasparri, M. G., Pipinos, Kralovich, K. A., and Margolin, D. A. 2000. "Retrograde Jejunogastric Intussusception," Southern Medical Journal 93(5):499-500; Ciaccia, D., Quigley, R. L., Shami, P. J., and Grant, J. P. 1994. "A Case of Retrograde Jejunoduodenal Intussusception Caused by a Feeding Gastrostomy Tube," Nutrition in Clinical Practice 9(1):18-21; Dubinsky, T. J. and Kang, K. 1992. "CT Appearance of Retrograde Jejunoduodenogastric Intussusception: A Rare Complication of Gastrostomy Tubes," American Journal of Roentgenology 158(1):212-213 [comment on Weber and Nadel]; Weber, A. and Nadel, S. 1991. CT Appearance of Retrograde Jejunoduodenogastric Intussusception: A Rare Complication of Gastrostomy Tubes," American Journal of Roentgenology 156(5):957-959).

The reason is that the balloon prevents the tube from pulling out through the gastric entry wound, but unattached and not firmly connected to the tissue surrounding the wound, cannot prevent distal migration or progressively more irritating movement between the sides of the catheter and the wound. Other serious complications from the use of gastrostomy tubes have been reported (see, for example, Saavedra, H., Losek, J. D., Shanley, L., and Titus, M. O. 2009. "Gastrostomy Tube-related Complaints in the Pediatric Emergency Department: Identifying Opportunities for Improvement," Pediatric Emergency Care 25(11):728-732; Baskin, W. N. 2006. "Acute Complications Associated with Bedside Placement of Feeding Tubes," Nutrition in Clinical Practice 21(1):40-55; Friedman, J. N., Ahmed, S., Connolly, B., Chait, P., and Mahant, S. 2004. "Complications Associated with Image-guided Gastrostomy and Gastrojejunostomy Tubes in Children," Pediatrics 114(2):458-461).

As shown in FIG. 4, to hold fast despite abrupt and forceful excursions of a substrate gastric wall or myocardium, for example, especially where a gastropexy is contraindicated, a side-entry connector with additional tissue engaging snap-clasps 5 surrounding the catheter can be used. In FIG. 20, two connectors as shown in FIG. 4 are joined by spring loaded spanning stabilizer bar 33. A second such pairing positioned atop bar 33 perpendicular to that shown does not interfere with the shock absorption feature of either. In some instances, adhesion will be jeopardized because of a potential for changes in hardness of the subjacent tissue due to the disease treated itself or an intercurrent degenerative process. Where such a threat of progressive malacosis is present but a single side connector with mainline and sideline remains appropriate, additional adhesion is obtained by fastening additional faceplate-snap-clasp fastening pads as shown in FIG. 4 to those shown in FIG. 20.

Additional pads can be connected to those shown in either axial or perpendicular relation to crossover bar 33. Connection between adjacent pads is by a flat platform fixed to the surface of the adjacent pads by a suitable adhesive. Where additional adhesion is to be obtained with anchoring needles 6 such as those made of titanium and having a deep engraved or etched surface texture with undercuts to promote tissue ingrowth, wetting the underside of each pad with a surgical grade adhesive such as one glycolic (alpha-hydroxyacetic) acid based including dexamethazone to least interfere if not promote tissue infiltration will assist to stabilize the needles as ingrowth progresses. Otherwise, adhesives are broken down hydrolytically and enzymatically limiting the time these remain effective.

Each knife switch-configured snap-clasp can mount more than two needles along a span of the same or greater length. Before the attachment of a side-entry connector to anatomy of moderate mobility, the organ or tissue as a whole is best stabilized with suture as in a conventional nephropexy or gastropexy. Additional stabilization can be obtained through the use of a connecting span as shown in FIG. 19. Nonjacketing side-entry connectors as shown in FIGS. 1, 2, 4, 6, 7 thru 11, 13A thru 14, 17, and 20, and the catheter-to-catheter end-to-end diameter adapter connector shown in FIG. 22 include miniature shackle or shank-configured suture loops or eyelets 32, or small perforated bollards much as the proximal end of a sewing needle with eye, generally positioned toward or along the sides or edges, through which suture can be passed.

Suture loops are indicated in the drawing figures but might be increased in number, such as by adding suture loops along the side connector bounding sides of the pads in FIG. 20. When the organ is mobile, such as with nephroptosis, or floating kidney, a primary nephropexy is supported with suture placed through these small anchors. To treat an anterior lesion of the kidney, the patch-electromagnets can be placed at points about the pararenal fat, renal fascia, or Gerota's fascia, rather than at the outer surface, or cortex, of the kidney itself. Since to treat a posterior renal lesion, tissue expansion and subfascial or submuscular placement of the magnets would be necessary, treatment is best by dissecting the kidney free and stabilizing the kidney with suture.

Then mounting the side-entry connector and patch-electromagnets directly to the kidney substantially eliminates relative movement among these, as further addressed below in the section entitled Stereotactic Drug Steering by Magnetic Vectoring. The handles also allow placement of the side-entry connector where the needles are not used. The spanned side-entry connectors stabilize the tissue straddled by the connectors, while fixation with suture stabilizes the wider structure. However, where pulling forces are strong enough to tear out the connector, the suture is placed near to the connector, not through suture loops or suture loops or eyelets 32. For example, to stabilize the stomach, a conventional anterior gastropexy is used. Broadly, suture passed through suture loops or eyelets 32 should be oriented to pull in or support rather than to pull out and compromise side-entry connector retention.

While shown in its simplest form as joining two connectors, such a span can be three or four-armed and further extended to join three of four connectors, for example. The spans usually consist of one slightly smaller arm telescoped (intromitted, intussusepted) to reciprocate within that larger, the intended distance between the connectors set by a spring at the end of the inner span to act as a shock absorber that provides immediate return to the positioning intended. The problem of a progressive malacosis is addressed above in this section. When the disease process has rendered the site for placement of the nonjacketing side-entry connector malacotic, a stabilizing bar (brace, bridge, span) 33 in FIG. 20 is used to unite two or more nonjacketing side-entry connectors in straddling relation to the point for side connector insertion. Additional adherence is obtained by increasing the number of pads, as explained above.

The suture then prevents larger motions of the insertion site in relation to the baseplates. The apertures in the separate baseplates are used not to accept a side connector, hollow needle, hypotube, or other rod-shaped device, but rather a friction fitting bung at either end of a stabilizing spanner bar 33. The stabilizing bar friction fits into the apertures of the baseplate to either side and provides a central aperture for insertion of the catheter, hollow needle, electrode, side connector, or another rod-shaped device. Such a spanner bar can contain a compression spring to serve as a shock absorber. The foregoing subject does not arise with compact anatomy unsusceptible to jarring displacements such as pertains to the treatment of venous insufficiency or venous stasis ulcers (venous ulcers, chronic venous insufficiency ulcers, varicose ulcers, stasis ulcers, stasis dermatitis, ulcus cruris, ulcus cruris venosum).

Ulcers intended for treatment as described below have proven refractory to healing, take too long to heal, or repeatedly heal only to recrudesce despite standard of care measures to include the wearing of compression stockings (see, for example, Harlander-Locke, M., Lawrence, P., Jimenez, J. C., Rigberg, D., DeRubertis, B., and Gelabert, H. 2012. "Combined Treatment with Compression Therapy and Ablation of Uncompetent Superficial and Perforating Veins Reduces Ulcer Recurrence in Patients with CEAP 5 Venous Disease," Journal of Vascular Surgery 55(2):446-450; Chatterjee, S. S. 2012. "Venous Ulcers of the Lower Limb: Where Do We Stand?," Indian Journal of Plastic Surgery 45(2):266-274; Alamelu, V. 2011. "Is Chronic Venous Ulcer Curable? A Sample Survey of a Plastic Surgeon," Indian Journal of Plastic Surgery 44(1):104-109; Howard, D. P., Howard, A., Kothari, A., Wales, L., Guest, M., and Davies, A. H. 2008. "The Role of Superficial Venous Surgery in the Management of Venous Ulcers: A Systematic Review," European Journal of Vascular and Endovascular Surgery 36(4):458-465; van Gent, W. B., Hop, W. C., van Praag, M. C., Mackaay, A. J., de Boer, E. M., and Wittens, C. H. 2006. "Conservative Versus Durgical Treatment of Venous Leg Ulcers: A Prospective, Randomized, Multicenter Trial," Journal of Vascular Surgery 44(3):563-571; Tenbrook, J. A. Jr., Iafrati, M. D., O'donnell, T. F. Jr., Wolf, M. P., Hoffman, S. N., Pauker, S. G., Lau, J., and Wong, J. B. 2004. "Systematic Review of Outcomes after Surgical Management of Venous Disease Incorporating Subfascial Endoscopic Perforator Surgery," Journal of Vascular Surgery 39(3):583-589).

The embodiment of the invention and its application described in the section below entitled Venous Stasis Ulcers of the Lower Leg should reduce the need for drugs; that notwithstanding, the accessory channels seen as part number 13 in the enlarged view shown in FIG. 19 allow the direct targeting to the ulcerated tissue of drugs, and in so doing, materially improves the utility of these, averting side effects such as the gastrointestinal upset induced by pentoxifylline, adverse reactions, and allowing increased concentration (see, for example, O'Meara, S., Al-Kurdi, D., Ologun, Y., Ovington, L. G., Martyn-St James, M., and Richardson, R. 2014. "Antibiotics and Antiseptics for Venous Leg Ulcers," "Antibiotics and Antiseptics for Venous Leg Ulcers," Cochrane Database of Systematic Reviews CD003557; Jull, A. B., Arroll, B., Parag, V., and Waters, J. 2012. "Pentoxifylline for Treating Venous Leg Ulcers," Cochrane Database of Systematic Reviews 12:CD001733; Dale, J. J. 2000. "Pentoxifylline in the Treatment of Venous Leg Ulcers," Archives of Dermatology; 136( ):1142-1143).

Whether in preparation for skin grafting or epithelization (epithelialization), the accessory channel with supply pump reversed allows aspiration (Wen, H., Li, Z., Zhang, M., Wang, J., Wang, G., Wu, Q., and Tong, 5.2015. "Effects of Vacuum Sealing Drainage Combined with Irrigation of Oxygen Loaded Fluid on Wounds of Patients with Chronic Venous Leg Ulcers," (in Chinese, abstract at Pubmed) Zhonghua Shao Shang Za Zhi [Chinese Journal of Burns] 31(2):86-92), and when implanted subdermally, does not interfere with the placement of a skin graft, regardless of type as to artificial or autologous (Jones, J. E., Nelson, E. A., and Al-Hity, A. 2013. "Skin Grafting for Venous Leg Ulcers," Cochrane Database of Systematic Reviews 1:CD001737, Op cit.; Vytautas Jankunas; Rokas Bagdonas, Donatas Samsanavicius, and Rytis Rimdeika, 2007. "An Analysis of the Effectiveness of Skin Grafting to Treat Chronic Venous Leg Ulcers," Wounds 19(5):128-137.). More generally, the combination of skin grafting and use of the device shown in FIGS. 17 thru 19 should achieve positive results in more patients, more quickly, and allow the sustainment of the cure once achieved.

Long-standing non-healing venous ulcers pose an additional if small risk of undergoing malignant transformation to squamous, or rarely, basal cell carcinoma (see, for example, Sirbi, A. G., Florea, M., P{hacek over (a)}tracu, V., Rotaru, M., Mogo, D. G., Georgescu, C. V., and M{hacek over (a)}rg {hacek over (a)}ritescu, N. D. 2015. "Squamous Cell Carcinoma Developed on Chronic Venous Leg Ulcer," Romanian Journal of Morphology and Embryology 56(1): 309-313; Poccia, I., Persichetti, P., Febopras, G. F. M, Gigliofiorito, P. Campa, S., Del Buono, R., and Lamberti, D. 2014. "Basal Cell Carcinoma Arising in a Chronic Venous Ulcer: Two Cases and a Review of the Literature," Wounds 26(4):E30-E35, available at Medscape; Schnirring-Judge, M and Belpedio, D. 2010. "Malignant Transformation of a Chronic Venous Stasis Ulcer to Basal Cell Carcinoma in a Diabetic Patient: Case Study and Review of the Pathophysiology," Journal of Foot and Ankle Surgery 49(1):75-79; Lehnert, W, Kohl, K., Riebe, H., Junger, M., and Ladwig, A. 2008. "The Treatment of Malignant Tumors on Venous Leg Ulcers. Case Presentation and Lliterature Review," (in German, English abstract at Pubmed) Hautarzt 59(11):912-916; Baldursson, B. T., Hedblad, M. A., Beitner, H., and Lindelof, B. 1999. "Squamous Cell Carcinoma Complicating Chronic Venous Leg Ulceration: A Study of the Histopathology, Course and Survival in 25 Patients," British Journal of Dermatology 140(6):1148-1152; Baldursson, B., Sigurgeirsson, B., and Lindelof, B. 1995. "Venous Leg Ulcers and Squamous Cell Carcinoma: A Large-scale Epidemiological Study," British Journal of Dermatology 133(4):571-574; Blank, A. A. and Schnyder, U. W. 1990. "Squamous Cell Carcinoma and Basal Cell Carcinoma within the Clinical Picture of a Chronic Venous Insufficiency in the Third Stage," Dermatologica 181(3): 248-250).

A stabilizing bar 33 for connection of nonjacketing side-entry connectors to mobile substrate tissue is shown in FIGS. 20 and 21. Unless it includes an internal shock absorber on either side as shown and as described below in the section entitled Description of the Preferred Embodiments of the Invention, the stabilizing bar when not including the shock absorption feature as depicted is made bendable, allowing the operator to shape it to best conform to the anatomy. Such a double padded connector can also be made with a convexly or concavely bowed or cambered crossover arm 33, but angling of the pads is more versatile simply by altering the angle at which either end of bar 33 enters aperture 4, which is extended downward for more secure union. That both of these means for bending the embodiment shown in FIG. 20 might be combined and that the embodiment shown in FIG. 20 might be further compounded through the addition of a third radially directed arm to respond to a shock from any lateral direction is considered obvious.

When a more intense reaction is anticipated at the point of side connector entry into the subjacent tissue, aperture 4 through baseplate 1 is kept as centered as possible, and foam 2 immediately surrounding it omitted. The space created then serves as a cistern to receive a drip line as an accessory channel such as 34 in FIG. 21. If aperture 4 were too close to the edge of baseplate 1, the wall of foam 2 surrounding the drip tube would be missing or too thin, allowing the anti-inflammatory and/or antimicrobial medication, for example, to run out rather than be dammed about. The rate of the drip has a number of determinants medical and structural, to include the intensity of the adverse reaction and the dimensions of the cistern.

The placement of the entry wound at the body surface is the same as for a conventional gastrostomy, but the catheter led out through the body wall is passed through a body surface port as described in copending application Ser. No. 14/121,365, entitled Ductus Side-entry Jackets and Prosthetic Disorder Response Systems. Once this port at the body surface has been positioned, the internal (intracorporeal) entry wound, or circular incision surrounding the point of side connector insertion, can if necessary be protected by dripping antimicrobial, anti-inflammatory, and/or anticoagulative medication from a separate fine catheter as sideline or accessor channel in the manner of an oil drip to flow about and down into the wound. This, however, necessitates a means for preventing the medication from running off.

When a more intense reaction is anticipated at the point of side connector entry into the subjacent tissue, aperture 4 through baseplate 1 is kept as centered as possible, and foam 2 immediately surrounding it omitted. The space created then serves as a cistern to receive a drip line accessory channel such as 34 in FIG. 21. If aperture 4 were too close to the edge of baseplate 1, the wall of foam 2 surrounding the drip tube would be missing or too thin, allowing the anti-inflammatory and/or antimicrobial medication, for example, to run out rather than be dammed about. The rate of the drip has a number of determinants medical and structural, to include the intensity of the adverse reaction, the dimensions of the cistern, and open or closed cell structure, hence, porosity of the foam.

In a simpler case where only one or a number of side-entry connectors are to provide the same drug or combination of drugs at a time, the drip line, as any accessory channel, is led from a separate injection point on a portacath or a subcutaneously implanted Ommaya type reservoir implanted subcutaneously in the pectoral region, allowing full or closed-skin implantation with no lines passed through the integument. In a more complex case such as one involving the treatment of comorbid conditions where multiple drugs and destinations are essential, a body surface port described in copending application Ser. No. 14/121,365 is used. Such a multiport may be thought of as a nonjacketing side-entry connector for use at the body surface.

To assure that when jerked at by the contracting stomach the side connection tube cannot injure surrounding tissue or work its way loose from the side-connector, an anterior gastropexy, which the literature shows in a conventional context to be substantially free of complications, can be used, and/or the catheter provided with an outer layer of viscoelastic polyurethane foam. Suture loops 32 seen in FIGS. 1, 2, 4, 6 thru 11, 13A thru 14, 17, and 20, and at the junctions of the caliber incline of the catheter gauge adapter shown in FIG. 22 facilitate fixation to neighboring tissue. To place a nonjacketing side-entry connector, the operator gently presses down on baseplate 1, compressing foam 2, and rotates about knife switch-configured snap-clasps 5 shown in FIGS. 2 and 3, for example, to engage the underlying tissue. In FIG. 7, the side-entry connector has been positioned against the tissue before being pressed down and knife switch-configured snap-clasps 5 rotated about to engage the substrate tissue.

In FIG. 8, the same nonjacketing side-entry connector is shown after having been anchored into the substrate tissue so that foam lining 2 is compressed and needle rotating handles 8 now face away from the center of baseplate 1. That snap-clasps 5 might be reversed in direction is considered obvious. As may be noted in FIG. 7 thru 10, if locking collar 20 has not been tightened and trepan edge 21 is on line with the outer surface of foam 2, pressing down on the baseplate initiates incision into the subjacent or substrate tissue of the trepan. When the side connector is equipped with a crosshair cutting or grating wires 22, water jacket 31 is used to expel the tissue gratings out through the side connector. When the side connector is used to pass blood or urine so that crosshair cutting wires 22 are omitted as a platform for the accumulation of clot or uroliths respectively, water jacket 31 is turned on to expel the coherent tissue plug only after the tissue plug has been cut.

Once the needles have been inserted, the foam is released, whereupon it expands within the available space between the tissue and the baseplate. The foam urges the baseplate away from the surface of the subjacent or substrate tissue, and in so doing, exerts restorative force to keep the needles and baseplate firmly engaged, as well as accommodates any irregularities or unevenness along the surface of the tissue within the available space between the tissue and the baseplate. As nonuniformities along the surface of the tissue, especially if fibrosal or adventitial will often be due to fine vessels and nerves, the foam, which is warmth responsive, prevent these fine but critical structures from undergoing compression and compression trauma.

As shown in FIGS. 8 and 10A, unless used to inject drugs or electrostimulate the underlying tissue, once fully rotated to engage the substrate tissue, the points of anchoring needles 6, made of a strong stainless steel or titanium to prevent fracture, are nestled within the foam, directed toward the underside of baseplate 1, eliminating these as a potential source of injury. If hollow for injection and/or aspiration and/or electrically conductive to allow use for electrostimulation therapy as shown in FIGS. 9 and 10B, then for strength, anchoring needles 6 ordinarily still include but do not consist entirely of these materials. For a patient sensitive to metals, these are replaced with a strong polymer, such as an implantable bearing grade nylon or poly(aryl-ether ether ketone) (see just below).

For injection and/or electrostimulation, the tips of needles 6 cannot continue up into foam 2, so that the use of suture loops or eyelets 32 to thinly secure the connector in position by fixation to neighboring tissue should be considered. Just as when stopped at points along the circular trajectory in the underlying tissue, when situated with tips in the foam, the needles can inject adverse tissue reaction counteracting medication Injection-capable needles can thus serve in lieu of a separate accessory channel such as line 34 shown in FIG. 21. With the double pad or footing connector shown, however, line 34 is needed because the anchoring needles stand off to a side of side connector 3, the catheter delivering medication at the central location.

Whereas 'dumb' needles without tip amid-tissue injection capability, for example, are made full length so that the tips of the needles continue up into the foam cushion underlining of the connector for safety, needles that do have injection and/or electrical discharge capability must do so while the needle tips remain mid-tissue. Such needles can be full length and made retractable when needed for injection or electrical discharge, or as shown in FIGS. 9 and 10B, made to a specified length for continued injection or electrical discharge at the needle tips at the end of the needle trajectory with the needles fully extended. Needles made to inject once at intervals along the trajectory before knife-switch configures snap-clasp 5 is fully 'thrown' can be full length, and/or made to electrically discharge over their entire surface. Functional needles secured with a nonjacketing side-entry connector such as that shown in FIG. 4, especially when additional fixation is imparted by passing suture through suture loops or eyelets 32 and neighboring tissue should seldom if ever result in injury to the tissue treated.

A connector as shown in FIG. 4 with additional needles can have all needles injection-aspiration and electrical discharge functional, or all 'dumb,' or some functional and some not so in any combination. That is, in most instances, a nonjacketing side-entry connector with anchoring needles 6 capable of injection and/or electrostimulation as shown in FIGS. 9 and 10B and described below will provide sufficient retention and stability for the needles to remain extended with tips mid-tissue and ready for injection, for example, at any moment, without significant risk of injury upon impact. For these reasons, rather than made rotatable after placement, needles are usually either of shorter injection and/or electrostimulation length or of full length.

However, in some cases, it will be beneficial if full length functional needles can not only be retracted into the foam after each use but additionally indexed incrementally to any extent of deployment along the semicircular trajectory and paused to inject and/or electrically discharge before proceeding to the next detent or stopping point or the needle tip retracted into the foam. When used with a radioactive tracer and/or chemotherapeutic, the nonjacketing side-entry connector is radiation shielded much as the shielding shown in FIGS. 10A and 10B. Where post implantation intermittent injection and/or electrostimulation at any interval is required once or on a regular basis, the full length needles are made rotatable from one detent to a next until fully rotated or extended, effectively retracted, into the foam following each such use. Isolated or repetitive administration of drugs and/or electrostimulation is applied automatically by the microcontroller implant according to its prescription program.

Starting with the tips of the needles nestled within the foam, successive injections or discharges can be applied either when the needles are rotated down and out of the foam and into the subjacent tissue, upon return, or during both descent and return. Whenever injection or electrostimulation are required at any point or points along the needle trajectory-established by the semicircular shape of the needles and the knife switch-configured snap-clasp 5, withdrawal from the foam to accomplish this action can be effected once or intermittently in either direction at intervals. Use of detents and a dc rotary solenoid under the control of the microcontroller implant coaxially attached to cam axle 9 is addressed below in the section entitled Description of the Preferred Embodiments of the Invention. In the quadruple snap-clasp 5 embodiment shown in FIG. 4, each cam axle 9 is connected to a rotary solenoid (not shown), that to either side wired for opposing polarity, positioned between the snap-clasps to either side, with 'breathing' apertures 36 are arranged about these.

To avoid interference with the passage of superparamagnetic iron oxide nanoparticles acting as drug carriers, needles made of a stainless steel should be austenitic and nonmagnetic. For temporary use, the needles are generally made of a strong and nonbrittle polymer such as implantable poly(aryl-ether ether ketone) (PEEK), such as Solvay Zeniva® Brussels, Belgium, or a self-reinforced polyphenylene such as Solvay Proniva® Brussels, Belgium, or a pliant nylon. A smooth nylon surface will resist tissue infiltration without the need for a coating to prevent ingrowth (Chegini, N., von Fraunhofer, J. A., Hay, D. L., Stone, I. K., and Masterson, B. J. 1987. "The Use of Nylon Pouches to Prevent Cellular Attachment to Implanted Materials," Biomaterials 8(4):315-319), but is still wetted with phosphorylcholine or dexamethazone, for example, to forestall an adverse tissue reaction.

Stainless steel needles are wetted with a transcatheter lubricant such as ACS Microslide®, Medtronic Enhance®, Bard Pro/Pel® or HydrolPel®, Cordis SLX®, or Rotaglide®. For permanent use, the needles are generally larger in dimensions, provided with an etched deep texture to include undercuts, and coated to promote tissue infiltration. To expedite placement with the aid of imaging equipment, a side-entry connector such as that shown in FIG. 5 or other rod-shaped device is coated at its distal trepan edge and for two or so millimeters short of its free end with high imaging contrast such as tantalum (Danfoss Tantalum Technologies Danfoss Coating,® for example).

This allows the trepan to be seen as it is inserted to the desired depth into an organ or tissue, allowing the delivery of drugs to a lesion at a certain depth within the medulla or parenchyma of an organ or other tissue. The ability of a nonjacketing side-entry connector to position the tip of a catheter at a certain depth within tissue and maintain it there indefinitely makes feasible certain therapeutic options. If sufficient slack can be given the line or lines, connections made in childhood can gradually extend as the patient grows thus avoiding the need for replacement. Contrast coating of the connectors or fasteners and the catheteric lines with tantalum, for example, allows periodic reexamination of these by imaging.

Ductus and nonjacketing side-entry connectors avoid direct apposition or anastomotic junction as would allow capillary ingrowth, intimal overgrowth, and stricture (see, for example, Krishnan, L., Chang, C. C., Nunes, S. S., Williams, S. K., Weiss, J. A., and Hoying, J. B. 2013. "Manipulating the Microvasculature and Its Microenvironment," Critical Reviews in Biomedical Engineering 41(2): 91-123; Huang, C., Wang, S., Qiu, L., Ke, Q., Zhai, W., and Mo, X. 2013. "Heparin Loading and Pre-endothelialization in Enhancing the Patency Rate of Electrospun Small-diameter Vascular Grafts in a Canine Model," American Chemical Society Applied Materials and Interfaces 5(6):2220-2226; Whited, B. M., Hofmann, M. C., Lu, P., Xu, Y., Rylander, C. G., Wang, G., Sapoznik, E., and 4 others 2013. "Dynamic, Nondestructive Imaging of a Bioengineered Vascular Graft Endothelium," Public Library of Science One 8(4):e61275; Jeschke, M. G., Hermanutz, V., Wolf, S. E., and Koveker, G. B. 1999. "Polyurethane Vascular Prostheses Decreases Neointimal Formation Compared with Expanded Polytetrafluoroethylene," Journal of Vascular Surgery 29(1): 168-176; Dardik, A., Liu, A., and Ballermann, B. J. 1999. "Chronic in Vitro Shear Stress Stimulates Endothelial Cell Retention on Prosthetic Vascular Grafts and Reduces Subsequent in Vivo Neointimal Thickness," Journal of Vascular Surgery 29(1):157-167; Golden, M. A., Hanson, S. R., Kirkman, T. R., Schneider, P. A., and Clowes, A. W. 1990. "Healing of Polytetrafluoroethylene Arterial Grafts is Influenced by Graft Porosity," Journal of Vascular Surgery 11(6): 838-845; Clowes, A. W., Zacharias, R. K., and Kirkman, T. R. 1987. "Early Endothelial Coverage of Synthetic Arterial Grafts: Porosity Revisited," American Journal of Surgery 153(5):501-504; Clowes, A. W., Gown, A. M., Hanson, S. R., and Reidy, M. A. 1985. "Mechanisms of Arterial Graft Failure. 1. Role of Cellular Proliferation in Early Healing of PTFE Prostheses," American Journal of Pathology 118(1): 43-54; Clowes, A. W., Kirkman, T. R., and Clowes, M. M. 1986 "Mechanisms of Arterial Graft Failure. II. Chronic Endothelial and Smooth Muscle Cell Proliferation in Healing Polytetrafluoroethylene Prostheses," Journal of Vascular Surgery 3(6):877-884; Clowes, A. W., Kirkman, T. R., and Reidy, M. A. 1986. "Mechanisms of Arterial Graft Healing. Rapid Transmural Capillary Ingrowth Provides a Source of Intimal Endothelium and Smooth Muscle in Porous PTFE Prostheses," American Journal of Pathology 123(2):220-330).

A shunt created from a native vessel is less susceptible to coagulation, the formation of biofilm, and intimal overgrowth at the anastomosis susceptible to stricture. However, the ability to use exogenous (synthetic) tubing makes possible application of the procedure in a patient unable to contribute a usable bypass vessel and avoids the risk of a graft versus host reaction of a homologous graft. In an otherwise healthy patient, the use of an adventitious line of the dimensions required not only avoids much dissection, trauma, and the diversion of an otherwise uninvolved artery, but spares procedural time and reduces the overall risk. Other advantages are that if necessary to oxygenate tissue where trauma has destroyed much of the blood supply, a single takeoff or source artery can supply multiple shunts, the takeoff can be remote from the territory supplied, the shunt can be placed beginning at either end and made tough walled to resist deformation from encroachment.

The significance of a nonjacketing side-entry connector in this connection is that the baseplate allows the tip of tissue engineered vessel or a catheter to be brought to a certain depth within the substrate tissue and securely held there. Absent preventive treatment, some intimal overgrowth from native tissue can be expected; however, the nonanastomotic junctions created with the use of ductus side-entry connectors are less susceptible to stricture, and if necessary, the service channel allows the application of an antiproliferative drug. Intrinsic motility and normal endothelial and immune function are unlikely with a current state of the art tissue engineered vessel, and would not obtain with a catheter.

When the application makes necessary the continued targeted delivery of supportive substances, a pump-pack is used to meter the medication, which will include an angiogenic, anticoagulant and antimicrobial into current state of the art tissue engineered or catheteric arterial and venous shunt lines. The direct delivery to a prosthetic bypass of anticlotting and antimicrobial substances through the sideline or water jacket/accessory line allows continued maintenance with a dose that is very small compared to the systemic dose. Such lines can be applied in a manner analogous to Vineberg's myocardial reperfusion procedure whereby blood is shunted to chronically hypoxic or more recently ischematized tissue from a slit in the side of a closed-ended internal thoracic artery as blood supply, or sometimes, with the artery open-ended; Vineberg and others tunneled the internal thoracic with the side slit and the end seldom left open.

To allow the healing of a venous stasis ulcer, for example, the lines are tunneled subcutaneously and jogged to a deeper path where venous obstruction is more pronounced. Both side and end release used. The measures described below are intended primarily for patients unable to contribute a disease-free native graft vessel, or who are not sufficiently healthy to undergo a more radical or double harvesting and bypass procedure, or who would likely develop adverse sequelae in the supply or drainage territory of the harvested vessel, or where standard of care medical management and bypass surgery had proven not sufficiently effective. Whatever the means, ulceration, especially arterial, in the lower leg that does not resolve with conventional treatment indicates systemic vascular disease that could lead to a myocardial or cerebral infarction and/or locally result in gangrene and the need for amputation.

Application of the means to be described to the treatment of arterial rather than venous ulceration simpler, it is the latter that is addressed. For this reason, hypoxia in the legs is best eliminated as early as possible. Here, both terminal flow and flow more closely aligned to the majority of Vineberg's operations through a side slit, side-slits, or side holes in the 'arterial' (and 'venous') lines tunneled into the hypoxic tissue are contemplated. In the lower leg, ulceration due to venous insufficiency presents crus-distad, toward the medial malleolus, or inside ankle. For that reason, ductus side-entry jackets with two side connectors, each with a sideline for the delivery of medication are used. Otherwise—especially where differences in the extent or character of disease recommend a difference in the volumetric flow rate—separate jackets for the medial and lateral line pairs are chosen.

To take advantage of any available pumping action in the calf as would reduce the need to implant an assist pump, the 'arterial' and 'venous' lines are run subcutaneously alongside the gastrocnemius or in most individuals, to a point proximal or craniad to the calf pump, then plunged to run parallel to the large vessels in parallel with the tibial vessels, or along to soleus, essentially, down through the calf pump in the lower leg, where no side slits or holes are placed. If passed through the calf pump, this section of the venous line can be made of a larger caliber softer walled tubing, attached at either end by means of a catheter gauge adapter connector of the kind shown in FIG. 22 and described in the section below entitled Description of the Preferred Embodiments of the Invention. More strongly walled tubing with parallel side slits or small holes cut along the medial facing sides where perfusion is needed then continues downward to a level short of the ulcer.

If not having been run subcutaneously along the medial head of the gastrocnemius, the lines are then brought subcutaneous to run in parallel down to the belt supported nonjacketing double side connector side-entry connector shown in FIG. 17. The belt shown in FIG. 17 is reserved for lesions that malacotic or carrying the risk of degeneration, would not allow anchoring needles 6 to remain securely fastened; whenever possible, the belt, which necessitates additional dissection and procedural time, is omitted. Above the ankle, the nonjacketing side-entry connector is inserted directly into the substrate tissue, the belt positioned subcutaneously toward the lower margin of the ulcer. Also, unless multiple drugs must be delivered to different treatment sites, body surface multiport 39 is not used but rather delivery is closed skin by injection through a portacath, such as portacath 46 diagrammatically shown in FIGS. 12A and 12C.

Side connection tube sockets 38 are shown in FIGS. 17 and 18 as co-molded and unitary with baseplate 1 and in FIG. 19 as bonded to baseplate 1. In FIG. 17, the incurrent and excurrent catheters securely engaged within the two double knife switch-configured snap-clasp 5 to either side of side connector 3 assists to prevent pulling forces against the side connectors 3 where these penetrate into the ulcerated tissue and would result in migration. The patient should therefore be left with no impediment to movement, and when implanted subcutaneously, little if any effect on outward appearance, any protrusion slight and covered over with hosiery or socks.

Thus, fixation is entrusted neither to the snap-clasps nor to the belt alone but rather to the two in combination, suture loops 32 additionally provided to prevent displacement or migration as an edematous crus gradually subsides and the leg reverts to normal size. Where edema is pronounced so that displacement down to the ankle must ensue, suture is passed through suture loops 32, allowing the side-entry connector to be tacked to a higher point in the crus. If loose, the rear hook and loop belt fastener is easily accessed under a local anesthetic through a small incision allowing the belt to be suitably adjusted. In FIG. 17, which for clarity defers showing the accessory channels to the detailed view of FIG. 19, the incurrent and excurrent lines are open-ended within or slightly deep to the ulcerated tissue. Insertion of the device does not require that the accessory channels provide a water jacket.

To treat an irreversible condition or one certain to recur, lines 34 and 35, along with their respective accessory channels 13, are positioned subdermally. FIG. 17 is diagrammatic in that the side connectors of the ductus side-entry jackets about the supply artery and draining vein are actually angled to achieve minimally turbulent confluent flow from the artery into catheteric side connector 34 and minimize sheer stress for the vein. Also, in FIG. 17, the connector-incurrent arrow to the left indicates the blood supply or 'arterial' side connection, or side connector line, while the excurrent or departing arrow to the right denotes the drainage or 'venous' side connection line.

The detail in FIG. 19 then, does show the accessory channels or sidelines where these empty into their respective side connectors to support the incurrent and excurrent blood lines 3 with medication as necessary, while FIG. 18 provides a vertical longitudinal section view through one of the line receiver or terminal portions of the side connectors, the ribbing along the external surface along the distal segment of the lines 3 and complementary ribbing along the internal surface of receivers or sockets 38 not shown. FIG. 18 depicts the side connection lines 3 and belt seen at the bottom of FIG. 17 as positioned about the outside of the leg; however, in most cases, the chronic and recurrent nature of venous ulcers recommends that the side connection lines 3 be tunneled subdermally (subcutaneously) and the belt situated likewise. In FIG. 18, the side connectors of the side-entry connector can be fixed at any depth.

Within the leg, the lines pursue the same course but are kept sufficiently separated that flow is never directly from incurrent into excurrent side slits as would bypass the microvasculature in and about the ulcer that is the intended target of perfusion. Running through the calf, however, the lines are without slits and can run appositely in parallel. Where Vineberg diverted the internal thoracic artery and sometime omentum, the procedures to be described use prosthetic tubing supported by anti-inflammatory, antimicrobial, and/or angiogenic medication as necessary, delivered from a pump directly into the blood supply, or arterial takeoff mainline, through its sideline (accessory channel, service channel), introduced in copending application Ser. No. 14/121,365, entitled Ductus Side-entry Jackets and Prosthetic Disorder Response Systems. Here, these openings are placed in the sides of fine flexible catheters with the distal end open proximate to the ulcer nidus.

To avert accidental impacts and present little visual evidence, the nonjacketing side-entry connector as shown in FIG. 17 has a low-profile, and to facilitate arterial-venous exchange at the ulcer, places the arterial and venous ostia in adjacent relation. Upon placement, the side connectors are driven just deeply enough to create lacuae when withdrawn to the fixed position. This bathes the hypoxic tissue, which is known to actively recruit arterial blood in proportion to the deficit thereof, with oxygenated and medicated blood. When the ends are closed, the nonjacketing side-entry connector anchors the lines so that the action of walking does not pull these up and away from the site of ulceration over time. This assumes an interval preceding more vigorous activity during which the side-entry connector becomes integrated into the surrounding tissue. When only the ends of the lines are open or are also open, the side-entry connector also expedites the formation.

Some hypoxic tissue will provide vacuities or voids that can be used in lieu of Vineberg's sinusoids without the need for such voids to be introduced iatrogenically. Flow through these vacuities or lacunae from side slits and/or the ends of the catheters is intended to stimulate the development of more extensive collateral circulation to reperfuse the tissue more widely and provide relief from venous hypertension. While to minimize trauma, the arterial and venous lines are best run subcutaneously or 'extraanatomically,' the pumping action of the lower leg muscles, if less forceful than the skeletal muscle, or calf pump, provides some compression-relaxation pumping action, although it is not constant or forceful as is that of the myocardium against the tunneled internal thoracic artery in Vineberg's procedure.

Vineberg trusted to the native vasculature to supply venous drainage; however, venous stasis ulcers result from venous incompetence, indicating the need for a complete arterial-venous circuit. Chronic arterial or venous insufficiency can also induce a condition of disuse atrophy in both the local arterial and venous vasculature. Rather than to depend upon a favorable recovery in venous function, reperfusion best provides supply and return lines ab initio. Adaptation of the Vineberg procedure to relieve hypoxia in the lower leg, for example, is addressed below in the section entitled Novel Applications.

To minimize reperfusion injury from an inflammatory immune response and the liberation of reactive oxygen free radicals (see, for example, Sivaraman, V. and Yellon, D. M. 2014. "Pharmacologic Therapy that Simulates Conditioning for Cardiac Ischemic/Reperfusion Injury," Journal of Cardiovascular Pharmacology and Therapeutics 19(1):83-96;

Buchholz, B., Donato, M., D'Annunzio, V., and Gelpi, R. J. 2014. "Ischemic Postconditioning: Mechanisms, Comorbidities, and Clinical Application," Molecular and Cellular Biochemistry 392(1-2):1-12. Minamino, T. 2012. "Cardioprotection from Ischemia/Reperfusion Injury: Basic and Translational Research," Circulation Journal 76(5):1074-1082; Carden, D. L. and Granger, D. N. 2000. "Pathophysiology of Ischaemia—Reperfusion Injury," Journal of Pathology 190 (3):255-266), such a procedure is performed under hypothermic conditions (see, for example, Polderman, K. H. 2004. "Application of Therapeutic Hypothermia in the ICU," Intensive Care Medicine 30(4):556-575) with hydrogen sulfide (see, for example, Predmore, B. L. and Lefer, D. J. 2011. "Hydrogen Sulfide-mediated Myocardial Pre- and Postconditioning," Expert Review of Clinical Pharmacology 4(1):83-96; Elrod, J. W., Calvert, J. W., Morrison, J., Doeller, J. E., Kraus, D. W., Tao, L., Jiao, X., and 6 others 2007. "Hydrogen Sulfide Attenuates Myocardial Ischemia-reperfusion Injury by Preservation of Mitochondrial Function," Proceedings of the National Academy of Sciences of the United States of America 104(39):15560-15565; Elrod, J. W., Calvert, J. W., Duranski, M. R., and Lefer, D. J. 2006. "Hydrogen Sulfide Donor Protects against Acute Myocardial Ischemia-reperfusion Injury," Circulation 114(18): II172) King, A. L. and Lefer, D. J. 2011. "Cytoprotective Actions of Hydrogen Sulfide in Ischaemia-reperfusion Injury," Experimental Physiology 96(9):840-846; Dongo, E., Hornyak, I., Benko, Z., and Kiss, L. 2011. "The Cardioprotective Potential of Hydrogen Sulfide in Myocardial Ischemia/Reperfusion Injury (Review)," Acta Physiologica Hungarica 98(4):369-381; Calvert, J. W., Coetzee, W. A., and Lefer, D. J. 2010. "Novel Insights into Hydrogen Sulfide-mediated Cytoprotection," Antioxidants and Redox Signaling 12(10):1203-1217; and cyclosporine (see, for example, Gill, R. S., Bigam, D. L., and Cheung, P. Y. 2012. "The Role of Cyclosporine in the Treatment of Myocardial Reperfusion Injury," Shock 37(4):341-347; Sullivan, P., Sebastian, A., and Hall, E. 2011. "Therapeutic Window Analysis of the Neuroprotective Effects of Cyclosporine A after Traumatic Brain Injury," Journal of Neurotrauma 28(2):311-318; Cook, A. M., Whitlow, J., Hatton, J., aand Young, B. 2009. "Cyclosporine A for Neuroprotection: Establishing Dosing Guidelines for Safe and Effective Use," Expert Opinion on Drug Safety 8(4):411-419; Piot, C., Croisille, P., Staat, P., Thibault, H., Rioufol, G., Mewton, N., Elbelghiti, R., and 14 others 2008. "Effect of Cyclosporine on Reperfusion Injury in Acute Myocardial Infarction," New England Journal of Medicine 359 (5):473-481) administered. The avoidance of nephrotoxicity of cyclosporine made possible by targeting the drug to a non-kidney transplant is addressed above in the section entitled Background of the Invention.

Turning now to FIG. 19, the more recent development of angiogenic drugs—which can be directly targeted to the ulcer through accessory channel 13 of side connection line 34—should facilitate collateralization. For serious cases, a technique that averted necrosis would spare the need for abscission or resection. Where primary hypoxia and not a temporary condition such as an infection or freezing are the source of injury, the catheter should remain in place indefinitely, perhaps permanently. Provided placement is firm and supported by sustaining medication, where a suitable vessel is unavailable, a tissue engineered artery or catheter can take the place of a diseased or lost vessel. If necessary to repair a defect or void, the replacement to the innate conduit is combined with collateral therapy with which the device of FIGS. 17 thru 19 is compatible, subdermal placement can be carried out during the same procedure. Otherwise, placement is deferred until healing, when the device can still be applied subdermally. Placement with the jacket shown in FIG. 17 positioned superdermally as an 'anklet' still requires that lines 34 and 35 and their respective accessory channels 13 shown in FIG. 19 be subdermally, or subcutaneously, tunneled.

Remedial measures compatible with the device shown in FIGS. 17 thru 19 to facilitate the healing of leg wounds have been developed (see, for example, Saaiq, M., Hameed-Ud-Din, Khan, M. I., and Chaudhery, S. M. 2010. "Vacuum-assisted Closure Therapy as a Pretreatment for Split Thickness Skin Grafts," Journal of the Coll Physicians and Surgeons—Pakistan 20(10):675-679; Boggio, P., Tiberio, R., Gattoni, M., Colombo, E., and Leigheb, G. 2008. "Is There an Easier Way to Autograft Skin in Chronic Leg Ulcers? 'Minced Micrografts', A New Technique," Journal of the European Academy of Dermatology and Venereology 22(10):1168-1172. Oien, R. F., Hakansson, A., Hansen, B. U., and Bjellerup, M. 2002. "Pinch Autografting of Chronic Leg Ulcers in Primary Care: Fourteen Years' Experience," Acta Dermato-Venereologica 82(4):275-278; Schmeller, W. and Gaber, Y. 2000. "Surgical Removal of Ulcer and Lipodermatosclerosis Followed by Split-skin Grafting (Shave Therapy) Yields Good Long-term Results in "Non-healing" Venous Leg Ulcers," Acta Dermato-Venereologica 80(4): 267-271; Bolivar-Flores, Y. J. and Kuri-Harcuch, W. 1999. "Frozen Allogeneic Human Epidermal Cultured Sheets for the Cure of Complicated Leg Ulcers," Dermatologic Surgery 25(8):610-617; Dunn, R. M., Fudem, G. M., Walton, R. L., Anderson, F. A. Jr., and Malhotra, R. 1994. "Free Flap Valvular Transplantation for Refractory Venous Ulceration," Journal of Vascular Surgery 19(3):525-531). Fill tissue may be used in conjunction with debridement (see, for example, Ahnlide, I., Bjellerup, M., and Akesson, H. 2000. "Excision of Lipodermatosclerotic Tissue: An Effective Treatment for Non-healing Venous Ulcers," Acta Dermato-Venereologica 80(1):28-30) and/or skin grafing (see, for example, Schmeller, W. and Gaber, Y. 2000. "Surgical Removal of Ulcer and Lipodermatosclerosis Followed by Split-skin Grafting (Shave Therapy) Yields Good Long-term Results in "Non-healing" Venous Leg Ulcers," Acta Dermato-Venereologica 80(4):267-271; Ward, D. J., Bennett, J. P., Burgos, H., and Fabre, J. 1989. "The Healing of Chronic Venous Leg Ulcers with Prepared Human Amnion," British Journal of Plastic Surgery 42(4):463-467).

3. Applications Made Possible by Ductus Side-Entry Jackets and Nonjacketing Side-Entry Connectors Because nonjacketing side-entry connectors allow synthetic catheters to be fastened to native tissue at stable junctions and ductus side-entry jackets form stable junctions with native conduits, and because both include the features enumerated above in the section entitled Concept of the Invention, can accessory or service channel to reach the junction or catheter from outside the body with drugs or line maintenance substances such as antimicrobials and anti-inflammatories, these make possible several new applications of synthetic materials to shunting, bypassing, and drainage.

a. Auger Therapy

A temporary process such as precision magnetic vector targeting of a superparamagnetic nanoparticle drug carrier-hound radionuclide, with or without an adjuvant drug or drugs at a tumor, whether in conjunction with tracking external beam radiation, uses a nonjacketing side-entry connector with motorized adjustable depth side-stem, catheter or hollow (injection/aspiration) needle, and is devised for relative ease of recoverability despite long term placement. When not motorized, side-connector 3 can be made absorbable. An external beam process, for example, is generated and adjusted at a control console, and despite a need for extreme proximity to the target tissue to conserve energy, achieve effective range, and avoid scatter onto healthy tissue, cannot itself be implanted. Radiotherapy currently tends to be either external beam photonic or nonparticulate, or internal particulate.

Used with radionuclides, the configuration shown in FIGS. 13A without and 13B with local magnetic vectoring using clasp-electromagnets 40 are long term or permanently radiation shielded as shown in FIG. 10A or temporarily radiation shielded s shown in FIG. 10B. The need for shielding with external beam radiation varies with the specifics. Referring now to FIG. 13B, cells out to about 10 nanometers surrounding the tip of the injection needle or hypotube as side connector are affected by the radionuclide emitted. In this situation, the needle is advanced in up to 10 nanometer increments. It is then paused, and the magnets fastened about the organ, here shown as a kidney, individually and jointly pulsed to draw the magnetically susceptible radionuclide radially outward along a very large number of radial trajectories to kill the cells and disintegrate the blood supply out to about a 5 nanometer radius surrounding each trajectory.

This tedious process, untenable had the patient to remain hospitalized or a medical professional had to remain in attendance, and oppressive were the patient bedridden, is enabled because it can be fully automated in a system that includes a portacath, shielded line leading to a shielded radionuclide storage reservoir, pump, electromagnets, pump and magnet coordinating microcontroller, shielded side connector line, motorized nonjacketing side-entry connected injection needle or hypotube, and transdermal charging system, all fully implanted. If otherwise ambulatory, the patient is free to go about his normal activities while radiation is used to eradicate the tumor without injury to healthy tissue.

Such means have application to endoradiotherapy (radionuclide Auger therapy or mega Gray dose molecular therapy or magnetically targeted peptide receptor radionuclide therapy (see, for example, Su, X. Y., Liu, P. D., Wu, H., and Gu, N. 2014. "Enhancement of Radiosensitization by Metal-based Nanoparticles in Cancer Radiation Therapy," Cancer Biology and Medicine 11(2):86-91; Hossain, M. and Su, M. 2012. "Nanoparticle Location and Material Dependent Dose Enhancement in X-ray Radiation Therapy," Journal of Physical Chemistry. C, Nanomaterials and Interfaces 116 (43):23047-23052; Sofou, S. 2008. "Radionuclide Carriers for Targeting of Cancer," International Journal of Nanomedicine 3(2):181-199; Howell, R. W. 2008. "Auger Processes in the 21st Century," International Journal of Radiation Biology 84(12):959-975, errata at 89(1):67 and 89(7): Chang, M. Y., Shiau, A. L., Chen, Y. H., Chang, C. J., Chen, H. H., and Wu, C. L. 2008. "Increased Apoptotic Potential and Dose-enhancing Effect of Gold Nanoparticles in Combination with Single-dose Clinical Electron Beams on Tumor-hearing Mice," Cancer Science 99(7):1479-1484; Kassis, A. I. 2005. "Radiotargeting Agents for Cancer Therapy," Expert Opinion on Drug Delivery (6):981-991; Kassis, A. I. 2003. "Cancer Therapy with Auger Electrons: Are We Almost There?," Journal of Nuclear Medicine 44(9):1479-1481) accomplished through direct targeted delivery from a very slowly advanced delivery tube rather than by injection or infusion of the radionuclide. To achieve the proximity required for necessitates a stable anchor and motive means as will be described for moving the tube or other delivery implant under precise control.

While spillover of radiation beyond the intended boundaries for treatment, or 'bystander effect', and some abscopal exposure prove beneficial (see, for example, Boyd, M., Sorensen, A., McCluskey, A. G., and Mairs, R. J. 2008. "Radiation Quality-dependent Bystander Effects Elicited by Targeted Radionuclides," Journal of Pharmacy and Pharmacology 60(8):951-958; Boyd, M., Ross, S. C., Dorrens, J., Fullerton, N. E., Zalutsky, M. R., and Maks, R. J. 2006. "Radiation Induced Biologic Bystander Effect Elicited in Vitro by Targeted Radiopharmaceuticals Labeled with .alpha.-, .beta.-, and Auger electron-emitting Radionuclides," Journal of Nuclear Medicine 47(6):1007-1015), rigidity of the intracorporeal source of radiation at the treatment site is necessary to minimize the exposure of healthy tissue and to maintain as rigidly as may be achieved, exactitude of the drug, radiation, or radioactive drug locus of release where the distance to the target is very small and the angle of radiation critical.

Endoradiotherapy can be facilitated through the precisely positioned implantation within the lesion of a shielded radionuclide fluid targeting delivery tube or hollow needle with contrast coated emissive tip. In a combined higher energy external beam to target larger structure/internal radiation at low energy to disrupt nuclear DNA, the implant also serves to facilitate aiming of the external beam. The use of an external beam to excite an implanted hollow needle or tube-targeted substance to the energy level at which the substance transitions into a radionuclide or otherwise frees a radionuclide it contains to emit Auger electrons, for example, would alleviate dependency upon the uncontrollable spontaneity of emission. X-ray generators for auger therapy are currently under development.

In any such external/internal combined approach, the efficacy of treatment depends upon the cooperation of a radionuclide or radionuclide-containing fluid delivery tube implant with its point of radionuclide emission, or the emitting surface of a radiation relay implant rigidly fixed in position. For radiation that acts over a very small distance to the target cellular nuclei, the implant is provided with motive means. For combined internal/external radiation methods, the external beam can be aimed under the control of an automatic tracking system. Neither microwave thermotherapy nor photodynamic therapy demand anything like the stringent tolerances required by Auger therapy.

Where a beta-particle emitting, alpha-particle emitting, Auger electron, or Coster-Kronig electron following electron capture emitting radionuclide not transported in a ferrofluid without an inherent affinity for the target tissue must be delivered to a precise location, the ability to accurately release (see, for example, Sadeghi, M., Enferadi, M., and Shirazi, A 2010. "External and Internal Radiation Therapy: Past and Future Directions," Journal of Cancer Research and Therapeutics 6(3):239-248) such radiopharmaceuticals and substances susceptible to external beam radiation on a replenishable basis without the use of magnetic means for forcibly steering the substance into the functional position, as addressed in copending application Ser. No. 13/694,835 published on 12 Jun. 2014, depends upon the positional stability of the release point.

For Auger therapy, this requires maintaining extreme proximity to the target cells over a long period. In a 2-stage process, a superparamagnetic nanoparticle drug carrier-bound platin, or coordination complex of platinum, such as cisplatin (cismaplat, cis-diamminedichloroplatinum (CDDP), cisplatinum, platamin, neoplatin), carboplatin, or oxaliplatin, is first released in precise and immediate proximity to the targeted cells of the malignant neoplasm using the motorized side connector shown in FIGS. 14 thru 16 shown applied in FIG. 13B and forcibly drawn toward and into the cells under the force of a magnetic field. With the patient ambulatory, the release of a small amount of the ferrofluid through the hollow needle is automatically controlled. The needle is advanced in small increments and the ferrofluid emitted by the disorder response system, which additionally coordinates the energization of one or a combination of patch or clasp-electromagnets in a set, each positioned at different point about the outer surface of the organ or tissue.

The ability to target a tumor within the kidney while minimizing exposure to the rest of the same kidney, much less the rest of the body, is intended to significantly reduce the risk of nephrotoxicity and substantially eliminate neurotoxicity, impaired vision, and ototoxicity which at least during treatment, can lead to severely impaired hearing. Also eliminated are the hemolytic anemia which can develop over time, bone marrow suppression, disturbances in electrolyte balance, nausea which to overcome necessitates the administration of other problematic drugs, such as corticosteroids, ondansetron, and granisetron, and forceful vomiting which can result in an hiatal hernia.

Stage 2 commences once dispersal of the platin has been completed and allowed to take effect, and consists of the release of Auger electrons by X-ray bombardment of the heavy metal, here platinum. When the agent is radioactive, the delivery path is shielded as described below. The direct proximity and targeting of an advancing hollow needle as shown in FIG. 16 serves both the requirement for extreme proximity of the Auger effect and by targeting the cisplatin or similar antineoplastic to the extent possible, minimize the dosing, dispersal, and side-effects that often interfere with the most effective use of the drug.

When the drug is infused, nephrotoxicity (Sanchez-Gonzalez, P. D., Lopez-Hernandez, Lopez-Novoa, J. M., and Morales, A. I. 2011. "An Integrative View of the Pathophysiological Events Leading to Cisplatin Nephrotoxicity," Critical Reviews in Toxicology 41(10):803-821; Yao, X., Panichpisal, K., Kurtzman, N., Nugent, K. 2007. "Cisplatin Nephrotoxicity: A Review," American Journal of the Medical Sciences 334(2):115-124; Daugaard, G. 1990. "Cisplatin Nephrotoxicity: Experimental and Clinical Studies," Danish Medical Bulletin 37(1):1-12; Fillastre, J. P. and Raguenez-Viotte, G. 1989. "Cisplatin Nephrotoxicity," Toxicology Letters 46(1-3):163-175) is dose limiting (see, for example, Seker, M. M., Deveci, K., Seker, A., Sancakdar, E., Yilmaz, A., Turesin, A. K., Kacan, T., and Babacan, N. A. 2015. "Predictive Role of Neutrophil Gelatinase-associated Lipocalin in Early Diagnosis of Platin-induced Renal Injury," Asian Pacific Journal of Cancer Prevention 16(2): 407-410; Mi, I., Wani, W. A., Saleem, K., and Haque, A. 2013. "Platinum Compounds: A Hope for Future Cancer Chemotherapy," Anti-cancer Agents in Medicinal Chemistry 13(2):296-306; Hartmann, J. T. and Lipp, H. P. 2003. "Toxicity of Platinum Compounds," Expert Opinion on Pharmacotherapy 4(6):889-901)

Life-changing side effects of systemic platin administration, sometimes irreversible and severe, which are avoided, include disrupted vision (Li, Y., Li, Y., Li, J., Pi, G., and Tan, W. 2014. "Paclitaxel- and/or Cisplatin-induced Ocular Neurotoxicity: A Case Report and Literature Review," Onco Targets and Therapy 7:1361-1366. Fischer, N., Stuermer, J., Rodic, B., and Pless, M. 2009. "Carboplatin-induced Bilateral Papilledema: A Case Report," Case Reports in Oncology 2(1):67-71; Kwan, A. S., Sahu, A., and Palexes, G. 2006. "Retinal Ischemia with Neovascularization in Cisplatin Related Retinal Toxicity," American Journal of Ophthalmology 141(1):196-197; Watanabe, W., Kuwabara, R., Nakahara, T., Hamasaki, O., Sakamoto, I., Okada, K., Minamoto, A., and Mishima, H. K. 2002. "Severe Ocular and Orbital Toxicity after Intracarotid Injection of Carboplatin for Recurrent Glioblastomas," Graefes Archive for Clinical and Experimental Ophthalmology 240(12):1033-1035), and hearing loss, traceable to a genetic predisposition (Choeyprasert, W., Sawangpanich, R., Lertsukprasert, K., Udomsubpayaku, I. U., and 4 others 2013. "Cisplatin-induced Ototoxicity in Pediatric Solid Tumors: The Role of Glutathione S-transferases and Megalin Genetic Polymorphisms," Journal of Pediatric Hematology and Oncology 35(4):e138-e143; Mukherjea, D. and Rybak, L. P. 2011. "Pharmacogenomics of Cisplatin-induced Ototoxicity," Pharmacogenomics 12(7):1039-1050; Rybak, L. P., Mukherjea, D., Jajoo, S., and Ramkumar, V. 2009. "Cisplatin Ototoxicity and Protection: Clinical and Experimental Studies," Tohoku Journal of Experimental Medicine 219(3): 177-186).

That the nausea and emesis associated with the systemic administration of a platin, for example, necessitate the further administration of chemotherapy-induced nausea and vomiting antiemetics, either or both of which can intensify or produce additional adverse side effects, is avoided, (see, for example, the 5-HT3 receptor antagonist granisetron at Cakir, F. B., Yapar, O., Canpolat, C., Akalin, F., and Berrak, S. G. 2012 "Cardiac Effects of Granisetron in a Prospective Crossover Randomized Dose Comparison Trial," Supportive Care in Cancer 20(10):2451-2457; the dopamine antagonist olanzapine at Brafford, M. V. and Glode, A. 2014. "Olanzapine: An Antiemetic Option for Chemotherapy-induced Nausea and Vomiting," Journal of the Advanced Practitioner in Oncology 5(1):24-29), with NK1 receptor antagonists, antihistamines, cannabinoids, benzodiazepines, anticholinergics, and corticosteroids (see, for example, Nakamura, Y., Momokawa, K., Sasaki, T., Sakayauchi, T., Watanabe, T., Mikami, T., and Matsumoto, T. 2005. "Effect of a Steroid as an Antiemetic in Anticancer Chemotherapy," (in Japanese; English abstract at Pubmed) Gan To Kagaku Ryoho (Cancer and Chemotherapy) 32(3):401-404), is a significant advantage. All chemotherapeutic drugs at systemic doses pose similar or different adverse side effects.

While some moderating measures have been developed, another serious side effect of cisplatin is myelotoxicity, or myelosuppression (Ueda, Y., Sonoda, Y., Fujiki, H., Harada, S., Kimura, T., Itoh, T., Imura, K., and 4 others 2004. "Mobilization of Peripheral Blood Stem Cells (PBSCs) after Etoposide, Adriamycin and Cisplatin Therapy, and a Multimodal Cell Therapy Approach with PBSCs in Advanced Gastric Cancer," Oncology Reports 12(2):323-332; Gelderblom, H., Loos, W. J., Verweij, J., van der Burg, M. E., de Jonge, M. J., and 4 others 2002. "Modulation of Cisplatin Pharmacodynamics by Cremophor EL: Experimental and Clinical Studies," European Journal of Cancer 38(1):205-213; Gelderblom, H., Verweij, J., Nooter, K., and Sparreboom, A. 2001. "Cremophor EL: The Drawbacks and Advantages of Vehicle Selection for Drug Formulation," European Journal of Cancer 37(13):1590-1598; Badary, O. A., Abdel-Naim, A. B., Khalifa, A. E., and Hamada, F. M. 2000. "Differential Alteration of Cisplatin Cytotoxicity and Myelotoxicity by the Paclitaxel Vehicle Cremophor EL," Naunyn-Schmiedeberg's Archives of Pharmacology 361 (3): 339-344).

Another side effect of platins is electrolyte imbalances (Assadi, F. 2010. "Hypomagnesemia: An Evidence-based Approach to Clinical Cases," Iranian Journal of Kidney Diseases 4(1):13-19; Panichpisal, K., Angulo-Pernett, F., Selhi, S., and Nugent, K. M. 2006. "Gitelman-like Syndrome after Cisplatin Therapy: A Case Report and Literature Review," Bio Med Central Nephrology 7:10; Lajer, H. and Daugaard, G. 1999. Cisplatin and Hypomagnesemia," Cancer Treatment Reviews 25(1):47-58; Mehrotra, R., Nolph, K. D., Kathuria, P., and Dotson, L. 1997. "Hypokalemic Metabolic Alkalosis with Hypomagnesuric Hypermagnesemia and Severe Hypocalciuria: A New Syndrome?," American Journal of Kidney Diseases 29(1):106-114; Lam, M. and Adelstein, D. J. 1986. "Hypomagnesemia and Renal Magnesium Wasting in Patients Treated with Cisplatin," American Journal of Kidney Diseases 8(3):164-169; Schilsky, R. L. and Anderson, T. 1979. "Hypomagnesemia and Renal Magnesium Wasting in Patients Receiving Cisplatin," Annals of Internal Medicine 90(6):929-931), and hemolytic anemia (see, for example, Betensky, M., Witmer, C., Fisher, M. J., Nance, S., Weiss, M. J., and Sesok-Pizzini, D. A. 2014. "Immune Hemolytic Anemia with Drug-induced Antibodies to Carboplatin and Vincristine in a Pediatric Patient with an Optic Pathway Glioma," Transfusion 54(11):2901-2905. Wong, J. T., Ling, M., Patil, S., Banerji, A., and Long, A. 2014. "Oxaliplatin Hypersensitivity: Evaluation, Implications of Skin Testing, and Desensitization," Journal of Allergy and Clinical Immunology. In Practice 2(1):40-45; Marani, T. M., Trich, M. B., Armstrong, K. S., Ness, P. M., Smith, J., Minniti, C., and Sandler, S. G. 1996. "Carboplatin-induced Immune Hemolytic Anemia," Transfusion 36(11-12):1016-1018; Maloisel, F., Kurtz, J. E., Andres, E., Gorodetsky, C., Dufour, P., and Oberling, F. 1995. "Platin Salts-induced Hemolytic Anemia: Cisplatin- and the First Case of Carboplatin-induced Hemolysis," Anti-cancer Drugs 6(2): 324-326).

b. Vineberg Derived Prevention of Hypoxia, and Reperfusion (1). Venous Stasis Ulcers of the Lower Leg Vineberg devised a coronary bypass distinct from those to follow, in that rather than surgically anastomosed to a point downstream on the obstructed coronary artery, the distal terminus of the diverted internal thoracic artery with one or more side slits was tunneled into the myocardium. Oxygenated blood then seeped out directly into small voids in the surrounding tissue through a side slit or slits along the bypass. The procedure may be seen as having wider applicability to hypoxic tissue of which the microvasculature has become impaired so that the need for direct-to-tissue delivery of oxygenated blood through a bypass is indicated. In the present context, a ductus side-entry jacket is used as the tap, or takeoff, and a nonjacketing side-entry connector is used to create a stable junction at the outflow end at or within the hypoxic organ or tissue.

That the embodiment depicted in FIGS. 17 thru 19 is compatible with dermagrafting and other therapies addressed above in this section, can actually provide pharmaceutical and electrostimulatory therapy, and can be placed subdermally or externally, should reduce the time for intractable ulcers to heal. No reflow and reperfusion injury addressed above, the embodiment shown in FIGS. 17 thru 19 can restore perfusion for as much of the native fine vasculature as will reflow to reperfuse, and when connected to electrical and fluid supply lines as depicted in FIG. 9 without and FIG. 10B with radiation shielding described in conjunction with those figures, can directly target drugs and electrotherapy to the affected site. The healing of intractable ulcers obtained with drugs and the application of electricity, skin transplantation, and fill tissue grafts is addressed above in the section entitled Concept of the Invention.

Pharmaceutical and electrical therapy with nonjacketing side-entry connectors has potential application to both venous stasis and gastrointestinal ulcers. Referring now to FIG. 19, deeper delivery of drugs and electricity is through an accessory channel or channels 13 and/or electrodes run alongside side connectors 34 and 35 not shown in FIG. 19 but shown in FIGS. 9 and 10B. In an alternative embodiment, these can be run down through a common conduit side connector. That the reinstatement of circulation has not been developed is due to problems of clotting and infection associated with small caliber synthetic tubing. However, side-entry connectors include at least one accessory channel for the directly targeted delivery into the line of anticoagulants, anti-inflammatory drugs, and antimicrobials as necessary. In this, accessory lines or service channels of ductus and nonjacketing side-entry connectors are central to the long term functioning of catheteric lines. The targeted release into the conduit of drugs is used to support the conduit itself or to treat the tissue to which the conduit is directed.

The use of synthetic lines with a tap, or takeoff, on a vessel with arterial blood intake through a nonjacketing side-entry connector eliminates the need to divert a native vessel such as the internal thoracic, which prerequisite procedure can leave the normal supply territory of the artery hypoxic and expands the risk of infection. FIG. 17 shows such a connection, whereby a ductus side-entry jacket as the takeoff feeds into a prosthetic line as side connector led to a nonjacketing side-entry connector. In the application shown, both arterial and venous blood is moved, and unlike direct to organ or tissue surface applications, side slits at intervals along the length of these lines are provided to oxygenate and drain tissue to the sides. The higher level vessels and miniature assistance pumps if necessary for either or both lines 34 and 35 in FIG. 17 are usually remote.

FIGS. 17 thru 19 provide a detailed view of the incurrent and excurrent lines, FIG. 19 showing the inferior or caudal segments to include the sidelines. FIG. 18 provides a side sectional view of such a line, which is ribbed about its outer surface along its distal segment. The interior of the extension from baseplate 1 serving as a socket 38 is likewise ribbed about its interior (not shown), allowing the operator to push the line down and around into the ulcer to the depth desired where it remains fixed in position. These ribs along the distal segment of the catheter serving as side connector 3 are seen as part number 44 in FIGS. 17, 18, and 19.

Whether hypoxic tissue can be oxygenated in the manner of a Vineberg procedure 1. When the native supply artery is proximate so that to divert a portion of its flow can be accomplished without the aid of a fully implanted transcutaneous energy transfer resonance recharged pump; 2. When the native supply artery is remote so that to divert a portion of its flow cannot be accomplished without the aid of such a pump; or 3. When a belt-worn pump-pack with port at the body surface is already justified to treat comorbid disease warrants comment. The best artery to use as origin (takeoff, tap) and/or the best vein to use as insertion (runoff, drain) by placement of ductus side-entry jackets are those most proximal and encircleable with minimum trauma. Since the local microvasculature will usually have become deteriorated as to prompt its bypass, the term 'perfusion' and not 'reperfusion' applies.

When the hypoxic tissue is at a site which due to distance and restriction in caliber of the catheters that can be used is difficult to access, such as a venous stasis ulcer in the lower leg, catheteric circulation can be assisted by an entirely implanted transcutaneous energy transfer resonance recharged pump. Such a pump, or if necessary, multiple pumps, can be placed in the presacral space and/or the parietal cavity. That the dysfunctional venous paths do not simply atrophy and resorb indicates some residual function. However, the creation of a competent drainage path should initiate the abandonment, atrophy, and resorption of vestigially functional and probably occluded native venous paths. Since the diseased paths are bypassed and autologous tissue can be transplanted to the wound, no-reflow and reperfusion injury should not arise. The diseased native vasculature circumvented, the need for a compression stocking during healing may prove unnecessary.

A pathophysiologically distinct condition, peripheral arterial occlusive disease is due not to venous incompetence but rather occlusive disease of larger vessels by atheroroscerotic plaque, vasospasm, and/or diabetic endothelial angiopathy to include microangiopathy. If bypass as described herein for venous stasis ulcers would appear inadequate, then this can be combined with or replaced by neurostimulation. Electrotrodes and leads readily incorporated into nonjacketing side-entry connectors and ductus side-entry jackets fix the site of stimulation more durably than, and can be used together with tines or barbs (see, for example, Ubbink, D. T. and Vermeulen, H. 2013. "Spinal Cord Stimulation for Non-reconstructable Chronic Critical Leg Ischaemia," Cochrane Database of Systematic Reviews 2:CD004001; Colini Baldeschi, G. and Carlizza, A. 2011. "Spinal Cord Stimulation: Predictive Parameters of Outcome in Patients Suffering from Critical Lower Limbs Ischemia. A Preliminary Study," Neuromodulation 14(6): 530-533; Gersbach, P. A., Argitis, V., Gardaz, J. P., von Segesser, L. K., and Haesler, E. 2007. "Late Outcome of Spinal Cord Simulation for Unreconstructable and Limb-threatening Lower Limb Ischemia," European Journal of Vascular and Endovascular Surgery 33(6): 717-724; Ubbink, D. T. and Vermeulen, H. 2006. "Spinal Cord Stimulation for Critical Leg Ischemia: A Review of Effectiveness and Optimal Patient Selection," Journal of Pain and Symptom Management 31(4):S30-S35). Whereas long term diabetes will have affected the entire vascular tree down to the capillary level, the caliber of vessel susceptible to atherosclerosis is considerably larger than that of the microvasculature in the legs, for example, where arterial insufficiency or ischemic ulcers arise.

Where reperfusion remains possible, the means described herein and illustrated in FIGS. 17 thru 19 allow revascularization otherwise not possible (see, for example, Melillo, E., Nuti, M., Buttitta, F., and Balbarini, A. 2006. "Medical Therapy in Critical Lower Limb Ischemia when Immediate Revascularization is Not Feasible," (in Italian, abstract at Pubmed), Giornale Italiano di Cardiologia (Rome).7(5):317-335). When an arterial ulcer is the result of atherosclerosis without significant microangiological impairment, the treatment of arterial ulcers with a bypass as described herein is to a level higher than the local capillaries and is ordinarily able to reperfuse the native arterial tree leading up to the muscles with adequate venous runoff. Except for that of Vineberg upon which it is based, a bypass of the kind to be described is distinct from the conventional in that the terminus is not surgically anastomosed.

Where degradation is substantially arterial with supply intended for the microvasculature, and an end-to-end anastomosed bypass at a higher level is not expected to accomplish healing of the microvasculature, the microvasculature is bypassed with oxygenated blood delivered to the ischemic tissue. Except in diabetic angiopathy, a bypass after Vineberg can usually be limited to the arterial leg with side slits or small holes provided to deliver oxygenated blood along the line. Where an arterial ulcer is the result of diabetes, both legs will probably have been affected necessitating a complete circuit. A direct-to-microvasculature method of treatment as proposed for the treatment of hypoxia as presented by venous stasis ulcers, however, is not pertinent to this condition where the fine vessels remain functional.

More often, bypass of the microvasculature presumes that injury to the one has induced impairment of the other as justify support through a complete circuit wherein blood is diverted from a source artery to a destination vein through ductus side-entry jackets that allow delivery through accessory channels of medication to support the circuit. For this purpose, the medication can be injected into a subcutaneously placed portacath or Ommaya type reservoir. Unlike conventional applications, when comorbid conditions disallow limitation to a single port, a port for placement at the body surface with multiple fluid and electrical lines, each targeted to a different treatment site, is used. Such a port is described in copending application Ser. No. 14/121,365, entitled Ductus Side-entry Jackets and Prosthetic Disorder Response Systems.

Using the ductus side-entry connectors described in copending nonprovisional application Ser. No. 14/121,365, entitled Ductus Side-entry Jackets and Prosthetic Disorder Response Systems, any prosthetic bypass, whether aorto-bifemoral, femoral-popliteal, femoral-tibial, subcutaneous, or 'extraanatomic' axillo-femoral-femoral, or femorofemoral (see, for example, Brewster, D. C. 1997. "Aortoiliac Disease," Chapter 84 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven; Taylor, L. M. Jr., Porter, J. M., and Masser, P. A. 1997. "Femoropopliteal and Infrapopliteal Occlusive Disease," Chapter 85 in Greenfield, L. J., Mulholland, M. W., Oldham, K. T., Zelenock, G. B., and Lillemoe, K. D. (eds.), Surgery: Scientific Principles and Practice, Philadelphia, Pa.: Lippincott-Raven; Gewertz, B. L., Graham, A., Lawrence, P. F., Provan, J., and Zarins, C. K. 1992. "Diseases of the Vascular System," in Lawrence, P. F., Bell, R. M., and Dayton, M. T. (eds.), Essentials of General Surgery, Baltimore, Md.: Williams and Wilkins, pages 332-337) will be superior than if anastomosed with suture.

The direct delivery of medication into extraanatomic bypasses responsive to arterial trauma should extend the long term patency rate. Using ductus side-entry jackets avoids direct anastomotic contact of synthetic materials with the native tissue, if necessary, contact between the foam cushion and adventitia can be drip fed phosphorylcholine or dexamethazone, for example, to ameliorate an adverse reaction, and the jacket can establish an acute angle of confluence that if sutured would be more susceptible to the development of a leak. Significantly, ductus and nonjacketing side-entry connectors provide a sideline or accessory channel for the delivery of medication directly into the ductus. Equally important, these connectors readily incorporate electrical features such as a heating element to warm flow through the junction and for these reasons are readily integrated into a comprehensive therapeutic control system.

This factor of readiness for integration into an automatic control system that is able to coordinate the treatment of interrelated comorbid disease should such become necessary of wider therapeutic should. In an automatic ambulatory prosthetic disorder response system, sensors strategically positioned in the body signal the need for different drugs to be delivered into different ductus (mostly blood vessels) in a coordinated manner according to the control program. The subcutaneously implanted double nonjacketing side-entry connector shown in FIG. 17 can fix the destination, or insertion, of the supply or 'arterial' line and the origin of the outflow, or 'venous,' return line where—the veins dysfunctional—bypass must be directly to the local microvasculature or vascular bed where the vessels are far too small to be encircled with ductus side-entry jackets. Use of the belt should be limited to cases where additional fixation in position is necessary.

The arterial tap or take-off preferably at the highest level in the arterial tree consistent with the least trauma to encircle, where the opening, or 'ostium'; into the side connector is wide, the catheteric or tissue engineered vessel large in caliber, the pressure gradient is high, and gravity is in support, the need for an arterial assist pump is usually averted. Whether the 'venous' return line requires an assist pump is too dependent upon patient anatomy and physiology to predict. Compared to the energy requirements of a ventricular assist device, for example, the energy requirements of a pump to treat localized hypoxia are small and the consequences of failure not tied to survival.

While the side connectors in FIG. 17 interface with the microvasculature in the lower leg, the blood supply at the native artery take-off and native vein return are preferably at a high level. The caliber of the tubing at the upper ends is therefore considerably larger than at the lower ends. This is preferably remedied by using catheteric or tissue engineered tubing that gradually changes in diameter. Alternatively, size adapters of the kind shown in FIG. 22 allow end to end connections between catheters different in caliber and/or materials. The connecting or inclined segment is made long enough to minimize turbulent flow moving from one caliber to the other. The adapter provides suture eyelets or loops for fastening the lines along a route selected to avoid the risk of tissue or organ strangulation. Where the catheters in FIG. 17 are channeled through the calf pump without side slits, the caliber of the catheters is intermediate between that at the takeoff and end drain and the inferior segments at the crus.

It is advantageous to somewhat expand the caliber using tubing with highly elastic walls that best comply with the compressive force exerted by the calf pump. For this purpose, the size adapter shown in FIG. 22 allows the interposition through the calf pump of a wider and more elastic length of tubing without an abrupt step up or step down in luminal caliber. Where subcutaneous, the catheters are made of material sufficiently resilient to thwart damage from accidental impact. The catheters are not sufficiently elastic to propagate the pulse but should respond to the greater compressive force of the skeletal or calf pump Thus, to gain the advantage of the intrinsic pumping of the skeletal muscle or calf pump, the wall is thinned and the material changed to one more elastic and readily compressible.

Unless subcutaneous placement medial to the medial head of the gastrocnemius will provide pumping assistance, the lines are run down through the sural region adjacent to the soleus, parallel to the peroneal and tibial veins, then led out and resumed with stronger walled material for insertion into the excurrent or 'venous' side connector on the belt at the bottom of FIG. 17, which depending upon which leg is treated, can in this bilaterally symmetrical arrangement be either that to the left or to the right. The 'venous' or excurrent line follows the reverse course in parallel to the incurrent line. Deep incision is needed only at the calf, the lines otherwise tunneled subcutaneously with no need to cut through the integument except when the lower margin of the cutaneous lesion is reached.

There an incision at the lateral may be needed to position the double connector, and an incision at the medial maleolus to fasten the belt. When both lateral and medial paired supply and drainage lines must be placed, each pair of lines originates at separate side connectors on the arterial ductus side-entry jacket and end on parallel side connectors on the outflow or 'venous' side-entry jacket. The medial and lateral maleolar line pairs generally take off and return to side connectors at the same level; however, distinctions in the state of disease medially and laterally can justify the placement of separate ductus side-entry jackets at different levels.

As open-ended with a terminal slit or hole too small to reduce the upstream or back pressure needed to expel blood through the more proximal slits, the nonjacketing side-entry connector shown in FIGS. 17, 18, and 19 differs from the majority, but not all, of Vineberg's procedures. Another strategy is to place primary inflow and outflow jackets at the higher level and secondary jackets at lower level where branch lines can be attached to carry blood to and from the diseased tissue at lesser pressure. When pressure cannot be obtained by passive bypass means, an arterial and more likely, venous assist pumps, recharged by transcutaneous energy transfer, are implanted.

When the catheter must be long with a wall that must be thicker and inelastic to pass over a bone, for example, a slight increase in the caliber is used to offset abrupt changes in the systolic and diastolic pressure. An essential factor in adapting the approach to drug assisted synthetic catheters or current state of the art tissue engineered vessels, which treatable to encourage overgrowth, angiogenesis, and tissue infiltration, for example, are still incapable of anastomosing with native vessels, is the need to avoid pull-up displacement, or migration, during walking, for example, that is, to maintain constancy of position. Positional stability in the lower leg should allow the patient to jog and participate in non-collision sports, for example.

Stem cell research and improved tissue engineered vessels will eventually overcome this limitation; but some measure of relief can be attained by perfusion of the hypoxic tissue through bypass to the small vasculature of the muscles through lacunae analogous to Vineberg's myocardial sinusoids. The method interrupts and bypasses the native microvasculature local to the ulcer or obstruction, the lack of anastomosis and more particularly the delay for it to develop is inconsequential. With synthetic catheters, flow through the lacunae must be preserved. Vineberg established that the propensity of local vessels in hypoxic tissue to grow toward a source of oxygenated blood varied in proportion to the degree of hypoxia.

Nonjacketing side-entry connectors can be used to fix the depth into an organ or tissue, such as skeletal muscle, of a native artery after the general scheme taught by Vineberg, and the use of a ductus side-entry connector makes it possible to tap into any convenient vessel and not divert a native vessel to access a blood supply or drain. The supply vessel and return vein can therefore be remote and selected on the basis of larger caliber least affected by the diversion therefrom or delivery thereinto of blood. The catheteric lines from the supply artery to the treatment site and venous return must be sufficiently pliant to avoid pressing against the neighboring tissue. Vineberg tunneled the internal mammary (since redesignated the internal thoracic) into hypoxic myocardium, allowing blood to drip into endothelium lined venous sinusoids. Reperfusion injury and clotting proved less problematic than one might have been led to suppose.

Access to oxygen and nutrients stimulated the tissue bounding the endothelium lined myocardial sinusoids to collateralize (see, for example, Katrapati, P. and George, J. C. 2008. "Vineberg Operation: A Successful Case 35 Years Later," Annals of Thoracic Surgery 86(5):1676-1677; Filho, J. G., Forte, A. J., Leitao, M. C., Filho, H. G., Silva, A. A., and Machado, J. J. 2006. "Vineberg's Procedure Modified Technique: Flow Analysis, Immediate Postoperative Results and Angiographic Evaluation," Journal of Cardiac Surgery 21(4):370-376; Rozsival, V. 2006. "Outcome of Vineberg's Operation after 31 Years," Heart 92(8):1070; Marx, R., Jax, T. W., Kelm, M., Schoebel, F. C., and Strauer, B. E. 2001. "Vineberg Graft: Flow Reserve of Bilateral Implantation after 27 Years," Annals of Thoracic Surgery 71(1):341-343; Krabatsch, T., Grauhan, O., and Hetzer, R. 2000. "Unilateral Vineberg Arterial Graft with a Patency of 30 Years," Circulation 102(14):1724-1725; Thomas, J. L. 1999. "The Vineberg Legacy: Internal Mammary Artery Implantation from Inception to Obsolescence," Texas Heart Institute Journal 26(2):107-113; Nasu, M., Akasaka, T., Chikusa, H., and Shoumura, T. 1996. "Flow Reserve Capacity of Left Internal Thoracic Artery 23 Years after Vineberg Procedure," Annals of Thoracic Surgery 61(4):1242-1244; Shrager, J. B. 1994. "The Vineberg Procedure: The Immediate Forerunner of Coronary Artery Bypass Grafting," Annals of Thoracic Surgery 57(5):1354-1364; Dobell, A. R. 1992. "Arthur Vineberg and the Internal Mammary Artery Implantation Procedure," Annals of Thoracic Surgery 53(1):167-169; Topaz, O., Pavlos, S., Mackall, J. A., Nair, R., and Hsu, J. 1992. "The Vineberg Procedure Revisited: Angiographic Evaluation and Coronary Artery Bypass Surgery in a Patient 21 Years Following Bilateral Internal Mammary Artery Implantation," Catheterization and Cardiovascular Diagnosis 25(3):218-222; Vineberg, A. 1958. "Coronary Vascular Anastomoses by Internal Mammary Artery Implantation," Canadian Medical Association Journal 78(11): 871-879).

The procedure was eventually supplanted by coronary artery bypass surgery, which feeding into the native end arterial microvasculature, averted a delay for angiogenic collateralization and proved more effective in immediately achieving a higher volumetric arterial flow rate (see, for example, Katrapati, P. and George, J. C. 2008. "Vineberg Operation: A Review of the Birth and Impact of this Surgical Technique," Annals of Thoracic Surgery 86(5):1713-1716; Shrager, J. B. 1994. "The Vineberg Procedure: The Immediate Forerunner of Coronary Artery Bypass Grafting," Annals of Thoracic Surgery 57(5):1354-1364). Since the myocardium is unique in its end arterial blood supply, a Vineberg approach may yet have pertinence to the reperfusion of ordinary vascular beds with an impaired or destroyed blood supply.

Vascular connection to the tunneled artery was not noted until 3 months later when the tunneled and coronary arteries were seen to have anastomosed, no new capillaries having branched off from the tunneled artery (see, for example, Sparks, C. H. 1967. "Factors Responsible for Success of the Vineberg Operation: An Experimental Study," Annals of Thoracic Surgery 3(5):455-459); the angiogenic activity took place in the tissue bounding the sinusoids, long before the advent of angiogenic drugs. An anticlotting factor unique to implantation within the myocardium is the constant pulsation of the beating heart, of which the lack in quiescent tissue necessitates the addition of a thrombolytic or anticoagulant to be offset. Some overgrowth notwithstanding, end-to-side and end-to-end connections of synthetic catheter and native vessels is referred to as, but is not actually or histologically anastomosis.

Problems of vascular insufficiency are addressed by standard of care autologous vessel grafting, synthetic bypass, endarterectomy, angioplasty, stenting, and for venous stasis ulcers, endovenous ablation and foam sclerotherapy. When refractory to conventional therapy, the use of a compression stocking is refused, and/or suspension of treatment results in reulceration, oxygenation and the relief of hypertensive pressure can be relieved through a Vineberg-derivative tunneled shunt. In this case, the shunt is a prosthesis that eliminates the need to divert a native artery, which is an additional procedure subject to risks and adverse sequelae in its own right. Medication is supplied via the accessory channel or sideline of the incurrent or 'arterial' line by injection into a subcutaneously placed portacath.

The use of a port at the body surface fed from a pump-pack is generally reserved for conditions that demand the concurrent treatment using like means of comorbid disease. Procedures that make use of prosthetic lines most benefit patients who do not have a usable native vessel, or in whom a procedure to divert the vessel would be ill advised, or in whom the vessel had already been diverted. Large caliber prosthetic lines have been used with some success for decades, medical support introduced into the systemic circulation so that the entire body is exposed; the ability to deliver an antimicrobial and anticlotting medication directly into the prosthetic line eliminates this factor of indiscriminateness and allows extension in the use of prosthetic vessels to small calibers.

Rather than to approach long standing venous stasis ulcers from the standpoint of attempting to clear what are likely long occluded, hypertension distended, and degraded local vessels (see, for example, Negus, D. 2005. "Venous Return from the Lower Limb: Muscle Pumps, Normal and Disordered Function, Chapter 4, page 26 in Negus, D. Coleridge Smith, P. D., and Bergan, J. J. 2005. Leg Ulcers, Boca Raton, Fla.: Taylor and Francis Group/Hodder Arnold Publications, Chemical Rubber Company Books), both the blood supply and drainage catheters should be placed to bypass the vasculature local to the ulcer at the outset. In such cases, the no-reflow phenomenon, or no-reflow syndrome (see, for example, Kloner, R. A. 2011. "No-Reflow Phenomenon: Maintaining Vascular Integrity," Journal of Cardiovascular Pharmacology and Therapeutics 16(3-4):244-250; Niccoli, G., Cosentino, N., Lombardo, A., Sgueglia, G. A., Spaziani, C., Fracassi, F., Cataneo, L, and 6 others 2011. "Angiographic Patterns of Myocardial Reperfusion after Primary Angioplasty and Ventricular Remodeling," Coronary Artery Disease 22(7):507-514; Reffelmann, T. and Kloner, R. A. 2002. "The "No-reflow" Phenomenon: Basic Science and Clinical Correlates," Heart 87(2):162-168; Nanobashvili, J., Neumayer, C., Fuegl, A., Blumer, R., Prager, M., and 4 others 2003. "Development of 'No-reflow' Phenomenon in Ischemia/Reperfusion Injury: Failure of Active Vasomotility and Not Simply Passive Vasoconstriction," European Surgical Research 35(5):417-424), may not only fail to reperfuse, but whether accomplished with thrombolytics, anticoagulants, thermally, with the aid of growth factors, or by any other means, is likely to prompt reperfusion injury and reocclusion that perpetuate the inability to reperfuse.

Reperfusion injury with respect to venous stasis ulcers would likely occlude the deep calf perforating veins as well as the arterioles and capillaries. Except in the case of very short term hypoxia, it is wise to presume as much and place both supply and drainage lines ab initio. There are then, two reasons to furnish a direct arterial shunt from a proximal artery of large caliber. The first is that the native fine vessels are probably incapable of recovery to a state of supply sufficiency, various partial remedies notwithstanding (see, for example, Neumayer, C., Fugl, A., Nanobashvili, J., Blumer, R., Punz, A., Gruber, H., Polterauer, P., and Huk, I. 2006. "Combined Enzymatic and Antioxidative Treatment Reduces Ischemia-Reperfusion Injury in Rabbit Skeletal Muscle," Journal of Surgical Research 133(2):150-158; Nanobashvili J, Neumayer C, Fuegl A, Punz A, Blumer R, Mittlbock M, and 5 others 2004. "Combined L-arginine and Antioxidative Vitamin Treatment Mollifies Ischemia-Reperfusion Injury of Skeletal Muscle," Journal of Vascular Surgery 39(4):868-877).

The second reason to furnish a direct arterial shunt from a proximal artery of large caliber is that agents to counter the development of a biofilm and clogging must be delivered through the 'arterial' (incurrent, affluent) catheter in order to gain entry into the 'venous' (excurrent, effluent) catheter. If the condition is not of such long standing that the small supply vessels are still competent, it may be possible to avoid the delivery of arterial blood and thus the need to tap a larger artery with a ductus side-entry jacket. Drugs to treat the catheter itself are added to its flow at the source, while those to treat the native ductus which the catheter empties into are fed through the sideline or water jacket.

When crus ulceration is incipient or short term so that the native small vessels are recoverable without injury, eliminating blood from the supply line eliminates clotting, reduces the risk of infection, and allows the use of a subcutaneously implanted reservoir with the drugs injected rather than pumped from an extracorporeal pump pack requiring a larger power source. Drugs to treat the outflow or drainage line are supplied through the 'arterial' or supply catheter, either by inclusion in the flow or through the 'arterial' sideline.

These drugs will normally consist of warfarin, danaparoid, lepirudin, or argatroban, which can be delivered intermittently, or sodium heparin, which has a half-life of an hour or a low molecular weight or unfractionated heparin with a half-life of 4.5 hours, such as dalteparin, enoxaparin, or tinzaparin can be used (Presta, M., Leali, D., Stabile, H., Ronca, R., Camozzi, M., and 4 others 2003. "Heparin Derivatives as Angiogenesis Inhibitors," Current Pharmaceutical Design 9(7):553-566). The targeted dose of heparin is insufficient to induce or significantly aggravate osteoporosis. Critically, the risk of heparin-induced thrombocytopenia, which can cause death or compel an amputation, is minimized. Because the dose in terms of total body mass is small, the lack of a counteractant or reversal agent with newer anticoagulants such as dabigatran, rivaroxaban, and apixaban poses no bleeding problem for surgery or accidental trauma.

Other applicable anticoagulants include fondaparinux, hirudin, ximelegatran or melagatran formulated as a liquid, or danaparoid. To guard against the inadvertent under administration of clot preventive medication, additional protection against clotting is obtained by adding a thrombolytic such as synthetic tissue plasminogen activator, streptokinase, or urokinase. Targeted at the prosthetic circuit, the concentration of the thrombolytic poses little if any risk of hemorrhage, thrombocytopenia, osteroporosis, or alopecia. These drugs are introduced into the accessory channel or sideline of the supply or arterial ductus side-entry jacket to flow through the prosthetic circuit, consisting of both the 'arterial' and 'venous' arms, or lines.

Ionic copper facilitates (Harris, E. D. 2004. "A Requirement for Copper in Angiogenesis," Nutrition Reviews 62(2): 60-64; Gullino, P. M., Ziche, M., and Alessandri, G. 1990. "Gangliosides, Copper Ions and Angiogenic Capacity of Adult Tissues," Cancer Metastasis Reviews 9(3):239-251; Raju, K., Alessandri, G., Ziche, M., and Gullino, P. M. 1982. "Ceruloplasmin, Copper Ions, and Angiogenesis," Journal of the National Cancer Institute 69(5):1183-1188) and corticosteroids counter (Folkman, J. and Ingber, D. E. 1987. "Angiostatic Steroids. Method of Discovery and Mechanism of Action". Annals of Surgery 206(3):374-383) the angiogenic action of heparin (Folkman, J. 1985. "Regulation of Angiogenesis: A New Function of Heparin," Biochemical Pharmacology 34(7):905-909), and should not be given to reduce inflammation when heparin is used. Nonsteroidal drugs for reducing inflammation include diclofenac, fenoprofen, nabumetone, oxaprozin, and tolmetin. The relatively tiny dose allowed by directly targeting the prosthetic circuit means that the usual caveats specified for each of these is unlikely to apply.

The corticosteroid dexamethasone ordinarily recommended as an anti-inflammatory, such use should dissuade the use of heparin. In an exigent circumstance, rather than to confirm supply, drainage, or both as dysfunctional or counterperfusive, it is best to bypass the local vasculature by placing supply and drainage lines ab initio. Otherwise, venous function is impaired and only an excurrent or 'venous' return line placed. Incurrent and excurrent lines are run in parallel but at a distance that precludes the direct flow of blood from the incurrent to the excurrent line. Similarly, the transport of drugs via the oral route and systemic circulation is of advantage only if an extracorporeal pump and body surface port are eliminated. When protracted disuse and chronic obstruction have resulted in a disabling or atrophy of the blood supply heparinized and thrombolytic-treated blood is delivered through the arterial catheter. Vacuities equivalent to cardiac sinusoids not available local to the ulcer, a laser is used to introduce small vacuities, or voids.

This is done immediately before initiating flow through the lines that incorporates anticoagulants, thus preventing a buildup of clot or stenosing inflammation of the fine vasculature. The small vacuities or sinusoids upon which the Vineberg procedure is posited to have depended are introduced with the aid of a laser, much as in transmural laser revascularization, with small side slits in the supply catheter finding these. This allows the catheter to be inserted without hunting for these. Slits that align will flow, while those that do not will not flow. The subsequent application of heparin and other anticoagulative drugs will flow through the patent slits, and the nonflowing slits obstructed, the blood will follow the course of least resistance. For this reason, the formation of a localized iatrogenic hematoma is unlikely.

At this level of minimal pressure, the angle at which the lines approach and enter the paired side connectors is important from the standpoint of achieving minimal projection to avoid irritation as well as an acceptable cosmetic result. Loosening locking collars or nuts 20 allows these not only to be moved inward to incise the tissue plugs and then retracted, but to be rotated to face into any radial angle that will minimize the projection of the catheters as these approach and enter the side connectors. Thus, while represented in FIG. 18 as angled acutely craniad, rotating the side connectors allows line approach and entry from the sides, below, or any angle in between. The nonjacketing double side-entry connector shown in FIGS. 17 thru 19 is lined with a double layer of foam as described above and placed toward the lower margin of the ulcer where it is held in position subcutaneously by means of a foam-lined adjustable belt with spaced holes and wide head narrow waist snap in lugs or studs to obtain a snug fit. Shown with the belt or anklet cinched about the external surface of the leg, the device can also be implanted subcutaneously.

The lines connected to it exit subcutaneously and to rise up through the diseased tissue, the incurrent line 'bleeding' oxygenated blood and the excurrent line drawing off deoxygenated blood. As with the use of catheters to shunt blood generally, the advantages gained when clot and biofilm can be prevented, are that 1. The native artery and vein are not dissected for diversion from the tissue normally supplied and drained, effectively representing a second procedure, but only tapped into by ductus side-entry jackets, and 2. In the treatment of venous stasis ulcers, which appear above the ankle at the lateral surface of the crus, the points or levels of takeoff at the artery and return to the vein will usually be remote to allow input and output at the highest initial pressures and at a level where the side connectors and lines connected to these can be wider and set at the proper angle for optimal flow-through.

When pressure can be preserved between the ulcer, and the origins of the lines, the need to implant a pump or two, necessitating period recharging of the batteries is averted as a major improvement. The lines are run subcutaneously along the inner surface of the thigh and knee, making certain to flex the knee and allow sufficient slack for the knee to bend without placing the lines under tension, which can result in pull-up displacement of the special dual side connector side-entry connector cinched along the lower margin of the wider (visible, discolored) lesion. Shifting of the lines is also prevented by placing simple interrupted sutures at points where the lines would shift during movement of the leg.

Below the knee, the lines diverge, that arterial continuing to the side-entry connector subcutaneously. The venous line is continued subcutaneously until a short distance above the superior margin of the visible lesion where it plunges to run between the soleus and gastrocnemius muscles. Once inferior to the calf or skeletal muscle pump, the venous line is led subcutaneously to connect to its side connector in the special dual side connector side-entry connector. In a wider sense, FIG. 17 shows an reperfusion set for the treatment of a local hypoxia likely to have resulted in deterioration of the local microvasculature and probably some of the local vasculature anywhere in the body.

Such deterioration is characteristic of a long standing venous stasis ulcer. Standard of care measures for the treatment of venous stasis ulcers are generally effective; however, these measures, to include the wearing of compression stockings and the use of diuretics to control edema, are often unacceptable, but if suspended, result in reulceration. While standard of care measures for the treatment of peripheral arterial occlusive disease usually prove effective, with cases refractory to conventional treatment, a similar reperfusion set is used. The difference in the sets is that in peripheral artery disease, the local vasculature is often sufficiently intact that the bypass can be placed at a higher level along the vascular tree.

When positioned higher in the vascular tree, the inferior or caudal connections, as are the arterial takeoff and venous drain connections, accomplished with ductus side-entry jackets rather than a special nonjacketing side-entry connector, and the caliber of the tubing used is larger. Ulceration inherently indicative of a failure to develop collateral circulation, where venous stasis and hypertension have impaired drainage, it is likely that the arterioles and capillaries associated with the hypoxic tissue have also deteriorated. For this reason, and because the prospect of reperfusion injury and no-reflow loom were reperfusion attempted, the diseased microvasculature is bypassed, both inflow (incurrent, supply, 'arterial') and outflow (excurrent, drainage, 'venous') lines placed from the outset.

In the diagrammatic representation of FIG. 17, this Vineberg-derivative perfusion process uses small diameter catheters, the incurrent or 'arterial' line or catheter pliant as to bend easily after exiting the side connector to avoid encroaching upon neighboring tissue. This catheter is tunneled subcutaneously to the upper margin of the ulcer and to resist compression if struck, has a thick wall. The incurrent line is then passed through the diseased tissue proximate if not alongside the return or venous' line. While passing through the diseased tissue, both distally open-ended lines are also slit or have holes to allow blood to pass through. The excurrent or 'venous' line or catheter is made of the same material and is also tunneled subcutaneously.

The incurrent or 'arterial' accessory channel or sideline shown in FIG. 19 is used to run antimicrobial, anticlotting, anti-inflammatory, and if appropriate, diuretic medication through the entire circuit. Blood is bypassed directly to the hypoxic tissue from the highest level artery and returned to the highest level vein consistent with minimizing trauma. This is because these vessels are more readily accessible, dissectable, provide higher blood pressure, and allow sufficient clearance for the ductus side-entry jacket with properly angled side connectors. By the same token, the extension of incision is best lessened. The popliteal vessels offer proximity with clearance optimized by vertically offsetting the arterial and venous jackets.

As in the treatment of popliteal artery entrapment and compartment syndromes, entry is into the popliteal fossa by posterior approach and fasciotomy (see, for example, Jacobs, L. A. 1997. "Arterial Compression Syndromes," in Greenfield, L. J., Mulholland, M. W., Oldham, K. T., Zelenock, G. B., and Lillemoe, K. D. (eds.), Op cit. pages 1639-1643; Gulli, B. and Templeman, D. 1994. "Compartment Syndrome of the Lower Extremity," Orthopedic Clinics of North America 25(4):677-684; Power, R. A. and Greengross, P. 1991. "Acute Lower Leg Compartment Syndrome," British Journal of Sports Medicine 25(4):218-220; Mubarak, S. J. and Hargens, A. R. 1981. Compartment Syndromes and Volkmann's Contracture, Philadelphia, Pa.: W.B. Saunders). "The best surgical approach is an S-shaped incision in the popliteal fossa, which enables complete exposure of the popliteal artery and its surrounding structures" (page 87 in Gourgiotis, S., Aggelakas, J., Salmis, N., Elias, C., and Georgiou, C. 2008. "Diagnosis and Surgical Approach of Popliteal Artery Entrapment Syndrome: A Retrospective Study," Vascular Health and Risk Management 4(1):83-88; Rollins, D. L., Bernhard, V. M., and Towne, J. B. 1981. "Fasciotomy: An Appraisal of Controversial Issues," Archives of Surgery 116(11):1474-1481).

Popliteal artery and vein jacketed, the lines are run subcutaneously along the medial calf or down through the calf, to bypass and follow the posterior tibial artery and vein down to the nonjacketing side-entry connector shown in FIG. 17, the belt mounting used only when necessary. If the ulcer is not extensive so that slits in the lines are not essential and the gastrocnemius muscles will provide pumping action, the lines are run subcutaneously down the inside (medial surface) of the calf to the nonjacketing side-entry connector shown in FIG. 17. Placement of the side connector at the proper angle results in the least turbulent and greatest flow rate at the maximum pressure through the entry or ostium leading into the side connector and catheter it holds. The use of a double lumen catheter to draw diagnostic testing samples requires a ductus side-entry jacket with two side connectors. A central object sought in using vessels at a high pressure level that will persist through a catheter is to eliminate the need for implanted assist pumps.

In a reperfusion set as shown in FIG. 17 and further described below in the section entitled Description of the Preferred Embodiments of the Invention, the incurrent or 'arterial' line can be made of less flexible, more strongly walled tubing subcutaneously tunneled to the lesion with little concern for accidental impacts. The return (outflow, excurrent, 'venous') line, however, moving blood at lower pressure, is made of a pliant polymer placed deep within the calf to take advantage of the skeletal muscle pump (tricipital pump, calf pump, sural pump, 'peripheral heart'). Provided the patient is appropriately conformed, to take advantage of its pumping function the return line is run subcutaneously against the gastrocnemius (see, for example, Casey, D. P. and Hart, E. C. 2008. "Cardiovascular Function in Humans during Exercise: Role of the Muscle Pump," Journal of Physiology 586(Part 21):5045-5046; Sheriff, D. 2005 "Point: The Muscle Pump Raises Muscle Blood Flow during Locomotion," Journal of Applied Physiology 99(1):371-375).

On the outflow or 'venous' side, the delivery of blood into the native vein is with the least shear stress. The lower leg or crus especially susceptible to atherosclerotic degradation, the ductus side-entry jacket side connectors are angled to minimize shear stress. While the incurrent, that is, the inflow or arterial bypass is a prosthesis invulnerable to arterial degradation, the correct angle expedites good outflow from the source artery. Veins more susceptible to injury from sustained nonlaminar flow, the correct angle is more significant for the excurrent, that is, outflow or venous bypass, the administration of antiatherosclerotic and anti-inflammatory medication notwithstanding.

Ductus side-entry jackets are always provided with fenestra to expose the adventitia. This serves further to avert atherosclerotic degradation at both the arterial origin or takeoff and the outflow or venous connection. Also advantageous is the nonanastomotic connection of the prosthetic tubing to the outflow vein in reducing the risk of atherosclerotic degradation without the need for a statin in a high dose even as targeted, much less were it systemic. Generally, an anticoagulant, ordinarily warfarin, heparin sodium, or more likely a low molecular weight heparin derivative, and if clotting is a problem, then a thrombolytic, such as tissue plasminogen activator are given. So that these flow entirely through the circuit, this medication is delivered directly into the tubing through the accessory channel of the ductus side-entry jacket on the artery.

Both sidelines or accessory channel lines are subcutaneously tunneled to either a singular subcutaneous portacath or a port placed at the outer surface of the body for connection to an external pump. Such a surface port is described in copending application Ser. No. 14/121,365, entitled Ductus Side-entry Jackets and Prosthetic Disorder Response Systems. More specifically, for intermittent administration, access to the sideline is by injection into a subcutaneously implanted portacath or Ommaya type reservoir conventionally positioned subcutaneously in the pectoral region. For continuous administration, delivery is from a pump suspended from a waist belt and through a port at the body surface.

(2). Targeted Interdiction of a Cirrhosis-Inducing Cascade

Except that a cinch or belt mounting is not used, therapy to truncate degeneration of the liver, for example, employs substantially the same formation of elements as is shown in FIG. 17. The delivery of medication into the liver to treat an intrinsic hepatic deficiency, such as chloroquine, beta carotene, luteinizing hormones, and/or contraceptives to treat erythropoietic porphyria, is accomplished thus to suffuse the parenchyma, and/or with ductus side-entry jackets placed on the hepatic arteries and/or portal vein to arrive through the innate blood supply. Broadly, the liver can be targeted for the delivery of any drug, to include antiviral vaccines.

Unbelted nonjacketing side-entry connectors are shown in FIGS. 1, 2, 4, 7, 8. 9, 10A, 10B, 14, 20, and 21 among others. When the number of drugs needed is considered to invite human error with subdermally placed ports, a body surface multiport with clearly labeled insertion holes, diagrammatically represented in FIG. 17 as port 39 described in copending application Ser. No. 14/121,365 is used. Reference to the liver and progression to cirrhosis should not be interpreted in a limiting sense: the means shown for the treatment of a refractory venous stasis ulcer in FIG. 17 are no less applicable to the targeting of antiviral drugs, for example, to the liver or any other organ or tissue site.

Unless the number of drugs militates against the implantation of the components and lines that would be required and invite errors in administration, the external multiport is not preferred. Placement at the surface allows relegating these components to a belt-worn power, pump, and control pack, as well as allows each port entry hole to be clearly labeled. The reliability and adjustability of state of the art electromechanical implants is such that external access is no longer preferable to full implantation or complete closure. In any application where the number of drugs are few and the port entry clear, subdermally placed ports are preferred.

The progression of degenerative transition in the liver can be indicated by means of sensor implants, as addressed below in the section entitled Discrete Point, and Point to Point through Tissue Transmission, Measurement and Telemetry. The object is to target drugs directly into the liver within oxygenated blood, thus alleviating local stagnant hypoxia and supplying degeneration-counteracting therapy at the same time. Drugs for intrahepatic application are mechanically targeted by direct catheteric delivery, while extrahepatic tissue and organs are either targeted separately using the same means or are administered systematically according to convention. Where the liver is targeted so that extrahepatic tissue is unexposed, the targeted dose can be more concentrated.

Significantly, drugs targeted to extrahepatic sources, or niduses (nidi), of liver disease or to comorbid niduses as hepatotoxic can be kept substantially clear of the liver. Conversely, the liver may have become impaired by any of the large number and types of hepatotoxic drugs when prescribed for conditions not involving the liver see, for example, The Merck Manual 18th edition, 2006, Chapter 24, Drugs and the Liver, Table 24-1, page 208; Dienstag, J. L. and Isselbucher, K. J. 2005. "Toxic and Drug-induced Hepatitis," in Harrison's Principles of Internal Medicine, New York, N.Y.: McGraw-Hill, 16th Edition, Table 286-2, page 1840). Thus, unless the injurious medication must be systemically dispersed, direct targeting of the diseased organ allows hepatic exposure and impairment to be avoided, and where a systemic disorder generates localized lesions, these are targeted, if necessary, at a higher dose, a background bolus then applied at lower dose, minimizing adverse side effects, drug drug, and drug food interactions for all non-targeted tissue.

Anti-inflammatory and antifibrotic drugs intended for but prone to induce adverse side effects, such as ursodeoxycholic acid and corticosteroids, are delivered directly into the liver. Where targeting the liver allows a reduction in a background systemic dose to treat extrahepatic tissue related or unrelated to the liver disease, adverse side effects, to include adverse drug drug and drug food interactions are reduced if not eliminated. In cases refractory to conventional treatment, the truncation of degenerative transition in the liver may serve to prevent the numerous symptoms associated with a given stage in the disease, and avoid the need for procedures such as the placement of a portacaval shunt (postcaval shunt, portal venous shunt), transjugular intrahepatic portosystemic, or portal systemic, shunt, or a distal splenorenal shunt, all of which risk hepatic encephalopathy.

Avoiding a liver transplant averts the life long need for immunosuppressive medication that places the patient at risk for other disease. Moreover, failure to suppress or eliminate an extrahepatic etiological source of damage to the innate liver will result in the same damage to the transplant. The multifarious functions of the liver render it vulnerable to many extrahepatic disorders, to include cardiac, biliary, and pancreatic, while reciprocally, impairment of the liver as the result of a genetic defect in copper or iron metabolism affects the liver itself and therewith, extrahepatic functions that depend upon a healthy liver. Untreated liver disease progresses to involve additional organ systems with increasing severity, which if left untreated, can lead to death. The centrality and life-dependency to which this attests makes prompt and effective interdiction of progressive degenerative transition of the liver from normal to fibrosed, then cirrhosed, crucial.

Cirrhosis, to include that cholestatically induced by primary biliary cirrhosis, cholestatic liver disease that originates within the intrahepatic bile ducts and is commonly associated with other autoimmune conditions, rather than due to a neoplasm or gallstone) (see, for example, Floreani, A., Franceschet, I., Cazzagon, N. 2014. "Primary Biliary Cirrhosis: Overlaps with Other Autoimmune Disorders," Seminars in Liver Disease 34(3):352-360; The Merck Manual 18th edition, 2006, page 218), can also be treated through the delivery of ursodiol, or ursodeoxycholic acid, through ductus side-entry jackets placed on the hepatic arteries, portal vein, and/or the hepatic, cystic, or common bile ducts. The gallbladder is drug targeted through a nonjacketing side-entry connector fastened to the fundus or body.

Primary sclerosing cholangitis (see, for example, Hirschfield, G. M. and Gershwin, M. E. 2013. "The Immunobiology and Pathophysiology of Primary Biliary Cirrhosis," Annual Review of Pathology 8:303-330; The Merck Manual 18th edition, 2006, page 246), likely an aberrant immune response that affects the intrahepatic and extrahepatic bile ducts and almost always associated with irritable bowel syndrome, may represent an example of a sequelary or secondary disseminated comorbidity suited to automated treatment as delineated in copending application Ser. No. 14/121,365, entitled Ductus Side-entry Jackets and Prosthetic Disorder Response Systems. Copending application Ser. No. 13/694,835 had previously addressed the use of permanent magnet jackets at skip lesions, the use of electromagnet jackets allowing sequential energization. Targeted delivery to the gut of neomycin to reduce ammonia-generating microbiota thereby alleviating hepatic encephalopathy (hepatic coma, portal systemic encephalopathy) is through a ductus side-entry jacket.

c. Stereotaxic Drug Steering by Magnetic Vectoring (1). With magnets fastened about to move as one with the organ or tissue under treatment. Must adapt for irregularities in conformation or profile and apportionment of tractive vectors (see, for example, Klostergaard, J. and Seeney, C. E. "Magnetic Nanovectors for Drug Delivery," 2012. Nanomedicine 8 Supplement 1:S37-S50; Klostergaard, J., Bankson, J., Yuill, W., and Seeney, C. E. 2007. "Magnetic Vectoring of Magnetically Responsive Nanoparticles (MNP) within the Murine Peritoneum," Journal of Magnetism and Magnetic Materials 311(1):330-335; Seeney, C., Ojwang, J. O., Weiss, R. D., and Klostergaard, J. 2012. "Magnetically Vectored Platforms for the Targeted Delivery of Therapeutics to Tumors: History and Current Status," Nanomedicine (London) 7(2):289-299; Tietze, R., Lyer, S., Dun, S., and Alexiou, C. 2012. "Nanoparticles for Cancer Therapy Using Magnetic Forces," Nanomedicine (London) 7(3):447-457; Chen, B., Wu, W., and Wang, X. 2011. "Magnetic Iion Oxide Nanoparticles for Tumor-targeted Therapy," Current Cancer Drug Targets 11(2):184-189; Tran, P. H., Tran, T. T., Vo, T. V., and Lee, B. J. 2012. "Promising Iron Oxide-based Magnetic Nanoparticles in Biomedical Engineering," Archives of Pharmacol Research 35(12):2045-2061; Babincova, M. and Babinec, P. 2009. "Magnetic Drug Delivery and Targeting: Principles and Applications," Biomedical Papers of the Medical Faculty of Palack University, Olomouc, Czech Republic 153(4):243-250; Naqvi, S., Samim, M., Dinda, A. K., Iqbal, Z., Telagoanker, S., Ahmed, F. J., and Maitra, A. 2009. "Impact of Magnetic Nanoparticles in Biomedical Applications," Recent Patents on Drug Delivery and Formulation 3(2):153-161; Namdeo, M., Saxena, S., Tankhiwale, R., Bajpai, M., Mohan, Y. M., and Bajpai, S. K. 2008. "Magnetic Nanoparticles for Drug Delivery Applications," Journal of Nanoscience and Nanotechnology 8(7): 3247-3271) to pull in the direction wanted. In less intricate applications, steering can proceed under open loop control.

(2). With magnets fastened about the body. Same as for fastened to organ but with the advantage that the magnets can be radially equiangular and the disadvantage that the control system must compensate for deviations in position of the target due to physiological and pathophysiological movement. This is, however, no greater in pediatric or veterinary practice where the patient is under a general anesthetic. On adult humans, almost all of the procedures referred to herein can be done under local anesthesia. This type of stereotactic body radiotherapy must compensate for numerous sources of displacements intervening between the target and magnets, in deference to which it is conducted under closed loop control.

d. Discrete Point, and Point to Point Through Tissue, Transmission, Measurement and Telemetry Whether functioning independently as passive sensors or related as a matched transmitter and pickup or pickups, the positional stability afforded by nonjacketing side-entry connectors makes possible the infixion within tissue of sensors for which positional stability is essential for accuracy. Materials testing type diagnosis of affected tissue can be used to indicate the status in progression of any pathophysiological process. The minor invasive procedure to position the transmitter and pickup or pickups accepted, allowed is continuous data read-out in the progression, for example, of nonalcoholic fatty liver disease (nonalcoholic hepatic steatofibrosis, steatosis, hepatosteatosis, nonalcoholic steatohepatitis, steatonecrosis), progressive fibrosis, these in combination, and cirrhosis.

The configuration shown in FIG. 6 without patch-electromagnets or with these as shown in FIG. 13B allows the rigid infixion of a stationary sensor, probe, electrode, or combination of sensors, while that shown in FIGS. 13A thru 16 allows the signal transmitter to be precisely advanced and retracted. This might be a microminiature hardness testing gauge stylus or probe, or a hypotube used to release a radionuclide for use in Auger therapy, in which case the catheter as side connector and side-entry connector are shielded as shown in FIG. 13A or 13B. As applied to the liver, for example, the types of sensors available numerous, the initial differential diagnosis in preparation to place implanted sensors is by conventional liver biopsy.

Notwithstanding recent advancements, for acquiring precise quantitative information concerning the state of the tissue tested, biopsy and direct-contact sensor implants are critically superior to noninvasive means of diagnosis such as external ultrasound (see, for example, Gerstenmaier, J. F. and Gibson, R. N. 2014. "Ultrasound in Chronic Liver Disease," Insights Imaging 5(4):441-455). For liver disease, the sensors can report aminotransferase levels and/or changes in the mechanical properties of the tissue at discrete points, between discrete points, or moving through trajectories between discrete points. For unpredictably or rapidly progressive disease, an advantage over monitoring in the clinic or radiology laboratory is that rather than intermittent, the data is continuous, from an ambulatory patient in whom the sensor or sensors are fully or closed-skin implanted.

In some instances such as for infrared laser absorption spectroscopy of molecular trace gases or for the quantification of cytochrome P450 and NADPH-cytochrome P450 reductase (see, for example, Zanger, U. M. and Schwab, M. 2013. "Cytochrome P450 enzymes in drug metabolism: Regulation of gene Expression, Enzyme Activities, and Impact of Genetic Variation," Pharmacology and Therapeutics 138(1):103-141; Guengerich, F. P., Martin, M. V., Sohl, C. D., and Cheng, Q. 2009. "Measurement of Cytochrome P450 and NADPH-Cytochrome P450 Reductase," Nature Protocols 4(9):1245-1251), the signal from the sensor implant is sent to a remote spectrometer. Another advantage in the stabilization afforded by nonjacketing side-entry connectors is that even if the organ or tissue shifts in position during measurement, the relative positions of the organ or tissue and the sensors remain substantially if not entirely unchanged. This is true even if the organ or tissue is subject to intrinsic motility, shifting during the use of joints, or is anomalous in this regard, such as a floating kidney.

Transmitter and pickup or pickups measurements include thermal conductivity, diffusivity, inertia, dimensional stability with change in temperature, sonic transmission, or transonance, ultrasound velocity, absorption, and scatter, acoustic nonlinearity factor, electrical conductivity and permittivity, bioimpedance, electromagnetic radiation, reflection, and absorption, oxygenation, perfusion, perfusion rate, point of release to point of detection transit time of superparamagentic nanoparticles, and numerous other type measurements (see, for example, Duck, F. A. 2012. Physical Properties of Tissues: A Comprehensive Reference Book, York, England: Institute of Physics and Engineering in Medicine; Nowak, K. W. and Markowski, M. 2013. "A Comparison of Methods for the Determination of Sound Velocity in Biological Materials: A Case Study," Ultrasonics 53(5):923-927; Byram, B. C., Trahey, G. E., and Jensen, J. A. 2012. "A Method for Direct Localized Sound Speed Estimates Using Registered Virtual Detectors," Ultrasonic Imaging 34(3):159-180; Athanasiou, K. 2008. Introduction to Continuum Biomechanics (Synthesis Lectures on Biomedical Engineering), San Rafael, Calif.: Morgan and Claypool.).

Numerous applications, explicit and implicit appear in the literature (see, for example, au, Y., Zheng, Y., Shen, Y. Y., Chen, X., Zhang, X. Y., Lin, R M., Guo, Y. R., Wang, T. F., and Chen, S. P. 2014. "Analyzing and Modeling Rheological Behavior of Liver Fibrosis in Rats Using Shear Viscoelastic Moduli," Journal of Zhejiang University. Science B 15(4): 375-381; Dai, Z., Peng, Y., Henry, B. M., Mansy, H. A., Sandler, R. H., and Royston, T. J. 2014. "A Comprehensive Computational Model of Sound Transmission through the Porcine Lung," Journal of the Acoustical Society of America 136(3):1419; Nowak, K. W. and Markowski, M. 2013. "A Comparison of Methods for the Determination of Sound Velocity in Biological Materials: A Case Study," Ultrasonics 53(5):923-927; Lakshmanan, S., Koch, T., Brand, S., Mannicke, N., Wicke, M., Morlein, D., and Raum, K. 2012. "Prediction of the Intramuscular Fat Content in Loin Muscle of Pig Carcasses by Quantitative Time-resolved Ultrasound," Meat Science 90(1):216-225; Byram, B. C., Trahey, G. E., and Jensen, J. A. 2012. "A Method for Direct Localized Sound Speed Estimates Using Registered Virtual Detectors," Ultrasonic Imaging 34(3):159-180; Chatelin, S., Oudry, J., Perichon, N., Sandrin, L., Allemann, P., Soler, L., and Willinger, R. 2011. "In Vivo Liver Tissue Mechanical Properties by Transient Elastography: Comparison with Dynamic Mechanical Analysis," Biorheology 48(2):75-88; Aid, T. J. Long, R., Mc Shane, M. J., Ericson, M. N., Wilson, M. A., and Cote, G. L. 2011. "Optimizing Probe Design for an Implantable Perfusion and Oxygenation Sensor," Biomedical Optics Express 2(8):2096-2109; Hirasaki, K. K., Watts, J. A., and Suhocki, P. V. 2010. "Wireless Surveillance for Transjugular Intrahepatic Portosystemic Shunts (TIPS): A Feasibility Study," Academic Radiology 17(4):418-20; Baba, J. S., Letzen, B. S., Ericson, M. N., Cote, G. L., Xu, W., and Wilson, M. A. 2009. "Development of a Multispectral Tissue Characterization System for Optimization of an Implantable Perfusion Status Monitor for Transplanted Liver," Conference Proceedings of the IEEE Engineering in Medicine and Biology Society 2009:6565-6568. Mudaliar, A. V., Ellis, B. E., Ricketts, P. L., Lanz, O. I., Scott, E. P., and Diller, T. E. 2008. "A Phantom Tissue System for the Calibration of Perfusion Measurements," Journal of Biomechanical Engineering 130(5):051002; Hargitai, B., Szijarto, A., Kupcsulik, P., and Darvas, K. 2004. "ICG [indocyaninegreen]-densitometry Investigation of Liver Function during Hepatic Resection," European Journal of Anaesthesiology 21:87; Athey, P. A., Sax, S. L., Lamki, N., and Cadavid, G. 1986. "Sonography in the Diagnosis of Hepatic Artery Aneurysms," American Journal of Roentgenology 147(4): 725-727).

With the implementation of recently developed intra-body communication (see, for example, Akl, T. J., Wilson, M. A., Ericson, M. N., Farquhar, E., and Cote, G. L. 2014. "Wireless Monitoring of Liver Hemodynamics in Vivo," PLoS [Public Library of Science] One 9(7):e102396; Chen, X. M., Mak, P. U., Pun, S. H., Gao, Y. M., Lam, C.-T., Vai, M. I., and Du, M. 2012. "Study of Channel Characteristics for Galvanic-Type Intra-Body Communication Based on a Transfer Function from a Quasi-Static Field Model," Sensors 12(12):16433-16450; Estudillo, M. A. Naranjo, D. Roa, L. M. and Reina-Tosina, J. 2009. "Intrabody Communications (IBC) as an Alternative Proposal for Biomedical Wearable Systems, in Cruz-Cunha, M. M., Tavares, A. J., and Simoes, R. (eds.), Handbook of Research on Developments in E-Health and Telemedicine: Technological and Social Perspectives, Hershey, Pa.: IGI [Idea Group, Incorporated] Global, pages 1-28; Wegmueller, M. S. 2007. "Intra-Body Communication for Biomedical Sensor Networks, Dissertation, Zurich, Switzerland: Swiss Federal Institute of Technology) and body area networks, numerous indicia previously limited to the clinic can be continuously monitored and/or used to control an autonomous prosthetic disorder response system, itself often fully implanted. Such sensors include thermistors, electrodes; ultrasonic, electrohydraulic, and laser probes and scopes, and such transmitters include hollow (injection/aspiration) needles, hypotubes, lasers; and heating elements as already mentioned.

e. Urethra-Noncompressive Reinstatement of Urinary Continence

A primary advantage in drug targeting is the avoidance of side effects in tissue not targeted. This applies to chemotherapeutics, immunosuppressives, and antibiotics, which can cause as much if not greater harm as benefit. Confining immunosuppressives to an organ transplant, for example, avoids systemic dispersal and a generalized degradation in resistance to disease. Targeting antibiotics as to avoid the gut and thus conserving its microbiota, eliminates the risk of infection with *Clostridium difficile*, while targeting chemotherapeutics to avoid the scalp avoids the loss of hair, for example. Incorrect treatment as mislocated has other expressions. Side effects result not only when unintended tissue is intolerant to the drug but when tissue is inappropriately extracted from its normal function.

For this reason, the appropriation of one kind of healthy tissue to perform an alien function should be done away with in favor of using synthetic materials. Surgically displaced tissue may adapt to its new environment to some degree, but not enough to avert adverse long term sequelae that necessitate revision (reoperation). Compression of nonsphincteric urothelium to reinstate continence in simpler cases, such as stress, effort, or exertion incontinence, is avoided through the use of a stopper ball check valve mechanism which is simpler and less traumatizing to implant than is an hydraulic artificial sphincter having three parts, each to be separately positioned in highly innervated and vascularized locations.

Where the bladder is missing following an anterior exteneration, cystoprostatectomy, or trauma, so that diversion is required, compression is avoided by placing the sphincter along the diversion line, not along the urethra, for example. Whereas the unique geometry of the bladder means that the stopper ball check valve device is limited to this application, the bypass sphincter, is applicable to any bodily conduit. If the native sphincter must be excised, then the electromagnetic pinch valve sphincter is positioned orthotopically. Orthotopic placement by end to end anastomosis is still supported with medication on as needed basis through a side-entry connector with service or accessory channel or channels.

Gut is adapted for absorption and unsuitable for conducting urine, and urothelial tissue not adapted to virtually constant compression as lining a sphincter will eventually atrophy, erode, or fistulize. The harvesting and reconfiguration of tissue to perform an alien, countergenomic function comprises two procedures, not one, both involving trauma and risk often too pronounced to allow application to the very young or very old. Because side-entry connectors and jackets make possible the dependable connection of synthetic lines to native tissue, and allow the direct delivery to the lines of therapeutic and line maintenance substances, the multiple deficiencies inherent in harvesting healthy tissue and misplacing it, along with the trauma and risks in doing so—especially in the very young and old—can be avoided.

Despite the fact that the urothelium is adapted to withstand sustained pinching or clamping compression only at the sphincters, marketed devices have sought to simulate native function using artificial sphincters that must be positioned aside from either the internal or the external urinary sphincter. As a valving function, this choice of mechanism for an artificial sphincter was ill advised, surgical complexity, risk, and repeated compression limiting the use of these devices. Multicomponent hydraulic prostheses government approved and tooled, the original error is now firmly ingrained. However, the compressive approach should be supplanted by alternative means for on-off valving the flow of urine, especially because this allows a reduction in the need for surgical precision and reduces the need for later attention (see, for example, Van der Aa, F., Drake, M. J., Kasyan, G. R., Petrolekas, A., and Cornu, J. N. 2013. "The Artificial Urinary Sphincter after a Quarter of a Century: A Critical Systematic Review of Its Use in Male Non-neurogenic Incontinence," European Urology 63(4):681-689).

Referring now to FIG. 12B, shown is in essence a ball check valve adapted to suppress urinary incontinence without the need to place the urethra in virtually constant compression that will eventually erode or atrophy it. The device of FIG. 12B is shown separately from the application of nonjacketing side-entry connectors shown in FIG. 12A for clarity. To avoid concentrating weight at one location, an electromagnet is usually mounted separately from fluid or electrical lines passed through nonjacketing side-entry connectors. Electromagnets 66 in FIG. 12B and 69 and 70 in FIG. 12D are shown fastened to the subjacent tissue as clasp-electromagnets, which in many instances will be situated beside nonjacketing side-entry jackets.

For that reason, the delivery of drugs or other therapeutic substances to the same organ or region, whether used independently of the magnet, or controlled for coordination with magnet when magnetically susceptible carrier-bound, is separate, through a nonjacketing side-entry connector placed as the upper of the two connectors 61 in FIG. 12A. Medication might be needed or later become needed to treat detrusor areflexia, hyperreflexia (hyperactivity, overactivity), pressure, leak point pressure, cystodynia, cystolith, and/or urinary tract infection with cystitis and/or cystistaxia, for example. In such cases, the arrangements shown in FIGS. 12A thru 12D are used in various combinations as dictated by the specific disorder.

Hydraulic artificial sphincters that fail or cause injury to the urethra can be replaced by the check valve device shown in FIG. 12B, which operating on a different principle, does not maintain the urethra in compression. Upon replacement, the constricting cuff of the hydraulic artificial sphincter is explanted. Provided injury to retrieve the reservoir and pump following tissue ingrowth and adhesion will not be significant, these are explanted as well. When the urethra distal to the bladder neck is obstructed or missing, the neck can be bypassed as shown in FIG. 12C. Such a bypass allows a urethral enlargement and meatorrhaphy, for example, to be deferred, avoided, or to heal more quickly.

Neurological problems, such as detrusor-sphincter dyssynergia, or neurogenic detrusor overactivity, and cystoplegia (cystoparesis) may be remediable by sending current (see, for example, Taweel, W. A. and Seyam, R. 2015. "Neurogenic Bladder in Spinal Cord Injury Patients," Research and Reports in Urology 7:85-99) through half-round needles 6, addressed above in the section entitled Applications Made Possible by Ductus Sde-entry Jackets and Nonjacketing Side-entry Connectors. Targeted Electrical and/or Chemical Autonomic Motor Assistance. As shown in FIGS. 9 and 10B, half-round anchoring needles 6 if hollow and connected to a sideline 13 can be used to inject drugs directly into the detrusor with or without the simultaneous delivery of electrical current, thus in a combined form of electrostimulatory neuromodulation of which an electrical sacral pulse device is incapable. A double lumen sideline 13 allows the same of different fluid delivery through any of the hollow half-round needles 6. When only electrical stimulation is sufficient, fluid lines not likely to be needed for a time are omitted. Electrostimulation of an organ such as the bladder is almost always through separately placed connectors and according to strategically timed patterns of discharge among the needles of a given connector and those of neighboring connectors.

Depending upon the dose rate, half life, and inadequacy of immediately flushing the line through once a radioactive drug such as chemotherapeutic has been administered, the upper connector shown in FIG. 12A portacath, line, and connector are permanently radiation shielded as shown in FIG. 10A or disintegrably shielded as shown in FIG. 10B. Hushing through when the patient is continent is through upper connector 61 with voiding normal. When the patient has an external collection bag, flushing is from the pump; through upper connector 61, and out to the bag through lower connector 62 and drain line 51. Compatible with the check valve device shown in FIG. 12B are not only combined arrangements that include components taken from FIGS. 12A, 12C, and 12D, but nonjacketing side-entry connectors used to position an imaging device, electrode, heating element, diagnostic and/or therapeutic probe, laser, and so on.

The same combinability of components applies when the arrangement shown FIG. 12A, 12C, or 12D is that primary. In FIGS. 12A and 12C, a single pump 49 might be switched among inputs, that is, different pre-pump drug delivery reservoirs and lines, and/or different outputs, meaning different post-pump drug delivery lines and destination connectors such as 61. For simplicity, conditions that affect a single organ best use a single channel to target any number of compatible drugs to the same destination. Primarily for reasons of reliability and secondarily for reasons of cost, when the number of drugs required is few enough to allow it, that each drug delivery channel be discrete from origin to destination is to be preferred. When, however, drugs are required that should not sharp the same line or are intended for different destinations, the increased potential for malfunctions associated with pump switching are overridden by the elimination of components which involve added expense, and more significantly, are likely to create discomfort.

Where minimal mixture of drugs that should be kept separate takes place within the pump, the pump is flushed through with water before switching from one drug input to the next. Pump output switching would also be justified were a single connector at the organ in a superior position to deliver different drugs. Switching among inputs if required is at the pump input, and switching among outputs if required at the pump output; other elements or connections junctions such as entry ports, fluid lines, reservoirs, and connections of drug delivery lines as themselves or as connected to the side connector are stationary. Consistency thus facilitates not only simplifies system architecture and production, but expedites maintenance or troubleshooting were a switching malfunction to occur. Also to expedite repair, the pump with switchable inputs and/or outputs is built as an interchangeable module that allows immediate replacement with diagnostics and repair of that recovered to be carried out after the implant system has been returned to proper function.

The side-entry connector atop the bladder can be set at any angle that avoids encroachment on the ureters or neighboring tissue. Temporary placement in an open surgical field where retractors can be applied can be at any point about the bladder accessible thus. In FIG. 12B, check valve stopper ball 65, generally 1 to 1.5 centimeters in diameter, can be made of any suitable polymer, to include nitrocellulose (cellulose nitrate, pyroxylin) using the same process as is used to produce table tennis balls to obtain a sphere that is strong and light in weight. Prior to bonding the hemispheres of ball 65 together, each hemisphere is coated internally with a layer of iron-silicon crystal and externally with a thin layer of a slippery fluoropolymer, such as polytetrafluoroethylene. To facilitate rolling, the internal layer of iron powder is of uniform thickness. An alternative stopper ball has an elemental iron core surrounded by polytetrafluoroethylene.

The internal layer of iron-silicon crystal is of a thickness that imparts the degree of magnetic susceptibility required while contributing enough weight so that ball 65 rolls down into the bladder outlet at the neck without becoming lodged in a ruga or any other irregularity along the internal surface, or becomes stuck to the mucosal lining. Unless the rugae are abnormally deep, no need for an additional magnet or magnets toward the bottom of the bladder is needed. The weight of ball 65 is not allowed to accede to the threshold at which the pressure sensing nerve endings in the trigone induce a sense of urgency. Dependable traction with the least weight also allows the electromagnet to be smaller, weigh less, and [lar] less likely to distract the wearer.

During micturition, the action of the detrusor muscle continuously adjusts the internal volume of the bladder. For this reason, a solid connection between the side-entry connector and ball 65, such as by a tube or rod, would require a needlessly complex telescoping action, one more costly to manufacture, and likely to result in malfunctions. Because of the continuously varied dimensions of the bladder cavity as the detrusor contracts and relaxes, a physical connection between the points to be brought close during voiding and released thereafter is avoided. In FIG. 12B, small traction clasp-electromagnet 66 and magnetically susceptible check valve stopper ball 65 eliminate the problems of mechanical adaptation to bladder function. Clasp-electromagnet 66 is fastened to the superior surface of the bladder in facing relation to and in axial alignment with the bladder outlet. If the superior surface of the bladder is irregular in tissue strength, a more extended connector, such as that shown in FIG. 4 is used.

If irregular in anatomical conformation, axial alignment between the angle of orientation of the pole of magnet 66 and ball 65 is by bending the clasp mounting as necessary and inserting a strip or strips of viscoelastic polyurethane foam beneath the clasp platform. When the detrusor muscle is fully contracted, the ball at the magnet pole must remain out of contact with the internal surface of the bladder. If contact is at the outlet, any remaining urine will be prevented from draining, while if off to a side of the outlet, a spurious sense of urgency may result. If necessary with a small bladder, contact between ball 65 attached to the pole of small configured traction electromagnet 66 and the internal surface of the bladder is avoided through the use of a specially wound 'pancake'-configured electromagnet 66 which is shorter in the axial direction.

The space constraint is not so pronounced as to justify the cost of a silver wire wound solenoid. If there is concern that the weight of magnet 66 will be annoying once the entry wounds have healed and the patient had time to acclimate to the sensation if any, the weight of the electromagnet can be evenly distributed for upright, prone, and supine positions using suture by connection to neighboring tissue, preferably tissue less highly innervated, such as connective. The patient withdraws check valve stopper ball 65 from the bladder outlet by means of one button switch, and releases it to close off the outlet with a second button keyless entry type radio switch, which can be worn or implanted anywhere. The switches are smaller but much the same and based upon the same remote keyless entry short range radio keyless entry transmission system used in remote control car keys.

Urinary incontinence can be treated as one channel in an ambulatory prosthetic disorder response system which is able to treat other conditions as these arise or have channels removed when a comorbid or intercurrent condition subsides. Access is through a laparoscopic entry wound with a second entry wound into the superior surface bladder. In not compressing the urethra, the mechanism described avoids the fundamental defect in an hydraulic sphincter. This mechanism is far simpler in structure, far less susceptible to malfunction, is inserted through a path far less inclusive of small nerves and reproductive ducts, is therefore considerably less complicated to put in place, and is less costly to produce and market.

Unless a dysfunctional sphincter can be encircled by a prosthetic sphincter which limits the segment under compression to that native or the function of a missing sphincter must be replaced, or a pinch valve sphincter can be placed orthotopically along the tract, an extraanatomic bypass with in-line electromagnetic sphincter, or bypass sphincter, is placed. When the origin of the bypass is a sheet of tissue, a nonjacketing side-entry connector is used. FIG. 12C provides a diagrammatic representation of the urinary bladder with nonjacketing side-entry connector 62 at the origin of drain line 51.

When the origin is at a native conduit such as a ureter or along the intestine, a ductus side-entry jacket is used, and reconnection to the tract at the destination or insertion is with a ductus side-entry jacket. The insertion or return to the tract is through a ductus side-entry jacket. Connection to the distal colon where the diameter is considerably larger, connection if difficult with a ductus side-entry jacket is with a nonjacketing side-entry connector. Because of the intrinsic motility of this substrate, a connector such as shown in FIG. 4 or FIG. 20 without the shock absorption feature is used. If the bladder is atonic, or dyssynergic (ataxic), timed electrical shocks are delivered through the nonjacketing side-entry connector half round anchoring needles 6 in the drawing figures.

If along the ureter or gut, peristalsis is impaired or missing distad the bypass, an electrode is included in the side connector for this purpose. Origin or takeoff at the ureter is through a ductus side-entry jacket, and insertion into the bladder through a nonjacketing side-entry connector. When the bladder is missing, continent function without the need for a urostomy and external collection bag or intermittent catheterization is obtained by placing a prosthetic bladder. Such a prosthesis is not currently reconnected to the urethra, does not incorporate a sphincter and pressure detecting sensors at the outlet, or the electronics required to signal the patient of the need to void.

Neither is a functional tissue engineered bladder in the offing. The outlet line of the synthetic reservoir, or prosthetic bladder, is connected to a shunt with an electromagnetic sphincter inserted along it as described above in this section. The distal end of the line, not the sphincter, is then joined to the intracorporeal urethra through a ductus side-entry jacket. A surgically constructed neobladder is not preferred for the reasons stated above. Future prosthetic bladders may incorporate an outlet line with sphincter. A native conduit prone to atrophy, erode, and/or fistulize when placed under compression to which it is not adapted, insertion of a segment of elastic or rubbery tubing along the bypass encircled by an electromagnetically actuated artificial sphincter effects compression aside from the native conduit.

If the pressure sensors in the bladder trigone induce urging, the patient has a radio remote control switch to the release the sphincter. Because the insertion is to the urethra when present, no external collection bag is needed, voiding performed normally. If for any reason the patient cannot sense the need to void or is unable to control the sphincter, control is by a microcontroller implant sent pressure data by strain gauges at the level proximal to the native sphincter. In that case, a vibrator signals the patient the need to go to the bathroom. The patient unable to respond to such a prompt will not benefit from a bypass in-line, or shunt, sphincter and must, as the least preferred option, be diverted to an external collection bag.

f. Targeted Electrical and/or Chemical Autonomic Motor Assistance

Nonjacketing side-entry connectors allow peristaltic adjustment or restitution using electrical and/or pharmaceutical means of neuromodulation, alone or together, and concurrently or separated by brief or long intervals. The delivery of timed electrical discharges with or without the concurrent delivery of medication into subjacent muscle through the side connector and/or the hollow anchoring half round needles can be used to stimulate the muscle to contract. Site specific, or local, rather than higher level stimulation of innervating nerve, omits any rami, or branches, which innervate other structures as might lead to their unintended stimulation. Where the contraction is traveling, or peristaltic, a train of discharge-delivering side-entry connectors is energized in the timed sequence of normal function.

To minimize the presence of these as might encroach upon neighboring tissue and arouse disturbing internal sensation, the majority of these will connect only a wire. Much peristaltic action, most prominently the contraction of the stomach, is too energetic to entrust to a less penetrating and less securely engaging clasp as used to fasten a permanent magnet or electromagnet, or clasp-electromagnet. The use of nonjacketing side-entry connectors to maintain the position of implanted electrical nerve stimulation neuromodulator electrodes was mentioned above in the section entitled Concept of the Invention. Peristaltic tracts encircled at intervals with nonjacketing side-entry connectors equipped with injection and electrical discharge-capable anchoring needles and dysfunctional sphincters can be prodded to contract with functional timing.

Along a larger ductus, such as the esophagus or gut, connectors are ringed about at intervals along the length, generally three to each separately energized series-wired ring. In a prosthetic esophagus, for example, when simulated without the aid of overlapping mechanical elements, the smooth continuous traveling contractive wave of peristalsis rather than a disjunctive incremental pattern of contraction is obtained by selecting the synthetic tubing used to replace the native esophagus for the elasticity needed to smooth out the incremental contractions. Until neuromuscular sufficiency is achieved in a tissue engineered prosthesis, the same approach must apply to a tissue engineered as does to a synthetic prosthesis. In an assist device, the resting tonus of the smooth muscle tunics is adjusted.

Implanted sacral neuromodulation has been used to treat neurogenic lower urinary tract dysfunction, to include urinary incontinence, chronic retention, and overactive bladder for four decades, and came into more general practice a quarter century ago (see, for example, Noblett, K. L and Cadish, L. A. 2014. "Sacral Nerve Stimulation for the Treatment of Refractory Voiding and Bowel Dysfunction" American Journal of Obstetrics and Gynecology 210(2):99-106; Bullock, T. L and Siegel, S. W. 2012. "Neuromodulation," in Smith, J. A. Jr., Howards, S. S., McGuire, E. J., and Preminger, G. M., Hinman's Atlas of Urologic Surgery, Philadelphia, Pa.: Elsevier/Saunders, pages 599-604; Hubsher, C. P., Jansen, R., Riggs, D. R., Jackson, B. J., and Zaslau, S. 2012. "Sacral Nerve Stimulation for Neuromodulation of the Lower Urinary Tract," Canadian Journal of Urology 19 (5):6480-6484).

Tined, or barbed, leads such as passed through the third or fourth sacral foramen, through which pass the S3 [third sacral nerve] and S4 nerves respectively, to affect the relative strength and coordination among sacral reflexes thereby restoring more nearly normal bladder and internal and external urinary sphincter function have been known to cause pain, migrate, fracture, or both, or dislocate when the patient does not comply with advice to avoid bending movements, necessitating reimplantation or explantation (see, for example, Thar, A. P. 2014. "Sacral Neuromodulation and Peripheral Nerve Stimulation in Patients with Anal Incontinence: An Overview of Techniques, Complications and Troubleshooting," Gastroenterology Report (Oxford) 2(2):112-120; Cannel, M. E., Vasavada, S. P., and Goldman, H. B. 2012. "Troubleshooting Sacral Neuromodulation Issues," Current Urology Reports 13(5)363-369; Kohli, N. and Patterson, D. 2009. "InterStim Therapy: A Contemporary Approach to Overactive Bladder," Reviews in Obstetrics and Gynecology 2(1):18-27; Deng, D. Y., Gulati, M., Rutman, M., Raz, S., and Rodriguez, L V. 2006. "Failure of Sacral Nerve Stimulation Due to Migration of Tined Lead," Journal of Urology 175(6):2182-2185).

Capable of eluting only anti-inflammatory and adverse tissue reaction suppressing drugs for early acceptance by the sacral tissue, current neuromodulators are not able, configured, or implanted in the position necessary to deliver drugs to the treatment site on a long term basis, much less coordinate drug delivery with the electrical stimulation. By comparison, the componentry shown in FIGS. 12A and 12C, to include subdermally implanted injection portacath 46, drug storage reservoir 47, drug delivery pump 49, charging circuitry 50, microcontroller 53, battery 54, and included in FIG. 12C but not FIG. 12A, transdermal (transcutaneous, transintegumentary) battery charging secondary coil and optional diagnostic sensor readout telemetry antenna denoted by 64, where the anchoring needles 6 of exemplary nonjacketing side-entry connector 61 are hollow for injection, allow the delivery of drugs on a continuous basis for as long as necessary. Anchoring needles 6 hollow for injection and/or aspiration where each is connected to a drug delivery line and a wire supplying current are shown in FIGS. 9 and 10B.

Neither artificial urinary sphincters nor implanted neuromodulator pulse generators incorporate means for the delivery of drugs, much less coordinated with the electrical discharge. Nonjacketing side-entry connectors incorporate three means for delivering pulsed electrical discharges. These include an electrode as side connector or included in a common conduit as side connector, electrified anchoring needles, and the coordinated use of these. The electrode can be adjusted to any depth and is capable of transmitting greater energy, while the needles are limited to the outer layers of the underlying organ or tissue. Therefore, in the use of one or more side entry connectors to stimulate a dysfunctional sphincter, for example, the choice of which mode to employ depends upon the specific sphincter.

Autonomic motor assistance with the means described herein include neurostimulation through 1. Electrified anchoring needles for shallow muscle, 2. Microelectrode or electrode, comprising the side connector or passed through a common conduit with drug delivery lines as the side connector for less shallow to deep muscle, 3. Either of the foregoing two with the addition of an electromagnet and disk attractant positioned opposite thereto usually in pairs when the muscle would be too weak to function normally if electrostimulated, and 4. Clasp-electromagnets where electrostimulation is inadequate because the muscle cannot provide sufficient force or where normal function was never present, as in a surgically constructed neobladder or a prosthetic bladder.

Due to the abruptness of magnetic attraction and the likelihood that this will produce a disconcerting internal sensation, the use of electromagnets is reserved for cases where electrical stimulation would not work, such as with a surgically constructed neobladder or a prosthetic bladder. However, impaired motor function is usually accompanied by impaired sensory function, in which case this would not apply. For a sphincter with a deep adluminal area of specialized contractile cells and relatively nonparticipatory outer tissue, the electrode or microelectrode is inserted into that area. Where the contractile muscle is not confined to such a depth, both needles and electrode can be used together. Along the gut, the relatively shallow situation of the Auerbach (myenteric) and Meissner (submucosal) plexuses allow treatment using electrified anchoring needles. The application of electricity can be further coordinated with the delivery of medication through the same side connector.

In multimodal use thus, the electrode—or any other cabled or styloid device to enter alongside fluid and electrical lines—are conveyed through a common conduit as overall input line and side connector. For the treatment of urinary dysfunction, the placement of nonjacketing side-entry connectors is deep and well away from exposure to any forces that might dislodge them, this in contrast to the relatively superficial and vulnerable placement of a sacral neuromodulator. Large in size compared to side-entry connectors fitting in relatively little space, and not likely to encroach upon neighboring tissue, side-entry connectors and jackets are less prone to cause pain. Implanted pulse generators are more highly susceptible to complications and the need for surgical revision or explantation.

Positioned just outside the pelvic girdle, a sacral nerve stimulator (neuromodulator, neurostimulation pulse generator) is subject to compression under the weight of the body, limiting freedom of movement, and superficially situated, is vulnerable to collision. In a thrombophilic patient, the result can be significant bleeding (Kalyanaraman, B. and Mandy, A. 2012. "Extensive Gluteal Hematoma Following InterStim Implant: A Case Report," International Urogynecology Journal 23(12):1805-1807). Furthermore, because the target site is the sacral root and not the detrusor itself, lead misplacement, especially following dislodgement due to discouraged bending movements that interfere with free movement, can lead to the loss or misdirection of stimulation meant for the detrusor, necessitating reentry.

Neurological or neuromuscular problems may be remediable by sending timed and pulse shaped electrical discharges through the half-round needles 6 used to fasten the nonjacketing side-entry connector to the subjacent tissue. Biphasic discharge having been established as most effective for cardiac application, which is unique, the electrical discharge and pulse shape delivered from each needle and/or electrode if used can be coordinated in any pattern to deliver monophasic, biphasic, or polyphasic shock (see, for example, Keener, J. P. and Lewis, T. J. 1999. "The Biphasic Mystery: Why a Biphasic Shock is More Effective than a Monophasic Shock for Defibrillation," Journal of Theoretical Biology 200(1):1-17; Zhou, X., Knisley, S. B., Smith, W. M., Rollins, D., Pollard, A. E., and Ideker, R. E. 1998. "Spatial Changes in the Transmembrane Potential during Extracellular Electric Stimulation," Circulation Research 83(10):1003-1014), which subject in the literature remains unrelated to the coordinated release of a prodrug or drug and substantially limited to discharge-discharge interaction in cardiac resynchronization, rather than to discharge in relation to membrane permeability and prodrug or drug assimilation.

Whether used independently or in combination with needles 6, an electrode inserted into baseplate aperture 4 can be inserted to any depth. In contrast to conventional neuromodulation which targets higher level nerve, the needles or electrode are not situated at a distance, or neuroanatomical level superior to the target tissue, such as along the spinal cord or a larger peripheral nerve where branches to other tissue might be affected, but deliver the current at the target. At the same time, the sacral roots can stimulated through a lead or leads fixed in position by nonjacketing side-entry connectors. Conventional transcutaneous electrical nerve stimulation to remediate bladder problems such as overactive bladder and urge incontinence, targets the sacral or pudendal nerves. Moreover, to this immediacy, the nonjacketing side-entry connector adds a rigidity or fixation of positioning that even the contracting urinary bladder or stomach cannot dislodge. Increased density of discharge per cubic centimeter is obtained through the use of more than two needles per snap-clasp 5; a connector of the kind shown in FIG. 4; or that shown in FIG. 20. The motility of the bladder less abrupt and forceful than the beating of the myocardium or the motility of the stomach, the shock absorption feature shown in FIG. 20 is ordinarily unnecessary.

The choice of connector as between those shown in FIGS. 1, 4, and 20 with the required number of half round needles 6, might also respond to a preferred arrangement of current and drug delivering needles. The primary object of achieving secure attachment to tissue accomplished, the number of half round needles 6 per snap-clasp 5 is variable where all anchor the connector, but only some deliver current and/or a drug. With respect to the urinary system, for example, a detrusor-sphincter atonia (atony), dyssynergia, or ataxia, post prostectomy incontinence, or neurogenic bladder may respond to the delivery of a mild shock or train of timed synchronizing shocks directly to the detrusor or indirectly to the innervating nerve, while an excitation shock might alleviate a cystoplegia, or cystoparesis, or cystospasm (see, for example, Hubsher, C. P., Jansen, R., Riggs, D. R., Jackson, B. J., and Zaslau, S. 2012, Op cit.).

A nonjacketing side-entry jacket fastened to the bladder and/or the external urinary sphincter can be provided with hollow injection half round anchoring needles with beveled or chisel points. The needles can also be sent current to deliver timed electric discharges, or pulses, and/or mount an injection needle as side connector. To minimize connector size, electrical connection is by wire to the implanted power source; however, once sufficient miniaturization of a receiver is realized, this will be supplanted by radio remote control. The fine wire or wires have nonresilient insulation to flex without resistance and are given only so much slack as allows the patient to adopt any posture without pulling at the wires or entangling or ensnaring tissue. When the current would affect the injectant, electrical and drug delivery uses of the half round needles are not simultaneous. The injectant can be supplied from a portacath, and if necessary, an implanted reservoir with transdermal energy transfer charged pump and pump battery.

Internal power storage frees the patient from the frequent need to use external charging apparatus, affording independent movement. Half round needles able to deliver electrical shocks and botulinum toxin type A injections applied to the bladder and/or external urinary sphincter can ameliorate neurogenic bladder and post prostectomy incontinence, for example. That reversing the current to the electromagnets in FIG. 12B will more securely stop the outflow or leaking of urine; the reversal of current to the electromagnets in 12D force open a collapsed bladder; that the same in miniature form could be applied to the gallbladder; and that the reversal of any of the pumps to include those connected to the injection anchoring needles in FIGS. 9 and 10B would allow the use of these to aspirate, and that any of these could be programmed to work thus in conjunction with the more usual applications thereof as specified herein, is considered obvious.

SUMMARY OF THE INVENTION

Provided are means for joining fluid and electrical lines, electrodes, and diagnostic probes to nontubular anatomical structures. The intake of diagnostic sensor data as the basis for the delivery of drugs or other therapeutic substances, or the application of an ionotropic electrical discharge, for example, by an automatic ambulatory prosthetic disorder response system requires the durable positioning of sensors and infusers. The rigid fixation in position of a catheter allows the direct delivery of drugs, drawing of diagnostic test samples, or drainage. To place such diagnostic and therapeutic elements is intermediate in trauma between percutaneous methods as in a suprapubic cystostomy and surgical construction of a catheter channel and stoma as in a urostomy.

Compared to conventional percutaneous insertion, the means described avert the irritation and exposure at the mobile interface between the sides of the catheter and the internal edges of the internal organ or tissue entry wound that causes irritation, facilitates infection, and unless corrected, structural degradation. This limits a suprapubic cystostomy, for example, to the temporary. The firm connection of a catheter to the edges of the tissue or organ entry wound mean that the tip of the catheter can be stably positioned at a depth that will allow treatment, whether automated, to continue indefinitely. Compared to a stomal reconstruction that appropriates healthy tissue, the means described achieve permanence without the extension of trauma or risk of functional impairment or infection to unaffected tissue and without the need to change catheters, which degrades the quality of life.

OBJECTS OF THE INVENTION

An object of the invention is to make possible the direct and permanent connection of synthetic tubing to native tissue, and in so doing, eliminate the need for a surgical anastomosis less likely to prove successful over time.

Another object of the invention is to make possible connections between synthetic materials and native tissue where the junction is readily accessible for the direct targeting of drugs to the junction and outlet line, thereby countering the infection, biofilm, clot, inflammation, adverse tissue reaction, crystal deposition, anastomotic stricture, or any combination of these that has discouraged such connections in the past, and in so doing, discourage the harvesting and spurious repositioning of vessels, gut, and segments of the colon, for example, necessitating the diversion of tissue of distinct functional specialization for a different function in a different environment and conformation, predisposing to adverse sequelae.

Yet another object of the invention is to furnish means for interconnecting implants as allows long term or permanent, full or closed-skin implantation as essential for the implementation of an automatic ambulatory disorder response control system to serve as an adaptive prosthetic immune system.

An equally important object of the invention is a means for selectively targeting and eradicating a solid tumor from within an organ or tissue with significantly less intrusion or trauma than any alternative method, considerably increasing the prospect for sparing the organ and avoiding the need for a transplant with the need for immunosuppressive drugs to the end of life.

Another object of the invention is to provide a type fastener for connecting diagnostic and therapeutic electrodes; prosthetic conduits, such as hollow needles and catheters; and/or any similar device to nonductal native tissue so that the device and the tissue into which the device has been inserted move as one, the junction between the two free of play or relative movement at the interface as eventually leads to abrasive injury, increases the chances for dislodgement, or migration, and results in a need to reenter for maintenance or replacement, thus precluding the possibility of a percutaneously placed line that can remain in place indefinitely.

An associated object is to provide a tissue connector that will allow positioning the tip of a prosthetic conduit, such as an hollow needle, hypotube, catheter, or that of an electrode, at a precise inclination and depth to target drugs, for example, directly to an original source or nidus of disease or a secondary site that has become severely affected in a patient whose freedom of movement will be little if at all imposed upon by this treatment, and continue as such for years.

A related object is the optimization of drug targeting made possible by directly aimed and dependably infixed drug delivery means such as hollow needles, hypotubes, or catheters to allow delivery of the drug at a higher concentration right at the source or nidus of disease, where such a dose if systemically circulated would induce toxicity, adverse side effects, adverse drug food interactions, and/or interfere with other medication.

Another object of the invention is to stably and precisely position implants to work in coordination with nonimplantable processes such as radiological, and to fix the position of a fully implanted passive warming implant, reactive or relay device, or receiving antenna for energization by the external source.

Yet another object of the invention is to provide prosthetic means for the drainage of urine or deoxygenated blood, the delivery of arterial blood, and/or and drug delivery to dysfunctional internal organs which means are capable of remaining in place with minimal maintenance to the end of life.

An associated object is to provide the foregoing means with a durability, precision, and invulnerability to deformation or degradation that exceeds, and with fewer complications, surgical reconstructions which appropriate, or harvest, and traumatize healthy tissue, diverting blood vessels, for example, from their normal territory or field of supply, and so involve tissue in a disease that had been unaffected by that disease.

Another object is to make possible the use of synthetic or prosthetic conduits that can continue all the way to the fine vasculature of hypoxic tissue without limitation to a distal anastomosis to an upstream artery large enough to apply suture wherewith the distal disease can then progress to the point of necessitating amputation.

Another object is to achieve the foregoing with trauma no greater than intermediate between that least, associated with temporary devices such as suprapubic cystostomy and nephrostomy catheters, and that greatest, associated with reconstructive surgery.

Another object of the invention is to provide such means in a form which lends itself to electronic control, whether separately or as one channel or axis of control in a hierarchical control system that automatically effects the targeted delivery of drugs to the site or sites of disease, in such a manner that an ambulatory patient will seldom be distracted, whether by the condition or the response system.

Yet another object of the invention is to provide tissue connectors, which secure and dependable, allow the use of an automatic ambulatory control system to automatically deliver treatment to one or a number of target sites on the basis of implant sensor based diagnostic inputs without dependency upon the patient or a medical worker.

Where blood is diverted through the catheteric line fastened to an organ or tissue by means of a nonjacketing side-entry connector, an object is to effectively simulate collateral circulation, alleviating dependency upon a dysfunctional microvasculature too damaged and fine to ameliorate.

To provide connectors that make it possible to reinstate urinary continence and dispose of the need for an external urine collection bag whether a comparatively minor stress incontinence, or severe, as following an anterior or total pelvic exenteration.

An object of the invention is to promote the advancement of pharmaceutical science by making possible the direct delivery of drugs to diseased or dysfunctional tissue thereby allowing novel uses for old drugs, hormones, and enzymes.

Another object of the invention is to promote the advancement of pharmaceutical and electrical neuromodulation by making possible the direct delivery of these, apart or in combination, simultaneously or intermittently, to diseased or dysfunctional tissue.

DESCRIPTION OF THE DRAWINGS

FIG. 1 provides an overall perspectival view of a nonjacketing side-entry connector with bilaterally opposed dual round needle driving knife switch-configured snap-clasps 5 used to engage the substrate tissue, shown in typical applications in FIGS. 6, 11, and 12, wherein the needles respective of each pair of each snap-clasp are mounted toward either end of a supporting bridge or spanner strip.

FIG. 2 shows a side view of a nonjacketing side-entry connector semicircular needle knife switch-configured snap-clasp as shown in FIG. 1, taken just to the fore of the half round needles to the right and along the midline at the center, to allow the fastening engagement of substrate tissue with positive click or snap action toggling after the operator lightly presses the nonjacketing side-entry connector down against the substrate tissue, thus compressing the foam cushion and inserting the anchoring needles into the tissue.

FIG. 3 shows an overhead view of the lever arm and cam component of a knife switch-configured snap-clasp.

FIG. 4 shows a baseplate with four knife switch-configured needle snap-clasps, each mounting two anchoring needles, and suture loops arranged to allow long term connection of the side-entry connector to a structure undergoing abrupt displacements, as the myocardium or to secure a gastrostomy tube to the stomach despite forceful peristaltic excursions, with or without an anterior gastropexy.

FIG. 5 shows a perspective view of the distal end of a side connector, or side stem with trepan distal edge to incise the substrate tissue, crosshair tissue cutter to reduce or grate the tissue when twisted from side to side, and water jacket to eject the tissue debris and flush through the line, where following tissue insertion, the water jacket line remains as an accessory line (accessory channel, sideline, service channel, service line) for the delivery of adjuvant drugs, therapeutic solutions, or line maintenance substances for example, into the side connector mainline or if continued to the distal terminus, into the tissue.

FIG. 8 shows a side view of a nonjacketing side-entry connector for connection of a catheter such as shown in FIGS. 5 and 7 within a baseplate such as shown in FIG. 1, taken just to the fore of the nonmotorized half round needles laterally and along the midline at the center, after it has been fixed in position by insertion of the semicircular tissue needles and side connector into the underlying tissue, so that the side connector is inserted within, and the round needles engaged within the tissue, and the foam compressed.

FIG. 9 shows an off-center, or sagittal, transection through a nonjacketing side-entry connector as shown in FIG. 8 taken just to the fore of the half round needles laterally and along the longitudinal midline at the center, where the needles are used not only to anchor the connector into the subjacent tissue, but each is connected to a separate fluid drug delivery line to inject nonradioactive substances and wired to deliver electrical discharge pulses or another form of electrically generated ablative energy.

FIG. 10A shows an off-center, or sagittal, transection through a nonjacketing side-entry connector as shown in FIG. 8 taken just to the fore of the half round needles laterally and along the longitudinal midline at the center, here used exclusively to anchor the connector into the underlying tissue, rather than serving also to inject drugs and wired to deliver electrical discharge pulses, but where to allow the delivery of moderate dose rate radioisotopes or radionuclides having a long half life, the connector and its feedline or side connector enclosed from the surrounding body cavity within a nondisintegrable, permanent radiation shield.

FIG. 10B shows an off-center, or sagittal, transection through a nonjacketing side-entry connector as shown in FIG. 9 taken just to the fore of the half round needles laterally and along the longitudinal midline at the center, where these needles not only anchor the connector into the underlying tissue, but are connected to accessory fluid lines (accessory channels, service lines, service channels, sidelines) to inject drugs, wired to deliver electrostimulatory discharge or ablative pulses, and enclosed within a temporary disintegrable radiation shield that will afford sufficient protection for the delivery of moderate dose rate radioisotopes or radionuclides having a half life shorter than the duration of the shielding.

FIG. 11 shows a catheteric side connector such as shown in FIG. 5 (which might also be a hollow needle, electrode, or probe) in use as a urinary diversionary drainage line, its distal end rigidly fixed in depth and angle within the renal pelvis by a nonjacketing side-entry connector as shown in FIG. 1 to serve as a urinary diversion nephrostomy and if double luminal, deliver drugs to a transitional or squamous cell carcinoma, or to serve as the inlet to a nephroureteric (pelvis to ipsilateral or contralateral ureter), or a nephrocystic (pelvis to bladder) shunt, or if necessary, to an external collection bag, thus serving to bypass a congenitally deformed, missing, diseased, stenosed, or otherwise obstructed renal pelvis outlet or ureter.

FIG. 12A shows a nonjacketing side-entry connector toward the bottom, or aside the neck, of a urinary bladder diagrammatic in omitting histology, and above the level of the prostate, in use to connect a permanent excurrent cystostomy line to treat retention or voiding dysfunction, by rechanneling urine either to a point distal along the tract as shown in FIG. 12C, or to an external collection bag through a port at the body surface, a second nonjacketing side-entry connector placed toward the superior surface of the bladder, to connect a drug delivery catheter to a manually injected internal port, or portacath.

FIG. 12B shows a clasp-electromagnet in use to affix a ball check valve nonsphincteric and noncompressive urinary incontinence remediation device to the superior surface of the urinary bladder, with a nonjacketing side-entry connector off to a side thereof to connect a catheter injectable at a portacath to deliver medication into the bladder as side connector and/or optional electrical conducting wire to provide electrostimulation generated by an implant microcontroller through the half round anchoring needles devised for neuromodulation as those shown in FIGS. 9 and 10B, to treat detrusor atony or native sphincter dyssynergia, for example.

FIG. 12C shows a partly sectional view of a nonjacketing side-entry connector positioned along the surface of the urinary bladder as close to the bladder outlet, or neck as possible, or as close as the prostate gland will allow, in use to affix a urinary diversion catheter with noncompressive bypass line pinch valve, or bypass inline sphincter, as urinary incontinence remediation device, a catheteric line secured by a nonjacketing side-entry connector toward the superior surface of the bladder injectable at a portacath to deliver medication into the line and optionally as shown in FIGS. 9 and 10B, electrification of the half round anchoring needles for neuromodulation to treat detrusor atony or native sphincter dyssynergia, for example, optional, convergence with the bulbar urethra through a ductus side-entry jacket affording meatal emission.

FIG. 12D shows patch-electromagnets fastened to the superior surface of the urinary bladder with opposing iron-silicon crystal disks encapsulated for chemical isolation placed subserously toward the bladder outlet or neck to allow the patient with an atonic or ataxic bladder to push a small radio remote wristband switch or switch implanted subcutaneously at the wrist causing the bladder to contract, combination with any of the foregoing FIG. 12 series implants to treat incontinence or outlet obstruction, for example, at the same time to be understood.

FIG. 13A shows an overall view of the nonjacketing side-entry connector detailed in FIGS. 14 thru 16 without the radiation shielding shown in FIGS. 10A and 10B or the clasp-electromagnets shown in FIG. 13B with an electrode inserted as side connector suitable for sideration, electro-cautery, or use as a radiofrequency scalpel, for example, a fuller description provided in the section above entitled Background of the Invention.

FIG. 14 shows an overall perspective view of a nonjacketing side-entry connector with motorized side connector or side stem as shown in FIGS. 13A and 13B for close proximity therapy that demands the precise retraction and advancement through tissue of a direct drug delivery catheter, hollow injection/aspiration needle, hypotube, electrode, probe, or a close proximity radiation source such as used for Auger therapy, whether in cooperation with external beam radiation, or for advancing an antineoplastic drug-delivering hollow needle at a controlled rate to and through a solid tumor, for example.

FIG. 15 shows an diagrammatic overhead view of the motor housing in a nonjacketing side-entry connector with motorized side connector or side stem shown in FIG. 14, with the top cut away, the direct-drive stepper motor connected to a high traction biconcave roller urged by springs toward its contralateral counterpart to compress while rolling to advance or retract the side connector hollow needle, electrode, or other styliform or rod-shaped device interposed between the rollers for precisely controlled advancement and retraction, the stepper motor, voltage doubler, rectifier, battery, and voltage regulator used for transcutaneous energy transfer shown diagrammatically.

FIG. 16 shows a diagrammatic side view of the motor housing in a nonjacketing side-entry connector with motorized side connector or side stem shown in FIGS. 14 and 15, shown with the side wall cut away, the motor used to precisely advance the styliform device, here shown as a hollow needle interposed between the rollers, to a precise depth within the tissue, with stepper motor, voltage doubler, rectifier, battery, and voltage regulator used for transcutaneous energy transfer shown diagrammatically.

FIG. 17 shows incurrent (intake, supply, inflow artery-connected, 'arterial') and excurrent (outlet, outflow, runoff, drainage, vein-connected, 'venous') catheteric bypass lines connected to a nonjacketing side-entry belt connector that accommodates the two side connectors, in use to supply blood through a ductus' side-entry jacket mediated tap or take-off on a native artery to the left with return to a native vein to the right, thereby to alleviate a chronic localized hypoxia, here shown with the connector held in position by a belt encircling the lower crus or placed subcutaneously or subdermally without the belt to secure the side-entry connectors for treatment of a venous stasis ulcer in the lower leg.

FIG. 18 is a detailed side view of the nonjacketing side-entry connector with intake or arterial and outlet or venous side connectors mounted to a belt as shown in FIG. 17 for placement about the lower leg when used to treat a temporary condition so that subdermal placement is unnecessary.

FIG. 19 is a detailed front view showing the two side connectors in the belt-supported nonjacketing side-entry connector shown at the bottom of FIG. 17, in which small caliber arterial and venous catheters are tunneled cranially to higher level vessels, the connector placed above the ankle to treat a venous stasis ulcer through an adaptation of Arthur Vineberg's procedure, the detail showing that each side connector is provided with an accessory channel (service channel, sideline) for the delivery of adjuvant drugs, for example.

FIG. 20 shows a cutaway, partially 'ghost,' or show-through perspectival view, of a double pad, double footing, or two point anchored coupling span (brace, bar) for connecting separate nonjacketing side-entry baseplates, or pads, such as shown in FIG. 4, across substrate tissue allowing direct viewability of the side connector entry wound into the substrate tissue and/or to maintain greater stability of the side connector entry point by means of bilateral internal shock absorbers and suture loop tie-downs which allow suture to be passed through for fixation to stable tissue, cover 37 shown in FIG. 21 removed.

FIG. 21 shows an external view of the intersection between the side-entry connector, which might be a catheter, hollow needle, electrode, laser, or other styliform device at the center, and the crossover stabilizing bar or span that provides side to side shock absorption between the two-point, double pad or double footing baseplates shown in FIG. 20 with the enclosure at the intersection to allows locking collar or nut 20 to be tightened flush down against its upper surface.

FIG. 22 shows an adapter for connecting catheters different in caliber and/or materials, so that the internal diameter is increased or decreased gradually thus minimizing turbulent flow, shear, and to the extent possible, sustaining laminar flow as reduces the propensity for clot when conducting blood or the accretion of crystal when conducting urine, for example.

DESCRIPTION OF THE PREFERRED EMBODIMENTS OF THE INVENTION

Figure 6:
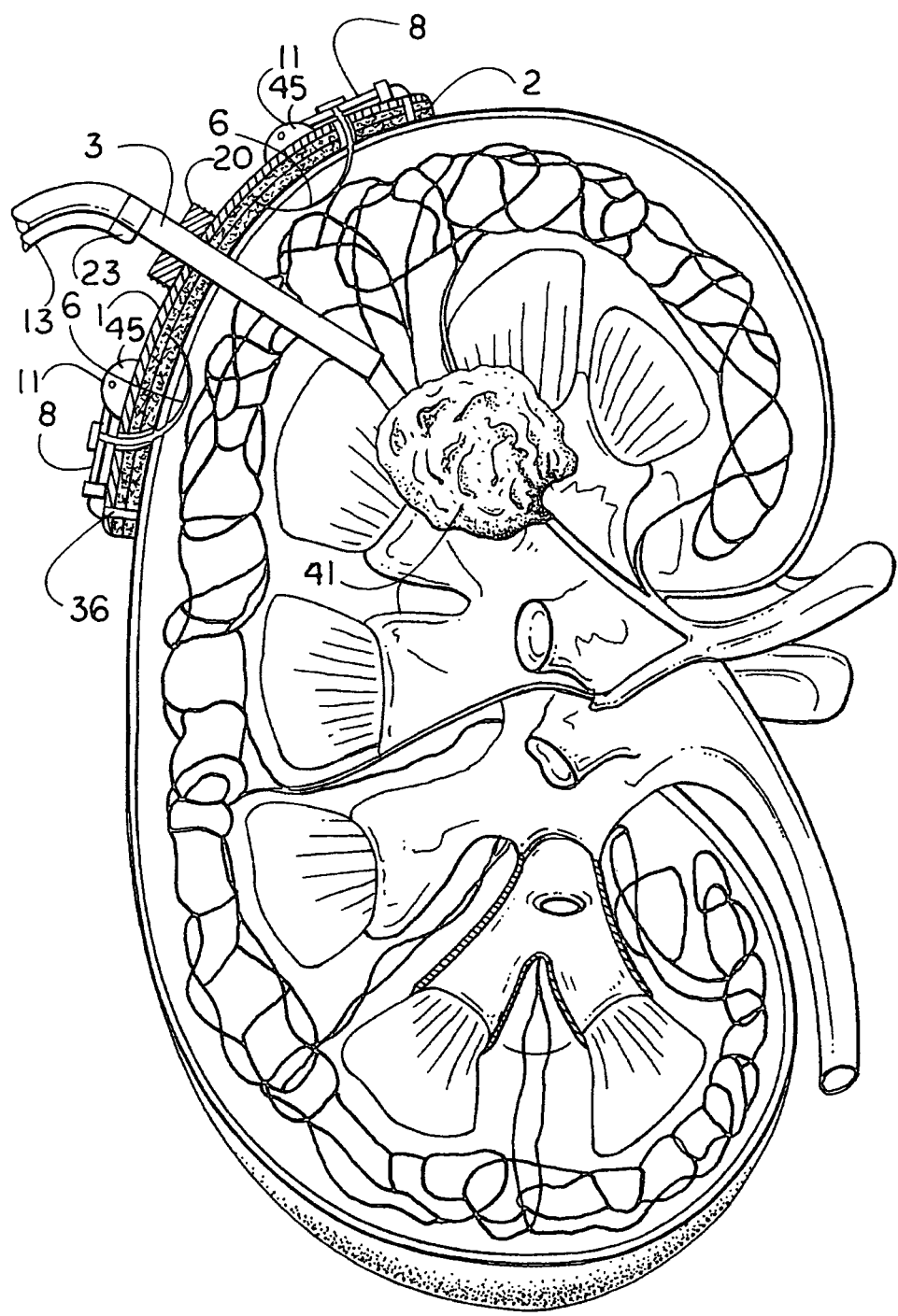
FIG. 6 shows a side view of a nonjacketing side-entry connector as shown in FIG. 1, less radiation shielding, positioned to target a drug or drugs directly at a solid organ tumor, here renal, a fuller description provided in the section above entitled Background of the Invention.

Structural features essential to explain the concept behind nonjacketing side-entry connectors are addressed above in the section entitled Background. Turning now to the perspectival view of a nonjacketing side-entry connector with bilaterally opposed double needle knife switch-configured snap-clasps 5 shown in FIG. 1; the side view of a snap-clasp in FIG. 2; and the overhead detailed view of a dual needle knife switch-configured snap-clasp proper, or cam and lever arm-mechanism 5, needle-mounting cross-bridge or spanner strip 7, and needles 6 shown in FIG. 3, baseplate 1 is cushioned beneath with a double layer of foam 2. The inner layer of foam in contact with the subjacent tissue is made of high density viscoelastic polyurethane.

Referring now to FIGS. 1, 2, 4, 6 thru 11, 13A, 13B, 14, 17, 20, and 21, it being critical that anchoring needles 6 never fracture, nonelectrified needles solid and hollow to allow injection are made from a strong stainless steel or titanium. Those to be electrified are overlain with copper separated from the steel or titanium by a bimetallic electron blocking shield and coated to isolate the copper from tissue. Spanner strip 7 is made of a tough polymer such as bearing grade nylon. Whether solid or hollow, needles 6 have a broad flange (not shown) toward the end to attach to spanner strip 7. Needles 6 are included in the mold used to produce spanner strip 7, so that the flange is embedded within the strip. If hollow for injection, the needle continues to a distance beyond the outer surface of spanner strip 7 sufficient to securely fasten a fluid line thereto.

Where heat buildup is best avoided, a low density viscoelastic polyurethane is used. The basic part numbers shown in FIG. 1 are applicable to all embodiments of nonjacketing side-entry connectors and are consistent for the equivalent parts in all of the drawing figures. The foam is die cut to produce side connector aperture 4, 'breathing' slits or openings 36, and as will be described, a passage to stow drug delivery lines when hollow and/or electrical connection lines to the anchoring needles as necessary. The outer layer, or that against the underside of baseplate 1, made of biocompatible, such as cyanoacrylate cement bonded polyurethane rebonded, or rebond, foam with high resilience contributes restorative force to urge baseplate 1 against the substrate tissue and thus more securely engage half round needles 6.

The degree of restorative force is suited to the hardness of the substrate tissue, whether predominantly fibrous or fascial, adipose, or muscular. When placed to span a convex surface such as the outer margin of the kidney, a restorative force backup layer of the two foam layers is unnecessary. The second foam layer is not beneficial in ductus side-entry jackets but is included in wraparound or belt-mounted nonjacketing side-entry connectors such as shown in FIGS. 17 thru 19. Snap-clasps 5 are fastened down to baseplate 1 by wide head rivets no fewer than one at each corner (not shown) in the base of lever arm and cam housing 45, which is the only part of snap-clasps 5 fastened down to baseplate 1. The use of nonreticulated open cell viscoelastic polyurethane foam allows periodic saturation with phosphorylcholine or dexamethazone, for example, to suppress an adverse inflammation reaction on a continued basis.

Such a drip line is shown in FIG. 21 as part number 34. Baseplate 1 consists of a strip or band of pliant material, typically, an implantable poly(aryl-ether ether ketone) (PEEK), such as Solvay Zeniva® Brussels, Belgium, or a self-reinforced polyphenylene such as Solvay Proniva® Brussels, Belgium, or a pliant nylon. To minimize the risk of incisions due to abrasive contact or accidental impact, baseplate 1 has all corners and all edges rounded, and to allow gas exchange between the outer fibrosal or adventitial layer, or other substrate tissue, small 'breathing' apertures in the form of slits or holes 36 which pass entirely through baseplate 1 and double layer foam 2.

When space allows so that neighboring tissue is not encroached upon or too many anchoring half round needles would be needed, an electromagnet to be accompanied by means for the direct delivery of medication and/or electrical discharges to the substrate tissue—allowing the microcontroller to coordinate the action of each modality—the electromagnet is mounted as a separate clasp-electromagnet. If space is limited, the baseplate mounts the magnet and side connector in adjacent relation. A nonjacketing side-entry connector with such a side by side arrangement, hollow anchoring needles able to deliver drugs by injection, and electrically connected to allow neurostimulation, can be used to apply any of these in a coordinated manner. The addition of radiation shielding as depicted in FIGS. 10A and 10B allows the coordinated use of radioactive substances as well.

Reciprocally, when an electromagnet hut not a side connector aperture 4 or other fluid or electrical connections to the anchoring needles 6 will is needed, a clasp-electromagnet is used instead. For example, in FIG. 12B, if only the electromagnet to lift check valve stopper ball 65 out of the bladder outlet is needed; a clasp-electromagnet is used. If a need for a drug arises at a later date, a nonjacketing side-entry connector such as 61 in FIG. 12A is added. When the expectation that a need for drugs or pulsed electrical discharge at the superior surface will become beneficial, a connector that includes the necessary accessory lines is placed at the outset. Where effective neurostimulation calls for discharge at numerous points about the urinary bladder, for example, to least draw attention or cause problems, the plurality of connectors are made as unobtrusive as possible.

Such a connector consists of a baseplate 1 with a die cut passage through the foam 2 to stow a coiled electrical wire, which connected to an anchoring needle 6, deploys as the operator rotates snap-clasp 5 to fasten the connector. If anchoring needles 6 used as electrodes are to deliver pulses in the same spatial and/or timing pattern, then these can be wired in series for connection to the implanted microcontroller and power source. If a differential pattern of pulses is to be generated by coordinating the action among the needles 6 as separate channels of control, then a separate conductor is connected to each set of needles to discharge in unison. In either case, the only connection to baseplate 1 an electrical cord, aperture 4, more often used to connect a fluid than an electrical line, is smaller in diameter.

As shown in FIGS. 12A and 12C, reservoir 47 can hold a single fluid drug or therapeutic solution or compatible mixture of these at a given time. An intervening flush by injecting and aspirating water through body surface port type side-entry connector 46 can clean reservoir 47 for a following substance to be kept apart from the first. This has the advantage of using a single reservoir 47 and pump 49. That various switching mechanisms can be situated at each junction along the line—between a subdermally implanted portacath 46 and line leading to reservoir 47 as shown in FIGS. 12A and 12C, between the line leading from the port to different reservoirs, and between different reservoirs and the outlet line respective of each, is considered obvious.

The same applies to a body surface type nonjacketing side-entry multiport with plural entry holes such as that shown in FIG. 17 and described in copending application Ser. No. 14/121,365. However, for medical use, any nonessential connection capable of break down or conducive to error on the part of the patient or medical personnel is best eliminated. For this reason, drug delivery channels are preferably kept exclusive, each including a respective portacath, line to reservoir, reservoir, line from reservoir to pump 49, and line 48 from pump 49 to side-entry connector, such as that shown as 61 in FIGS. 12A and 12C. A surface port with plural entry holes, each clearly marked, as shown in FIG. 17 is suitable for patients with multiple health problems who need several different drugs targeted to different sites as makes the use of separate subdermally implanted portacaths more amenable to errors in administration than the single multi-hole surface port.

Injection capable anchoring needles 6 if to function independently for electrical discharge must each have a separate control channel with independent connection to the microcontroller. If additionally to function independently for the injection of medication, then each must have a separate control channel comprising a separately controlled pump and fluid drug catheteric supply line. If different drugs which should not be mixed are to be injected by the different needles, then each must come at the end of a discrete channel that includes the components along the drug delivery control path. As shown in FIGS. 12A and 12C, this includes a subdermally implanted portacath 46 or easily distinguished injection point thereof, catheteric fluid line from port 46 to an exclusive reservoir 47, fluid line from reservoir 47 to a separate pump 49, and a separate catheteric line from pump 49 through catheter drug supply line 48 as side connector to and through nonjacketing side-entry connector 61, as shown in FIGS. 12A and 12C fastened to the urinary bladder.

While the compatibility of most drugs used together allows adding an adjuvant or supply line maintenance agent to the mainline or side connector, eliminating the need for a separate channel to the same connector, when this is not so, each sideline or accessory channel must likewise be constituted as a discrete channel. Pump switching and flush-through are addressed above in the section entitled Urethra-noncompressive Reinstatement of Urinary Continence. It warrants emphasis that unless the additional expense is considerable, components not immediately required but likely to become so are placed at the outset. For example, in FIGS. 12A and 12C, microcontroller 53 will usually remain overrated for a time, but within the context of the cost to accomplish the procedure overall, the electronics to include transdermal (transcutaneous, transintegumentary) battery charging secondary coil and optional diagnostic sensor readout telemetry antenna 64 charging circuitry 50, and so on are justified as to cost and the avoidance of a body surface socket or jack to recharge battery 54.

Along with a primary fluid delivery catheter as mainline side connector 3, a nonjacketing side-entry connector can receive a wire or wires to electrify, and accessory or service channels to deliver adjuvants for injection through anchoring needles 6. Referring now to FIG. 1—which omits electrical and/or fluid connections to half round anchoring needles 6, and to FIGS. 9 and 10B which include fluid lines 72—wires 91, when present, follow the same path, run alongside, or as shown, are spiral wound about to run with fluid lines 72. In FIGS. 9 and 10B, wires 91, shown as wound about fluid lines 72 beneath baseplate 1, have passed from the microcontroller (not shown in FIGS. 9 and 10B) to contact 79 down through additional accessory channel lines 83 within side connector 3.

Full implantation adds less expense than return to the clinic to treat an infection or adverse tissue reaction to a body surface positioned connector. FIG. 9 shows a nonductus side-entry connector without radiation shielding, while FIG. 10B shows the same connector having been adapted to allow an outer radiation shield, here one disintegrable. Fluid drug or therapeutic solution delivery accessory channels or sidelines 13 run down through side connector 3 as an enveloping conduit, and each accessory channel 13 is connected to its respective injection needle 6. Running alongside each accessory channel 13 within side connector 3 for connection to the same needle to deliver electrical current is a wire respective of each accessory channel 13 and any additional accessory channel lines 83 made necessary by the need to supply each needle 6 independently. These fluid and electrical lines terminate within side connector 3, those fluid with a miniature coupling, those electrical with contacts for connection to corresponding extension lines respective of each stored beneath baseplate 1 and unstowed from recesses in foam 2 as the operator rotates snap-clasp handle 8.

While inside side connector 3, the electrical wires are not shown, the extensions respective of each are shown each coiled about its respective fluid line. As no longer a part of side connector 3, the fluid extension lines beneath baseplate 1 are shown as 72 and the electrical lines as 91. Accessory channels 31 generally reserved for adjuvants, anticlotting agents, and antimicrobials, if the delivery from the reservoir is to be separately controlled by the prescription program, then these too must be provided as discrete control channels from portacath hole to the respective injection capable anchoring needles 6. Also in FIGS. 12A and 12C, a single channel is shown because the crystallization suppressive or other medication can be mixed with the primary drug. By contrast, the propensity for synthetic materials to allow the accretion of clot, the ductus side-entry jackets shown in FIGS. 17 thru 19 as encircling blood vessels are provided with accessory channels 13 to drip-feed an anticoagulant.

In most instances, a single accessory channel 13 allows compatible adjuvants to be delivered into side connector 3. Where adjuvants must be kept apart and the delivery of each into side connector 3 or through separate accessory channels alongside side connector 3, or through needles 6 for injection coordinated with delivery along each of the other drug delivery lines—if not with electrical stimulation or radiation during the same interval—the addition of adjuvants must be coordinated in time. For electrical discharge, the needles if made of copper are covered with an electrically conductive outer coating to prevent copper from entering the surrounding tissue. To prevent copper from entering the surrounding tissue, copper needles if coated with another metallic substance are first passivated to prevent a bimetallic effect with an intervening layer of a fluoropolymer, polyurethane, or lightly dip or sputter coated with a nonmetallic electrically conductive material.

An outer coating of a conductive material such as platinum-iridium is then applied. Where the implanted energy source is sufficient to sustain the reduction in conductivity, the needles are made of titanium or stainless steel. If also hollow for injection, a polymeric capillary tube or tube slightly larger in caliber is passed through the copper needle to the beveled opening toward the needle tip so that the drug does not come into contact with copper. The small caliber fluid and electrical lines are juxtaposed within a common cable for insertion through baseplate aperture 4. Unless a connector with multiple anchoring needles such as those shown in FIGS. 4 and 20 are required, baseplate aperture 4 will be smaller in diameter. Preserving the circularity of aperture 4 simplifies production.

When each needle is to be provided with independent drug and electrical discharge capability, upon passing through to the underside of baseplate 1, each electrical and fluid line transitions into a coiled extension that remains stowed within its passage beneath baseplate 1, each aimed toward its respective target needle through a passage die cut into foam baseplate lining 2. When this means that a number of electrical and or drug delivery lines must exit in a more or less circular formation, the foam on the underside of baseplate 1 surrounding the primary side connector 3 if present or the common cable is removed in a die cut continuous circle. The length of the coiled terminal section or segment of each electrical and/or fluid line is based upon the distance to its respective needle after snap-clasp 5 is rotated to anchor the connector in tissue.

To connect to its respective needle, the distal end of each coiled section is then passed up through a hole in baseplate 1 through needle mounting crossbar or bridge 7. A needle for injection only is reduced in length so that it's beveled or chisel point exit hole will remain in the substrate tissue rather than continue up into the foam, and the distal end of the delivery tube is pressed over the proximal end of hollow needle 6. The wire for electrical discharge is soldered inside the end of the coated copper needle. When both injection and electrical discharge are required, the fluid drug line is connected to the needle in the same way but with longer overlap. The insulated wire is run alongside the fluid line, and soldered to a noninsulated copper contact plate exposed beneath a slit through the fluid tube overlap. Once the electrical connection is made and the slit flap to either side is released, the contact is covered over and out of contact with tissue.

The components of the 12-series figures combined as appropriate, the charging, drug storage, and control means shown in FIGS. 12A and 12C are the same for each configuration. Thus, drug delivery can be added to the configurations depicted in FIGS. 12B and 12D. Which are implanted depends upon the prognosis. Since along with the autonomic motor assist devices shown in FIGS. 12B and 12D, almost every patient will further benefit if not require targeted pharmaceutical support for the same and/or a comorbid condition or conditions, in almost every case, the entire complement of drug and power delivery components should be placed from the very start. To prevent a need for later reentry to place a drug delivery line, in a situation where the need therefor is predicted, the line or lines should likewise be placed ab initio. By the same token, because drug delivery adds portacath 46, drug storage reservoir 47, and reversible drug delivery pump 49, where the probability for future benefit is doubtful, the placement of these is deferred until needed.

In order to prevent rocking movement when the nonjacketing side-entry connector is to be connected to a mildly concave or convex surface, such as along the lateral border of a kidney, baseplate 1 is made of a material sufficiently plasticized (see, for example, Bey, S., Benamor, M., and Drioli, E. 2013. "Surface Modification of PEEK-WC Membranes by Wet Phase Inversion for Ni(II) Adsorption," American Journal of Analytical Chemistry 4:33-39; Yurchenko, M. E., Huang, J., Robisson, Agathe, McKinley, G. H., and Hammond, P. T. 2010. "Synthesis, Mechanical Properties, and Chemical/Solvent Resistance of Crosslinked Poly (aryl-ether-ether-ketones at High Temperatures," Polymer 51:1914-1920; Cogswell, F. N. and Staniland, P. A. 1985. "Method of Producing Fibre-reinforced Composition," U.S. Pat. No. 4,541,884), hence, pliant material that it conforms to the surface of the subjacent or substrate tissue 16 readily without significant restorative force that would apply stress to the pull at the semicircular tissue retention needles 6, inevitably pulling these through the tissue.

FIGS. 6, 11, 13A, and 13B, wherein the side-entry connector must comply with the curved margin of the kidney as exemplary illustrates but two instances of the need for pliancy of baseplate 1. The catheter side connector shown in FIG. 6 and the hollow needle side connector shown in FIGS. 13A and 13B directly target the kidney, and for stereotactic vectoring within the kidney to target a hard tumor, for example, the drug is paramagnetic nanoparticle carrier-bound, and snap clasp 5 in FIGS. 1 thru 3 secured or clasp-electromagnets 40 fastened about the kidney are used to draw the drug toward and through the tumor. Thus, a drug or combination of drugs can be targeted to the parenchyma, precise targeting within the parenchyma obtained by positioning patch-electromagnets to subtend the lesion targeted.

Figure 13B:
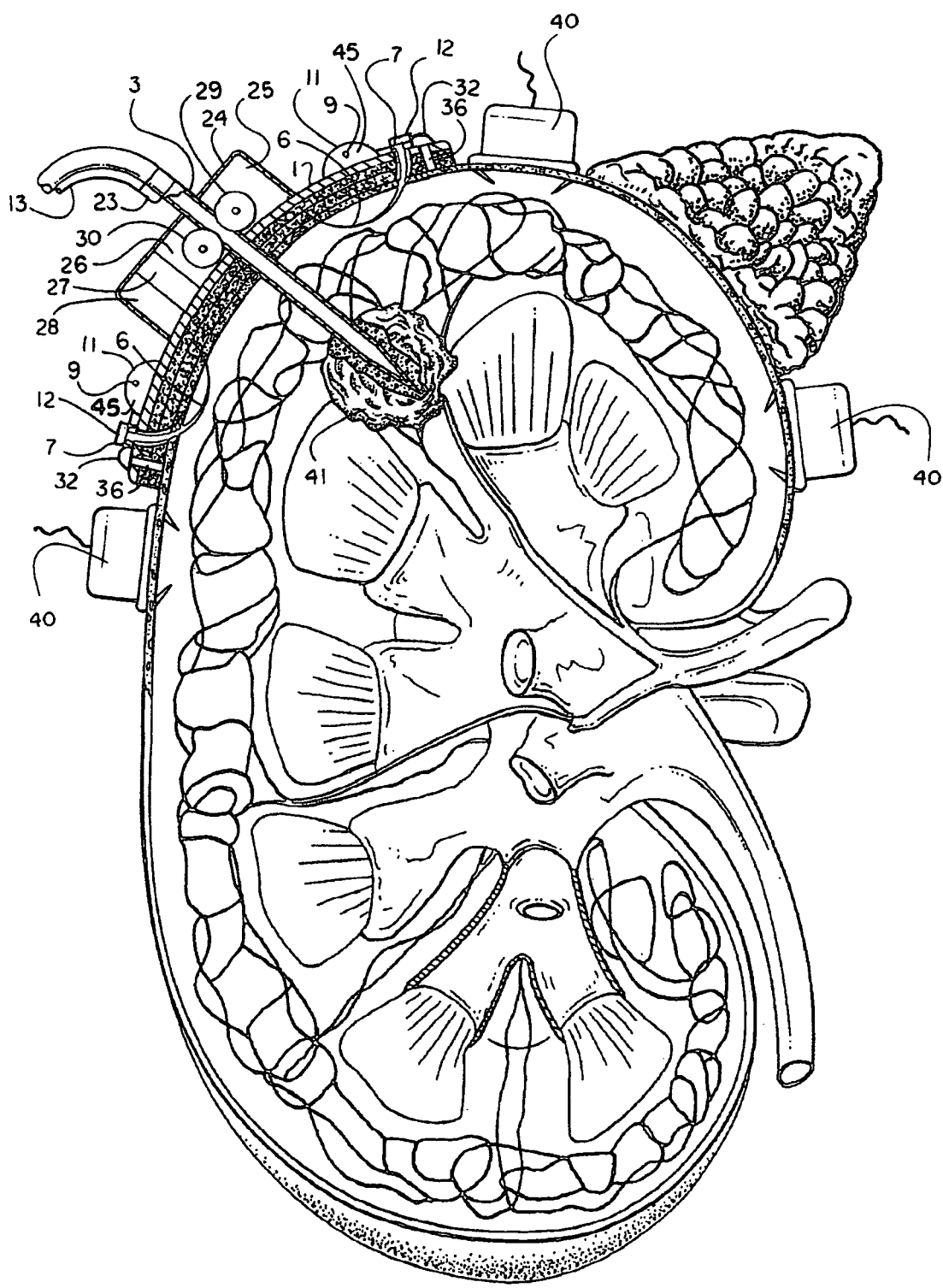
FIG. 13B shows the nonjacketing side-connector shown in FIG. 13A without radiation shielding as shown in FIGS. 10A and 10B with an electrode and/or hollow injection and aspiration needle to target a superparamagnetic nanoparticle carrier bound drug at a solid tumor, here represented as an inchoate nephroblastoma (embryonal adenomyosarcoma, Wilms' tumor) or a TNM (Tumor-[lymph] Node-Metastasis) Stage TIb (tumor less than 7 centimeters across) adenocarcinoma or a renal cell carcinoma in a kidney, with clasp-electromagnets added to assist in the magnetically susceptible drug carrier steering to and through the tumor under the control of the microcontroller implant.

Clasp-electromagnets 40, while shown only in FIG. 6 and radiation shielding, while shown only in FIGS. 10A and 10B, are not shown in FIG. 6 but are no less applicable to FIG. 6 as to FIGS. 13A thru 16. Also omitted for visual clarity from FIG. 13A are the continuations of the side connector 3 and accessory channel 13 craniad to their respective source pumps 49, and from FIG. 13B both these fluid lines and the wires connecting clasp-electromagnets 40. These electromagnet wires and any used to connect a sensor or sensors embedded between baseplate 1 and form 2, for example, must be fully flexible to include flexible insulation are run alongside side connector 3 in a common sheath.

Use of a radionuclide necessitates that lines of which the distal segment serves as side connector or a separate side connector associated with baseplate 1 be radiation shielded. When magnetic carrier bound radionuclides without an intrinsic affinity for the target tissue are administered, magnetic vectoring is used to direct the radionuclide at the lesion. When this is so, applications such as depicted in FIGS. 6, 13A, and 13B for example, must be understood to include both radiation shielding a clasp-electromagnets 40. Plasticizers pose toxicity problems for implantation, must be completely washed away following polymerization, and implants containing even trace amounts of plasticizer passivated or chemically isolated with a outer coating of a biocompatible polymer.

Double foam layered cushion 2 must be thick enough to accommodate small nonuniformities along the surface of subjacent or substrate tissue 16 in FIG. 2, and to compensate for larger nonconformities of substrate tissue 16 as would prevent down-flat or flush apposition of baseplate 1 to tissue 16, baseplate 1 must be pliant. Knife switch-configured snap-clasps 5 in FIGS. 1 thru 4, 7, 13, and 17 mount nonmagnetic and noncorroding stainless steel semicircular tissue engaging needles 6, mounted to cross-bridge or spanner strip 7, so that rotating lever arm 8 lifts strip 7 rotating needles 6 about their center of rotation through baseplate needle holes 19, through baseplate-subjacent foam 2, then into to encircle subjacent tissue 16. The restorative force of foam 2 is not sufficient to induce ecompression necrosis.

In less trauma-susceptible sites, opposing prongs might be substituted for fine half round needles to fix the connector in place. Similarly, patch or clasp magnets, as described in copending application US2014/0163664A1 or patch- or clasp-electromagnets 40 as described in copending application Ser. No. 14/121,365 can be fixed in place with a foam lined baseplate fastened to the substrate tissue by means of snap-clasps 5. When the device which the nonjacketing side-entry connector is to fix in position with its distal end held fast is a catheter to be brought to the desired end point by manual rotation and advancement using the side connector or side stem 3, locking collar or nut 20, in FIGS. 1, 2, 4, 6 thru 8, 10A, 11, and 21 is loosened.

As shown in FIGS. 9 and 10B, when the fluid and electrical line terminals in side connector 3, diagrammatically represented as 79 must align with their respective receiving or takeoff terminals or contacts shown as 80 beneath baseplate 1 to secure sound connections through vertical and rotational alignment, stabilization bell or collar 73 is used. This allows side connector or side stem 3 to be moved longitudinally and rotated, after which locking collar 20 or alignment, stabilization bell or collar 73 as appropriate is rotated to lock connector or side stem 3 in position. Locking collar 20, usually not threaded but rather forced down against the top of baseplate 1 or the upper surface of motor housing 24 in FIG. 14 and then twisted to lock it in place, will usually work as do ordinary natural gas line couplings by compression against an internal conical bushing or tapered collar 20 when screwed down tight along the distal segment of side connector 3.

Tissue surfaces without sufficient hardness at the entry point to allow stable connection and those with more pronounced rates of curvature are engaged with the aid of a stabilizing bar 33 in FIGS. 20 and 21, briefly addressed in the section above entitled Concept of the Invention as well as below in this section. If necessary suture loops 32 are used to pass suture through the side-entry connector and if present, its outrigger baseplate connectors as shown in FIGS. 20 and 21 to -pexy these to stable neighboring tissue. In FIG. 17, when a condition likely to promote migration, such as malacosis or a steep change in crus diameter is present, connection, typically about the lower ems, is with the aid of the belt shown. Otherwise, the belt is omitted, the connector fastened to the crus peripheral to the lesion, suture loops 32 at either end of baseplate 1 available if a lesser degree of migration thwarting fixation appears necessary. Fixation with the aid of suture is best to fascia where discomfort is less likely.

Turning now to FIG. 20, stabilizing crossover or spanning bar 33 is configured to securely anchor one or more side connectors through the center of the span by engaging the substrate tissue at points surrounding a weak entry point or an apex of curvature, for example. Stabilizing bars with a downward curve at either end to for insertion into the apertures of the spanned baseplates or pads can be bent to more closely conform to the tissue surface, the degree of bending determined by whether the bar includes a compression spring to serve as a shock absorber, if so, the length of the spring, and within the degree of bending preceding vector based resistance, the coefficient of friction between the outer surface of the inner telescoped section containing the spring and inner surface of the bar. Depending upon the detailed contour of the tissue surface, a second bar may be needed to protect against perpendicular displacements. In that case, the side connector or side connectors pass through the center of the crossover or spanner bar 33.

The degree of bending limited by friction passing through apertures 4 can be increased by coating the contacting surfaces with a fluoropolymer, such as a thin layer of polytetrafluoroethylene. In FIGS. 1, 2, 5, 7 thru 10B, and 20, the water jacket/accessory line is part number 13, the water jacket inlet 23, and the water jacket proper, that is, the internal concentric chamber within the side connector 3, is 31. Adaptation to more significant curvature is with a straight stabilizing bar provided with rod or dowel shaped piling projections or extensions in lieu of studs or bosses, for example. These extensions can be bent to any degree. The foregoing means, to include the use of suture, baseplates having multiple knife switch-configured snap-clasps, stabilizing bars, bendable stabilizing bars, pile like extended bosses or bungs, and the bending of these when the internal side to side shock absorber shown in FIG. 20 is omitted, make possible the formation of a secure junction to any surface however altered in strength and/or distorted in conformation by disease.

As shown in FIG. 5, whether made as part of the catheter at its side-entry connector inserting end or associated with the side-entry connector to which any number of different catheters might be connected, the working end ordinarily includes a trepan distal edge 21, crosshair tissue cutter 22, water jacket/service or accessory channel, or sideline 13, water jacket/accessory line inlet 23, and water jacket 31. The side connector 3 with trepan distal edge 21, water jacket/accessory line 13, water jacket/accessory line inlet 23, and water jacket proper 31 is generally made of a length of thin-walled nonmagnetic stainless steel tubing, for most applications, 2 to 4 centimeters in length. Unless forcing the excessive use of anticlotting agents to prevent clogging when used to pass blood or agents to prevent the formation of calculi when used in the urinary tract, crosshair tissue cutter 22 is provided to allow tissue to be grated by side to side rotation of side connector 3.

Tissue gratings less prone to adhesion than avulsion of a solid plug by undercutting jet flushing action and ejection as a coherent plug out through the catheteric line, crosshair tissue cutter 22 facilitates extraction of the tissue. Inside side connector 3, water jacket 31 outlet ejects around the outer surface of the tissue plug. Therefore, when crosshair tissue cutter 22 is omitted so that the tissue plug is not removed in gratings, to undercut and drive the plug outwards, the force of the irrigating jet must be sufficient to force water down and around the sides of the plug and avulse it at the terminus of the cut down. The side connector can be provided either as connected to the catheter for insertion through a side-entry connector that omits the side connector, or as part of the side-entry connector.

Only a minimum length side connector is used, a length of inelastic catheter used as an extension if necessary to expedite manipulation during insertion of the side connector. Once placed, the extension is replaced with a compliant permanent catheter. The first option allows the use of adapters for joining catheter of different luminal diameters to a side connector meant to fit a certain aperture. Of the two options, providing the side connector as a part of the side-entry connector is preferred as more dependably providing a water jacket/accessory line of the correct size to fit through aperture 4, an adapter for introducing a side connector of different diameter into aperture 4 not amenable to dependable correction through the use of an adapter. In most instances, the locking collar is pressed down against the flat underlying surface, and rotating it then locks it onto the tube it surrounds, thus preserving the downward force as well without the need for threading.

Provided it does not employ a elastomeric or rubbery lining as would allow a hollow needle, for example, passed through it to flex, or would unduly hinder the adjustment to the proper position of the needle point, a friction fit joint can be used in lieu of a locking collar. Because the device to be fixed in position in baseplate aperture 4 midprocedurally must allow unhindered rotation and longitudinal movement, to fix the position by friction fit requires that the distal segment of the device be off-round in cross section, have rough interfacing surfaces, and/or rhomboidal to achieve the resistance to coming loose required, which by definition must not come loose except intentionally with the aid of long nose pliers as was used to achieve this tightness in the first place. Friction fitting is substantially reserved for fine caliber devices such as hollow needles that would be awkward to manipulate midprocedurally.

By compliant or adaptive apposition through noncompressive investment that accommodates and compensates for any unevenness along the foam-tissue interface, cushion 2 serves as an aligning and protective layer, as well as to safely nestle round needles 6 when fully engaged. Smaller nonuniformities will usually consist of irregularities in contour of the tissue itself or the presence of small vessels and/or nerves that course along the surface of the substrate tissue 16. Larger nonuniformities which necessitate bending baseplate 1 include vestiges of normal connective tissue attachment or adhesions resulting from earlier surgery following removal. Lever and locking cam housings 45 in FIGS. 1 thru 4, 6 thru 11, 13A thru 14, 17, 20, and 21, made of biocompatible and nondegradable plastic and fastened down to baseplate 1 by wide head rivets, lack the length to significantly interfere with the flexibility of baseplate 1, flexibility primarily seen to either side, that is, medially and laterally, of these.

To place such fine support vessels in compression would induce hypoxia with atherosclerotic degradation, for example, and to compress such nervelets and plexi can induce neurological impairment of autonomic function. As shown in FIG. 1, baseplate 1 has side connector or side stem 3 with sharp trepan distal edge, crosshair tissue cutter, and water jacket provided within aperture 4. The operator advances the side connector into the substrate tissue by applying force in the forward direction while rotating the side connector from side to side. The gratings enter side connector 3 where the water-jacket 31 flushes these out of the line.

The aperture is normally central but can be peripheral to the snap-clasps when the anatomy does not afford the space for the side connector to be distant enough to allow interposition of a snap-clasp. FIGS. 1, 2, 5, 7, 8, 10A, 10B, and 20 show the side-entry connector with water-jacket 31 inlet 23 for connection of a water jacket/accessory line or sideline 13. Depending upon the function of the catheter or other device inserted into the tissue, which might include heating the material flowing through the catheter, for example, electrical lines are run alongside accessory line 13. FIG. 6 depicts a nonjacketing side-entry connector in use to stably position a catheter, hollow needle, hypotube, or other styloid or rod-shaped device at a certain depth within tissue or a solid organ, here within the renal medulla or perenchyma.

Eliminating levering movements at the side-entry connector is important for preventing growing tissue irritation that will limit the time the implant can remain in place. Generally, a catheter is fixed in depth with a conventional side-entry connector such as that shown in FIG. 1. Depending upon the mobility of the organ, a multiple snap-clasp side-entry connector such as shown in FIG. 4 or a number of these joined by stabilizing bars such as shown in FIGS. 20 and 21 are used. For controlled adjustment in depth, however, a motorized side-entry connector is used. That shown diagrammatically in FIGS. 14 thru 16 is a motorized version of the side-entry connector shown in FIG. 1.

The essential difference between a usually larger embodiment such as that shown in FIG. 6 with catheteric side connector 3 and one intended for Auger or transfective therapy, for example, as that hollow needle based in FIGS. 13A and 13B is one of size; either the stationary side-entry connector shown in FIG. 6 or that motorized in FIGS. 13A and 13B can connect a catheter, hollow needle, hypotube, laser, or any other miniature cabled device. The catheter or injector entering into the side-connector can be inflexible only over a short length, beyond which a steel hollow needle, for example, must be connected to a pliant nonirritating polymeric catheter. When a ferrofluid containing a magnetic carrier-bound drug is used with either, clasp-electromagnets 40 stereotactically position about the surface of the organ or tissue can be used to steer the ferrofluid into any direction between any two magnets 40.

When the volume of fluid allows, access is through a subcutaneously placed portacath or Ommaya type reservoir. Since unlike an Ommaya reservoir, the subcutaneous reservoir is placed in the pectoral region, it can extend to a considerable distance in every direction. An implanted reversible pump can meter the drug from the reservoir to the ductus or nonjacketing side-entry connector. Unless the energy required by the implanted pump necessitates a battery within the motorized nonjacketing side connector in FIGS. 13A thru 16 which is too large in size to prevent encroachment upon the neighboring tissue, the same battery, recharged by transcutaneous energy transfer, is used to power the pump as well as the stepper motor. Similarly, if the sum of energy requirements justifies it, the size of the motor and transdermal recharging system housing 24 in FIG. 14 is reduced by positioning the battery in a pocket created elsewhere within the body.

To prevent the dissipation of heat into the surrounding tissue, motor and transdermal charging electronics housing 24 consists of a strong by light weight plastic grid, enclosed or encapsulated within a non-silica based aerogel having very low thermal conductivity. Unless treated hydrophilic, to waterproof the aerogel, housing 24 is submerged within a bath containing a biocompatible aliphatic based coating that replaces the hydroxyl groups at the surface of the aerogel with non-polar groups. The edges and corners of housing 24 are rounded and blunted. The need for an external pump feeding through a port mounted at the body surface from a belt-worn pump pack is therefore limited to applications requiring a high volumetric flow rate.

FIG. 15 provides an overhead and FIG. 16 a diagrammatic side view of the components within the motor and transdermal recharging system housing 24, the components of the recharging system addressed below. To reduce the risk of irritation to neighboring tissue, housing 24 has blunted or rounded corners and edges. Notwithstanding this, and the common sheathing of fluid and electrical lines wherein the lines and sheath are highly flexible and the sheath made of material least likely to arouse an antixenic response, should the outer surface of the connector come into contact with neighboring tissue susceptible to abrasion erosion, a covering of a nonirritating material is applied. Encroachment is more likely when the connector shown in FIG. 14 is doubly anchored by a two point footing or anchor as shown in FIGS. 20 and 21, and the more so when this is doubled as explained below.

The basic part numbers shown in FIG. 1 apply. In FIG. 14, direct-drive stepper motor or piezomotor 25 responds to feedback sent to the microcontroller or respective node subordinate thereto as addressed in copending nonprovisional application Ser. No. 14/121,365, entitled Ductus Side-entry Jackets and Prosthetic Disorder Response Systems. In FIGS. 15 and 16, part number 26 is the battery, 27 a voltage regulator, and 28 a voltage rectifier-doubler. Stepper motor 25 rotates high traction biconcave roller 29 against the side of catheter, hollow needle, hypotube, or other rod-shaped device as side connector 3, contralateral or complementary biconcave roller 30 urged against the opposite side or side connector 3.

The urging or the biconcave roller against opposite sides results from the spring loading applied to these at the floor of motor mechanism housing or enclosure 24. When the motorized side-entry connector shown in FIG. 14 must be fastened to highly mobile tissue, the precision required will necessitate additional stabilization. This can be achieved by combining the embodiment shown in FIG. 14 with the dual baseplate or pad configuration depicted in FIGS. 20 and 21. More specifically, the proximal portion of side connector 3 in hollow injection and aspiration needle serving as side connector 3 in FIG. 13B is passed down through the larger side connector 3 in FIG. 20. In such use, side connector 3 in FIG. 20 is empty, and no lines 13 or 34 run alongside it.

Neither is locking collar or nut 20 used. Housing 24 in FIG. 14 then rests atop enclosure 37 in FIG. 21. This combination embodiment affords the protection of the spring loaded shock absorption feature but requires the all components be made with minimal height to avoiding encroachment upon neighboring tissue. The motorized side connector and the outrigger or side pads are also provided with suture loops, which can be used to achieve additional stability by connection or -pexy to stable neighboring tissue. In the 'ghost' view in FIG. 20, the medial spring retainers and stops of internal springs 87 are shown as part number 88 and the lateral as part number 89.

In FIGS. 20 and 21, the internal crossover bar shown as part number 90 is stationary. The addition of more than two outrigger baseplates to stabilize the styloid or cabled device controlled in depth of insertion by motorized injection needle 3 in FIG. 14 is addressed below. When the device to be fitted into baseplate-centered aperture 4 is a catheter rather than a hollow needle for injection and/or aspiration or fine trocar-configured insert as would clear its own path through substrate tissue 16, the trepan edge assists to incise the tissue as rotation of the side connector causes the crosshair tissue cutter to slice through the tissue at right angles to the long axis of the side connector.

In situations where it is preferred to eliminate the crosshair cutter as a platform for the accretion of crystals or the buildup of clot, the water jacket is used to direct a forceful jet at the base of the plug cut with the trepan, the plug then removed in a coherent piece. If the plug resists extraction through use of the water jet alone, a hooked guidewire or small catheter connected to a vacuum pump is passed down the line to forcibly extract the plug. When difficulty in extraction is anticipated, the presence of the crosshair cutter might lead to complications, and/or the use of a hooked guidewire or aspiration line is not preferred, a side connector or side stem with crosshair cutter is used to grate the plug, extraction effected by the forceful undercutting water jet irrigation of the water jacket then usually sufficient to wash the gratings out through line 13.

The plug extracted, the side connector is removed and reinserted after the crosshair cutter has been snipped or nibbled away, or another side connector without crosshair cutter is inserted. If bleeding is a problem, this action is best accomplished quickly. The water-jacket is used first to assist in insertion of side connector or side stem 3 into the substrate tissue 16 by freeing and ejecting the plug or gratings of the substrate tissue 16 and thereafter serve as an accessory channel (service channel, sideline) for the delivery of fluid drugs or other therapeutic substances into or withdraw diagnostic test sample through catheter side-connector stem 3 as necessary.

Much tissue is internally cohesive as to offer resistance to removal as a coherent or solid plug. Removal thus is with a side connector equipped with a trepan distal edge 21, water jacket/accessory line inlet 23, and line 13, connected for undercut-flushing and ejecting the cut tissue out through the catheteric line such as shown in FIG. 5 but not a crosshair cutter 22. When blood is to pass through the side connector, omitting crosshair cutter 22 significantly reduces the rate of delivery of heparin and/or other anticoagulants that will continue to be essential to suppress obstruction due to the buildup of clot. Otherwise, crosshair cutter 22 allows the operator to rotate from side to side while forcing the side connector more deeply into the target site.

Figure 7:
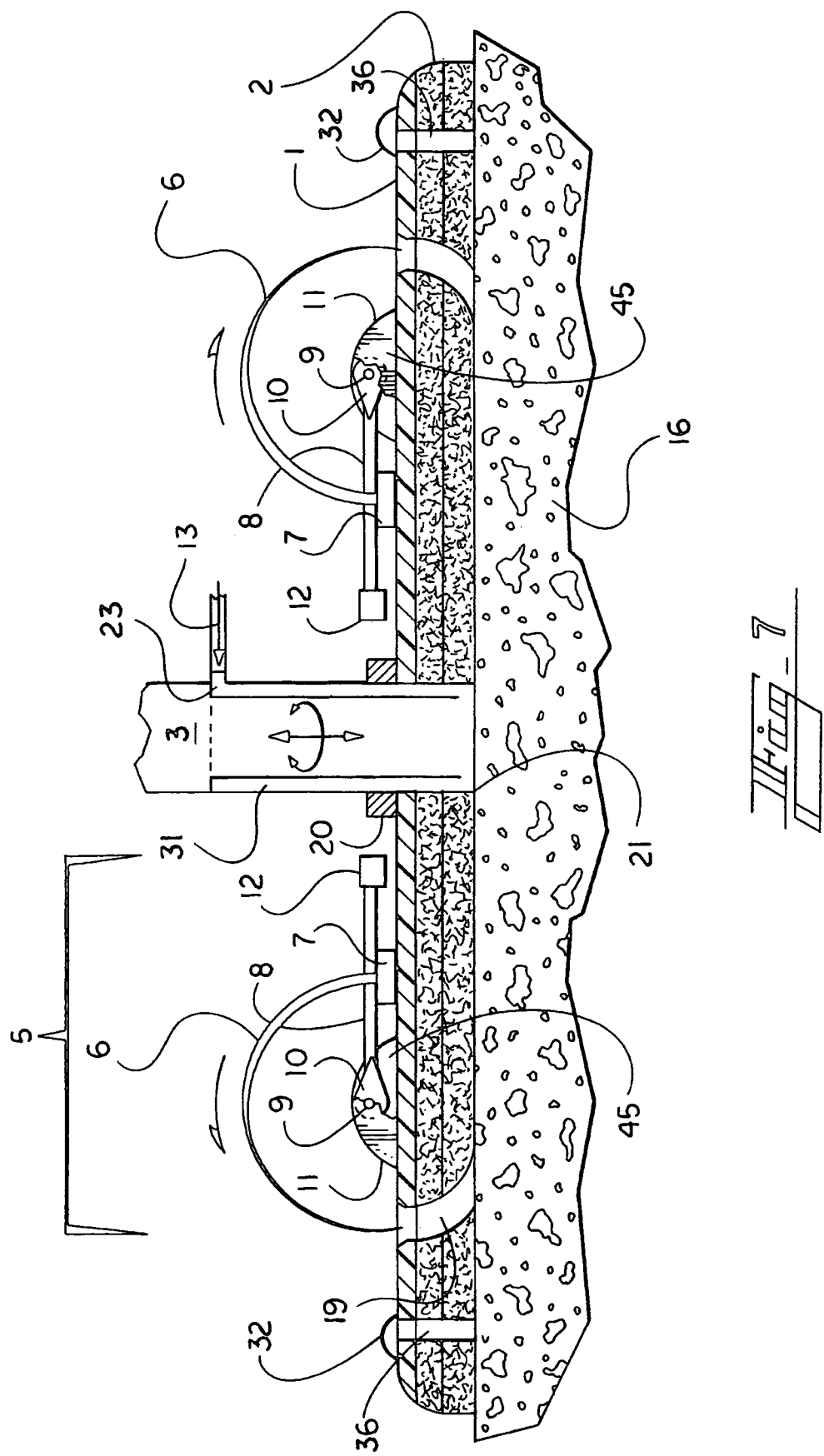
FIG. 7 shows a more inclusive side view than does FIG. 2 of a nonjacketing side-entry connector with catheteric side connector such as shown in FIG. 5, taken just to the fore of the nonmotorized half round needles laterally and along the midline at the center, before the connector is fixed in position by insertion of its semicircular tissue needles, after which the trepan tip at the distal end of the side connector will be used to insert the side connector into the underlying tissue.

FIG. 7 provides a detailed view of a side connector 3 such as shown in FIG. 5 upon initial abutment on the target site, and FIG. 8 shows the same side-entry connector having been placed by rotating about snap-clasp lever arms 8, causing half round needles 6 to penetrate through and undercut tissue 16. Referring now to FIG. 9, side connector 3 consisting of a conduit conveying internal fluid and/or electrical current delivery lines 83 which require to be connected to baseplate-internal counterpart lines 72 within the baseplate component of the nonjacketing side-entry connector, are separate components such that the baseplate component is fastened down and into the underlying tissue first.

This accomplished, the side connector 3 is then inserted through connector aperture 4. Insertion is by rotationally reciprocating incision using sharp trepan edge 21, the cutting action of crosshair cutter 22, and the flushing jet action of water jacket 31 shown in FIGS. 1 and 5, the debris additionally forced up and out through side connector 3 under the force of aspiration. When the side connector 3, in this instance, a conduit conveying fluid and/or electrical lines 83 (as well as its own lumen and water jacket 31) must connect to receiving lines respective of each needle 6 just beneath baseplate 1 within the connector, the proper alignment and forming of a secure contact for each such connection is essential. In FIGS. 9 and 10B, electrical conductors 91 are shown coiled about to stow and run with fluid lines 72. To avoid the need to reenter the patient as well as to achieve the economy of uniformity, fluid and electrical lines are included even when a need for the one or the other is not immediately apparent.

In FIGS. 9 and 10B, the view at the center is through the longitudinal midline, while at the sides, the view is a section just to the fore of half round needles 6, so that for side a side-entry connector with a length twice its width seen from above, the lines radiate outward from side connector 3, each to its respective half round needle 6 at an angle of about 30 degrees in relation to the longitudinal axis. In FIGS. 9 and 10B, needles 6 are made shorter to end within the underlying tissue, are hollow, and connected to drug delivery lines and/or electrical conductors 72 for delivery of the drug to be injected through each needle. Fluid and/or electrical current lines 72 connected to needles 6 automatically unstow from storage recesses or chambers 81 die cut in foam 2 wherein the lines are coiled, through openings 82 in baseplate 1 for extension as the operator engages knife switch-configured snap-clasp levers 8 to engage needles 6.

FIG. 10A shows a nonjacketing side-entry connector with permanent, that is, nondisintegrating radioactive shielding adequate for the continued delivery of radioactive diagnostic and therapeutic substances, while FIG. 10B shows temporary radiation shielding shows and this configuration altered to allow accessory channels to feed adjuvant drugs for injection through the half round anchoring needles 6 when hollow. Temporary shielding affords flexibility according to the formulation of the matrix, whereas permanent tungsten shielding is much less flexible. Certain plastic based shielding materials afford greater flexibility for a given thickness. As shown in FIGS. 9 and 10B, anchoring needles 6 can also be electrified to deliver neuromostimulatory discharge pulses, which can, moreover, be coordinated with the delivery of drugs through the side connector and needles; this tiny structure is described but omitted from the drawing figures.

FIG. 10B shows the same connector with injection and electrical discharge capability as that shown in FIG. 9 but with disintegrating shielding that consists of small overlapping or imbricated plates of tungsten, each encapsulated within an outer layer of polyethylene terephthalate within an adhesive matrix as binder similar in composition to glycolic acid based tissue engineering scaffolding and absorbable suture. Such materials include polyesters, primarily homopolymers and copolymers of poly(lactic acid) and poly(glycolic acid) with poly(amino acids), polyanhydrides, polyorthoesters, polyurethanes, polycarbonates, copolyesters of e-caprolactone, trimethylene carbonate, and paradioxanone. The disintegration of radiation shielding is hydrolytic or enzymatic. When not spontaneous within the internal milieu, dissolution is accelerated by injection.

Disintegrating shielding for the baseplate cap is made of imbricated tungsten plates temporarily bonded together in layers with sugar syrup or molasses, for example, and then permeated by heated matrix. While still plastic, the layered shielding is placed over the inner or positive form or mandrel of a mold and the outer or negative form is brought down to form and die cut the edges. The matrix binder is formulated to dissolve or disperse after the last radioactive dose has sufficiently decayed. Depending upon the position within the body, disintegration of such a temporary radiation shield may result spontaneously from hydrolytic or enzymatic action by the interval environment, or if not, then induced by deliberately applying a hydrolytic or enzymatic coating of known dissolution rate when placed, or to allow removal in response to the diagnostic condition or end point sought or whenever clinical judgment recommends, by injection of a solvent to wet the shielding.

Using needles 6 as shown in FIG. 9, any application of nonjacketing side-entry connectors, to include those depicted in FIGS. 6, 11, 13A, 13B, 16, and 17, can include the near surface or shallow depth injection of drugs and/or electrical discharge. Deeper drug delivery and/or electrical discharge is through side connector 3, which can consist of or include as its conduit, an injection needle, electrode, laser, or these run alongside one another within side connector 3, for example. If the injectant is radioactive, the embodiment shown in FIG. 10A with permanent shielding or that in FIG. 10B with disintegrating shielding is used according to the decay rate of the substance. Each side-entry connector can therefore incorporate the means for delivering electrical stimulation and/or drug delivery, or the two in coordination to any depth.

Where the adequacy of any one mode of treatment or a combination of these cannot be predicted, this prepositioning capability means that the implants can be placed and the patient closed without first engaging in much time consuming and inconclusive testing before the procedure is ended and the patient discharged. The optimizing that would otherwise take much time can then be conducted, tested, and monitored remotely through a network that allows an ambulatory patient to go about his ordinary business. Wireless body area networks with wireless transmission or telemetry is addressed with references provided in copending application Ser. No. 14/121,365, entitled Ductus Side-entry Jackets and Prosthetic Disorder Response Systems, filed on 25 Aug. 2014.

In FIG. 10B, when each needle is to constitute and independent channel for drug and electrical discharge delivery, it is essential that delivering fluid 13 and fluid or electrical line 83 distal contacts or terminals inside side connector 3 and the receiving terminals just below the baseplate of the connector correctly align and connect. Otherwise, the drug or drugs and/or electrical discharge respective of each needle will be lost or directed into the wrong receiving line, whereup other complications will arise. In fine action to affect the tissue subjacent to the side-entry connector, a misalignment that resulted in the misdirection of substances, leakage, or loss of coordination between injection and electrical discharge of each needle would nullify the treatment intended and possibly foul the connector.

Unless each fluid line of side connector 3 is precisely aligned to its respective receiving line in the connector, the drug conveyed, rather than passed through its respective needle 6 for injection, will either be delivered to the wrong injection needle, obstructed, or most likely, leak at the junction between the lines respective of the side connector 3 and those respective of the connector. Similarly, when needles 6 are to deliver electrical discharge pulses, the fluid line as accessory channel or electrical conductor 83 contacts 79 within side connector 3 and those stowed beneath baseplate 1 in a stowage area created by removal of foam 2 must align. As shown in FIG. 9, exact depth of penetration into the subjacent tissue is fixed by alignment and stabilization collar 73, firmly bonded to side connector 3 so that its bottom edge constitutes a stop to further penetration.

Precise depth of penetration is essential to bring fluid feedline and/or electrical conductor outlet line 83 terminals 79, located inside side connector 3 and corresponding inlet terminals located beneath baseplate 1 into exact vertical and rotational alignment to assure electrical contact and leak free fluid delivery. The vertical distance from the bottom of alignment and stabilization collar 73 to the upper surface of baseplate 1 the same as that separating the line outlets or input line 83 terminals 74 within side connector 3 from the inlet or input line terminals beneath baseplate 1, when both fluid and electrical contact is to be made, the contacts appurtenant of fluid and/or electrical terminals are adjacent, the exactitude of alignment afforded by the bolt action to be described assuring that both electrical and fluid contacts will be properly aligned.

In viewing FIG. 9, it should be understood that bolt 77 and bolt receiver 78 can be positioned anywhere about alignment and stabilization collar 73, but for clarity, are shown in the plane of the figure. The impression that the placement of these would obstruct throwing knife switch-configured snap-clasp lever 8 is thus misperceived. Also not to be misperceived in viewing FIGS. 10A and 10B is that radiation shielding cap 71 would obstruct the rotation of snap-clasp lever 8. Prior to pressing the shield down over the side-entry connector, side connector 3 is inserted through the central hole in shield cap 71. Once the baseplate component of the connector has been engaged within the subjacent tissue and the side connector 3 inserted, baseplate 1 is prevented from pressing down into the underlying tissue by supporting baseplate 1 from compressing the subjacent tissue by supporting baseplate 1 with the aid of a probe or dental pick.

Upon removal of radiation cap 71, side connector 3 fastened to baseplate 1 by locking collar 20, stabilizing side connector 3 with the aid of a pliars or hemostat allows a second such tool to grasp radiation cap 71 at the sides to remove it from baseplate 1. With respect to FIGS. 9, 10A, and 10B, reentry to remove a side-entry connector without radiation shield cap 71 should seldom prove necessary, and where the use thereof may again prove beneficial, should be avoided. If the side-entry connector remains or would likely become necessary after radiation shielding is no longer necessary but to leave radiation shield cap 71, which covers over 'breathing holes' 36 in place would risk degradation in the subjacent fibrosa or adventitial tunic, then cap 71 is removed. Since nonjacketing side-entry connectors will often remain in place after cap 71 has been removed, suture loops 32 are not omitted from those shown in FIGS. 10A, and 10B.

Radiation shielding cap 71 is then pressed down over baseplate 1 so that its apron like sides 84 with integral inwardly directed half round configured molding 85 running about the inside of its lower edge is pressed down over the yielding tapered outer edge of baseplate 1 to undercut baseplate 1. This causes half round molding 85 to slip beneath and undercut baseplate 1 and to become locked in place so that molding 85 protrudes into foam 2. Whether a continuous catheter or the line from the pump to which it is connected, side connector 3 must be shielded 86. Further penetration is thereafter stopped by contact between the bottom edge of alignment and stabilization collar 73 with the upper surface of baseplate 1. When the operator senses that further penetration is not possible, he releases compression spring 76 pull ring 75.

In FIGS. 9 and 10B, alignment and stabilization bell or collar 73 is shown just after having been stopped by compression spring 76 loaded bolt 77, then extended out of bolt housing 74, whereupon to continue downward penetration by trepan edge 21, the operator has had to retract bolt 77 by drawing compression spring 76 pull ring 75 to overcome the force of compression spring 76, thus clearing the path of descent for alignment and stabilization collar 73 to continue down to baseplate 1 where side connector 3 is brought to the correct depth for aligning contacts 79 and 80 without bolt 77 engaged within bolt receiver 78. Bolt 77 and bolt receiver 78 are square in cross section and precisely complementary in dimensions so that bolt 77 must be perfectly aligned to bolt receiver 78 axially for bolt 77 to engage alignment and stabilization collar 73.

Now in vertical alignment, the operator rotates alignment and stabilization collar 73 until bolt 77 under the restorative force of compression spring 76 slides into bolt receiver 78. Engagement of bolt 77 in bolt receiver 78 thus rigidly fixes alignment and stabilization collar 73, hence, side connector 3 both at the precise depth and angle of rotation required. Bolt 77 serves first to detain, or decent, further descent of side connector 3, and thereafter rigidly lock alignment and stabilization collar 73 in both vertical and rotational position. It will thus be seen that bolt 77 and bolt receiver 78 effectively key side connector 3 into the correct depth and rotational angle for the fluid and electrical lines in the side connector 83 to align to their otherwise separate respective receiving fluid fittings or couplings and/or electrical contacts within side-entry connector 3.

While nonjacketing and ductus side-entry connectors are primarily intended for long term if not life long use, for temporary treatment or otherwise necessary, side connector 3 can be removed. When use is to be less than long term, measures to increase retention, such as etching or engraving an undercut tissue surface texture to allow tissue ingrowth and/or applying an absorbable surgical adhesive are not used. To remove the nonjacketing connector, a probe is used to hold down the connector so that the underlying tissue is not injured when the connector is removed. The connector stabilized thus, draw compression spring 76 pull ring 75 is pulled outward to release bolt 77 from hold receiver 78. Snap-clasps are then rotated back to the open position and pliers or a hemostat used to pull off the connector. To minimize its weight, alignment and stabilization collar 73 is hollow and made of a light tough polymer such as polyester, as is bolt housing 74.

With this design, no separate action of and no dependency upon the operator other than to insert the side connector using slight to moderate downward force and rotational reciprocation finds the precise depth and angle of rotation without needles complexity at greater expense. As shown in FIGS. 8 and 10A, anchoring needles 6 incapable of injection and aspiration are made to a length that places the tips of the needles out of harms way within the foam underlining the connector. As shown in FIGS. 9 and 10B, so that their tips will lie within the subjacent tissue, anchoring needles capable of injection and aspiration and/or electrical discharge must be shorter. With an injection and/or electrostimulation-capable needle of the same full length as the equivalent purely anchoring needle, a 'speed bump' type detent along the inner surface of steel strip spring and cam retaining guide 11 is used to mark off the depth of needle insertion for injection and/or electrostimulation.

The detent requires that current to the solenoid be increased for the rubbery apex of the cam to pass. Any other points along the needle trajectory where the needle must pause are likewise indexed by a detent. Responsive to surges in current, a small dc rotary solenoid with shaft coaxially connected to cam axle 9 under the control of the implant microcontroller prescription program effects switching from one detent to the next in either direction. These deployments to effect injection and/or electrostimulation therapy can take place once or repeatedly at intervals regular or successively more distant. The drugs injected, the pattern of electrical discharges among the needles and the needles of other connectors if present, and the coordination of pharmacological and electrostimulatory functions by the prescription program warrant study.

To deliver adverse tissue reaction counteracting medication, sidelines, or service channels, may end in the foam lining 2 the underside of the baseplate 1 itself, toward the distal terminus of the mainline to add an adjuvant or prodrug conversion substance, or connect to the proximal end of half round needles 6 when hollow to allow injection. Radioactive substances can be delivered to the foam underside of the connector or to the underlying tissue through a shielded mainline and/or accessory channels, or when hollow and connected to a delivery service channel, by injection through half round needles 6. These are enclosed in the mainline as side connector or with the mainline inside a common shielded conduit which continues to below baseplate 1 whereupon the accessory channels exit the conduit and each proceeds to its respective connection or delivery site.

The tissue underlying the connector to be injected with the radioactive substance, shielding as shown in FIGS. 10A and 10B is needed only at the top and sides of the connector and the side connector containing the fluid and electrical delivery lines. The composition of permanent and disintegrating radiation shielding is specified in copending application Ser. No. 14/121,365. Briefly, permanent radiation shielding is tungsten-based, and disintegrating shielding consists of small tungsten plates set in overlapping relation within an absorbable adhesive matrix such as one glycolic acid-based. Whether continuous in permanent shielding or present in small overlapping plates in disintegrated shielding, tungsten, toxic to tissue, must always be encapsulated within an outer chemically isolating layer, such as one polyester-based.

Still referring to FIG. 10A, nondisintegrating tungsten connector radiation shield cap 71, applied to baseplate 1 after anchoring needles 6 have been inserted into the subjacent tissue, affords enclosure of the upper surface of the connector otherwise open to the surrounding body cavity. If no spillage of a radioactive substance occurred during insertion of side connector 3 and side connector shielding 86 is brought flush down into contact with the upper surface of baseplate 1, then according to the specific application, shielding cap 71 may be unnecessary. FIG. 10B shows a shielded embodiment of the connector shown in FIG. 9, a disintegrable radiation shield cap 71, injection, and electrical discharge-capable needles connected to drug delivery lines 72 and electrical wires 91 added.

Even though cap 71 is applied after needle insertion, drug lines 72 and electrical wires 91 necessitate more headroom or overhead clearance beneath radiation shielding cap 71 than is needed in the embodiment shown in FIG. 10A without injection, aspiration, and electrical discharge-capable anchoring needles. And since placement of cap 71 always follows the rotation of snap-clasp handles 8 to rotate about and insert needles 6 into the subjacent tissue, cap 71 does not interfere with this preliminary action. Otherwise, withdrawal of lines 72 with wires 91 from the storage recesses 81 beneath baseplate 1 wherein these remain coiled until deployed would necessitate additional overhead clearance beneath cap 71. Placing cap 71 only after insertion of needles 6 thus allows a significant reduction in the profile height of the connector.

To prevent any abnormal sensation once the placement procedure has healed, or if initially and for a while thereafter sensed, then to expedite habituation, radiation shielding is minimized in weight, and to prevent abrasion against and injury to neighboring tissue, it is minimized in dimensions and with no sharp corners or edges. As shown in FIGS. 10A and 10B, radiation shield cap 71 engages connector faceplate 1 when cap-integral inwardly protrusive bottom half-round nosing 85, which runs entirely about the lower edge of radiation shield cap 71, undercuts highly flexible and tapered or feather-edged baseplate 1, which also runs entirely about as the outer edge of baseplate 1. The embodiments shown in FIG. 8 and in FIG. 10A, which shows the embodiment shown in FIG. 8 with permanent shielding added, have anchoring needles 6 which are solid, not hollow for injection and not wired for electrostimulation capability.

Because the electrical and fluid lines to be connected to the needles need not precisely align vertically and rotationally, the side connector 3 in these is inserted to the depth the operator desires and lock nut 20 tightened to fix side connector 3 in position. Also, locking collar or nut 20 fits flush down against the upper surface of baseplate 1; however, when conduit side connector 3 is radiation shielded, radiation shield cap 71 stands between conduit side connector 3 and baseplate 1, preventing access to a tightening collar or nut 20 in FIG. 10A. In FIGS. 9 and 10B, the side connector is locked in depth and rotational angle by insertion of bolt 77 into bolt receiver 78. To allow the distal end of conduit side connector 3 shielding 86 to fit flush down against the upper surface of radiation shield cap 71, a tightening collar or nut, such as shown in FIGS. 1, 2, 7, 8, 10A and 21, among others, as part number 20 is eliminated.

In both FIGS. 10A and 10B, the distal end of conduit side connector shielding 86 serves as the vertical or depth of insertion setting stop. In the unshielded embodiment incorporating injection and electrostimulatory needles 6 shown in FIG. 9, alignment and stabilization shell, bell or collar 73 must be brought flush down against baseplate 1. In the corresponding shielded version shown in FIG. 10B, alignment and stabilization bell or collar 73 must be brought flush down against the shielding cap 71. In both, to allow descent past compression spring-76 loaded bolt 77, the operator draws pull ring 75 to withdraw bolt 77 to the rear of bolt housing 74 thus clearing the way for the alignment and stabilization bell or collar 73 to be brought flush down against the baseplate in FIG. 9 or radiation cap 71 in FIG. 10B.

Whether for, examination, repair, or explantation, the connector must be exposed, the shield must lift away without pulling at the connector or underlying tissue. Removal of radiation shield cap 71 is by grasping shielded side connector 3 with pliers or a hemostat, thereby stabilizing the side connector so that it does not lift and pull at the underlying tissue, as a second pliers is used to pull off the cap. Radiation shielding necessarily omitting any path for radiation to pass, in a location where the tissue underlying the connector would be injured by sustained enclosure that denies contact with the surrounding gas through "breathing holes," slits or circular cutouts 36, shielding is limited to that which will disintegrate prior to a stage in degradation not readily healed.

Because it allows aperture 4 to remain circular, fluid delivery lines and electrical wires as accessory channels (service channels, sidelines) which run down through baseplate 1 (usually to deliver adjuvants or other drugs separately, such as through injection half round needles) are run inside side connector 3 as a common conduit. Side connector 3 can thus represent either an outer conduit or sheath that conveys all fluid and electrical lines to pass down through the baseplate 1 to include a mainline, where the lumen of the conduit itself conveys no fluid, or it can serve as the mainline itself. If the latter, then the sidelines are situated about the lumen of the mainline, flow through the mainline wetting their external surfaces.

As shown in FIGS. 10A and 10B, when side connector 3 is provided with radiation shielding, even the water jacket 31 accessory channel 13, which is ordinarily made to run down along the outside of side connector 3 as shown in FIG. 1, is run down the inside of side connector 3 as a conduit. To be situated within the underlying tissue and not the foam, needles for injection must be shorter than those used purely to anchor the baseplate. FIG. 10A shows such a side connector with nondisintegrating radioactive shielding adequate for the continued delivery of moderately radioactive diagnostic or therapeutic substances of long half life, while FIG. 10B shows disintegrating shielding that consists of small overlapping, or imbricated, plates bound within an absorbable matric formulated to drop away after the last radioactive dose has decayed to a safe level. Tungsten is toxic and therefore encapsulated to chemically isolate it from tissue, polyester family polymers such as polyethylene terephthalate suitable.

Absorbable materials suitable for use as a matrix are specified just above in this section. In most instances, it will be best not to depend upon spontaneous degradation of the bonding agent through hydrolysis and enzymatic breakdown but rather control the time of disintegration by coating the shielding with a noncaustic solvent such as hydrolytic or enzymatic. Previously described in copending nonprovisional application Ser. No. 14/121,365, entitled Ductus Side-entry Jackets and Prosthetic Disorder Response Systems, filed on 25 Aug. 2014, to reduce the weight and increase the shielding ability, both the permanent shielding in FIG. 10A and the disintegrating shielding in FIG. 10B are made of tungsten encapsulated within a polymeric shell, such as one polyethylene based (International Journal of Toxicology 2007. "Final Report on the Safety Assessment of Polyethylene," International Journal of Toxicology 26 Supplement 1:115-127) to prevent the presumptive potential contact toxicity of tungsten.

The toxicity associated with elemental tungsten appears questionable, species dependent, as by bioaccumulation in fish, and more likely attributable to the nickel with which tungsten is often alloyed (see, for example, Witten, M. L., Sheppard, P. R., and Witten, B. L. 2012. "Tungsten Toxicity," Chemico-biological Interactions 196(3):87-88; Strigul, N., Koutsospyros, A., and Christodoulatos, C. 2010. "Tungsten Speciation and Toxicity: Acute Toxicity of Mono- and Poly-tungstates to Fish," Ecotoxicology and Environmental Safety 73(2):164-171; Strigul, N. 2010. "Does Speciation Matter for Tungsten Ecotoxicology?," Ecotoxicology and Environmental Safety 73(6):1099-1113; Thomas, V. G., Roberts, M. J., and Harrison, P. T. 2009. "Assessment of the Environmental Toxicity and Carcinogenicity of Tungsten-based Shot," Ecotoxicology and Environmental Safety 72(4):1031-1037; Peuster, M., Fink, C., Wohlsein, P., Bruegmann, M., Gunther, A., and 4 others 2003. "Degradation of Tungsten Coils Implanted into the Subclavian Artery of New Zealand White Rabbits is Not Associated with Local or Systemic Toxicity," Biomaterials 24(3): 393-399).

Radiation shielding cap 71 in FIG. 10B is made up of particulate tungsten encapsulated thus in as many overlapping or imbricated layers as the radionuclide necessitates. The encapsulated particles are bound together with a bonding agent such as a glycolic acid-based adhesive formulated to yield to hydrolysis and intrinsic or iatrogenically introduced enzymes. For standardization and cost reduction of connectors of any one conformation and set of dimensions, aperture 4 can be made the same in diameter, friction fitting annular adapters fitted about smaller caliber inserts such as hollow needles and therapeutic and/or diagnostic electrodes to firmly secure these within aperture 4. The combined rotational and long axial action used to bring a trepan and crosshair tipped side connector or side stem such as shown in FIG. 5 to the depth wanted is made difficult when locking collar or nut 20 is omitted, reliance for fixation in place instead entrusted to a friction fit.

So that the aperture 4 through baseplate 1 for insertion of the side connector 3 sets the spot for insertion of the styloid device as side connector 3, the contrast coated side-entry connector is positioned before the catheter is led from the portacath or pump to and inserted into baseplate 1. Entry at the body surface is through a small or 'keyhole incision' under the guiding assistance of a suitable imaging system through the most direct path the anatomy will allow without posing a risk of strangulating an organ along the route. When the optimal point for entry into the tissue to be treated would result in excessive trauma to access, binding the drug to superparamagnetic drug carriers and magnetically vectoring the drug to the target with the aid or organ peripherally attached patch-electromagnets 40 is considered. The catheter, marked off along its length with contrast is then inserted into the body through the same small incision or through a different point of entry and tunneled to insert through aperture 4.

The terms 'locking nut;' 'locking collar', and 'locking bushing' 20 in the present context are intended to denote not a nut with bottom locking washer to achieve rotational fixation when tightened flush down against the subjacent surface, but rather a collar or nut with an internal bushing that conical, eccentric, and/or elastomeric, expands circumferentially as the collar is rotated. Combined with threading, a side connector 3 that expands when heated, or a side connector that friction fits through aperture 4, tightening nut 20 fixes side connector 3 in position both longitudinally and rotationally along side connector 3 so that it will not pull free of aperture 4. When placement is not to be revised or explanted for the foreseeable future, this joint can be made secure over and above the mild friction fit and locking collar by running a surgical cyanoacrylate cement around the junction.

Of these options, a friction fit is least preferred as posing some resistance to adjustment during placement. Such locking collars are many in detailed mechanism, well known among those skilled in the art, the type used for the present purpose relevant only to the extent that the locking feature must not spontaneously or as the result of sterilization during manufacture degrade over time when the assembled side-entry connector is placed in a steam autoclave or treated with ethylene oxide just before it is placed in an hermetically sealed package.

While not preferred for tubular inserts without a pointed or very narrow gauge leading end, where the removal of a plug from the substrate tissue 16 is uninvolved, a friction fit in lieu of a lock nut affords a reduction in cost and increased production yield. Depending upon the cohesiveness of the tissue 16 penetrated, a plug thereof may be extracted spontaneously upon withdrawal of side-connector stem 3, or may require forceful irrigation toward the trepan edge with the aid of the built in water jacket to be described. Allowing for alteration in normal tissue hardness due to the disease, intuitive realization as to the physical properties of the tissue 16 to be extracted will ordinarily allow selection of a suitably configured side connector at the outset.

If not, a more costly type with side stem rotation lock nut and crosshair cutter is prepositioned to replace the simpler type at the outset. Whether in a solid plug or grated, the accumulated tissue is usually forced out through side connector or side stem 3 by the water jet alone, without the need for tissue grating by wire or crosshair cutter 22. However, if side stem 3 lacks a water jacket so that tissue adheres inside it or retrieval or retraction of the tissue plug to the exterior through the catheter connected to side stem 3 is not accomplished by the undercutting force of the water jet from the water jacket, then a capillary tube-caliber catheter connected to an aspiration pump or fine guidewire with a hook at the distal tip is run down the catheter to extract the tissue plug.

Shown to either side of side connector, or side stem, 3 in FIGS. 1, 7 thru 10, 14, and 18 and surrounding side connector 3 in FIGS. 4 and 20 are dual-needle knife switch-configured snap-clasps 5 mounted in bilaterally opposed pairs to the upper surface of baseplate 1. In FIGS. 1, 5, and 7, side connector or side stem 3 is catheteric. In FIG. 18, no locking collar, whether of a natural gas line fitting or any other type such as one with and internal conical bushing or elastomeric expansion lining and thread need be used. Instead, the contrast-coated side connector catheters 3 that serve as the incurrent and excurrent lines are ribbed along their distal segment, allowing the operator to push these to the depth required incrementally by pushing each through its respective quarter-round tubular extension 38 which serves as its receiver or socket. Where the patient is more active or edema is expected to subside, a complementary ribbing is applied to the interior surface of the quarter round tube extensions.

In FIGS. 14 thru 16, side connector 3 consists of a hollow injection-aspiration needle, electrode, hypotube, excimer laser, or fine drug delivery catheter, for example. As shown in FIG. 4, where the site for placing the connector is subject to abrupt yanking or jerking forces, a connector mounting additional snap-clasps 5 and/or snap-clasps 5 mounting more than two tissue engaging needles, numerous such arrangements possible. If the site for insertion of any side-entry connectors is unstable, suture loops or eyelets 32 are used to pass through suture to allow connection to the nearest stable tissue, a multiple anchor arrangement as shown in FIG. 4, or a stabilizing bar that allows a second or more baseplates with snap-clasps as shown in FIG. 20 is used to tie the side connector to a stable anchor or anchors. If portions of the tissue or organ about that of the side connector are mobile, suture is used to stabilize the tissue.

To eliminate corners as a potential source of incisions in an accidental impact, baseplate 1 is preferably made continuous rather than cruciate with the intervening sections cut away. A continuous baseplate can sometimes be trimmed for improved conformity to the conformation and motional pattern of the underlying tissue. As shown in FIG. 14, shortening of baseplate 1 is by making lever arm 8 in the shape of an L not allowing it to extend closer to side connector 3 than round needle 6 mounting cross-bridge or spanner strip 7. Were the embodiment shown in FIG. 14 augmented in capability through the addition of hollow anchoring needles and an electrical feed as shown in FIGS. 9 and 10B to allow injection or aspiration at points along the needle trajectory so that cam axle 9 would be coaxially connected to the shaft of a dc rotary solenoid, this feature could be used to place the side-entry connector, allowing lever or throw arm 8 to be eliminated.

The operator would then engage the anchoring needles 6 by pressing a switch rather than using a probe or dental pick to 'throw' or rotate lever arm 8. This space is essential to interpose the electroactuator such as a piezomotor at the center, usually a direct drive micro stepper motor with voltage doubler, rectifier, battery, and voltage regulator for transcutaneous energy transfer. The object in this embodiment is to allow the precise control in penetration of a radionuclide releasing hypotube, for example. Representation in the drawing figures of the round needles as paired is exemplary, the use of snap-clasps provided with a larger number of needles considered obvious. A connector of such conformation should rarely require the elongation of baseplate 1 for increased resistance to levering forces. Operation of a pneumatic jack-hammer, for example, will violently jerk about even a well anchored kidney, but the motion sought to be suppressed is that between the side connector and the organ or tissue to which it is attached. A floating kidney is best stabilized by a nephropexy, and an affected stomach, for example, by a gastroplexy.

In FIGS. 1 thru 4, 6, and 7 thru 14 knife switch-configured snap-clasps 5 comprise round needles 6 mounted toward either end of cross-bridge or spanner strip 7, with cross-bridge or spanner strip 7 fastened at the center to lever arm 8 so that cross-bridge or spanner strip 7 can be rotated about its center of rotation at axle or rotary joint 9. Lever arm 8 rotates cam 10 about axle or rotary joint 9 beneath arcuate, or arciform, nonmagnetic stainless spring steel strip spring 11 within lever arm cam housing 45 so that upon lifting lever arm 8, the nose, or narrow side of cam 10, comes into contact with and is swept along the underside of strip spring 11 until it is advanced toward the opposite side, where the narrow edge of cam 10 reaches the point where it is separated from the underside of strip spring 11, whereupon strip spring 11 follows in descent against the upper surface of cam 10 to fix cam 10 in position at the opposite extreme of its run, or throw.

Multiple semicircular needles 6, usually two in number, are mounted to cross-bridge or spanner strip 7 for joint movement. Rotating lever arm 8 from the more central or medial to the outer or lateral position moves needles 6 from the retracted or open position, through substrate tissue 16, to the closed, or tissue needles-engaged, position. Fixed in position relative to baseplate 1, the orientation of snap-clasp mechanism 5 as a whole and thus the throw angle of lever arm 8 and the angle of penetration of needles 6 can be set to any angle. The length of cross-bridge or spanner-strip 7 and the number of needles 6 mounted to it are widely variable, as is the size and conformation of baseplate 1, and the number of snap-clasps 5.

As shown in FIG. 4, when the site for placement presents abrupt displacements, the number of snap-clasps and/or needles per cross-bridge or spanner-strip 7 is increased. Provided the nonjacketing side-entry connector is not made too long, lever arm 8 is provided with expanded hooked tool such as a probe or dental pick entry cup 12 at its free end that expedites rotation of lever arm 8 by allowing the tip of a hooked instrument such as a dental pick to be inserted. When the side-entry connector must be shortened overall, hooked tool entry cup is dispensed with the hook then inserted beneath cross-bridge or spanner strip 7, or if space allows, the free end of lever arm 8 is bent to either side.

In FIG. 3, strip spring 11 is folded, that is, brake bent when to be die cut from a sheet or bent in a small vise is made separately, and in either case, annealed toward either end and fastened down flush parallel to baseplate 1 by rivets, one at either corner toward the ends of strip spring 11. Included in FIG. 3, at the outer or lateral end of arcuate or arciform strip spring 11 where strip spring 11 fits down flush against baseplate 1, the rivets 14 that pass through slots 17 oriented parallel to the long axis of strip spring 11 in fold 15 are left just loose enough to allow that end of strip spring 11 to slide along slots 17 beneath the head of the rivets 14. Thus, as the operator rotates lever arm 8 vertically, the longer lifting apical or narrower end of cam 10 rises and slides along the underside of strip spring 11, exceeding its restorative force, lifting strip spring 11 by displacement at slots 17.

As the lifting narrow side, or nose, of cam 10 shown in FIGS. 1 thru 3 show, continuation of the cam nose past the center of strip spring 11, the latter recedes accordingly until the apical end reaches the limit of rotation to the opposite side, whereupon the restorative force of strip spring 11 decisively retains it in that position with a snapping effect. Also in FIG. 3, aperture 18 allows strip spring 11 to pass through lever arm 8, cam 10 beneath and strip spring 11 slid through and along aperture 18 in lever arm 8. For visual clarity, the fold with rivets at the medial or more central end of strip spring 11 has been omitted in FIG. 3. Referring now to FIG. 5, in tissue where crosshair cutter 22 to allow tissue to be grated as trepan 21 edge is driven into the tissue is omitted as conducive to obstruction due to clogging with clot or the accretion of a hard material, a solid tissue plug cut by a trepan without crosshair cutter is removed with a hooked guidewire or suction tube.

Whether due to disease or its inherent composition, when the substrate tissue 16 is indurated, or hardened, the number of needles is then increased to resist the pull of the solid tissue plug with a hooked guidewire or suction tube. Provided the water jacket is used to flush away the gratings, moderately indurated tissue should still allow the use of a rotationally grating side connector or side stem with crosshair cutter. That knife switch-configured snap-clasps 5 as shown in FIGS. 1 and 14, for example, could be journaled to allow these to be rotated by mounting these to baseplate 1 on a rotary joint, thereby allowing the angle of the side-entry connector or a given snap-clasp to be changed, and/or that snap-clasps 5 could be made adjustable by mounting on a raceway to allow linear shifting in position is not considered sufficiently advantageous as to warrant the additional expense. The former would necessitate increasing the width or 'beam' of the side-entry connector and extending needle holes 19 into semicircular slots through baseplate 1 to allow the needles to rotate.

This would satisfy the need for separate 'breathing holes' in the area of the slots. Since rotation thus would only be possible with the needles withdrawn from the substrate tissue, a rotary solenoid would also be required to rotate cam axles 9 to lift the needles out of the tissue. While readily practicable from a purely technical standpoint, seen medically, the benefits to be gained by such refinements would appear not to justify the increased cost and complexity. Nonjacketing side-entry connectors can thus be made adjustable, in an assortment of standardized configurations and sizes to accommodate any normal anatomy, or both to accommodate any contingency involving anomalous anatomy. The standardization of semicircular needle diameter allows the other elements of the connector to be standardized, resulting in a considerable reduction in unit cost. Large animal veterinary applications aside, three standard sizes will accommodate most requirements.

The round conformation of the needles, the fact that no fewer than two needles spaced apart toward opposite ends of a common bridge or spanner strip 7, and that each snap-clasp 5 is positioned at a distance from the other along an axis that passes through both, means that baseplate 1 is stabilized during movement in relation to the surface subjacent thereto. Significantly, this is so whether the needles 6 insert fully through the substrate tissue 16, as when applied to a solid organ, or penetrate into the interior of a hollow structure such as the urinary bladder. Where the site is more mobile and the depth into the structure to which the distal end of the inserted catheter, probe, or electrode, for example, must be placed is to be kept fixed, a baseplate with three or four radially equiangular snap-clasps will generally prevent movement of the catheter or electrode, for example, relative to the substrate tissue, even without extending the distance from the center to increase the counter-levering moments of force. However, if the movement forcibly impacts upon the side stem or device connected to it, the organ should be stabilized with suture as in a gastropexy or nephropexy.

Unless the substrate tissue must withstand abrupt impacts at various angles, as in an impact sport, a baseplate conformed as shown in FIG. 1 will suffice. Vulnerable positions can be reinforced by using multiple snap-clasp side-entry connectors such as shown in FIG. 4 connected with a brace or coupling bar. Fastening with needles 6 and if necessary, suture through suture loops 32, rather than with prongs of nonmagnetic noncorrosive stainless steel, as shown for clasp-permanent magnets in copending application Ser. No. 13/694,835 and clasp-electromagnets (shown here in FIG. 13B as part number 40) in Ser. No. 14/121,365, achieves more secure connection when the junction is subject to greater forces, as when the substrate tissue is motile, as is the stomach, especially when fluid is passed through the junction the side-entry connector is used to establish, or when intervening soft and/or uneven tissue is present—here, the adipose and fascial capsule surrounding the renal cortex.

As shown in FIG. 5, for cutting into and extracting tough (sclerotic, indurated, fibrosed) tissue, fine wire or crosshair cutter 22 is positioned to span the lumen slightly short of the distal trepan edge 21. Fine wire or crosshair cutter 22 is usually made of the same material as the tube or barrel of the side stem, most often a stainless steel or titanium. When the operator manually rotates side-connector stem 3 in a reciprocal manner, that is, twists it from side to side in oscillatory rotation, trepan 21 is pushed and cuts more deeply into the substrate tissue 16, wire or crosshair wires 22 progressively shaving or grating more of the tissue, which accumulates from the distal end of side connector 3 where the outlet circular jet of water jacket 31 forces the debris out through the line. The tissue approached pushes that previously cut and reduced up into side stem 3, the length of stem 3 limiting the depth to which the tissue can be bored into thus and accumulate.

It may be noted that the term renal 'capsule' is inconsistently defined as the fat and fascial layers surrounding and stabilizing the kidneys proper, or the outer fibrous layer of the renal cortex. Softer tissue that would allow needles of fine gauge to cut through over time must be avoided. Rather than to allow such an eventuality, it is preferable to use needles somewhat oversized in gauge and diameter to engage more of the substrate tissue. Other measures include increasing the number of needles and surfacing the needles to encourage tissue ingrowth or infiltration and integration. The sides of the needles may be coated with a procoagulent, such as thrombin, a zeolite, or fibrin glue to augment the antileak conformation of the needle which is sharp at the tip so that the trailing barrel.

Despite a general preference for standardization, to conform to a site where one knife switch-configured snap-clasp side or wing of baseplate 1 will not allow catheter or other device 3 to be at the center of baseplate 1 where it is needed, baseplate 1 has platform extensions, or 'wings,' that extend at other than 180 degrees. If necessary, side connector 3 can be positioned in a reentry with the wings extending away at an angle; however, this will almost always require fixation with suture that wraps about catheter or other device 3 and into tissue proximal to catheter or other device 3. That baseplate 1 can be made in two halves to rotate about catheter or device 3 is considered obvious. Baseplate 1 can also incorporate a cutout along the outer edge, allowing it to span about an intervening vessel, nerve, or anatomical attachment, for example.

Side connector 3 is not, however, allowed to be situated without at least one snap-clasp beside it. When rotated about its center of rotation by lever arm 8, needles 6 pass through holes 19 in baseplate 1. When baseplate 1 is lightly pressed against the subjacent tissue 16 and lever arm 8 fully rotated through the tissue 16, the tips of needles 6 are nestled within the viscoelastic polyurethane foam cushion 2 with the points directed toward the underside of baseplate 1 and cannot come into contact with tissue. While responsive to the radius of the tissue engaging needles, for most applications, baseplate 1 is typically 2 centimeters long, 1 centimeter wide, 2 millimeters thick, the thickness of foam cushion 2 typically 4 millimeters, and the radius of semicircular needles 6 typically 3.5 to 7.0 millimeters, depending upon the tissue.

With cross-bridge or spanner-strip 7 and semicircular needles 6 hollow, back to back spring-loaded pistons inside spanner-strip 7 just next to either side of lever arm 8, released by breaking a restraining tether fastened down to baseplate 1 when lever arm 8 is lifted, can be used to make needles 6 inject drugs automatically, coating the wall along the needle wounds as needles 6 pass through tissue 16. Such drugs typically include an anesthetic such as lidocaine; an anti-inflammatory such as prednisone, or cortisone, an antimicrobial such as amoxicillin, tetracycline; or doxycycline adverse tissue reaction-counteractant such as phosphorylcholine, dexamethasone, and/or curcumin. That any or all of these are directly targeted means that the conventional reservations concerning side effects, drug drug, and drug food interactions can be disregarded.

Injection through needles 6 is generally limited to medication helpful in ameliorating the trauma caused by the needles themselves. The back to back pistons (not shown) are prevented from traveling all the way to needles 6 by stops within their runs inside spanner strip 7. Once needles 6 contain only the trailing fraction of the injectant, the small rubbery portals allow the terminal segments of spanner strip 7 to be used as external or endoscopic injection chambers. These chambers can be used to inject just enough of a solution or plain water to inject the final portion of the drug were its decomposition to risk complications or to inject the same or different drugs. To this end, rubbery puncture seals of the kind seen at the top of injectable drug vials are provided to allow the sterile and nonleaking insertion of a hypodermic needle at either end of spanner strip 7.

These allow the use of a separate endoscope mounted hypodermic needle to introduce water to clear out the needles, a medicinal solution, or additional medication at any point along the trajectory of either semicircular needle 6 at which lever arm 8 is paused, either manually or by a rotary solenoid coaxially connected to cam axle 9. To prevent a subsequent rotation of lever arm 8 from failing to track the first trajectory of needle penetration or veering to reduce the rigidity of the final placement, the supplementary injection of medication is done only during the one and only rotation of lever arm 8. However, as an endoscope is available for injection unrestricted to the fixed trajectory of needles 6, or the volume or number of drugs or tissue to be medicated, and the additional mechanism increases the cost of manufacture, automatic injection is reserved for special circumstances where to coat the interior of the needle wounds offers a distinct benefit.

For example, with malacotic, or soft, tissue that can displace despite the rigid fixation of the needles, to prevent gradual sidewise incisions by the needles into the surrounding tissue, the foam cushion is wetted and the injectant provided with a stiffening agent (not a sclerosant such as used for embolization which kills the cells but rather a hardening agent) to harden the walls along the needle wounds. Especially when suture used to stabilize the organ by attachment to the body wall, for example, might tear through the organ, additional hardening agent, or sclerosant, is injected away from the needles.

The thickness of the bladder wall highly variable in health much less sickness (see, for example, Kanyilmaz, S., Calis, F. A., Cinar, Y., and Akkoc, Y. 2013. "Bladder Wall Thickness and Ultrasound Estimated Bladder Weight in Healthy Adults with Portative Ultrasound Device," Journal of Research in Medical Sciences 18(2):103-106; Blatt, A. H., Titus, J., and Chan, L. 2008. "Ultrasound Measurement of Bladder Wall Thickness in the Assessment of Voiding Dysfunction," Journal of Urology 179(6):2275-2279; Hakenberg, O. W., Linne, C., Manseck, A., and Wirth, M. P. 2000. "Bladder Wall Thickness in Normal Adults and Men with Mild Lower Urinary Tract Symptoms and Benign Prostatic Enlargement," Neurourology and Urodynamics 19(5):585-593; Chang, T. S., Bohm-Velez, M., and Mendelson, E. B. 1993. "Nongynecologic Applications of Transvaginal Sonography. American Journal of Roentgenology; 160:87-93; Jequier, S. and Rousseau, O. 1987. "Sonographic Measurements of the Normal Bladder Wall in Children," American Journal of Roentgenology 149(3):563-566), in pediatric and some adult patients, the segment of the semicircular needles within the bladder will be exposed to urine.

In FIG. 12A, drug delivery to the urinary bladder is through upper line and nonjacketing side-entry connector 61. Semicircular needles 6 that project into the bladder cavity, may serve as a platform for the deposition and accretion of calculus. In a 'stone former,' or calculus-prone patient, placing the connector on or beside the superior surface of the bladder toward the apex, or vertex, reduces contact with urine and any accretion of calculus. In this circumstance, drugs that encourage stones, such as indinavir and ritonavir (see, for example, Hess, B. 1998. "Drug-induced Urolithiasis," Current Opinion in Urology 8(4):331-334) should be avoided or supplemented with stone suppressive medication. Coating half round needles 6 with a fluoropolymeric film reduces mineral adhesion and accretion.

In general, medication best not introduced into the systemic circulation such as antibiotics or not at a dose equivalent to that if delivered directly to the bladder, is delivered through a nonjacketing side-entry connector positioned toward the apex, or vertex, of the bladder as shown in FIG. 12A. Where stone suppression is through dissolution, the dose and exposure to the solvent or mineralization neutralizer, such as citrate or bicarbonate (see, for example, The Merck Manual 18th edition, 2006, pages 1966, 1968), is minimized through a bladder-targeted, rather than a much larger systemic or background dose. Where the problem is metabolic, the mineral burden is controlled medically, first pass targeting of the liver through a ductus side-entry jacket placed about the hepatic portal vein. In general, solid organ, or whole organ targeting to perfuse the drug throughout the organ, such as the liver or an endocrine gland is through direct delivery into the supply artery or arteries.

Finer targeting of an affected portion within the parenchyma of the organ is by direct drug delivery through a nonjacketing side-entry connector, typical applications depicted herein in FIGS. 6, 13A, and 13B. To allow showing other components used for drug delivery and urinary diversion, FIG. 12A has been shown in cross section with the bladder diagrammatic in omitting histology. Further for clarity, the nonjacketing side-entry connectors have been shown vertically oriented; in most instances, the connectors are positioned horizontally, the upper just below the superior surface of the bladder, the lower just above the junction of bladder with the prostate or urethra. Also, only one upper or incurrent and one lower or excurrent line is shown; in fact, separate nonjacketing side-entry connectors or one designed to connect a number of catheters to the organ or tissue might be positioned at either location.

Compatible drugs or therapeutic solutions can share a line; if not, then separate lines are used. In FIG. 12A, the upper of the two nonjacketing side-entry connectors toward the apex of the bladder 61 allows the direct delivery from a subdermally implanted portacath 46 with reservoir 47 of an Ommaya reservoir of drugs to the lower urinary tract. Lower side-entry connector 62 serves as a long term or permanent cystostomy to bypass an obstruction to urinary drainage at any point from the cystic neck to the external urethral orifice, or meatus urinarius, through excurrent catheter 51. FIG. 12C, addressed in the section above entitled Background of the Invention and just below, however, will describe a bypass to allow meatal emission in almost any circumstance. Transdermal charging preferred, charging can also be accomplished by hard wire connection to a source of electrical power through a socket in a body surface type nonjacketing side-entry connector as described in copending application Ser. No. 14/121,365.

The medicinal contents of reservoir 47 are drawn from for delivery through catheter 48 by reversible drug delivery and recovery, or aspiration, pump 49, powered by battery 54 controlled by microcontroller implant 53, housed together as appropriate with transdermal charging electronics and/or charging circuitry 50 in a pocket usually created in the abdominal cavity, the transdermal battery charging receiving intracorporeal; secondary coil and optional diagnostic sensor readout telemetry antenna denoted by 64. Provided lower urinary diversion catheter, or line, 51 connected to nonjacketing side-entry connector 62 attached at the bladder neck or at the level of the trigone is double-lumened, a second portacath can delivery drugs to that level. If the patient requires the targeted delivery of drugs to other bodily systems, an externally positioned port with clearly labeled entry points as described in copending application Ser. No. 14/121,365 is used.

Preferably, access to the bladder for placement of nonjacketing side-entry connectors is directly through the suprapubic anterior surface and downward through the abdominal peritoneum overlying the superior surface of the bladder and into the paravesical space. Also indicated by dashed lines in FIG. 12C is an alternate urinary diversion line from the lower nonjacketing side-entry connector to the intrapelvic urethra 52. When this allows an obstruction at the bladder neck or proximal urethra to be bypassed, the need for an external collection bag is eliminated. If otherwise incontinent, the device described above in the section entitled Urethra-noncompressive Reinstatement of Urinary Continence is used in lieu of an ectopically placed hydraulic cuff.

In some instances, the same substance used to correct a metabolic anomaly, such as hypercalciuria, hyperoxaluria, or hypocitraturia, or any crystal chemodissolution substance according to the kind of stones involved (see, for example, Singh, S. K., Agarwal, M. M., and Sharma, S. 2011. "Medical Therapy for Calculus Disease," British Journal of Urology International 107(3):356-368; Micah, S., Grande, M., Sighinolfi, M. C., De Came, C., De Stefani, S., and Bianchi, G. 2006. "Medical Therapy of Urolithiasis," Journal of Endourology 20(11):841-847), can be delivered through either the accessory channel of the nonjacketing side-entry connector used to fasten the electromagnet at the top of the bladder or the upper nonjacketing side-entry connector shown in FIGS. 12A and 12C When through the accessory channel, medication for injection into the detrusor is through a hollow half round needle 6 connected to accessory channel 13. A double lumen accessory channel line 13 allows the same or different drugs to be injected. A single pump can simulataneously deliver the drug or drugs through both lumina and needles. If the drug to either needle follows a different schedule of administration, separate pumps are needed to feed either lumen.

Substances used to correct metabolic anomalies of the urinary tract include sodium citrate (see, for example, Caudarella, R. and Vescini, F. 2009. "Urinary Citrate and Renal Stone Disease: The Preventive Role of Alkali Citrate Treatment," in Italian with summary and abstract in English, Archivio italiano di urologia, nefrologia, andrologia [Italian Archive of Urology, Nephrology, and Andrology]; 81(3): 182-187; Pak, C. Y. 1994. "Citrate and Renal Calculi: An Update," Mineral and Electrolyte Metabolism 20(6):371-377), allopurinol (see, for example, Yasui, T., Sato, M., Fujita, K., Ito, Y., Nomura, S., and Kohri, K. 2001. "Effects of Allopurinol on Renal Stone Dormation and Osteopontin Expression in a Rat Urolithiasis Model.," Nephron 87(2): 170-176; Kohri, K., Kodama, M., Katayama, Y., Ishikawa, Y., Takada, M., and 4 others 1990. "Allopurinol and Thiazide Effects on New Urinary Stone Formed after Discontinued Therapy in Patients with Urinary Stones," Urology 36(4):309-314; Favus, M. J. and Coe, F. L. 1980. "The Effects of Allopurinol Treatment on Stone Formation on Hyperuricosuric Calcium Oxalate Stone-Formers," Scandinavian Journal of Urology and Nephrology. Supplementum 53:265-271), thiazides (Fernandez Rodriguez, A., Arrabal Martin, M., Garcia Ruiz, M. J., De Haro Munoz, T., and Zuluaga Gomez, A. 2001. "Effect of Thiazide Therapy in the Prophylaxis of Calcium Lithiasis," (in Spanish, English abstract at Pubmed), Archivos espanolcs de urologia 54(9): 1047-1054; Kohri, K. et al. 1990, just preceding; Yendt, E. R. and Cohanim, M. 1978. "Prevention of Calcium Stones with Thiazides," Kidney International 13(5):397-409), and Phillantus niruri (Asare, G. A., Addo, P., Bugyei, K., Gyan, B., Adjei, S., Otu-Nyarko, L. S., Wiredu, E. K., and Nyarko, A. 2011. "Acute Toxicity Studies of Aqueous Leaf Extract of Phyllanthus Niruri," Interdisciplinary Toxicology 4(4):206-210; Boim, M. A., Heilberg, I. P., and Schor, N. 2010. "Phyllanthus Niruri as a Promising Alternative Treatment for Nephrolithiasis," International Brazilian Journal of Urology 36(6):657-664).

If systemic medication ameliorates the blood mineral burden but the bladder and lower drain catheter shown in FIG. 12A persist in the accumulation of crystals, the upper line should be used to deliver a nephrolithiasis counteractant. Distal to the bladder apex or vertex, delivery through the water jacket (sideline, accessory line, service channel) of the side stem to which the lower or drainage diverting catheter is connected omits the upper bladder. Because it delivers drugs near to the bladder apex, or vertex, the upper line in FIG. 12A not only eliminates limitation to systemic antibiotics that tend to concentrate in the urine (see Seifter, J. L. and Brenner, B. M 2005. "Urinary Tract Obstruction," in Harrison's Principles of Internal Medicine, New York, N.Y.: McGraw-Hill, 16th Edition, page 1724), but allows the delivery of any drugs needed to protect the lower tract.

By contrast, a nephrostomy tube for urinary diversion positioned with its tip in the renal pelvis and higher in the urinary tract as shown in FIG. 11 but used instead to deliver drugs directly into the renal pelvis rather than for, urinary diversion allows treatment of the entire lower tract. In this case, the extrarenal tube from the injection syringes or pump, for example, is kept filled to prevent the inflow of urine. Used incurrently rather than excurrently for urinary diversion, the configuration depicted in FIG. 11 can be used to deliver antineoplastic drugs into the pelvis to treat a transitional or squamous cell carcinoma, for example, possibly averting the need for a radical nephrectomy, and working within it, conserving more of the kidney than any alternative method of tumor removal.

This given mounting evidence that tumor removal can be just if not more effective than a nephrectomy (see, for example, Scosyrev, E., Messing, E. M., Sylvester, R., Campbell, S., and Van Poppel, H. 2014. "Renal Function after Nephron-sparing Surgery versus Radical Nephrectomy: Results from EORTC [European Organization for Research and Treatment of Cancer] Randomized Trial 30904," European Urology 65(2):372-377; Cost, N. G., Sawicz-Birkowska, K., Kajbafzadeh, A. M., Tourchi, A., Parigi, G. B., Guillen, G., DeFoor, W. R. Jr, and Apoznanski, W. 2014. "A Comparison of Renal Cunction Outcomes after Nephron-sparing Surgery and Radical Nephrectomy for Nonsyndromic Unilateral Wilms Tumor," Urology 83(6):1388-1393. Li, W., Cheng, Y., Cheng, Y., Ren, H., and Han, N. 2014. "Clinical Efficacy of Radical Nephrectomy versus Nephron-sparing Surgery on Localized Renal Cell Carcinoma," European Journal of Medical Research 19:58; Osawa, T., Harada, H., Oba, K., Seki, T., and Togashi, M. 2013. "Clinical Factor Affecting the Recovery of Kidney Function in Clinically Localized Renal Cell Carcinoma Patients Who Underwent Nephron-sparing Surgery," (in English) Hokkaido Igaku Zasshi [Hokkaido Journal of Medical Science] 88(1):15-20; Ghavamian, R., Cheville, J. C., Lohse, C. M., Weaver, A. L., Zincke, H., and Blute, M. L. 2002. "Renal Cell Carcinoma in the Solitary Kidney: An Analysis of Complications and Outcome after Nephron Sparing Surgery," Journal of Urology 168(2):454-459; Thrasher, J. B., Robertson, J. E., and Paulson, D. F. 1994. "Expanding Indications for Conservative Renal Surgery in Renal Cell Carcinoma," Urology 43(2):160-168; Morgan, W. R. and Zincke, H. 1990. "Progression and Survival after Renal-conserving Surgery for Renal Cell Carcinoma: Experience in 104 Patients and Extended Follow-up," Journal of Urology 144(4):852-858).

When the drug is costly, it is inserted into the line first, with the balance of the line filled with a substance of lower cost, or a hollow needle or a hypotube is used. The use of a double lumen catheter allows medication to be delivered through one lumen and urine to be drained through the other lumen. Targeted thus, any suitable antibiotic can be used to prevent upper and lower tract infection, for example. By comparison, a ductus side-entry jacket placed high on the ureter protects the distal tract but leaves the calyces and pelvis unprotected, allowing the formation of a staghorn calculus, for example. The ability to deliver substances in either direction following placement almost always beneficial, side-connector stem 3 is usually provided with a water-jacket, even when the extraction of substrate tissue 16 is as a solid plug removed with the aid of a hook-ended guidewire or an aspiration line of fine caliber. FIG. 12A also shows nonjacketing side-entry connector 62 placed at the level of the trigone or slightly caudal or inferior thereto to passively drain the bladder.

Provided inflow line or catheter 48 and lower line or catheter 61 are biluminal, diagnostic bladder lavage is readily accomplished by inflow through upper connector 61 and outflow through lower connector 62, while lavage to wash the upper bladder is by inflow through lower connector 62 and outflow through upper line 48. As shown in FIG. 11, the delivery of drugs directly into and drainage of urine by nephrostomy directly from the renal pelvis likewise requires a biluminal side connector 3. Whether at the bladder or the renal pelvis, to prevent drugs from entering the diversion lumen, inflow and outflow are never simultaneous, plain water used to flush through both lumina prior to reinitiating the delivery of medication.

Incurrent flow can deliver not only drugs and other therapeutic substances, but imaging contrast, or if the lines and connectors are radiation shielded, even moderate dose rate therapeutic or scanning radionuclides, such applicable where periodic reevaluation is essential. Vascular concentration is obtained by delivery through a ductus side-entry jacket applied to the supply artery, in this case the renal artery. FIG. 12B shows an electromagnetically actuated check valve for the alleviation of urinary incontinence in a patient with intact trigonal pressure sensation. The mechanism consists of stopper ball 65 and clasp-electromagnet 66. Stopper ball 65 is made of any suitable polymer, such as nylon or of nitrocellulose (cellulose nitrate, pyroxylin).

Stopper ball 65 is lined with elemental iron-silicon crystal particulate of which the weight controls its descent to cut off urine outflow and its lifting determines the strength of electromagnet 66. For chemical isolation, minimal adhesion to the lining, or of trapping in a ruga lining the bladder, stopper ball 65 is encapsulated within an outer layer of polytetrafluoroethylene. When medication or electrical neurostimulation is to be added, electromagnet 66 is mounted with a nonjacketing side-entry connector rather than as a clasp-electromagnet. To lift stopper ball 65 from the bladder outlet, or neck, the patient presses a small radio remote control switch on a wristband, or attached to the band of a wristwatch, or implanted subcutaneously at the wrist to send current from the transdermally charged implanted battery 54 in FIG. 12A to electromagnet 66.

Since the weight of magnet 66 is slight, support by the umbilical ligaments not even needed, internal sensation due to its weight if any is soon habituated through stimulus decay. To minimize a sensation of abruptness when magnet 66 is energized, the field strength is kept to the minimum that testing establishes to be fully effective. Not only can the arrangement shown in FIG. 12B be combined with that shown in FIG. 12A, but should the patient present symptoms of any other bladder dysfunction or develop these at a later date, unlike an hydraulic artificial urinary sphincter, an electrically based systemic approach allows the addition of a few system components to remedy these symptoms as well. For example, as shown in FIG. 12D, initial or later atony or dyssynergia (ataxia) of the bladder is remedied by adding encapsulated bladder contracting iron-silicon crystal disks 67 and 68 subserosally to either side of the bladder outlet or neck. Disks 67 and 68 are positioned in opposition to the clasp-electromagnets 69 and 70 respective of each.

Should magnetic circuit diversion upset the simultaneous attraction of stopper ball 65 and disks 67 and 68 so that the bladder is not contracted at the same time that the outlet is opened, the paired magnets and attractants are offset anteroposteriorly. Also compatible with FIGS. 12A and 12B is the arrangement shown in FIG. 12C. Not subject to the adverse sequelae that follow placement of a stent or catheter, or a meatorrhaphy, bypass drainage of the bladder to the bulbar urethra when a dysfunctional or missing membranous urethra due to stricture following prostatectomy, or loss through trauma or following surgical excision necessitates, for example, eliminates the need for an external collection bag. As shown in FIG. 12C when possible, drainage is by convergence with the bulbar urethra through a ductus side-entry jacket.

If drainage to an external, or extracorporeal, bag is unavoidable, then using the means described herein, the conduit is not reconstructed ileum led to a rosebud stoma but rather a synthetic line exiting through a body surface type nonjacketing side-entry jacket as described in copending application Ser. No. 14/121,365, entitled Ductus Side-entry Jackets and Prosthetic Disorder Response Systems. Provided synthetics are provided with the means for preventing the formation of biofilm or clot, the superiority of such materials over the physiologically inappropriate diversion and reconstruction of tissue is considerable.

When the patient is incontinent, and outlet obstructed from the outset, the arrangement shown in FIG. 12C is combined with that shown in FIG. 12D. In this case, bypass line 52, fastened by nonjacketing side-entry connector 62 includes electromagnetic pinch valve 60, which functions as an artificial sphincter Thus, the arrangements shown in FIGS. 12A, 12B, 12C, and 12D can be used alone or in combination, FIG. 12A to delivery medication, allow lavage in either direction, and diversion to an external collection bag, 12B added to alleviate incontinence, 12C added to bypass an obstructed outlet, and 12D added to alleviate atony or dyssynergy. When the patient is incontinent and outlet obstructed from the outset, the arrangement shown in FIG. 12C includes sphincter 60 in bypass 52.

FIGS. 14 thru 16 show a nanometer range precision, such a piezoelectric, stepper-motorized hypotube or very fine gauge hollow (injection/aspiration) needle in use to release a superparamagnetic carrier-bound drug into a solid tumor, here depicted as situated within the kidney. The depth to which the tip of the needle is brought sets the point of drug release, and the patch-electromagnets 40 can be apportioned current to draw the susceptibly bound drug particles along any trajectory to any point subtended by the magnets with the needle tip as origin. For example, a superparamagnetic particle drug carrier-bound antineoplastic, usually a platin, can be steered into any direction subtended by electromagnets fastened about the periphery of the organ, here diagrammatically shown as within the renal medulla with renal fascia and surrounding fat omitted.

Advancement of the needle, emission of the ferrofluid, and proportional energization of the electromagnets are coordinated by an implanted microcontroller. The overall configuration is similar to the usually larger gauged hollow needle or catheter shown in FIG. 6, which can likewise have radiation shielding and clasp-electromagnets spaced about the outer surface of the organ or other tissue treated to allow the coordinated field strength of these magnetically vector the drug carrier nanoparticles into any direction the magnets subtend. The positioning of the point of release and emission of the ferrofluid are under the control of a microcontroller program. When the disease is singular with respect to the need for implants, the microcontroller and battery are implanted locally, with occasional provision of the ferrofluid through a subcutaneously placed portacath or Ommaya type reservoir.

With the battery implanted and recharged by transcutaneous (actually, transdermal) energy transfer, the apparatus is entirely intracorporeal (internal to the body), that is, fully or closed-skin implanted. When the delivery of the drug would best be continuous and/or multiple drugs must be provided so that the microcontroller coordinates the delivery of each to treat comorbid disease, a belt-worn pump-pack is used to supply the drugs through a port positioned in the pectoral region. This port, described in copending application Ductus Side-entry Jackets and Prosthetic Disorder Response Systems, filed on 25 Aug. 2014 Ser. No. 14/121, 365 is placed outside the body to allow continuous flow without a delivery tube or tubes exiting through the integument, creating a path for the incursion of microbiota and infection.

That this arrangement is easily extended to work in three dimensions with the addition of a magnet situated off-line with respect to the first two is considered obvious. FIG. 14 shows an overall perspectival view of a motorized hollow needle, electrode, excimer laser, hypotube, fine catheter, or other rod-shaped device. When the anatomy is compact or 'tight' so that the extent to which the connector protrudes is best minimized to prevent encroachment upon neighboring tissue, the battery, which is recharged by means of transcutaneous energy transfer regardless where implanted, is placed intracorporeally. FIG. 15 provides an overhead cutaway, and FIG. 16, a side cutaway view of the motorized side connector shown in FIG. 14 and in a typical application in FIGS. 13A and 13B.

FIG. 17 shows an adaptation of the Vineberg procedure for the reperfusion of myocardium to noncardiac tissue which has remained hypoxic over an interval such that sustained venous hypertension is assumed to have impaired venous runoff, or drainage, so that providing only an incurrent or 'arterial' blood supply line would not reinstate flow as did Vineberg. While not completely dysfunctional as to have atrophied and been resorbed, the native drainage will usually have become degraded, fibrosed and occluded with leukocytes, as to resist reperfusion and hinder healing, justifying its bypass from the outset. In FIG. 17, the ductus side-entry jackets toward the top of the drawing are used to create junctions with the native artery and vein.

In FIG. 17, small seepage perforation slits or holes through baseplate 1 and foam 2 if used would be positioned on the unseen opposite (far, deeper) side of lines 34 and 35 facing the hypoxic tissue, not along the outer surface shown which do not pass through hypoxic tissue but run close to the surface, whether submuscularly, subfascially, or subcutaneously. Also in FIGS. 17, 18, and 19, lines 34 and 35, of unique conformation compared to a typical nonjacketing side-entry connector such as shown in FIG. 1, have been distinguished from side connectors 3 as not just connected to and continuous therewith. In FIG. 17, port 39 placed inside the body wall when only one drug targeting destination is involved and on the outer surface of the body when different drugs must be delivered to different destinations, usually in the pectoral region, provides a separate labeled entry hole leading into each accessory drug targeting supply line.

In the adaptation of the Vineberg procedure addressed above in the section entitled Vineberg-derived Prevention of Hypoxia and Reperfusion shown in FIGS. 17, 18, and 19 one catheter each serves to deliver and drain blood. The connection of the two catheters to the side-entry connector in FIG. 17 differs in that baseplate 1 proffers quarter-round tubular extension line receivers 38 integrally molded with or bonded to baseplate 1 for receiving catheter side connector lines 3. Also, the bend along the distal segment of each line 3 disallowing clockwise and counterclockwise twisting, insertion is by trephination with aspiration and retention by adhesion of the ribbed or convoluted outer surface of the terminal segment within the extension line receivers 38 with complementary ribbing lining the internal surface of the lumen.

Such a port can often allow dispensing with the need for a belt worn or shoulder suspended pump pack. When only a single channel is needed and the volumetric rate of delivery does not additionally require a reservoir, a conventional subcutaneous port can be used. According to the scheme depicted in FIG. 17, each entry hole in body surface port 39 if not sufficiently replenished through periodic injection, is led to an implanted reservoir or bladder. Quite small implanted transdermally recharged, or transcutaneous induction powered, assist pumps each meter out the drug from the respective bladder according to the controller coordinated delivery drug prescription program.

Unless a more recently confirmed site for the placement of a cardiac assist device is used (see, for example, Maltais, S., Davis, M. E., and Haglund, N. 2014. "Minimally Invasive and Alternative Approaches for Long-term LVAD Placement: The Vanderbilt Strategy," Annals of Cardiothoracic Surgery 3(6):563-569; Krabatsch, T., Potapov, E., Stepanenko, A., Schweiger, M., and 4 others 2011. "Biventricular Circulatory Support with Two Miniaturized Implantable Assist Devices," Circulation 124(11 Supplement): S179-S186; Witkowski, C. J. and Saudek, C. 2008. "The Implantable Peritoneal Pump—A Patient's Perspective," Journal of Diabetes Science and Technology 2(4):703-706), when an eventual need for a cardiac assist device must be considered, the reservoirs and pumps are positioned to avoid the preperitoneal space or pocketing in the space between the posterior rectus sheath and the rectus abdominis of conventional placement (see, for example, Selzman, C. H. 2014. "Left Ventricular Assist Device Insertion Technique," at emedicine.medscape.com/article/1839658-technique).

Potential locations for the creation of a pocket to hold implants if isolated from the internal environment include the peritoneal cavity (see, for example, Witkowski, C. J. and Saudek, C. 2008. "The Implantable Peritoneal Pump—A Patient's Perspective," Journal of Diabetes Science and Technology 2(4):703-706; Icenogle, T., Sandler, D., Puhlman, M., Himley, S., Sato, D. J., and Schaefer, S. 2003. "Intraperitoneal Pocket for Left Ventricular Assist Device Placement," Journal of Heart and Lung Transplantation 22(7):818-821). A fully implanted or closed-skin prosthetic disorder response system to automatically coordinate the treatment of several comorbid conditions so that the patient is untethered by fluid or electrical lines and able to move about freely might require more pumps and reservoirs than there are sites or sites not requiring excessive dissection and trauma to create.

In this circumstance, well developed methods of skin expansion for use in plastic and reconstructive surgery allow the creation of a subcutaneously or more deeply situated pocket (Wagh, M. S. and Dixit, V. 2013. "Tissue Expansion: Concepts, Techniques and Unfavourable Results," Indian Journal of Plastic Surgery 46(2):333-348; Zhang, G. L., Zhang, J. M., Ji, C. Y., Meng, H., Huang, J. H., and 4 others 2013. "A Comparison of Skin Expansion and Contraction between One Expander and Two Expanders: A Preliminary Study," Aesthetic Plastic Surgery 37(6):1202-1208; Agrawal, K. and Agrawal, S. 2012. "Tissue Regeneration during Tissue Expansion and Choosing an Expander," Indian Journal of Plastic Surgery 45(1):7-15; Lasheen, A. E., Saad, K, and Raslan, M. 2009. "External Tissue Expansion in Head and Neck Reconstruction," Journal of Plastic, Reconstructive, and Aesthetic Surgery 62(8):e251-e254; Lasheen, A. E. 2006. "External Tissue Expansion Using Negative Pressure in Upper-extremity Reconstruction," Journal of Hand Surgery 31(10):1694-1696; Lasheen, A. E., Salim, A., Hefny, M. R., Al-Bakly, E. 2004. "External Tissue Expansion Successfully Achieved Using Negative Pressure," Surgery Today 34(2):193-196; Sharobaro, V. I., Moroz, V. Y., Starkov, Y. G., and Strekalovsky, V. P. 2004. "First Experience of Endoscopic Implantation of Tissue Expanders in Plastic and Reconstructive Surgery," Surgical Endoscopy 18(3):513-517).

Muscle is sufficiently stretchable to improve the range of motion about a joint. With highly miniaturized pumps and batteries, this might prove adequate in a few circumstances (see, for example, De Deyne, P. G. 2001. "Application of Passive Stretch and Its Implications for Muscle Fibers," Physical Therapy 81(2):819-827); however, the degree of expansion essential for larger or additional implants must depend upon autologous tissue engineering or if time does not allow, then bovine or porcine sheeting. Otherwise, the peritoneal cavity, dermal expansion, and miniaturization represent the avenues for progress (see, for example, Rodriguez, L. E., Suarez, E. E., Loebe, M., and Bruckner, B. A. 2013. "Ventricular Assist Devices (VAD) Therapy: New Technology, New Hope?," Methodist Debakey Cardiovasc Journal 9(1):32-37). A port described in copending application Ser. No. 14/121,365 incorporates means other than a conventional skin button or skin barrier for averting infection and instability. The port provides as many entry holes as accessory lines that require periodic drug replenishment.

Through this approach, the patient with multiple conditions under treatment, if not competent to replenish the drugs, reports periodically to the clinic where different specialists each replenish their respective drugs, the controller coordinating the release of each in coordination with each of the others. To achieve full implantation without a belt-worn pump and battery pack and thus allow unimpeded movement, tethering to stationary apparatus by fluid and/or electrical lines is eliminated. This is accomplished by placing the reservoir or reservoirs and/or pump or pumps respective of each drug entry supply line intracorporeally, replenishment then by periodic injection. In addition to allowing free movement, implanting the accessory line reservoirs and pumps results in a treatment that comfort permitting, is as unobtrusive and cosmetically acceptable as possible. Whether a number of these small, usually peristaltic pumps is energized by the same battery depends upon the space available without forces from neighboring bone that would cause discomfort and thus restrict movement.

Pump implants in contact with the skin can result in skin breakdown which the interposition of other tissue such as fascia or muscle (Tijerina, V. N., Saenz, R. A., Garcia-Guerrero, J. 2010. "Experience of 1000 Cases on Subfascial Breast Augmentation," Aesthetic Plastic Surgery 34(1):16-22; Hendricks, H. 2007. "Complete Submuscular Breast Augmentation: 650 Cases Managed Using an Alternative Surgical Technique," Aesthetic Plastic Surgery 31(2):147-153; Khan, U. D. 2007. "Muscle-splitting Breast Augmentation: A New Pocket in a Different Plane," Aesthetic Plastic Surgery 31(5):553-558; Atiyeh, B. S., Hayek, S. N., Skaf, G. S., Al Araj, A., and Chamoun, R. B. 2006. "Baclofen Pump Pocket Infection: A Case Report of Successful Salvage with Muscle Flap," International Wound Journal 3(1):23-28) or fascia (Ammar, A., Ughratdar, I., Sivakumar, G., Vloeberghs, M. H. "Intrathecal Baclofen Therapy—How We Do It," Journal of Neurosurgery. Pediatrics 2012 10(5):439-444; Ventura, O. D. and Marcello, G. A. 2005. "Anatomic and Physiologic Advantages of Totally Subfascial Breast Implants," Aesthetic Plastic Surgery 29(5):379-384; Kopell, B. H., Sala, D., Doyle, W. K., Feldman, D. S., Wisoff, J. H., and Weiner, H. L. 2001. "Subfascial Implantation of Intrathecal Baclofen Pumps in Children: Technical Note," Neurosurgery 49(3):753-757; Shahian, D. M., Williamson, W. A, Streitz, J. M. Jr., and Venditti, F. J. 1992. "Subfascial Implantation of Implantable Cardioverter Defibrillator Generator," Annals of Thoracic Surgery 54(1):173-174) serves to dispel. Site distribution of the components may allow subpectoralis major placement to reduce stress on the implant overlying skin (Asamura, S., Kurita, T., Motoki, K., Yasuoka, R., Hashimoto, T., and Isogai, N. 2014. "Efficacy and Feasibility of the Submuscular Implantation Technique for an Implantable Cardiac Electrical Device," Eplasty 14:e40).

Affixed to the outer surface of the body, the port described is not subcutaneous. However, especially since in the treatment of comorbid disease, separate teams may inject the drugs into different entries, the controller program coordinating the delivery of each, placement in plain view is imperative for clear definition of the entry hole or socket into each drug targeting line. While external, the port incorporates features to suppress infection and skin breakdown. Unless untenably traumatizing, placement of the reservoirs and pumps is subfascial rather than subcutaneous, thus interposing a protective layer of tissue between skin and implant pocket or pockets.

Sufficient muscle with which to enclose the reservoir and/or pump pocket or pockets can usually be obtained by autologous transplantation, tissue expansion or tissue engineering seldom if ever necessary. However, when the need to complete installation is exigent, the production of a pocket by tissue expansion, especially with fascia included, slows down an already slow process. In an obese patient, the skin is already stretched, allowing the preparation of a pocket or pockets to contain implants to be created without tissue expansion but rather suction lipectomy (liposuction).

This should, however, take into account the odds for skin breakdown at the location or locations contemplated.

Fascia included, the alternative options include autologous, homograft, cadaver, or xenographic transplantation, or the use of autologous muscle alone, or synthetic materials, such as polytetrafluoroethylene, polypropylene, or silicone sheet, or processed bovine or porcine pericardial sheeting or mesh materials (see, for example, Cobb, W. S., Kercher, K. W., and Heniford, B. T. 2005. "The Argument for Lightweight Polypropylene Mesh in Hernia Repair," Surgical Innovation 12(1):63-69; Demir, U., Mihmanli, M., Coskun, H., Dilege, E., Kalyoncu, A., Altinli, E., Gunduz, B., and Yilmaz, B. 2005. "Comparison of Prosthetic Materials in Incisional Hernia Repair," Surgery Today 35(3):223-227; Kapan, S., Kapan, M., Goksoy, E., Karabicak, I., and Oktar, H. 2003. "Comparison of PTFE, Pericardium Bovine and Fascia Lata for Repair of Incisional Hernia in Rat Model, Experimental Study," Hernia 7(1):39-43; Cilley, J. H. Jr., Cernaianu, A. C., Libby, J. A., Baldino, W. A., and DelRossi, A. J. 1991. "Silicone Pouch for Protection of Automatic Implantable Cardioverter-defibrillator Leads," Annals of Thoracic Surgery 51(3):504-505).

The production of fascia by expansion a slow process, and synthetics necessitating removal if infected (see, for example, Nakano, T., Yoshikawa, K., Kunieda, T., Arakawa, Y., Kikuchi, T., and 4 others 2014. "Treatment for Infection of Artificial Dura Mater Using Free Fascia Lata," Journal of Craniofacial Surgery 25(4):1252-1255), the preferred approach is the use of autologous tissue, muscle or fascia, such as fascia lata, as least susceptible to complications (see, for example, Alani, H. A. and Balalaa, N. 2013. "Complete Tissue Expander Coverage by Musculo-fascial Flaps in Immediate Breast Mound Reconstruction after Mastectomy," Journal of Plastic Surgery and Hand Surgery 47(5): 399-404).

Pumps larger than those contemplated, such as an intrathecal baclofen pump, are routinely placed in a subcutaneous pocket made in a lower quadrant of the abdomen at a sufficient distance from the anterior rib and iliac crest as not to cause discomfort (see, for example, Knight, K. H., Brand, F. M., Mehaourab, A. S., and Veneziano, G. 2007. "Implantable Intrathecal Pumps for Chronic Pain: Highlights and Updates," Croation Medical Journal 48(1):22-34), the infraclavicular fossa an alternative site (see Rocque, B. G. and Albright, A. L. 2010. "Infraclavicular Fossa as an Alternate Site for Placement of Intrathecal Infusion Pumps: Technical Note," Neurosurgery 66(2):E402-E403).

The nonanatomical or diagrammatic representation is of the tibial vessels below the popliteal artery at the popliteal fossa, with a subcutaneous belt used to mount the nonjacketing side-entry connector toward the ankle. This application is exemplary, the side-entry connector applied directly to the substrate tissue in most sites. When the native arterial or supply vasculature has become impaired, anticoagulant, thrombolytic and antimicrobial medication are delivered directly into the incurrent line 34. When the blood supply remains functional, anticoagulant, thrombolytic and antimicrobial medication are delivered directly into excurrent or 'venous' line 35. Venous' line 35 is used to return the blood to a relatively large vein, preferably one a high enough pressure to overcome the need to implant an assist pump.

If the excurrent vein is too low in pressure, then a miniature pump implanted within the lower pelvic area of the abdominal cavity, for example, is used to compensate for an inadequacy in the venous return pressure gradient. In FIG. 17, drugs as needed to encourage vascularization, prevent clotting, infection, and/or the formation of a biofilm are injected or pumped through a port mentioned above in the section entitled Concept of the Invention, placed at the body surface. The drugs pass through water jacket and accessory lines 13 and into respective destination line 34 or 35.

The greater distance to vessels larger in caliber is compensated for by the greater pressure at the prosthesis-vessel junctions. For a given level of arterial takeoff or origin and venous return, the need for an assist pump implant increases as the distance to be traversed with an inelastic catheter of fine caliber and without the valves of native veins increases. In placing this nonjacketing side-entry connector, to simulate a sinusoid, tissue plug removal by the side connectors is intentionally made deeper than usual, then retracted. If tissue remains separating the trepan ends of the side-connectors, it is removed by connecting either side connector to an aspiration pump. Clot avoidance is with heparin, and, if necessary, a thrombolytic.

If not, then an incurrent or 'arterial' catheter is also placed with the medication delivered through the catheter. The medication is delivered by the incurrent line as it must already be in the blood when entering the venous return line. Moving through the calf, the lines are without side slits or holes and plunged to run parallel to the large native vessels. Over this segment, optimal advantage is gained of the intrinsic calf pump action by increasing the caliber of the tubes with tubing having highly elastic walls, the end to end connections of this stretch with the smaller caliber tubes superior and inferior to the calf mediated with size adapters as shown in FIG. 20.

FIG. 18 provides a side view of the dual side connector nonjacketing side-entry connector shown in FIG. 17. At this low level, the pressure gradient is small, allowing the connector to make a sharp if not right angle when exiting the connector, thereby minimizing protrusion that would cause irritation and pose a cosmetic problem. This connector is but a variant of the embodiment shown in FIG. 1, with locking collar 20 that allows the side connectors and tubing connected to these to exit in any radial direction. As in FIG. 1, the baseplate is 1, the foam cushion 2, and the side connector 3.

FIG. 20 provides a cutaway, or partly internal, view of a compound nonjacketing side-entry connector with two connectors joined by a telescoping spring loaded span to allow the catheter or other side connector entry wound to be clearly viewed and/or more rigidly stabilize the tissue-catheter at its point of entry. A sudden impact or jolt is absorbed by the shockwave-ipsilateral sliding outer spring-loaded arm 33. To protect against more intense impacts, suture is passed through suture loops 32 to fix the connectors to the substrate tissue and the organ or tissue to connect or -pexy and thus stabilize the organ or tissue by connection to neighboring tissue.

The outside view of FIG. 21 shows the flat upper surface of crossbar housing 37, allowing locking collar 20 to be tightened down flush thereto. While side connector 3 can have its own baseplate with snap clasps, here it is shown as situated between two connectors for accessibility, viewability with imaging equipment, and pictorial clarity. Centering of the side connector between outrigger baseplates (footings, pads) as in FIGS. 20 and 21 does not pertain to the motorized embodiment shown in FIG. 14. If such a motorized nonjacketing side-entry connector as shown in FIG. 14 requires additional stabilization, it is provided with outrigger baseplates with spring loaded crossbar 33 as shown in FIGS. 20 and 21, and if necessary, the suture loops 32 of the central motorized side connector and the outriggers are used to connect or -pexy the compound connector to neighboring stable tissue.

Combination of the embodiments shown in FIGS. 14 and 21 with the connectors shown in FIGS. 4 and 21 are addressed above. If necessary, additional stabilization of a motorized connector such as shown in FIG. 14 is achieved by crossing over two crossbar bridge-connected double-fastener baseplates, or double outrigger type connectors of the kind shown in FIG. 20. To minimize the height of such an arrangement and thus the possibility of protrusion into neighboring tissue, the parts that stand proud at the center are kept as squat as possible and the formation consisting of the motorized side-entry connector of FIG. 14 with both side or outrigger pads enclosed within a cover with rounded corners and edges.

The spring loaded bars with injection needle side connector 3 in FIG. 14 passing therethrough as hub (rotary joint, journal) are crossed over in scissors conformation as to decussate in bias, rotation about side connector 3 made sufficiently frictional so that intentional twisting force must be applied to change the angle at which the flattened center pieces 42 intersect. To prevent round needles 6 from obstructing rotation of the bars should a force push the bars downward, the interval separating the upper surface of housing 24 and the bars filled with a bushing. The bars are positioned at the level along side connector 3 in FIG. 14 at the smallest distance from the upper surface of motor and charging electronics housing 24 that housing 24 and round needles 6 will allow.

A locking collar or ring can be used to prevent the bars from being pulled upward. Examination of FIG. 14 will make it apparent that if the bars rest against the roof of housing 24 so that needles 6 would obstruct rotation, then widening baseplate 1 would allow positioning needles 6 more widely apart, increasing the range of rotation even though the bars and needles are at the same level. The motorized side-entry connector with scissors-mounted crossbar bridge-connected double-fastener baseplates providing four footings or anchors is mounted at the angle that most likely disposes the spring loaded arms to respond to sidewise deflections. If necessary, the suture loops 32 of the motorized side-entry connector and both baseplates of each spring loaded crossover bar can be used to stabilize the formation with suture to neighboring stable tissue.

As also shown in FIG. 21, such an open-sided side connector not passing down through a baseplate with foam cushion is provided with a drip-tube 43 to allow antimicrobial and anti-inflammatory drugs to protect the entry wound. FIG. 22 shows a longitudinal section through an adapter tube for joining catheters of different caliber and/or different material in end to end relation. To minimize turbulence that an abrupt increase or decrease in diameter would impart, the passageway through the adapter gradually inclines between the two internal diameters. Such adapters allow a section of wider tubing with highly elastic walls to be run alongside the large vessels in the lower leg to take better advantage of the calf pump in the treatment of venous insufficiency ulcers, for example. The adapter is provided with suture loops or eyelets at the junctions of the caliber changing incline to allow fixation with suture to neighboring tissue.

In other locations, the interposition of a wider segment also allows the placement about this segment of a subsidiary or derivative ductus side-entry jacket to connect a branch line to the primary catheteric line. This approach can be applied to obtaining distinctions in blood pressure to treat more and less severely affected areas within a wider lesion, for example. Yet another situation in which a change in catheteric caliber can arise is in passing through compact anatomy, where the surrounding structures would be abraded or encroached upon unless the caliber were reduced. To pull the adapter in a preferred direction, suture is passed through the small suture loops and surrounding tissue. The suture loops are seen at the junctions of the wider and narrower sections with that inclined.

Having set forth structures and functions of nonjacketing side-entry connectors, the many significant improvements these make possible in conventional procedures, and the central need for these for the implementation of automatic prosthetic disorder response systems as second tier or backup artificial 'immune' systems.

The invention claimed is:

1. A tissue connector comprising a platform and a foam cushion; wherein the foam cushion is positioned beneath the platform wherein the platform is configured to securely engage a tissue; wherein the platform is configured to interchangeably engage one or more therapeutic and/or diagnostic devices thereby fastening said one or more therapeutic and/or diagnostic devices in working relation to the tissue; wherein said platform comprises at least one hole and a locking collar about said at least one hole, said locking collar configured to control the depth of a side connector placed therethrough; wherein said platform is configured to accept the side connector through said at least one hole at a right angles from the tissue connector; wherein the platform is configured to engage the tissue via a plurality of axially rounded rotatable tissue-undercutting and anchoring needles; wherein the plurality of axially rounded rotatable tissue-undercutting and anchoring needles are rotatable independently of the platform; and wherein a longitudinal axis of the plurality of axially rounded rotatable tissue-undercutting and anchoring needles moves circumferentially about an axis of rotation when rotating axially.

2. A tissue connector according to claim 1, wherein the issue connector is configured to securely fix said one or more therapeutic and/or diagnostic devices within the tissue thereby allowing long-term leak-free communication with the tissue in an ambulatory patient, and further allowing the direct mechanical conveyance of drugs and electrotherapy to the tissue so that adverse side effects, drug-food, and drug-drug interactions are avoided.

3. A tissue connector according to claim 1, wherein the foam cushion comprises a viscoelastic polyurethane foam.

4. A tissue connector according to claim 1, further comprising a pump, whereby the pump supplies fluid medicinals to said tissue connector; and wherein the pump is controlled according to a microcontroller program in response to the output of at least one physiological parameter sensor, said program and said sensor related through at least one closed feedback loop.

5. A tissue connector according to claim 4, configured for delivery of fluid drugs into the tissue and delivery of electrical discharge pulses under coordinated control of a microcontroller program responsive to output of at least one implanted physiological parameter sensor, wherein said microcontroller program and said sensor are related through at least one closed feedback loop.

6. A tissue connector according to claim 1, wherein the plurality of axially rounded rotatable tissue-undercutting and anchoring needles are hollow with a beveled tip and are configured to transmit an injectant pumped through the plurality of axially rounded rotatable tissue-undercutting and anchoring needles into the tissue, said injectant delivered to said anchoring needles through a fluid line inserted through said connector.

7. A tissue connector according to claim 6, configured for delivery of fluid drugs into the tissue and delivery of electrical discharge pulses under coordinated control of a microcontroller program responsive to output of at least one implanted physiological parameter sensor, wherein said microcontroller program and said sensor are related through at least one closed feedback loop.

8. A tissue connector according to claim 1, further comprising said one or more therapeutic and/or diagnostic devices selected from the group comprising fluid delivery lines, electrical wires, an electromagnet, an aspiration line, an electrode, a cabled device such as an endoscope, or excimer laser, or any combination thereof.

9. A tissue connector according to claim 8, wherein said one or more therapeutic and/or diagnostic devices comprises the fluid delivery lines; wherein the fluid delivery lines are configured to deliver medication selected from the group comprised of antimicrobials, anti-inflammatories, immunosuppressives, and anticoagulants.

10. An assemblage of tissue connectors, each according to claim 8, wherein the one or more therapeutic and/or diagnostic devices are configured to be mounted to a tissue connector of the assemblage of tissue connectors and are configured to be used individually or severally in coordination with another of those of the one or more therapeutic and/or diagnostic devices mounted to another tissue connectors of the assemblage of tissue connectors, thereby to provide diagnostics, medication, electrotherapy, radiation, and/or autonomic motor support to the tissue connected.

11. A tissue connector according to claim 1, whereby said tissue connector includes radiation shielding sufficient to protect the tissue from radiation exposure energy.

12. An assemblage of connectors, each according to claim 11, wherein the one or more therapeutic and/or diagnostic devices are configured to be mounted to a tissue connector of the assemblage of tissue connectors and are configured to be used individually or severally in coordination with another of the one or more therapeutic and/or diagnostic devices mounted to another tissue connector of the assemblage of tissue connectors, thereby to provide diagnostics, medication, electrotherapy, radiation, and/or autonomic motor support to the tissue connected.

13. A tissue connector according to claim 11, further comprising a shield conduit for conveying radioisotopes and radionuclides to the tissue.

14. A tissue connector comprising a platform and a foam cushion; wherein the foam cushion is positioned beneath the platform wherein the platform is configured to securely engage a tissue; wherein the platform is configured to interchangeably engage one or more therapeutic and/or diagnostic devices thereby fastening said one or more therapeutic and/or diagnostic devices in working relation to the tissue; wherein the platform is engaged to the tissue via a plurality of axially rounded rotatable tissue-undercutting and anchoring needles; wherein said platform includes at least one hole for the intromission therethrough of an intersecting tube having a sharp front edge and a locking collar about said hole that is configured to secure the depth of said intersecting tube, allowing said sharp front edge to be used as a trepan wherewith to excise a plug of the tissue.

15. A tissue connector comprising a platform and a foam cushion; wherein the foam cushion is positioned beneath the platform wherein the platform is configured to securely engage a tissue; wherein the platform is configured to interchangeably engage one or more therapeutic and/or diagnostic devices thereby fastening said one or more therapeutic and/or diagnostic devices in working relation to said tissue; wherein the platform is engaged to said tissue via a plurality of axially rounded rotatable tissue-undercutting and anchoring needles; wherein said plurality of axially rounded rotatable tissue-undercutting and anchoring needles are electrically conductive, connected to a source of electrical power, and configured to discharge electrostimulatory pulses under the control of a microcontroller.

16. A tissue connector according to claim 15, wherein the microcontroller is controlled according to a microcontroller program responsive output from at least one implanted physiological parameter sensor, where said microcontroller program and said sensor are related through at least one closed feedback loop.

17. A tissue connector according to claim 15, wherein said connector is radiation shielded.

* * * * *

UNITED STATES PATENT AND TRADEMARK OFFICE
CERTIFICATE OF CORRECTION

PATENT NO. : 11,013,858 B2
APPLICATION NO. : 14/998495
DATED : May 25, 2021
INVENTOR(S) : David S. Goldsmith It is certified that error appears in the above-identified patent and that said Letters Patent is hereby corrected as shown below:

In the Claims

Column 212, Line 13 for Claim reference numeral '1', "right angles from the tissue connector;..." should read -- "right angle from the tissue connector;..." --

Column 212, Line 2 for Claim reference numeral '2', "issue connector is configured to securely fix said one or more..." should read -- "tissue connector is configured to securely fix said one or more..." --

Column 213, Line 6 for Claim reference numeral '10', "...with another of those of the one or more therapeutic" should read -- "...with another of the one or more therapeutic" --

Column 213, Lines 7-8 for Claim reference numeral '10', "...tissue connectors of the assemblage of tissue connectors..." should read -- "..tissue connector of the assemblage of tissue connectors..." --

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*